(12) United States Patent
Manetti et al.

(10) Patent No.: US 9,102,740 B2
(45) Date of Patent: Aug. 11, 2015

(54) CNA-B DOMAIN ANTIGENS IN VACCINES AGAINST GRAM POSITIVE BACTERIA

(71) Applicants: Andrea Guido Oreste Manetti, Siena (IT); Immaculada Margarit Y Ros, Siena (IT); Guido Grandi, Siena (IT)

(72) Inventors: Andrea Guido Oreste Manetti, Siena (IT); Immaculada Margarit Y Ros, Siena (IT); Guido Grandi, Siena (IT)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 13/912,472

(22) Filed: Jun. 7, 2013

(65) Prior Publication Data

US 2014/0017727 A1 Jan. 16, 2014

Related U.S. Application Data

(62) Division of application No. 13/144,149, filed as application No. PCT/IB2010/050110 on Jan. 12, 2010, now Pat. No. 8,465,751.

(60) Provisional application No. 61/143,859, filed on Jan. 12, 2009.

(51) Int. Cl.
| | |
|---|---|
| C12N 15/03 | (2006.01) |
| C12P 21/04 | (2006.01) |
| C07H 21/04 | (2006.01) |
| C07K 14/315 | (2006.01) |
| C12N 15/63 | (2006.01) |
| A61K 39/085 | (2006.01) |
| A61K 39/09 | (2006.01) |
| C07K 16/44 | (2006.01) |
| A61K 39/00 | (2006.01) |

(52) U.S. Cl.
CPC .......... C07K 14/315 (2013.01); A61K 39/085 (2013.01); A61K 39/092 (2013.01); C07K 16/44 (2013.01); C12N 15/03 (2013.01); C12N 15/63 (2013.01); A61K 2039/55566 (2013.01)

(58) Field of Classification Search
CPC .......... A61K 39/092; A61K 2039/55566; A61K 2039/522; A61K 2039/55505; A61K 39/085; A61K 2039/523; A61K 39/0208; A61K 39/05; A61K 39/08; A61K 39/09; A61K 39/095; C07K 14/315; C07K 16/1275; C07K 16/40; C07K 16/1267
See application file for complete search history.

(56) References Cited

U.S. PATENT DOCUMENTS

| | | | |
|---|---|---|---|
| 6,777,547 B1 | 8/2004 | Podbielski | |
| 7,169,902 B2 * | 1/2007 | Podbielski et al. | ........ 530/387.1 |
| 7,838,010 B2 | 11/2010 | Bensi et al. | |
| 7,939,087 B2 | 5/2011 | Telford et al. | |

FOREIGN PATENT DOCUMENTS

| | | |
|---|---|---|
| WO | 97/43314 A2 | 11/1997 |
| WO | 01/70267 A1 | 9/2001 |
| WO | 2006042027 A2 | 4/2006 |
| WO | 2008/088822 A1 | 7/2008 |

OTHER PUBLICATIONS

Deivanayagam et al., Crystallization and preliminary X-ray analysis of B-domain fragments of a *Staphylococcus aureus* collagen-binding protein, Acta Crystallographica Section D: Biological Crystallography, vol. 55, No. 2, Feb. 1, 1999, pp. 525-527.
Deivanayagam et al.: "Novel Fold and Assembly of the Repetitive B Region of the *Staphylococcus aureus* Collagen-Binding Surface Protein," Structure, vol. 8, No. 1, Jan. 15, 2000, pp. 67-78.
Hartford et al.; Matrix-binding proteins of *Staphylococcus aureus*: Functional analysis of mutant and hybrid molecules, Microbiology, vol. 145, No. 9, Sep. 1999, pp. 2497-2505.
Josefsson et al.: "The binding of calcium to the B-repeat segment of SdrD, a cell surface protein of *Staphylococcus aureus*," Journal of Biological Chemistry, vol. 273, No. 47, Nov. 20, 1998, pp. 31145-31152.
Josefsson et al.: Three new members of the serine-aspartate repeat protein multigene family of *Staphylococcus aureus*, Microbiology, vol. 144, No. 12, Dec. 1998, pp. 3387-3395.
Otto: "Targeted immunotherapy for staphylococcal infections: Focus on anti-MSCRAMM antibodies," Biodrugs: Clinical Immunotherapeutics, Biopharmaceuticals and Gene Therapy, vol. 22, No. 1, Jan. 1, 2008, pp. 27-36.
Smeltzer et al.: "Molecular pathogenesis of staphylococcal osteomyelitis," Poultry Science, vol. 79, No. 7, Jul. 1, 2000, pp. 1042-1049.
Snodgrass et al.: "Functional analysis of the *Staphylococcus aureus* collagen adhesin B domain," Infection and Immunity, vol. 67, No. 8, Aug. 1999, pp. 3952-3959.
Zhou et al.: "An immunogenicity study of a newly fusion protein Cna-FnBP vaccinated against *Staphylococcus aureus* infections in a mice model," Vaccine, vol. 24, No. 22, May 29, 2006, pp. 4830-4837.
International Search Report, PCT/IB2010/050110, mailed May 17, 2010.

* cited by examiner

*Primary Examiner* — Padma V Baskar
(74) *Attorney, Agent, or Firm* — Banner & Witcoff, Ltd.

(57) ABSTRACT

The invention provides protective antigens which are useful in vaccine compositions to induce protection against gram positive bacteria, particularly against *S. agalactiae*, *S. pyogenes*, *S. pneumoniae*, *S. aureus*, *S. suis*, and *S. equi*.

3 Claims, 27 Drawing Sheets

FIG. 1
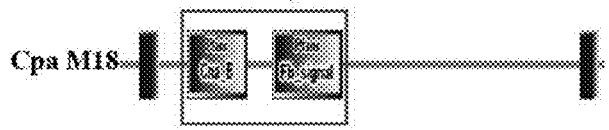
FIG. 1A
FIG. 1B
FIG. 2
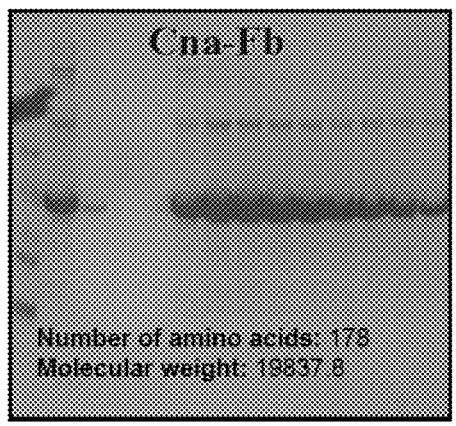

FIG. 3
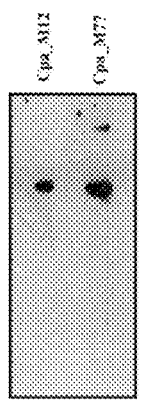 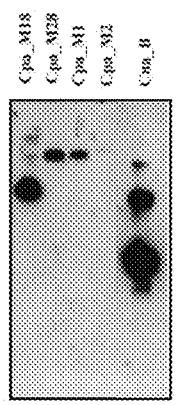 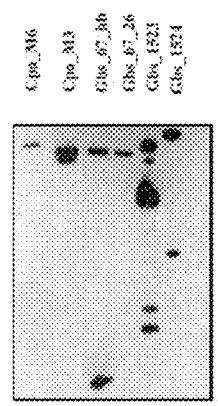 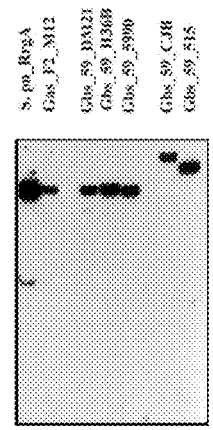
FIG. 3A     FIG. 3B     FIG. 3C     FIG. 3D
FIG. 4
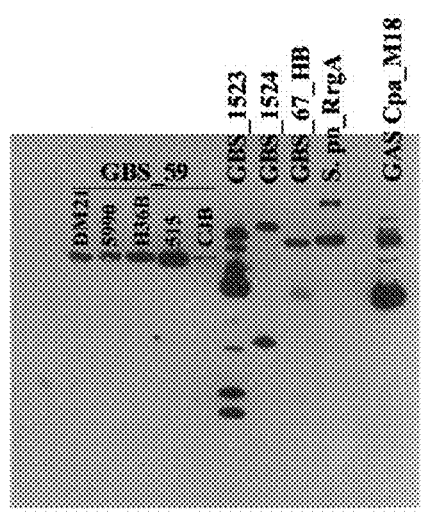 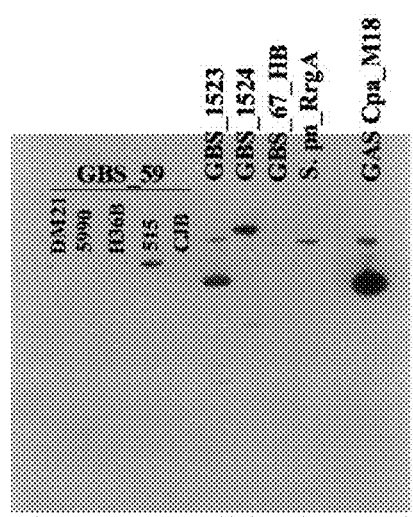
Anti-Cna_B        Anti-Cpa_M18
FIG. 4A        FIG. 4B

FIG. 7

```
CNA_B_GBS_52      LAGVVFHLYEKNGKTP-IPMNGVASQDIDAAK----------------HLEIDSSEHTRISG----  46
CNA_B_GBS_150     LSGVIFMLMD-NQNQP-VRFHKNGRFTIDQGIT---------------SLVIIDKCHEVEG-----  45
CNA_B_GBS_104_1   LGKAIFMLKNIND------------------KSEIS-------------HEIVEGSGEATFN----  32
CNA_B_67          LSKAIFMLKTIAHP-------------------ESKIE-----------KVIAELIGEATFIN---  33
CNA_B_GBS_1523    LQGAIFVLKNAIGQFINFNDINVEWGIEANAT---------------EMTIGADELIITIG----  47
CNA_B_GBS_1524    LAGAVDIYESDAEGN-----------------KASHPVS--------GLVINDKGILMDANNYL  42
CNA_B_GBS_80      LQGAEFDILASDIGTAVKWIDALIKANIIKNYIAGEAVIQPIKLKSHIDGIHEIKGLAYA     60
CNA_B_GBS_104_2   LLGAKFQLQIEKDISG-----------------YKQFVPEGS-----DVFIKNDGKIYFKA---   39
CNA_B_GBS_1521    LITKAVHKIQP----------------------LQIED---------NLPAEG-IVANN-----  26
                  *                                    *

CNA_B_GBS_52      ----LIFED---YVLKEIELQSGMDIQAETAVTIEKSKIVIVIL----  84
CNA_B_GBS_150     ----ILLGK---YIHREAKALTGYRTSMKDAVV---------------  71
CNA_B_GBS_104_1   ----IKIGD---YTLREEIAPIGYKIIDKIIWKVK-------------  59
CNA_B_GBS_67      ----LIIGD---YILSEETAEEGYKIIQIWQVKV--------------  61
CNA_B_GBS_1523    ----IKIGT---YYLVEKKAPLGMILIDNSQKVILGDGAIDTNS----  85
CNA_B_GBS_1524    S---IPIGK---YYLTEMKAPIGYILPKNDISVMVSIGVHKQ------  80
CNA_B_GBS_80      VIDNAIGTAVIYKIKETKAPEGYVIEDKEIEFI--------------  93
CNA_B_GBS_104_2   ----IQIEN---YKDYEISSEDGYEMKIPVVTFTIQNEEVINLK----  78
CNA_B_GBS_1521    ----LPYGI---YIFIQIKTAQGYMSPFTISIPKOGKMDTIIPIVIHQ  69
                  *       *                                   **

FIG. 8
```

```
CNA_B_GBS_80        LGGAEFDLLASDGTAVKWTDALIKANTNKNYTAGEAVTGQPIKLKSHTDG--TPEIKGLAY 59
CNA_B_GBS_52        LAGVVFELYEKNG------RTPIRVKNG----VESQDID-AAKHLETDSSG-HIRISGLIH 49
CNA_B_GBS_104_2     LLGAKFQLQIEKD------------FSG----YKQFVP-EGSDVTKNDG-KIYFKALQD 42
CNA_B_GBS_104_1     LGKATFVLKNDND------------KS-----EISHETVEGSG-EATPENIKP 35
CNA_B_M18           LEGATLKLAQIEG------------SG-----FQEQSFESSTSGKLQLSD-- 34
                    *                                        .   :

CNA_B_GBS_80        AVDANAEGTAVTYKLKETKAPEGYVIPDKE--IRFTVSQT 97
CNA_B_GBS_52        G-----DYVLKEIETQSGYQIGQAE--TAVTIERS 77
CNA_B_GBS_104_2     G-----NYKLYEISSPDGYIEVKTKPVVTFTIQNG 72
CNA_B_GBS_104_1     G-----DYTLREETAPIGYKKTDKT--WKVKVADN 63
CNA_B_M18           G-----TYILTETKSPQGYEIAEPI---TFKVTA- 60
                          .          *              *
```

FIG. 9

```
CNA_B_M18       LEGATLKLAQIEGS--GF-QEQS--FESSTSGQK----------LQLSLGTYILTETKS  44
CNA_B_GBS_1524  LAGAVFDIYESDAN--GN-KASHPMYSGLVTNDKGLLLVD-ANNYLSLPVGKYYLTETKA  56
CNA_B_GBS_1523  LQGAIFVLKNATGQFLNFNDTNNVEWGTEANATEYTTGADGITTTTGLKHGTYYLVEKKA  60
                *  **  :  :      *  :  :                    :    * *:**.*.:

CNA_B_M18       PQGYEIAEP-ITFKVTA--------  60
CNA_B_GBS_1524  PPGYLLPKNDISVLVISTGVTFEQ-  80
CNA_B_GBS_1523  PLGYNLLDNSQKVILGDGATDTTNS  85
                * **    :  :::           
```

→ G box

FIG. 11

```
Cna_B_M18    ----------------------------LEGATLKLAQIEGSG--------------------------FQEQSFESSTSGQK  29
Cna_B_RrgB   LAGAEFVIANADMAGQYLARKADKVSQEEKQLVTTKDALDPAVAAYNALTAQQTQQEK                            60
Cna_B_RrgA1  LGDAVFELKN-NTDG-------------------------------------------TTVSQRTEAQTGE              27
Cna_B_RrgC2  LQGAMPKVMK-EESGHYTP-----------------------------------------VLQNGKEVVTSGK            32
Cna_B_RrgA2  LRGAVPSLQKQHPDYPDIYG----------------------------------------AIDQNGTYQNVRTGE          35
Cna_B_RrgC1  LEGVGFKLVSVARDVSEKE-----------------------------------------VPLIGEYRYSSSGQ          33
                  *    :   :                                             ;
                                                                                                     ┌─────────────────────────┐
Cna_B_M18    ----------------------------------------------------------LQLS---IGTYILTETKS        44  │
Cna_B_RrgB   EKVDKAQAAYNAAVIAANNAFEWVADKIDNENVVKLVSDAQGRFEITGLLAGTYYLEETKQ                      120  │
Cna_B_RrgA1  ---------------------------------------------------------AIFSNIKHGTYYLTEAQP          45  │
Cna_B_RrgC2  D--------------------------------------------------GRFRVEGLEYGTPYYLWELQA            53  │
Cna_B_RrgA2  D--------------------------------------------------GKLTFKNLSLGKYRLFENSE             56  │
Cna_B_RrgC1  VG-------------------------------------------RTLYTDKNGEIFVTNLPIGNYRFKEVEP           63  │
                                                                            *   * . *            └─────────┐
                                                                                                            │
┌────────────────────────────────┐                                                                          ▼
│ Cna_B_M18    PQGMEIAEP---ITPKVTA----------  60                                                        G box
│ Cna_B_RrgB   PAGMALLTSR--QKFEVT----------  136                                                           ▲
│ Cna_B_RrgA1  PVGMKPSTKQ--WTVEVEKNGRTTVQ--  69                                                            │
│ Cna_B_RrgC2  PTGYVQLTSP--VSFTIGKDTRKELVTV  79
│ Cna_B_RrgA2  PAGMKPVQNKPTVAFQIVNGEVRDVT--  82
│ Cna_B_RrgC1  LAGYAVTTLD--TDVQLVDHQLVTITVV  89
└────────────────────────────────┘
              * :
```

FIG. 12

```
Ser-Asp_rich2   ISGVTVTLKNENGKVLQT------TKIDKDGKYQFTGLEN GTYKV-EFETPSGY PIQVG  53
Ser-Asp_rich3   ISGVTVTLKDENDKVLKT------VTTDENGKYQFTDLNN GTYKV-EFETPSGY PTSVT  53
Cna_B_cbp       IANVKFKLSKDGSVVKDNQKEIEIITDANGIANIKALPS GDYILKEIEAPAPY TDKDK  60
Cna_B_M18       LEGATLKLAQIEGSGFQE------QSFESSTSGQKIQLSI GTYILTETKSPQGY IAEPI  54
                   *:.  ::.:                   :   *   * *        *   **   *

Ser-Asp_rich2   SG--TDE--------- 58
Ser-Asp_rich3   SG--NDTEKDSNGLTTT 68
Cna_B_cbp       EYPFTMKDTDNQGYFT- 76
Cna_B_M18       TF--KVTA--------- 60
```

FIG. 13

```
Cna_B_AUTOTRANSPORTER      LTGAEFKLYDAANNGTEITVVKESDGVYPVAQADEQGVVIEAGEVVTKGL 50
Cna_B_                     LAGAVPGIYSDAETKQLVDIVTNADGYAISTKVGKG-------------- 37
Cna_B_CPA_M18              LEGATLKLAQIEGSGPQEQSFESSTSGQKLQLSDG--------------- 35
                            *          :   :  .

Cna_B_AUTOTRANSPORTER      VHSTTYYLEEMKAPNGYNILTEP-QSIE-- 77
Cna_B_                     ----TYYLKEITAPTGYSLNTNV-YTAEAS 62
Cna_B_CPA_M18              ----TYYILTETKSPQGYELAEPITFKVTA- 60
                               * *   :   ..**  .      
```

FIG. 16

```
CNA_B_bkb      -LEGAGPTLYILVKGDNGEEKY-QTVQEIKAGDTTSFPFVGLDAGDYKLSETTTPGGYNT 58
CNA_B_CPA_M18  -LEGATLKLAQIE-G-SGFQE--QSFESSTSGQK-------LQLSDGTYYILTETKSPQGYEI 50
CNA_B_ap1      -LYANDQKVNDKTTELSDFINSWQASFGKLDKYDS-------QNQKITYSVLEVMPVGYQS 53
CNA_B_ap2      LLKADGKVIREHQMTPDQQGKWEYTFDQLPVYQT------GKKISYSIEEKQVA-GYQA 52
                 .                                      *  *:

CNA_B_bkb      IA-DVMFSIVA 68
CNA_B_CPA_M18  AE-PITFKVTA 60
CNA_B_ap1      QV-EGDSGV-- 61
CNA_B_ap2      PVYEVDEGL-- 61
                   :        
```

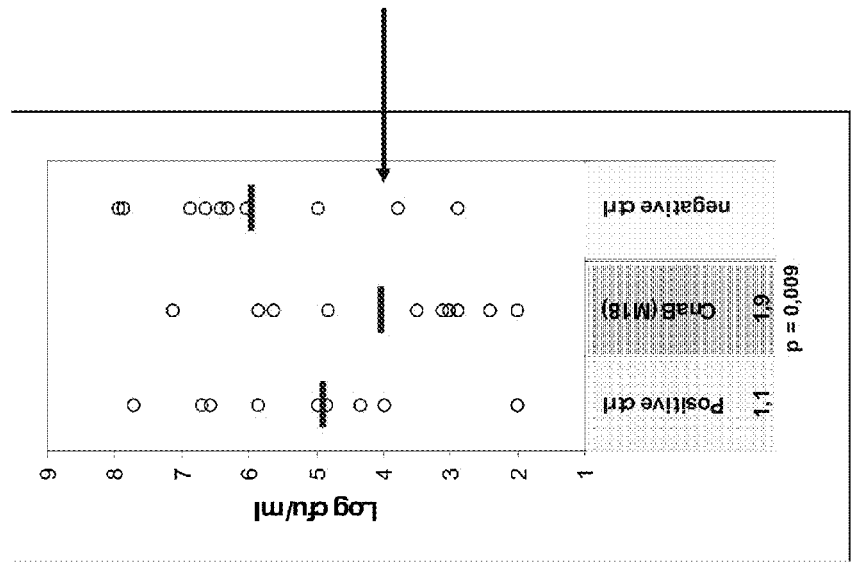
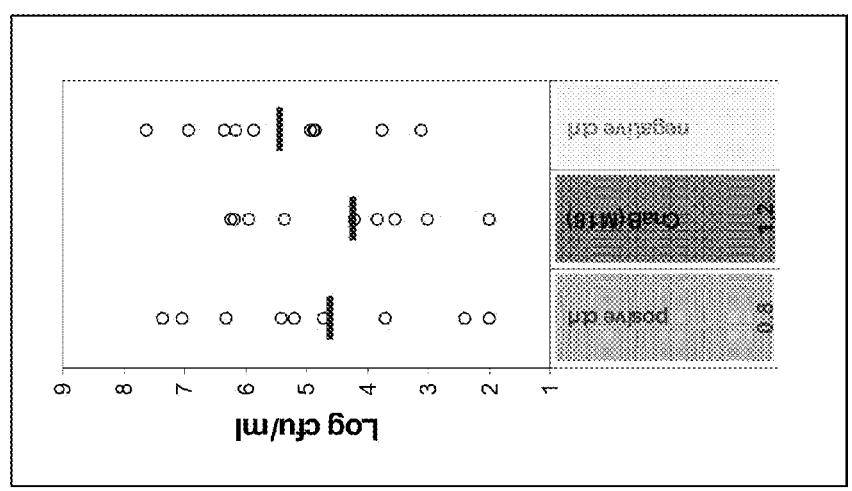
Figure 23
FIG. 23B
FIG. 23A

Sequences cut in SdrD52-592:
- Leader peptide and LPXTG motif (underlined and bold)
- SD repeats (italics)
- Cna_B domains (bold)

FIG. 27

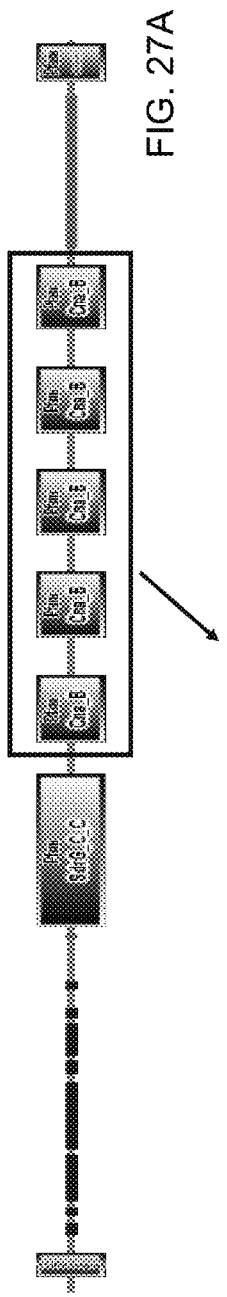

XXXXXXXVGNVTVTVFDNNTNTKVGEAVTKEDGSYLIPNLPNGDYRVEFS
NLPKGYEVTPSKQGNNEELDSNGLSSVITVNGKDNLSADLGIYKPKYNLG
DYVWEDTNKNGIQDQDEKGISGVTVTLKDENGNVLKTVTTDADGKYKFTD
LDNGNYKVEFTTPEGYTPTTVTSGSDIEKDSNGLTTTGVINGADNMTLDS
GFYKTPKYNLGNYVWEDTNKDGKQDSTEKGISGVTVTLKNENGEVLQTTK
TDKDGKYQFTGLENGTYKVEFETPSGYTPTQVGSGTDEGIDSNGTSTTGV
IKDKDNDTIDSGFYKPTYNLGDYVWEDTNKNGVQDKDEKGISGVTVTLKD
ENDKVLKTVTTDENGKYQFTDLNNGTYKVEFETPSGYTPTSVTSGNDTEK
DSNGLTTTGVIKDADNMTLDSGFYKTPKYSLGDYVWYDSNKDGKQDSTEK
GIKDVKVTLLNEKGEVIGTTKTDENGKYCFDNLDSGKYKVIFEKPAGLTQ
TVTNTTEDDKDADGGEVDVTITDHDDFTLDNGYFEEDT

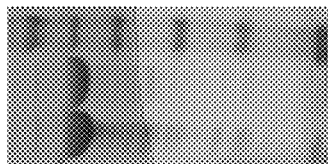

FIG. 27C

CNA-B DOMAIN ANTIGENS IN VACCINES AGAINST GRAM POSITIVE BACTERIA

This application is a division of Ser. No. 13/144,149, is a national phase application of PCT/IB/2010/050110 filed on Jan. 12, 2010, on which claims the benefit of U.S. 61/143,859, filed on 12 Jan. 2009. The complete contents of these applications are incorporated herein by reference.

This application incorporates by reference a 335 kb text file created on Oct. 11, 2011 and named "PAT052711substitutesequencelisting.txt," which is the sequence listing for this application.

FIELD OF THE INVENTION

This invention is in the fields of immunology and vaccinology. In particular, it relates to antigens derived from gram positive bacteria and their use in immunization.

BACKGROUND OF THE INVENTION

Gram positive bacteria include some of the most virulent human and animal pathogens and are responsible for a long list of severe diseases and subsequent sequelae. There is a continuing need in the art for effective vaccines against gram positive bacterial infections.

BRIEF DESCRIPTION OF THE FIGURES

FIG. 1A. Amino acid sequence (SEQ ID NO:1) of the Cna_B domain of S. pyogenes protein Cpa_M18 (Spy_M18_0126) cloned together with a flanking domain ("Fb signal") ("Cna_B-Fb"). FIG. 1B. Graphic representation of cloned domains. See Example 1.

FIG. 2. SDS-polyacrylamide gel containing purified recombinant His-tagged Cna_B-Fb domain. See Example 1.

FIGS. 3A-D. Western blots demonstrating that the S. pyogenes Cpa_M18 (Spy_M18_0126) Cna_B-Fb domain is immunogenic and that Cna_B-Fb domain antiserum recognizes Cpa and F2 (MGAS2096_SpyO119) proteins from various M strains of S. pyogenes (FIG. 3A, FIG. 3B, FIG. 3C) as well as pili components of S. agalactiae and S. pneumoniae (FIG. 3D). See Example 1.

FIGS. 4A-B. Western blots comparing reactivity of Cna_B-Fb antiserum (FIG. 4A) with Cpa_M18 antiserum (FIG. 4B). See Example 1.

Figure 7:
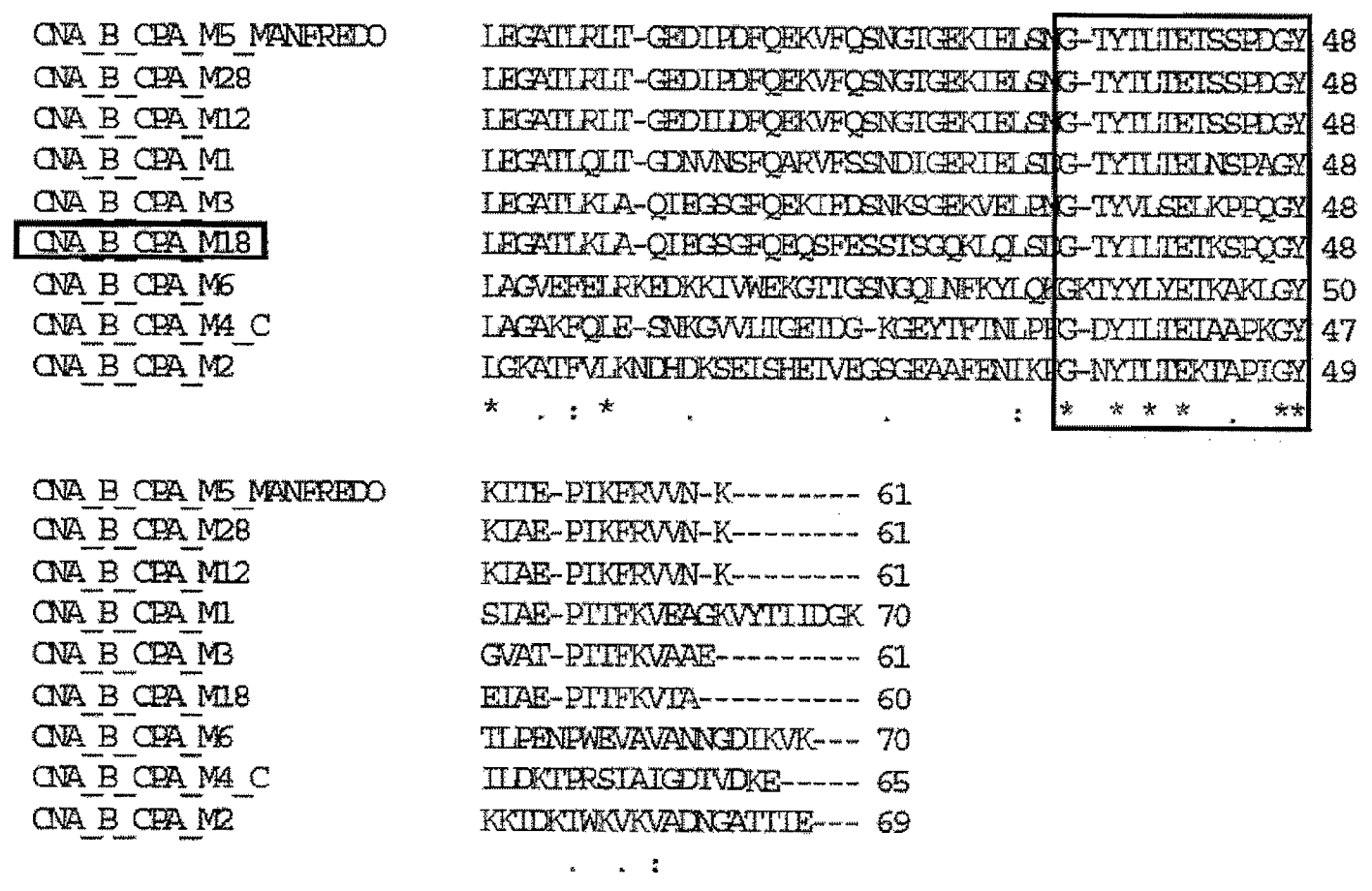

FIG. 7. Alignment of amino acid sequences of Cna_B domains of Cpa proteins from various S. pyogenes strains. Cna_B_Cpa_M5_Manfredo (Spy_M5_0104; SEQ ID NO:18), SEQ ID NO:2; Cna_B_Cpa_M28 (M28_SpyO107, SEQ ID NO:19), SEQ ID NO:3; Cna_B_Cpa_M12 (MGAS2096_Spy0113, SEQ ID NO:20), SEQ ID NO:4; Cna_B_Cpa_M1 (M5005_Spy_0107, SEQ ID NO:21), SEQ ID NO:5; Cna_B_Cpa_M3 (SpyM3_0098, SEQ ID NO:22), SEQ ID NO:6; Cna_B_Cpa_M18 (spyM18_0126, SEQ ID NO:23), SEQ ID NO:7; Cna_B_Cpa_M6 (M6_Spy0159, SEQ ID NO:24), SEQ ID NO:8; Cna_B_Cpa_M4_C (MGAS10750_Spy0115, SEQ ID NO:25), SEQ ID NO:9; Cna_B_Cpa_M2 (MGAS10270_Spy0113, SEQ ID NO:26), SEQ ID NO:10.

FIG. 8. Alignment of amino acid sequences of Cna_B domains of pili proteins from S. agalactiae. Cna_B_GBS_52 (SAG_0646, SEQ ID NO:45), SEQ ID NO:27; Cna_B_GBS_150 (SAL 1482, SEQ ID NO:26), SEQ ID NO:28; Cna_B_GBS_104_1 (SAG 0649, SEQ ID NO:47), SEQ ID NO:29; Cna_B_GBS_67 (SAL 1487, SEQ ID NO:48), SEQ ID NO:30; Cna_B_GBS_1523 (SAN 1518, SEQ ID NO:49), SEQ ID NO:31; Cna_B_GBS_1524 (SAN 1519, SEQ ID NO:50), SEQ ID NO:32; Cna_B_GBS_80 (SAG 0645, SEQ ID NO:51), SEQ ID NO:33; Cna_B_GBS_104_2 (SAG 0649, SEQ ID NO:47), SEQ ID NO:34; and Cna_B_GBS_1521 (SAN 1516, SEQ ID NO:52), SEQ ID NO:35.

FIG. 9. Alignment of amino acid sequences of GBS island 1 pili components with a Cna_B domain of S. pyogenes Cpa protein from strain M18. Cna_B_GBS_80 (SAG 0645, SEQ ID NO:51), SEQ ID NO:33; Cna_B_GBS_52 (SAG 0646, SEQ ID NO:45), SEQ ID NO:27; Cna_B_GBS_104_2 (SAG 0649, SEQ ID NO:47), SEQ ID NO:34; Cna_B_GBS_104_1 (SAG 0649, SEQ ID NO:47), SEQ ID NO:29; and Cna_B_CPA_M18 (Spy_M18_0126, SEQ ID NO:23), SEQ ID NO:7.

FIG. 11. Alignment of amino acid sequences of GBS island 3 pili components with a Cna_B domain of S. pyogenes Cpa protein from strain M18. Cna_B_CPA_M18 (Spy_M18_0126, SEQ ID NO:23), SEQ ID NO:7; Cna_B_GBS_1524 (SAN 1519, SEQ ID NO:50), SEQ ID NO:32; and Cna_B_GBS_1523 (SAN 1518, SEQ ID NO:49), SEQ ID NO:31.

FIG. 12. Alignment of amino acid sequences of S. pneumoniae pili strain TIGR4 components with a Cna_B domain of S. pyogenes Cpa protein from strain M18. Cna_B_CPA_M18 (Spy_M18_0126, SEQ ID NO:23), SEQ ID NO:7; RrgB (SP_0463, SEQ ID NO:63), SEQ ID NO:53; RrgA1 (SP_0462, SEQ ID NO:64), SEQ ID NO:54; RrgC2 (SP_0464, SEQ ID NO:65), SEQ ID NO:56; RrgA2 (SP_0462, SEQ ID NO:64), SEQ ID NO:57; and RrgC1 (SP_0464, SEQ ID NO:65), SEQ ID NO:58.

FIG. 13. Alignment of amino acid sequences of S. aureus proteins comprising a Cna_B domain with a Cna_B domain of S. pyogenes Cpa protein from strain M18. Ser-Asp rich2 (SdrD MW0517, SEQ ID NO:72), SEQ ID NO:66; Ser-Asp rich3 (SdrD MW0517, SEQ ID NO:72), SEQ ID NO:67; CBP (MW2612, SEQ ID NO:73), SEQ ID NO:68; and Cna_B_CPA_M18 (Spy_M18_0126, SEQ ID NO:23), SEQ ID NO:7.

FIG. 16. Alignment of Cna_B domains of S. pyogenes Cpa protein (Spy_M18_0126, SEQ ID NO:23) (SEQ ID NO:7) with Cna_B domains of two S. suis proteins. Cna_B_AUTOTRANSPORTER (SEQ ID NO:82), SEQ ID NO:80; Cna_B_(SEQ ID NO:83), SEQ ID NO:81.

FIG. 17. Alignment of Cna_B domains of S. pyogenes Cpa protein (Spy_M18_0126, SEQ ID NO:23) (SEQ ID NO:7) with Cna_B domains of two S. equi proteins. Cna_B_bkb (SEQ ID NO:88), SEQ ID NO:86; Cna_B_ap1 (SEQ ID NO:87), SEQ ID NO:84; Cna_B_ap2 (SEQ ID NO:87), SEQ ID NO:85.

FIG. 23A. Graph demonstrating that mice immunized with a Cna_B domain antigen show reduced nasopharyngeal colonization rates when challenged with S. aureus. FIG. 23B. Graph demonstrating that mice immunized with a Cna_B domain antigen show reduced nasopharyngeal colonization rates when challenged with S. aureus. See Example 9.

FIGS. 27A-C. Cloning, expression, and purification of Cna_B domains. FIG. 27A, Graphic representation of cloned Cna_B domains (SEQ ID NOS:134-138) of SdrD. FIG. 27B, amino acid sequence of the cloned domains (SEQ ID NO:133). FIG. 27C, SDS-polyacrylamide gel containing the purified Cna_B domains.

DETAILED DESCRIPTION OF THE INVENTION

Figure 5:
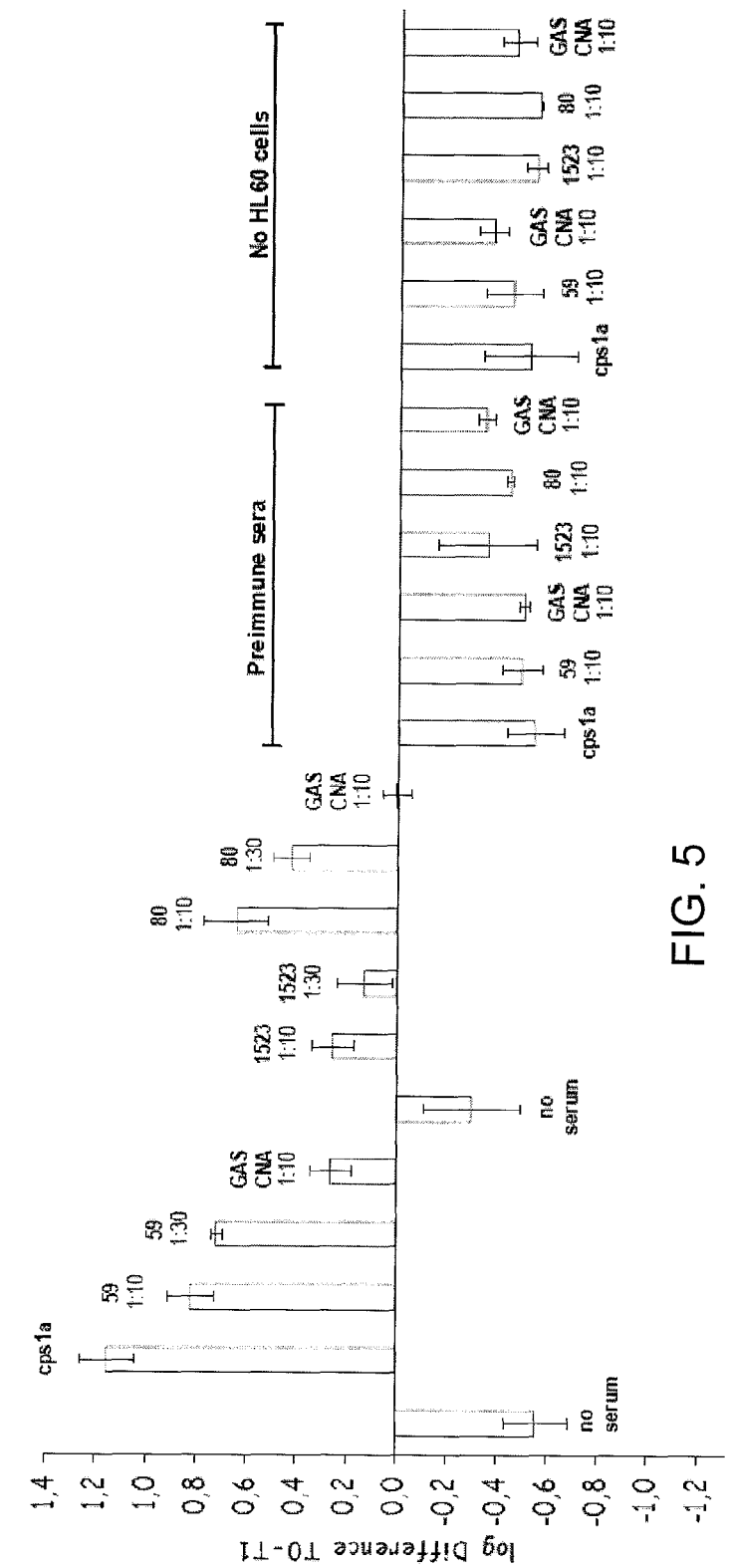
FIG. 5. Graph showing results of opsonophagocytosis assays for S. agalactiae strains 515 and JM using antiserum raised against recombinant Cna_B-Fb (see Example 1) and differentiated HL-60 cells. See Example 2.

A "Cna_B domain" was first described in an S. aureus collagen-binding surface protein as a region that does not mediate collagen binding. The structure of the repetitive B-region forms a beta sandwich structure. It is thought that this region forms a stalk in the S. aureus collagen-binding protein that presents the ligand binding domain away from the bacterial cell surface. Proteins containing a Cna_B domain are present in a variety of Gram positive pathogenic bacteria, including S. aureus, S. pneumoniae, S. agalactiae (GBS), S. pyogenes (GAS), S. equi, S. suis, C. perifringens, L. monocytogenes, B. thuringiensis, P. acidigallici, E. faceium, B. cereus, S. epidermidis, E. faecalis, C. difficile, C. diphtheriae, S. gordonii, S. dysgalactiae, and C. tetani.

As described in the specific examples, below, the Cna_B domain (SEQ ID NO:7) of S. pyogenes Cpa protein (Spy_M18_0126, SEQ ID NO:23) is immunogenic. Specific antibodies raised against it recognize recombinant proteins of S. pyogenes, S. agalactiae, S. pneumoniae, S. suis, and S. equi. About half of the antibodies contained in GAS_Cpa_M18 protein serum are specific for the Cna_B domain, and antiserum raised against the Cna_B domain of S. pyogenes Cpa protein from strain M18 ("anti-Cna_B serum") detects in a Western blot proteins which were not detected with antiserum raised against the entire protein ("GAS_M18_cpa") and mediates the phagocytic killing of S. agalactiae. The Cna_B domain of Spy_M18_0126 also mediates passive protection in GBS-challenged mice. Thus, there is an advantage to raising antibodies against streptococcal Cna_B domains or Cna_B domains of other gram positive bacterial proteins (e.g., S. aureus).

The invention provides Cna_B domain antigens which are useful in vaccine compositions to induce protection against gram positive bacteria, particularly against one or more of S. aureus, S. pneumoniae, S. agalactiae (GBS), S. pyogenes (GAS), S. equi, and S. suis. The invention also provides methods of using Cna_B domain antigens to induce antibodies and to treat or protect against gram positive bacterial infections, including cross-protection between various streptococcal and/or staphylococcal species.

Cna_B Domains

Cna_B domains from any gram positive bacterial protein can be used in compositions and methods of the invention. Amino acid sequences of Cna_B domains from various S. aureus, S. pneumoniae, S. agalactiae, S. pyogenes, S. suis, and S. equis proteins are shown in FIGS. 7-13, 16, and 17 and set forth in the sequence listing as SEQ ID NOS:2-10, 27-35, 53-57, 66, 67, 75, 76, 80, 81, 84-86, 110-117, 122-126, and 134-138. Examples of other proteins containing Cna_B domains are shown in SEQ ID NOS:89-102 and 132. The Cna_B domains typically contain one or more sequences identified in FIGS. 7-13 as a "G box." A consensus sequence amino acid sequence for the G boxes shown in FIGS. 7-13 is shown in SEQ ID NO:74.

Variants

In some embodiments, variants of Cna_B domains of the invention have amino acid sequences which are at least 90% identical, at least 95% identical, at least 96% identical, at least 97% identical, at least 98% identical, or at least 99% identical to any of SEQ ID NOS:2-10, 27-35, 53-57, 66, 67, 75, 76, 80, 81, 84-86, 110-117, 122-126, and 134-138. Typically any difference between the amino acid sequence of a Cna_B domain and the amino acid sequence of a variant of the Cna_B domain is due to one or more conservative amino acid substitutions (typically 1, 2, 3, 4, 5, 6, 7, or 8 substitutions). However, amino acid deletions or insertions also are possible.

In some embodiments conservative amino acid substitutions are based on chemical properties and include substitution of a positively-charged amino acid for another positively charged amino acid (e.g., H, K, R); a negatively-charged amino acid for another negatively charged amino acid (e.g., D, E); a very hydrophobic amino acid for another very hydrophobic amino acid (e.g., C, F, I, L, M, V, W); a less hydrophobic amino acid for another less hydrophobic amino acid (e.g., A, G, H, P, S, T, Y); a partly hydrophobic amino acid for another partly hydrophobic amino acid (e.g., K, R); an aliphatic amino acid for another aliphatic amino acid (e.g., A, I, L, M, P, V); a polar amino acid for another polar amino acid (e.g., A, D, E, G, H, K, N, P, Q, R, S, T, Y); an aromatic amino acid for another aromatic amino acid (e.g., F, H, W, Y); and a small amino acid for another small amino acid (e.g., D, N, T).

In some embodiments, conservative amino acid substitutions are determined using the BLOSUM62 table. The BLOSUM62 table is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915, 1992). The BLOSUM62 substitution frequencies can be used to define conservative amino acid substitutions that may be introduced into amino acid sequences of Cna_B domains. In these embodiments a conservative substitution preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2, or 3), while more preferred conservative amino acid substitutions are characterized by a BLOSUM62 value of at least 2 (e.g., 2 or 3).

Particular amino acid substitutions or alterations can be identified by aligning the Cna_B domains as shown in FIGS. 7-13. Cna_B domain antigens (described below) including any combination of such options is within the scope of the invention.

Cna_B Domain Antigens

"Cna_B domain antigens" comprise one or more Cna_B domains as described above and may or may not comprise additional amino acids at the N terminus, C terminus, or both. In some embodiments, Cna_B domain antigens consist of any of SEQ ID NOS:1-10, 27-35, 53-57, 66-68, 75, 76, 80, 81, 84-86, 110-117, 122-126, and 133-138. In other embodiments, Cna_B domain antigens comprise a Cna_B domain as well as other amino acid sequences which are not directly adjacent to a Cna_B domain in a native bacterial (e.g., streptococcal or staphylococcal) protein. That is, in such antigens the amino group of the N terminal amino acid of a Cna_B domain is not linked by a peptide bond to the carboxyl group of an amino acid to which it is linked in a native bacterial (e.g., streptococcal or staphylococcal) protein and/or the carboxyl group of the C terminal amino acid of the Cna_B domain is not linked by a peptide bond to the amino group of an amino acid to which it is linked in a native gram positive bacterial protein, e.g., a protein of *S. aureus, S. pneumoniae, S. agalactiae* (GBS), *S. pyogenes* (GAS), *S. equi*, or *S. suis*. "Native" gram positive bacterial proteins are proteins which are found in gram positive bacterial as they exist in nature; "native" streptococcal or staphylococcal proteins are proteins which are found in streptococcal or staphylococcal bacteria, respectively, as they exist in nature.

In still other embodiments, Cna_B domain antigens consist of a Cna_B domain as well as additional amino acids at the N and/or C terminal(s) of the domain, provided that the Cna_B domain antigen does not consist of a full-length bacterial (e.g., streptococcal or staphylococcal) protein (see Tables 1-32).

In other embodiments, Cna_B domain antigens consist of polypeptides of the formula:

A(LB)$_n$ wherein A is a first Cna_B domain; B is a second Cna_B domain; n is an integer (typically 1-10; e.g., 1, 2, 3, 4, 5, 6, 7, 8, 9, or 10); and L is independently absent or is an amino acid linker. The Cna_B domains in such antigens can be the same, different, or a mixture of some Cna_B domains which are the same and some which are different (i.e., all the Cna_B domains can be different or two or more of the Cna_B domains can be the same). For example, the Cna_B domains can be domains of two or more different gram positive proteins, particularly proteins of gram positive cocci, such as streptococcal proteins, staphylococcal proteins, or of proteins of two or more different species or strains (e.g., *S. agalactiae, S. pyogenes, S. pneumoniae, S. aureus, S. suis*, and/or *S. equi*).

The amino acid linker, if present between any of the Cna_B domains, typically contains between 6 and 12 amino acids (e.g., 6, 7, 8, 9, 10, 11, or 12). GSGGGG (SEQ ID NO:79) is an example of a useful linker. Linkers in a Cna_B domain antigen can be the same or different.

Examples of Cna_B domain antigens of formula A(LB)$_n$ include proteins comprising or consisting of SEQ ID NO:108. SEQ ID NO:108 comprises, from N to C terminus, a Cna_B domain of SAG_0645 (SEQ ID NO:112), the amino acid sequence VDS, a first amino acid linker (SEQ ID NO:79), a Cna_B domain of SAN__1518 (SEQ ID NO:113), a second amino acid linker (SEQ ID NO:79), a first Cna_B domain of SAL__1487 (SEQ ID NO:110), the amino acid sequence NSG, a second Cna_B domain of SAL__1487 (SEQ ID NO:111), and the amino acid KQI.

Other examples of Cna_B domain antigens of formula A(LB)$_n$ include proteins comprising or consisting of SEQ ID NO:109. SEQ ID NO:109 comprises, from N to C terminus, Cna_B domain of SAG__0645 (SEQ ID NO:112), the amino acid sequence VDS, a first amino acid linker (SEQ ID NO:79), a Cna_B domain of SAN__1518 (SEQ ID NO:113), a second amino acid linker (SEQ ID NO:79), a first Cna_B domain of SAL__1486 (114), the amino acid sequence LPL, a second Cna_B domain of SAL__1486 (SEQ ID NO:115), and the amino acid sequence DIE.

Other examples of Cna_B domain antigens of formula A(LB)$_n$ include proteins which comprise or consist of SEQ ID NOS:127, 128, 129, 130, 131, 133, 134, 135, 136, 137, or 138; see Examples 8 and 10.

In the Cna_B domain antigens described above, the amino acid sequences VDS, NSG, KQI, LPL, and DIE are included so as not to truncate a beta pleated sheet. It is well within the skill of the ordinary artisan to include other such amino acid sequences in Cna_B domain antigens of the invention to help preserve tertiary structure of Cna_B domains.

Still other examples of Cna_B domain antigens of formula A(LB)$_n$ comprise:

a. Cna_B domains of *S. pyogenes* Spy_M18__0126 (e.g., SEQ ID NO:7) and M6_Spy0159 (e.g., SEQ ID NO:8), and MGAS2096_Spy0119 (e.g., SEQ ID NO:121); these include Cna_B domain antigens which comprise fusions of the five Cna_B domains (SEQ ID NOS:122-126) of SEQ ID NO:121. A coding sequence for the Cna_B domain of Spy0159 is shown in SEQ ID NO:120. A coding sequence for Spy0119 is shown in SEQ ID NO:119. Nucleotides 181-390, 1576-1797, 1915-2127, 2281-2496, and 2716-2916 of SEQ ID NO:121 encode the Cna_B domains shown in SEQ ID NOS:122-126, respectively.

b. Cna_B domains of *S. aureus* SdrD (e.g., SEQ ID NOS: 134-138; SEQ ID NO:66 and/or 67; SEQ ID NO:139) and Cna_B cap (e.g., SEQ ID NO:68).

c. Cna_B domains of *S. pneumoniae* SP_0463) (e.g., SEQ ID NO:53), Cna_B_RrgA (SP_0462) (e.g., SEQ ID NO:54 and/or 56), and Cna_B RrgC (SP_0464) (e.g., SEQ ID NO:55 and/or 57).

d. Cna_B domains of Spy_M18_0126 (e.g., SEQ ID NO:7), SAG 0645 (SEQ ID NO:33), RrgB (SP_0463) (e.g., SEQ ID NO:53), and SdrD (e.g., SEQ ID NOS: 134-138; SEQ ID NO:66 and/or 67; SEQ ID NO:139).

Cna_B domain antigens of the invention also can comprise any of the Cna_B domain antigens described above. In some of these embodiments, the amino group of the N terminal amino acid of the Cna_B domain is not linked by a peptide bond to the carboxyl group of an amino acid to which it is linked in a native bacterial (e.g., streptococcal or staphylococcal) protein and/or the carboxyl group of the C terminal amino acid of the Cna_B domain is not linked by a peptide bond to the amino group of an amino acid to which it is linked in a native bacterial (e.g., streptococcal or staphylococcal) protein.

In some embodiments, one or more Cna_B domain antigens of the invention are part of a fusion polypeptide which comprises another bacterial antigen, preferably another bacterial (e.g., streptococcal or staphylococcal) antigen. Suitable antigens are disclosed, e.g., in WO 99/05447, WO 02/034771, WO 04/018646, WO 05/028618, WO 05/032482, WO 06/042027, and WO 06/078318.

Fusion polypeptides comprising one or more Cna_B domains and other domains, such as von Willenbrand Factor A (vWFA) domains (e.g., SEQ ID NOS:105, 106, 107), are also within the scope of the invention, such as:

a. a Cna_B domain of Spy_M18_0126) (e.g., SEQ ID NO:7) and vWFA_cpa_M6 (M6_Spy0159) (e.g., SEQ ID NO:105); and b. a Cna_B domain of SAG 0645 (e.g., SEQ ID NO:33) and vWFA_SAL_1487 (e.g., SEQ ID NO:106).

Such fusion polypeptides can include linker sequences between the various fusion partners and/or flanking sequences from each of the fusion partners, which can be selected from those disclosed in Tables 1-37 and 43-48, below.

TABLE 1

Cna_B domain antigens comprising SEQ ID NO: 2 (Spy_M5_0104, SEQ ID NO: 18; >gi|139472985|ref|YP_001127700.1| putative surface-anchored protein [*Streptococcus pyogenes* str. Manfredo])

| number of additional contiguous amino acids of SEQ ID NO: 18 at N terminus of SEQ ID NO: 2 | number of additional contiguous amino acids of SEQ ID NO: 18 at C terminus of SEQ ID NO: 2 |
|---|---|
| 0-70, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 | 0-390, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390 |

TABLE 2

Cna_B domain antigens comprising SEQ ID NO: 3 (M28_Spy0107, SEQ ID NO: 19; >gi|71902773|ref|YP_279576.1| collagen-binding protein [*Streptococcus pyogenes* MGAS6180])

| number of additional contiguous amino acids of SEQ ID NO: 19 at N terminus of SEQ ID NO: 3 | number of additional contiguous amino acids of SEQ ID NO: 19 at C terminus of SEQ ID NO: 3 |
|---|---|
| 0-294, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, | 0-390, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, |

TABLE 2-continued

Cna_B domain antigens comprising SEQ ID NO: 3 (M28_Spy0107, SEQ ID NO: 19; >gi|71902773|ref|YP_279576.1| collagen-binding protein [*Streptococcus pyogenes* MGAS6180])

| number of additional contiguous amino acids of SEQ ID NO: 19 at N terminus of SEQ ID NO: 3 | number of additional contiguous amino acids of SEQ ID NO: 19 at C terminus of SEQ ID NO: 3 |
|---|---|
| 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294 | 367, 368, 369, 370, 371, 372, 373, 374, 375, 376, 377, 378, 379, 380, 381, 382, 383, 384, 385, 386, 387, 388, 389, 390 |

TABLE 3

Cna_B domain antigens comprising SEQ ID NO: 4 (MGAS2096_Spy0113, SEQ ID NO: 20; >gi|94991610|ref|YP_599709.1| fibronectin-binding protein [*Streptococcus pyogenes* MGAS2096])

| number of additional contiguous amino acids of SEQ ID NO: 20 at N terminus of SEQ ID NO: 4 | number of additional contiguous amino acids of SEQ ID NO: 20 at C terminus of SEQ ID NO: 4 |
|---|---|
| 0-297, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297 | 0-396, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396 |

TABLE 4

Cna_B domain antigens comprising SEQ ID NO: 5 (M5005_Spy_0107, SEQ ID NO: 21; >gi|71909921|ref|YP_281471.1| fibronectin-binding protein [*Streptococcus pyogenes* MGAS5005])

| number of additional contiguous amino acids of SEQ ID NO: 21 at N terminus of SEQ ID NO: 5 | number of additional contiguous amino acids of SEQ ID NO: 21 at C terminus of SEQ ID NO: 5 |
|---|---|
| 0-310, e.g., 0, 1, 2, 3, 4, 5, 6,7, 8, 9, 10, 11,12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, | 0-380, e.g., 0, 1, 2, 3, 4, 5, 6,7, 8, 9, 10, 11,12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110,1 11, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, |

TABLE 4-continued

Cna_B domain antigens comprising SEQ ID NO: 5 (M5005_Spy_0107, SEQ ID NO: 21; >gi|71909921|ref|YP_281471.1| fibronectin-binding protein [*Streptococcus pyogenes* MGAS5005])

| number of additional contiguous amino acids of SEQ ID NO: 21 at N terminus of SEQ ID NO: 5 | number of additional contiguous amino acids of SEQ ID NO: 21 at C terminus of SEQ ID NO: 5 |
|---|---|
| 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310 | 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 |

TABLE 5

Cna_B domain antigens comprising SEQ ID NO: 6 (SpyM3_0098, SEQ ID NO: 22; >gi|21909634|ref|NP_663902.1| putative collagen binding protein [*Streptococcus pyogenes* MGAS315])

| number of additional contiguous amino acids of SEQ ID NO: 22 at N terminus of SEQ ID NO: 6 | number of additional contiguous amino acids of SEQ ID NO: 22 at C terminus of SEQ ID NO: 6 |
|---|---|
| 0-288, e.g., 0, 1, 2, 3, 4, 5, 6,7, 8, 9, 10, 11,12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288 | 0-393, e.g., 0, 1, 2, 3, 4, 5, 6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393 |

TABLE 6

Cna_B domain antigens comprising SEQ ID NO: 7 (Spy_M18_0126, SEQ ID NO: 23; >gi|19745301|ref|NP_606437.1| putative collagen binding protein [*Streptococcus pyogenes* MGAS8232])

| number of additional contiguous amino acids of SEQ ID NO: 23 at N terminus of SEQ ID NO: 7 | number of additional contiguous amino acids of SEQ ID NO: 23 at C terminus of SEQ ID NO: 7 |
|---|---|
| 0-70, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, | 0-392, e.g., 0, 1, 2, 3, 4, 5, 6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, |

TABLE 6-continued

Cna_B domain antigens comprising SEQ ID NO: 7 (Spy_M18_0126, SEQ ID NO: 23; >gi|19745301|ref|NP_606437.1| putative collagen binding protein [*Streptococcus pyogenes* MGAS8232])

| number of additional contiguous amino acids of SEQ ID NO: 23 at N terminus of SEQ ID NO: 7 | number of additional contiguous amino acids of SEQ ID NO: 23 at C terminus of SEQ ID NO: 7 |
| --- | --- |
| 43, 44, 45, 46, 47, 48, 49, 50, 51, 52, 53, 54, 55, 56, 57, 58, 59, 60, 61, 62, 63, 64, 65, 66, 67, 68, 69, 70 | 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392 |

TABLE 7

Cna_B domain antigens comprising SEQ ID NO: 8 (M6_Spy0159, SEQ ID NO: 24; >gi|50913505|ref|YP_059477.1| collagen adhesion protein [*Streptococcus pyogenes* MGAS10394])

| number of additional contiguous amino acids of SEQ ID NO: 24 at N terminus of SEQ ID NO: 8 | number of additional contiguous amino acids of SEQ ID NO: 24 at C terminus of SEQ ID NO: 8 |
| --- | --- |
| 0-906, e.g., 0, 1, 2, 3, 4, 5, 6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, | 0-58, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 |

TABLE 7-continued

Cna_B domain antigens comprising SEQ ID NO: 8 (M6_Spy0159, SEQ ID NO: 24; >gi|50913505|ref|YP_059477.1| collagen adhesion protein [*Streptococcus pyogenes* MGAS10394])

| number of additional contiguous amino acids of SEQ ID NO: 24 at N terminus of SEQ ID NO: 8 | number of additional contiguous amino acids of SEQ ID NO: 24 at C terminus of SEQ ID NO: 8 |
| --- | --- |

853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906

TABLE 8

Cna_B domain antigens comprising SEQ ID NO: 9 (MGAS10750_Spy0115, SEQ ID NO: 25; >gi|94993511|ref|YP_601609.1| Fibronectin-binding protein [*Streptococcus pyogenes* MGAS10750]

| number of additional contiguous amino acids of SEQ ID NO: 25 at N terminus of SEQ ID NO: 9 | number of additional contiguous amino acids of SEQ ID NO: 25 at C terminus of SEQ ID NO: 9 |
| --- | --- |
| 0-654, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654 | 0-646, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646 |

TABLE 9

Cna_B domain antigens comprising SEQ ID NO: 10 (MGAS10270_Spy0113, SEQ ID NO: 26; >gi|94989622|ref|YP_597722.1| collagen adhesion protein [*Streptococcus pyogenes* MGAS10270])

| number of additional contiguous amino acids of SEQ ID NO: 26 at N terminus of SEQ ID NO: 10 | number of additional contiguous amino acids of SEQ ID NO: 26 at C terminus of SEQ ID NO: 10 |
| --- | --- |
| 0-51, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 | 0-768, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768 |

TABLE 10

Cna_B domain antigens comprising SEQ ID NO: 27 (SAG_0646, SEQ ID NO: 45; >gi|22536815|ref|NP_687666.1| cell wall surface anchor family protein [*Streptococcus agalactiae* 2603V/R])

| number of additional contiguous amino acids of SEQ ID NO: 45 at N terminus of SEQ ID NO: 27 | number of additional contiguous amino acids of SEQ ID NO: 45 at C terminus of SEQ ID NO: 27 |
| --- | --- |
| 0-169, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169 | 0-52, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 |

TABLE 11

Cna_B domain antigens comprising SEQ ID NO: 28 (SAL 1482, SEQ ID NO: 46; GBS150 = SAL_1482 (ancillary2), jcvi.org/tigr-scripts/CMR/shared/GenePage.cgi?locus = SAL_1482 > SAL_1482

| number of additional contiguous amino acids of SEQ ID NO: 46 at N terminus of SEQ ID NO: 28 | number of additional contiguous amino acids of SEQ ID NO: 46 at C terminus of SEQ ID NO: 28 |
| --- | --- |
| 0-160, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 | 0-75, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 |

TABLE 12

Cna_B domain antigens comprising SEQ ID NO: 29 (SAG 0649, SEQ ID NO: 47; >gi|22536818|ref|NP_687669.1| cell wall surface anchor family protein, putative [*Streptococcus agalactiae* 2603V/R])

| number of additional contiguous amino acids of SEQ ID NO: 47 at N terminus of SEQ ID NO: 29 | number of additional contiguous amino acids of SEQ ID NO: 47 at C terminus of SEQ ID NO: 29 |
| --- | --- |
| 0-51, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 | 0-778, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778 |

TABLE 13

A. Cna_B domain antigens comprising SEQ ID NO: 110 or 30 (SAL 1487, SEQ ID NO: 48; GBS67 = SAL_1487 (ancillary 1), jcvi.org/cgi-bin/CMR/shared/GenePage.cgi?locus = SAL_1487 > SAL_1487

| number of additional contiguous amino acids of SEQ ID NO: 48 at N terminus of SEQ ID NO: 110 or 30 | number of additional contiguous amino acids of SEQ ID NO: 48 at C terminus of SEQ ID NO: 110 or 30 |
| --- | --- |
| 0-52, e.g., 0, 1, 2, 3, 4, 5, 6, 7, 8, 9, 10, 11, 12, 13, 14, 15, 16, 17, 18, 19, 20, | 0-786, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, |

TABLE 13-continued

| | |
|---|---|
| 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 | 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786 |

B. Cna_B domain antigens comprising SEQ ID NO: 111 (SAL 1487, SEQ ID NO: 48; GBS67 = SAL_1487 (ancillary 1), jcvi.org/cgi-bin/CMR/shared/GenePage.cgi?locus = SAL_1487 > SAL_1487

| number of additional contiguous amino acids of SEQ ID NO: 48 at N terminus of SEQ ID NO: 111 | number of additional contiguous amino acids of SEQ ID NO: 48 at C terminus of SEQ ID NO: 111 |
|---|---|
| 0-750, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, | 0-67, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67 |

TABLE 13-continued 274, 275, 276, 277, 278, 279, 280, 281, 282, 283, 284, 285, 286, 287,
288, 289, 290, 291, 292, 293, 294, 295, 296, 297, 298, 299, 300, 301,
302, 303, 304, 305, 306, 307, 308, 309, 310, 311, 312, 313, 314, 315,
316, 317, 318, 319, 320, 321, 322, 323, 324, 325, 326, 327, 328, 329,
330, 331, 332, 333, 334, 335, 336, 337, 338, 339, 340, 341, 342, 343,
344, 345, 346, 347, 348, 349, 350, 351, 352, 353, 354, 355, 356, 357,
358, 359, 360, 361, 362, 363, 364, 365, 366, 367, 368, 369, 370, 371,
372, 373, 374, 375, 376, 377, 378, 379, 380, 381, 382, 383, 384, 385,
386, 387, 388, 389, 390, 391, 392, 393, 394, 395, 396, 397, 398, 399,
400, 401, 402, 403, 404, 405, 406, 407, 408, 409, 410, 411, 412, 413,
414, 415, 416, 417, 418, 419, 420, 421, 422, 423, 424, 425, 426, 427,
428, 429, 430, 431, 432, 433, 434, 435, 436, 437, 438, 439, 440, 441,
442, 443, 444, 445, 446, 447, 448, 449, 450, 451, 452, 453, 454, 455,
456, 457, 458, 459, 460, 461, 462, 463, 464, 465, 466, 467, 468, 469,
470, 471, 472, 473, 474, 475, 476, 477, 478, 479, 480, 481, 482, 483,
484, 485, 486, 487, 488, 489, 490, 491, 492, 493, 494, 495, 496, 497,
498, 499, 500, 501, 502, 503, 504, 505, 506, 507, 508, 509, 510, 511,
512, 513, 514, 515, 516, 517, 518, 519, 520, 521, 522, 523, 524, 525,
526, 527, 528, 529, 530, 531, 532, 533, 534, 535, 536, 537, 538, 539,
540, 541, 542, 543, 544, 545, 546, 547, 548, 549, 550, 551, 552, 553,
554, 555, 556, 557, 558, 559, 560, 561, 562, 563, 564, 565, 566, 567,
568, 569, 570, 571, 572, 573, 574, 575, 576, 577, 578, 579, 580, 581,
582, 583, 584, 585, 586, 587, 588, 589, 590, 591, 592, 593, 594, 595,
596, 597, 598, 599, 600, 601, 602, 603, 604, 605, 606, 607, 608, 609,
610, 611, 612, 613, 614, 615, 616, 617, 618, 619, 620, 621, 622, 623,
624, 625, 626, 627, 628, 629, 630, 631, 632, 633, 634, 635, 636, 637,
638, 639, 640, 641, 642, 643, 644, 645, 646, 647, 648, 649, 650, 651,
652, 653, 654, 655, 656, 657, 658, 659, 660, 661, 662, 663, 664, 665,
666, 667, 668, 669, 670, 671, 672, 673, 674, 675, 676, 677, 678, 679,
680, 681, 682, 683, 684, 685, 686, 687, 688, 689, 690, 691, 692, 693,
694, 695, 696, 697, 698, 699, 700, 701, 702, 703, 704, 705, 706, 707,
708, 709, 710, 711, 712, 713, 714, 715, 716, 717, 718, 719, 720, 721,
722, 723, 724, 725, 726, 727, 728, 729, 730, 731, 732, 733, 734, 735,
736, 737, 738, 739, 740, 741, 742, 743, 744, 745, 746, 747, 748, 749,
750

TABLE 14

Cna_B domain antigens comprising SEQ ID NO: 31 or 113 (SAN 1518, SEQ ID NO: 49; >ORF01523 cell wall surface anchor family protein, putative {*Streptococcus agalactiae* COH1})

| number of additional contiguous amino acids of SEQ ID NO: 49 at N terminus of SEQ ID NO: 31 or 113 | number of additional contiguous amino acids of SEQ ID NO: 49 at C terminus of SEQ ID NO: 31 or 113 |
|---|---|
| 0-365, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365 | 0-50, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 |

TABLE 15

Cna_B domain antigens comprising SEQ ID NO: 32 (SAN 1519, SEQ ID NO: 50; >ORF01524 reticulocyte binding protein {*Streptococcus agalactiae* COH1})

| number of additional contiguous amino acids of SEQ ID NO: 50 at N terminus of SEQ ID NO: 32 | number of additional contiguous amino acids of SEQ ID NO: 50 at C terminus of SEQ ID NO: 32 |
|---|---|
| 0-1290, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, | 0-62, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 |

TABLE 15-continued

Cna_B domain antigens comprising SEQ ID NO: 32 (SAN 1519, SEQ ID NO: 50; >ORF01524 reticulocyte binding protein {*Streptococcus agalactiae* COH1})

| number of additional contiguous amino acids of SEQ ID NO: 50 at N terminus of SEQ ID NO: 32 | number of additional contiguous amino acids of SEQ ID NO: 50 at C terminus of SEQ ID NO: 32 |
|---|---|
| 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290 | |

TABLE 16

Cna_B domain antigens comprising SEQ ID NO: 33 or 112 (SAG 0645, SEQ ID NO: 51; >gi|22536814|ref|NP_687665.1| cell wall surface anchor family protein [*Streptococcus agalactiae* 2603V/R])

| number of additional contiguous amino acids of SEQ ID NO: 51 at N terminus of SEQ ID NO: 33 or 112 | number of additional contiguous amino acids of SEQ ID NO: 51 at C terminus of SEQ ID NO: 33 or 112 |
|---|---|
| 0-394, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394 | 0-65, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 |

TABLE 17

Cna_B domain antigens comprising SEQ ID NO: 35 (SAN 1516, SEQ ID NO: 52; >ORF01521 hypothetical protein {*Streptococcus agalactiae* COH1})

| number of additional contiguous amino acids of SEQ ID NO: 52 at N terminus of SEQ ID NO: 35 | number of additional contiguous amino acids of SEQ ID NO: 52 at C terminus of SEQ ID NO: 35 |
| --- | --- |
| 0-98, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 | 0-36, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 |

TABLE 18

A. Cna_B domain antigens comprising SEQ ID NO: 114 (SAL 1486, SEQ ID NO: 102; GBS59 = SAL_1486 (backbone), jcvi.org/cgi-bin/CMR/shared/GenePage.cgi?locus = SAL_1486 > SAL_1486

| number of additional contiguous amino acids of SEQ ID NO: 102 at N terminus of SEQ ID NO: 114 | number of additional contiguous amino acids of SEQ ID NO: 102 at C terminus of SEQ ID NO: 114 |
| --- | --- |
| 0-83, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 | 0-503, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503 |

B. Cna_B domain antigens comprising SEQ ID NO: 115 (SAL 1486, SEQ ID NO: 102; GBS59 = SAL_1486 (backbone), jcvi.org/cgi-bin/CMR/shared/GenePage.cgi?locus = SAL_1486 > SAL_1486

| number of additional contiguous amino acids of SEQ ID NO: 102 at N terminus of SEQ ID NO: 115 | number of additional contiguous amino acids of SEQ ID NO: 102 at C terminus of SEQ ID NO: 115 |
| --- | --- |
| 0-470, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, | 0-56, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56 |

TABLE 18-continued 176, 177, 178, 179, 180, 181, 182, 183, 184, 185, 186, 187, 188, 189,
190, 191, 192, 193, 194, 195, 196, 197, 198, 199, 200, 201, 202, 203,
204, 205, 206, 207, 208, 209, 210, 211, 212, 213, 214, 215, 216, 217,
218, 219, 220, 221, 222, 223, 224, 225, 226, 227, 228, 229, 230, 231,
232, 233, 234, 235, 236, 237, 238, 239, 240, 241, 242, 243, 244, 245,
246, 247, 248, 249, 250, 251, 252, 253, 254, 255, 256, 257, 258, 259,
260, 261, 262, 263, 264, 265, 266, 267, 268, 269, 270, 271, 272, 273,
274, 275, 276, 277, 278, 279, 280, 281, 282, 283, 284, 285, 286, 287,
288, 289, 290, 291, 292, 293, 294, 295, 296, 297, 298, 299, 300, 301,
302, 303, 304, 305, 306, 307, 308, 309, 310, 311, 312, 313, 314, 315,
316, 317, 318, 319, 320, 321, 322, 323, 324, 325, 326, 327, 328, 329,
330, 331, 332, 333, 334, 335, 336, 337, 338, 339, 340, 341, 342, 343,
344, 345, 346, 347, 348, 349, 350, 351, 352, 353, 354, 355, 356, 357,
358, 359, 360, 361, 362, 363, 364, 365, 366, 367, 368, 369, 370, 371,
372, 373, 374, 375, 376, 377, 378, 379, 380, 381, 382, 383, 384, 385,
386, 387, 388, 389, 390, 391, 392, 393, 394, 395, 396, 397, 398, 399,
400, 401, 402, 403, 404, 405, 406, 407, 408, 409, 410, 411, 412, 413,
414, 415, 416, 417, 418, 419, 420, 421, 422, 423, 424, 425, 426, 427,
428, 429, 430, 431, 432, 433, 434, 435, 436, 437, 438, 439, 440, 441,
442, 443, 444, 445, 446, 447, 448, 449, 450, 451, 452, 453, 454, 455,
456, 457, 458, 459, 460, 461, 462, 463, 464, 465, 466, 467, 468, 469,
470

C. Cna_B domain antigens comprising SEQ ID NO: 116 (SAG 1407, SEQ ID NO: 118)

| number of additional contiguous amino acids of SEQ ID NO: 118 at N terminus of SEQ ID NO: 116 | number of additional contiguous amino acids of SEQ ID NO: 118 at C terminus of SEQ ID NO: 116 |
|---|---|
| 0-20, e.g., 0, 1, 2, 3, 4, 5, 6, 7, 8, 9, 10, 11, 12, 13, 14, 15, 16, 17, 18, 19, 20 | 0-614, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614 |

TABLE 18-continued

D. Cna_B domain antigens comprising SEQ ID NO: 117 (SAG 1407, SEQ ID NO: 118)

| number of additional contiguous amino acids of SEQ ID NO: 118 at N terminus of SEQ ID NO: 117 | number of additional contiguous amino acids of SEQ ID NO: 118 at C terminus of SEQ ID NO: 117 |
|---|---|
| 0-489, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489 | 0-53, e.g., 0, 1, 2, 3, 4, 5, 6, 7, 8, 9, 10, 11, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 |

TABLE 19

Cna_B domain antigens comprising SEQ ID NO: 53 (SP_0463, SEQ ID NO: 63; >gi|15900379|ref|NP_344983.1| cell wall surface anchor family protein [*Streptococcus pneumoniae* TIGR4])

| number of additional contiguous amino acids of SEQ ID NO: 63 at N terminus of SEQ ID NO: 53 | number of additional contiguous amino acids of SEQ ID NO: 63 at C terminus of SEQ ID NO: 53 |
|---|---|
| 0-459, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459 | 0-68, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 |

TABLE 20

Cna_B domain antigens comprising SEQ ID NO: 54 (SP_0462, SEQ ID NO: 64; >gi|15900378|ref|NP_344982.1| cell wall surface anchor family protein [*Streptococcus pneumoniae* TIGR4])

| number of additional contiguous amino acids of SEQ ID NO: 64 at N terminus of SEQ ID NO: 54 | number of additional contiguous amino acids of SEQ ID NO: 64 at C terminus of SEQ ID NO: 54 |
|---|---|
| 0-60, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 | 0-762, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762 |

TABLE 21

Cna_B domain antigens comprising SEQ ID NO: 55 (SP_0464, SEQ ID NO: 65; >gi|15900380|ref|NP_344984.1| cell wall surface anchor family protein [*Streptococcus pneumoniae* TIGR4])

| number of additional contiguous amino acids of SEQ ID NO: 65 at N terminus of SEQ ID NO: 55 | number of additional contiguous amino acids of SEQ ID NO: 65 at C terminus of SEQ ID NO: 55 |
|---|---|
| 0-271, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271 | 0-41, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 |

TABLE 22

Cna_B domain antigens comprising SEQ ID NO: 66 (SdrD MW0517, SEQ ID NO: 72); >gi|21282246|ref|NP_645334.1| Ser-Asp rich fibrinogen-binding bone sialoprotein-binding protein [*Staphylococcus aureus* subsp. *aureus* MW2])

| number of additional contiguous amino acids of SEQ ID NO: 72 at N terminus of SEQ ID NO: 66 | number of additional contiguous amino acids of SEQ ID NO: 72 at C terminus of SEQ ID NO: 66 |
|---|---|
| 0-703, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, | 0-473, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, |

TABLE 22-continued

Cna_B domain antigens comprising SEQ ID NO: 66 (SdrD MW0517, SEQ ID NO: 72); >gi|21282246|ref|NP_645334.1| Ser-Asp rich fibrinogen-binding bone sialoprotein-binding protein [*Staphylococcus aureus* subsp. *aureus* MW2])

| number of additional contiguous amino acids of SEQ ID NO: 72 at N terminus of SEQ ID NO: 66 | number of additional contiguous amino acids of SEQ ID NO: 72 at C terminus of SEQ ID NO: 66 |
|---|---|
| 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473 | 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703 |

TABLE 23

Cna_B domain antigens comprising SEQ ID NO: 67 (SdrD MW0517, SEQ ID NO: 72); >gi|21282246|ref|NP_645334.1_| Ser-Asp rich fibrinogen-binding bone sialoprotein-binding protein [*Staphylococcus aureus* subsp. *aureus* MW2])

| number of additional contiguous amino acids of SEQ ID NO: 72 at N terminus of SEQ ID NO: 67 | number of additional contiguous amino acids of SEQ ID NO: 72 at C terminus of SEQ ID NO: 67 |
|---|---|
| 0-924, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, | 0-353, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, |

TABLE 23-continued

Cna_B domain antigens comprising SEQ ID NO: 67 (SdrD MW0517, SEQ ID NO: 72); >gi|21282246|ref|NP_645334.1_| Ser-Asp rich fibrinogen-binding bone sialoprotein-binding protein [*Staphylococcus aureus* subsp. *aureus* MW2])

| number of additional contiguous amino acids of SEQ ID NO: 72 at N terminus of SEQ ID NO: 67 | number of additional contiguous amino acids of SEQ ID NO: 72 at C terminus of SEQ ID NO: 67 |
|---|---|
| 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924 | 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353 |

TABLE 24

Cna_B domain antigens comprising SEQ ID NO: 68 (MW2612, SEQ ID NO: 73; >gi|21284341|ref|NP_647429.1| collagen adhesin precursor [*Staphylococcus aureus* subsp. *aureus* MW2])

| number of additional contiguous amino acids of SEQ ID NO: 73 at N terminus of SEQ ID NO: 68 | number of additional contiguous amino acids of SEQ ID NO: 73 at C terminus of SEQ ID NO: 68 |
|---|---|
| 0-344, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344 | 0-761, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761 |

TABLE 25

Cna_B domain antigens comprising SEQ ID NO: 1 (Spy_M18_0126, SEQ ID NO: 23; >gi|19745301|ref|NP_606437.1| putative collagen binding protein [*Streptococcus pyogenes* MGAS8232])

| number of additional contiguous amino acids of SEQ ID NO: 23 at N terminus of SEQ ID NO: 1 | number of additional contiguous amino acids of SEQ ID NO: 23 at C terminus of SEQ ID NO: 1 |
|---|---|
| 0-70, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 | 0-282, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 |

TABLE 26

Cna_B domain antigens comprising SEQ ID NO: 34 (SAG 0649, SEQ ID NO: 47; >gi|22536818|ref|NP_687669.1| cell wall surface anchor family protein, putative [*Streptococcus agalactiae* 2603V/R])

| number of additional contiguous amino acids of SEQ ID NO: 47 at N terminus of SEQ ID NO: 34 | number of additional contiguous amino acids of SEQ ID NO: 47 at C terminus of SEQ ID NO: 34 |
|---|---|
| 0-748, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748 | 0-62, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 |

TABLE 27

Cna_B domain antigens comprising SEQ ID NO: 57 (*S. pneumoniae* protein SP_0464; SEQ ID NO: 65)

| number of additional contiguous amino acids of SEQ ID NO: 65 at N terminus of SEQ ID NO: 57 | number of additional contiguous amino acids of SEQ ID NO: 65 at C terminus of SEQ ID NO: 57 |
|---|---|
| 0-161, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161 | 0-141, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141 |

TABLE 28

Cna_B domain antigens comprising SEQ ID NO: 80 (*S. suis* protein SSU05_0474[*Streptococcus suis* 05ZYH33; SEQ ID NO: 82)

| number of additional contiguous amino acids of SEQ ID NO: 82 at N terminus of SEQ ID NO: 80 | number of additional contiguous amino acids of SEQ ID NO: 82 at C terminus of SEQ ID NO: 80 |
|---|---|
| 0-348, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348 | 0-53, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 |

TABLE 29

Cna_B domain antigens comprising SEQ ID NO: 81 (*S. suis* protein DUF11: Surface protein from Gram-positive cocci, anchor region [*Streptococcus suis* 89/1591; SEQ ID NO: 83)

| number of additional contiguous amino acids of SEQ ID NO: 83 at N terminus of SEQ ID NO: 81 | number of additional contiguous amino acids of SEQ ID NO: 83 at C terminus of SEQ ID NO: 81 |
|---|---|
| 0-358, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358 | 0-124, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 |

TABLE 30

Cna_B domain antigens comprising SEQ ID NO: 84 (*S. equi* protein ancillary protein SEQ0935 undefined product 914186:916159 forward MW:73872 67; SEQ ID NO: 87)

| number of additional contiguous amino acids of SEQ ID NO: 87 at N terminus of SEQ ID NO: 84 | number of additional contiguous amino acids of SEQ ID NO: 87 at C terminus of SEQ ID NO: 84 |
|---|---|
| 0-350, e.g. 0, 1, 2, 3, 4, 5,

TABLE 32-continued

Cna_B domain antigens comprising SEQ ID NO: 86 (*S. equi* protein BKB SEQ0936 undefined product 916183:917625 forward MW:51902 46, 3; SEQ ID NO: 88)

| number of additional contiguous amino acids of SEQ ID NO: 88 at N terminus of SEQ ID NO: 86 | number of additional contiguous amino acids of SEQ ID NO: 88 at C terminus of SEQ ID NO: 86 |
|---|---|
| 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336 | |

TABLE 33

Cna_B domain antigens comprising SEQ ID NO: 122 (*S. pyogenes* protein F2, Spy0119; SEQ ID NO: 121)

| number of additional contiguous amino acids of SEQ ID NO: 121 at N terminus of SEQ ID NO: 122 | number of additional contiguous amino acids of SEQ ID NO: 121 at C terminus of SEQ ID NO: 122 |
|---|---|
| 0-59, e.g., 0, 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 | 0-1030, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, |

TABLE 34

**Cna_B domain antigens comprising SEQ ID NO: 123 (*S. pyogenes* protein F2, Spy0119; SEQ ID NO: 121)**

| number of additional contiguous amino acids of SEQ ID NO: 121 at N terminus of SEQ ID NO: 123 | number of additional contiguous amino acids of SEQ ID NO: 121 at C terminus of SEQ ID NO: 123 |
|---|---|
| 0-524, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524 | 0-561, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131,132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326,327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561 |

TABLE 35

**Cna_B domain antigens comprising SEQ ID NO: 124 (*S. pyogenes* protein F2, Spy0119; SEQ ID NO: 121)**

| number of additional contiguous amino acids of SEQ ID NO: 121 at N terminus of SEQ ID NO: 124 | number of additional contiguous amino acids of SEQ ID NO: 121 at C terminus of SEQ ID NO: 124 |
|---|---|
| 0-637, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, | 0-451, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, |

TABLE 35-continued

Cna_B domain antigens comprising SEQ ID NO: 124 (*S. pyogenes* protein F2, Spy0119; SEQ ID NO: 121)

| number of additional contiguous amino acids of SEQ ID NO: 121 at N terminus of SEQ ID NO: 124 | number of additional contiguous amino acids of SEQ ID NO: 121 at C terminus of SEQ ID NO: 124 |
|---|---|
| 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637 | 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451 |

TABLE 36

Cna_B domain antigens comprising SEQ ID NO: 125 (*S. pyogenes* protein F2, Spy0119; SEQ ID NO: 121)

| number of additional contiguous amino acids of SEQ ID NO: 121 at N terminus of SEQ ID NO: 125 | number of additional contiguous amino acids of SEQ ID NO: 121 at C terminus of SEQ ID NO: 125 |
|---|---|
| 0-759, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759 | 0-328, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328 |

TABLE 37

**Cna_B domain antigens comprising SEQ ID NO: 126 (*S. pyogenes* protein F2, Spy0119; SEQ ID NO: 121)**

| number of additional contiguous amino acids of SEQ ID NO: 121 at N terminus of SEQ ID NO: 126 | number of additional contiguous amino acids of SEQ ID NO: 121 at C terminus of SEQ ID NO: 126 |
|---|---|
| 0-904, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904 | 0-188, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 109, 110, 111, 112, 113, 114, 115, 116, 117, 118, 119, 120, 103, 104, 105, 106, 107, 108, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188 |

TABLE 43

**Cna_B domain antigens comprising SEQ ID NO: 134 (Cna_B domain of *S. aureus* SdrD protein, SEQ ID NO: 132)**

| number of additional contiguous amino acids of SEQ ID NO: 132 at N terminus of SEQ ID NO: 134 | number of additional contiguous amino acids of SEQ ID NO: 132 at C terminus of SEQ ID NO: 134 |
|---|---|
| 0-591, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, | 0-683, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, |

TABLE 43-continued

Cna_B domain antigens comprising SEQ ID NO: 134 (Cna_B domain of *S. aureus* SdrD protein, SEQ ID NO: 132)

| number of additional contiguous amino acids of SEQ ID NO: 132 at N terminus of SEQ ID NO: 134 | number of additional contiguous amino acids of SEQ ID NO: 132 at C terminus of SEQ ID NO: 134 |
| --- | --- |
| 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591 | 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683 |

TABLE 44

Cna_B domain antigens comprising SEQ ID NO: 135 (Cna_B domain of *S. aureus* SdrD protein, SEQ ID NO: 132)

| number of additional contiguous amino acids of SEQ ID NO: 132 at N terminus of SEQ ID NO: 135 | number of additional contiguous amino acids of SEQ ID NO: 132 at C terminus of SEQ ID NO: 135 |
| --- | --- |
| 0-703, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, | 0-572, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, |

TABLE 44-continued

Cna_B domain antigens comprising SEQ ID NO: 135 (Cna_B domain of *S. aureus* SdrD protein, SEQ ID NO: 132)

| number of additional contiguous amino acids of SEQ ID NO: 132 at N terminus of SEQ ID NO: 135 | number of additional contiguous amino acids of SEQ ID NO: 132 at C terminus of SEQ ID NO: 135 |
|---|---|
| 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703 | 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572 |

TABLE 45

Cna_B domain antigens comprising SEQ ID NO: 136 (Cna_B domain of *S. aureus* SdrD protein, SEQ ID NO: 132)

| number of additional contiguous amino acids of SEQ ID NO: 132 at N terminus of SEQ ID NO: 136 | number of additional contiguous amino acids of SEQ ID NO: 132 at C terminus of SEQ ID NO: 136 |
|---|---|
| 0-814, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, | 0-461, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, |

TABLE 45-continued

Cna_B domain antigens comprising SEQ ID NO: 136 (Cna_B domain of *S. aureus* SdrD protein, SEQ ID NO: 132)

| number of additional contiguous amino acids of SEQ ID NO: 132 at N terminus of SEQ ID NO: 136 | number of additional contiguous amino acids of SEQ ID NO: 132 at C terminus of SEQ ID NO: 136 |
|---|---|
| 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814 | 461 |

TABLE 46

Cna_B domain antigens comprising SEQ ID NO: 137 (Cna_B domain of *S. aureus* SdrD protein, SEQ ID NO: 132)

| number of additional contiguous amino acids of SEQ ID NO: 132 at N terminus of SEQ ID NO: 137 | number of additional contiguous amino acids of SEQ ID NO: 132 at C terminus of SEQ ID NO: 137 |
|---|---|
| 0-924, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924 | 0-351, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351 |

TABLE 47

**Cna_B domain antigens comprising SEQ ID NO: 138 (Cna_B domain of *S. aureus* SdrD protein, SEQ ID NO: 132)**

| number of additional contiguous amino acids of SEQ ID NO: 132 at N terminus of SEQ ID NO: 138 | number of additional contiguous amino acids of SEQ ID NO: 132 at C terminus of SEQ ID NO: 138 |
|---|---|
| 0-1035, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035 | 0-241, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241 |

TABLE 48

**Cna_B domain antigens comprising SEQ ID NO: 139 (Cna_B domains of *S. aureus* SdrD protein, SEQ ID NO: 132)**

| number of additional contiguous amino acids of SEQ ID NO: 132 at N terminus of SEQ ID NO: 139 | number of additional contiguous amino acids of SEQ ID NO: 132 at C terminus of SEQ ID NO: 139 |
|---|---|
| 0-598, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, | 0-225, e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, |

TABLE 48-continued

Cna_B domain antigens comprising SEQ ID NO: 139 (Cna_B domains of *S. aureus* SdrD protein, SEQ ID NO: 132)

| number of additional contiguous amino acids of SEQ ID NO: 132 at N terminus of SEQ ID NO: 139 | number of additional contiguous amino acids of SEQ ID NO: 132 at C terminus of SEQ ID NO: 139 |
|---|---|
| 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598 | 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225 |

Nucleic Acid Molecules

The invention includes nucleic acid molecules which encode Cna_B domain antigens of the invention. The invention also includes nucleic acid molecules comprising nucleotide sequences having at least 95% sequence identity to such molecules. Depending on the particular sequence, the degree of sequence identity is preferably at least 95%, 96%, 97%, 98%, or 99%. Identity between nucleotide sequences is preferably determined by the Smith-Waterman homology search algorithm as implemented in the MPSRCH program (Oxford Molecular), using an affine gap search with parameters gap open penalty=12 and gap extension penalty=1.

The invention also provides nucleic acid molecules which can hybridize to these molecules. Hybridization reactions can be performed under conditions of different stringency. Conditions which increase stringency of a hybridization reaction are widely known and published in the art. See, e.g., page 7.52 of Sambrook et al., Molecular Cloning: A Laboratory Manual, 1989. Examples of relevant conditions include (in order of increasing stringency): incubation temperatures of 25° C., 37° C., 50° C., 55° C., and 68° C.; buffer concentrations of 10×SSC, 6×SSC, 1×SSC, and 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art. See, e.g., Sambrook, 1989; Ausubel et al., eds., *Short Protocols in Molecular Biology*, 4th ed., 1999; U.S. Pat. No. 5,707,829; Ausubel et al., eds., *Current Protocols in Molecular Biology*, Supplement 30, 1987.

In some embodiments, nucleic acid molecules of the invention hybridize to a target under low stringency conditions; in other embodiments, nucleic acid molecules of the invention hybridize under intermediate stringency conditions; in preferred embodiments, nucleic acid molecules of the invention hybridize under high stringency conditions. An example of a low stringency hybridization condition is 50° C. and 10×SSC. An example of an intermediate stringency hybridization condition is 55° C. and 1×SSC. An example of a high stringency hybridization condition is 68° C. and 0.1×SSC.

Production of Cna_B Domain Antigens

Recombinant Production

The redundancy of the genetic code is well-known. Thus, any nucleic acid molecule (polynucleotide) which encodes a Cna_B domain antigen of the invention can be used to produce that protein recombinantly. Nucleic acid molecules encoding a Cna_B domain-containing protein can be isolated from the appropriate bacterium (e.g., a streptococcal or staphylococcal bacterium) using standard nucleic acid purification techniques or can be synthesized using an amplification technique, such as the polymerase chain reaction (PCR), or using an automatic synthesizer. See Caruthers et al., Nucl. Acids Res. Symp. Ser. 215 223, 1980; Horn et al. Nucl. Acids Res. Symp. Ser. 225 232, 1980; Hunkapiller et al., Nature 310, 105-11, 1984; Grantham et al., Nucleic Acids Res. 9, r43-r74, 1981.

cDNA molecules can be made with standard molecular biology techniques, using mRNA as a template. cDNA molecules can thereafter be replicated using molecular biology techniques well known in the art. An amplification technique, such as PCR, can be used to obtain additional copies of polynucleotides of the invention, using either genomic DNA or cDNA as a template.

If desired, polynucleotides can be engineered using methods generally known in the art to alter coding sequences for a variety of reasons, including but not limited to, alterations which modify the cloning, processing, and/or expression of a polypeptide or mRNA product. DNA shuffling by random fragmentation and PCR reassembly of gene fragments and synthetic oligonucleotides can be used to engineer the nucleotide sequences. For example, site directed mutagenesis can be used to insert new restriction sites, alter glycosylation patterns, change codon preference, produce splice variants, introduce mutations, and so forth.

Nucleic acid molecules can include a coding sequence for an N-terminal leader sequence (either the N-terminal leader sequence of a native protein comprising a Cna_B or another N-terminal leader sequence of choice). In some embodiments, sequence modifications, such as the addition of a purification tag sequence or codon optimization, are used to facilitate expression. For example, an expressed protein can comprise a tag such as polyhistidine (HIS) or glutathione S-transferase (GST). Such tags can be used to facilitate purification, detection, and stability of the expressed protein. Codons preferred by a particular prokaryotic or eukaryotic host can be selected to increase the rate of protein expression or to produce an RNA transcript having desirable properties, such as a half life which is longer than that of a transcript generated from the naturally occurring sequence. These methods are well known in the art and are described in WO 05/032582.

Expression Vectors

A nucleic acid molecule which encodes a Cna_B domain antigen can be inserted into an expression vector which contains the necessary elements for the transcription and translation of the inserted coding sequence. Methods which are well known to those skilled in the art can be used to construct expression vectors containing coding sequences and appropriate transcriptional and translational control elements. These methods include in vitro recombinant DNA techniques, synthetic techniques, and in vivo genetic recombination.

Host Cells

Host cells for producing Cna_B domain antigens can be prokaryotic or eukaryotic. *E. coli* is a preferred host cell, but other suitable hosts include *Lactococcus lactis, Lactococcus cremoris, Bacillus subtilis, Vibrio cholerae, Salmonella typhi, Salmonella typhimurium, Neisseria lactamica, Neisseria cinerea, Mycobacteria* (e.g., *M. tuberculosis*), yeasts, baculovirus, mammalian cells, etc.

A host cell strain can be chosen for its ability to modulate the expression of the inserted sequences or to process the expressed polypeptide in the desired fashion. Such modifications of the polypeptide include, but are not limited to, acetylation, carboxylation, glycosylation, phosphorylation, lipidation, and acylation. Post translational processing which cleaves a "prepro" form of the polypeptide also can be used to facilitate correct insertion, folding and/or function. Different host cells which have specific cellular machinery and characteristic mechanisms for post translational activities are available from the American Type Culture Collection (ATCC; 10801 University Boulevard, Manassas, Va. 20110-2209) and can be chosen to ensure the correct modification and processing of a foreign protein. See WO 01/98340.

Expression constructs can be introduced into host cells using well-established techniques which include, but are not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun" methods, and DEAE- or calcium phosphate-mediated transfection.

Host cells transformed with expression vectors can be cultured under conditions suitable for the expression and recovery of the protein from cell culture. The protein produced by a transformed cell can be secreted or contained intracellularly depending on the nucleotide sequence and/or the expression vector used. Those of skill in the art understand that expression vectors can be designed to contain signal sequences which direct secretion of soluble polypeptides through a prokaryotic or eukaryotic cell membrane.

Purification

Signal export sequences can be included in a recombinantly produced Cna_B domain antigen so that the antigen can be purified from cell culture medium using known methods. Alternatively, recombinantly produced Cna_B domain antigens of the invention can be isolated from engineered host cells and separated from other components in the cell, such as proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified Cna_B domain antigens is at least 80% pure; preferably, the preparations are 90%, 95%, or 99% pure. Purity of the preparations can be assessed by any means known in the art, such as SDS-polyacrylamide gel electrophoresis. Where appropriate, Cna_B domain antigens can be solubilized, for example, with urea.

Chemical Synthesis

Cna_B domain antigens can be synthesized, for example, using solid phase techniques. See, e.g., Merrifield, *J. Am. Chem. Soc.* 85, 2149 54, 1963; Roberge et al., *Science* 269, 202 04, 1995. Protein synthesis can be performed using manual techniques or by automation. Automated synthesis can be achieved, for example, using Applied Biosystems 431A Peptide Synthesizer (Perkin Elmer). Optionally, portions of a Cna_B domain antigen can be synthesized separately and combined using chemical methods to produce the complete molecule.

Pharmaceutical Compositions

The invention provides compositions for use as medicaments. Pharmaceutical compositions of the invention are useful for raising an immune response against gram positive bacteria, particularly streptococcal or staphylococcal bacteria (e.g., *S. agalactiae, S. pyogenes, S. pneumoniae*, and/or *S. aureus*). In some embodiments the compositions are useful for treating streptococcal and/or staphylococcal infections as well as reducing the risk of such infections.

Pharmaceutical compositions of the invention comprise at least one active agent, which can be a Cna_B domain antigen as disclosed herein or a nucleic acid molecule encoding the Cna_B domain antigen. The disease can be, for example, bacteremia, meningitis, puerperal fever, scarlet fever, erysipelas, pharyngitis, impetigo, necrotizing fasciitis, myositis, or toxic shock syndrome.

Compositions containing a Cna_B domain antigen or a nucleic acid molecule encoding a Cna_B domain antigen are preferably immunogenic compositions, and are more preferably vaccine compositions. Pharmaceutical compositions according to the invention can be either prophylactic or therapeutic, but will typically be prophylactic. A pharmaceutical composition is "prophylactic" if it reduces the risk of a gram positive bacterial (e.g., streptococcal and/or staphylococcal) infection or reduces the severity of a gram positive bacterial (e.g., streptococcal and/or staphylococcal) infection or a symptom of a gram positive bacterial (e.g., streptococcal and/or staphylococcal) infection. Accordingly, the invention includes methods for the therapeutic or prophylactic treatment of a gram positive bacterial (e.g., streptococcal and/or staphylococcal) infection. Animals, preferably mammals, most preferably humans, can be treated. The methods involve administering to the animal a therapeutic or prophylactic amount of an immunogenic composition of the invention.

The pH of such compositions typically is between 6 and 8, preferably about 7. The pH can be maintained by the use of a buffer. The composition can be sterile and/or pyrogen-free. The composition can be isotonic with respect to human tissue (e.g., blood).

Some compositions of the invention comprise one or more Cna_B domain antigens as described herein. Other compositions of the invention comprise one or more nucleic acid molecules which encodes the antigens and, optionally, other antigens which can be included in the composition (see below). See, e.g., Robinson & Torres (1997) Seminars in Immunology 9:271-283; Donnelly et al. (1997) Ann. Rev Immunol 15:617-648; Scott-Taylor & Dalgleish (2000) Expert Opin Investig Drugs 9:471-480; Apostolopoulos & Plebanski (2000) Curr Opin Mol Ther 2:441-447; Ilan (1999) Curr Opin Mol Ther 1:116-120; Dubensky et al. (2000) Mol Med 6:723-732; Robinson & Pertmer (2000) Adv Virus Res 55:1-74; Donnelly et al. (2000) Am J Respir Crit. Care Med 162(4 Pt 2):5190-193; Davis (1999) Mt. Sinai J. Med. 66:84-90. Typically the nucleic acid molecule is a DNA molecule, e.g., in the form of a plasmid. In some embodiments, compositions of the invention can comprise one or more Cna_B domain antigens and one or more nucleic acid molecules.

Additional Active Agents

In some embodiments, compositions of the invention can include one or more additional active agents. Such agents include, but are not limited to, (a) another Cna_B domain antigen of the invention, (b) a polypeptide antigen which is useful in a pediatric vaccine, (c) a polypeptide antigen which is useful in a vaccine for elderly or immunocompromised individuals, (d) a nucleic acid molecule encoding (a)-(c), an antibody which specifically binds to (a)-(c), and a GBS polysaccharide antigen as defined below.

Antibodies

Cna_B domains of gram positive bacterial (e.g., streptococcal and/or staphylococcal) proteins can be used to generate antibodies, preferably protective antibodies. "Antibody" as used herein includes, but is not limited to, intact immunoglobulin molecules, as well as fragments thereof which are capable of binding a Cna_B domain. "Antibodies" therefore can include monoclonal antibodies, hybrid (chimeric) antibody molecules (e.g., Winter et al., Nature 349, 293-99, 1991; U.S. Pat. No. 4,816,567); F(ab')2 and F(ab) fragments and Fv molecules; non-covalent heterodimers (e.g., Inbar et al., Proc. Natl. Acad. Sci. U.S.A. 69, 2659-62, 1972; Ehrlich et al., Biochem 19, 4091-96, 1980); single-chain Fv molecules (sFv) (e.g., Huston et al., Proc. Natl. Acad. Sci. U.S.A. 85, 5897-83, 1988); dimeric and trimeric antibody fragment constructs; minibodies (e.g., Pack et al., Biochem 31, 1579-84, 1992; Cumber et al., J. Immunology 149B, 120-26, 1992); humanized antibody molecules (e.g., Riechmann et al., Nature 332, 323-27, 1988; Verhoeyan et al., Science 239, 1534-36, 1988; and U.K. Patent Publication No. GB 2,276, 169, published 21 Sep. 1994); and any functional fragments obtained from such molecules, as well as antibodies obtained through non-conventional processes such as phage display.

An antibody binds specifically to a Cna_B domain according to the invention if it provides a detection signal at least 5-, 10-, or 20-fold higher than a detection signal provided with other proteins when used in an immunochemical assay. Preferably, an antibody that binds specifically to a Cna_B domain can immunoprecipitate that a Cna_B domain antigen from solution. In some embodiments, antibodies which bind specifically to a Cna_B domain induce opsonophagocytosis of GBS strain 515 by at least 30% (e.g., 30, 35, 40, 45, 50, 55, 60, 65, 70, 75, 80, 85, 90, 95, or 100%).

Additional Antigens

Compositions of the invention may be administered in conjunction with one or more antigens for use in therapeutic or prophylactic methods of the present invention. Preferred antigens include those listed below. Additionally, the compositions of the present invention may be used to treat or prevent infections caused by any of the below-listed pathogens. In addition to combination with the antigens described below, the compositions of the invention may also be combined with an adjuvant as described herein.

GBS Polysaccharide Antigen

In some embodiments compositions of the invention comprise a GBS polysaccharide antigen. *S. agalactiae* GBS carbohydrate typically features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings (Kreis et al., Int. J. Biol. Macromol. 17, 117-30, 1995). GBS polysaccharide antigens useful in compositions of the invention have the formula:

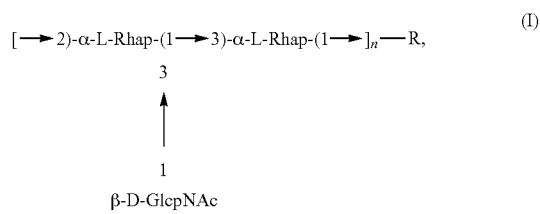

wherein R is a terminal reducing L-Rhamnose or D-GlcpNAc and n is a number from about 3 to about 30.

The GBS polysaccharide antigen used according to the invention may be a substantially full-length GBS carbohydrate, as found in nature, or it may be shorter than the natural length. Full-length polysaccharides may be depolymerized to give shorter fragments for use with the invention, e.g., by hydrolysis in mild acid, by heating, by sizing chromatography, etc. However, it is preferred to use saccharides of substantially full-length. In particular, it is preferred to use saccharides with a molecular weight of about 10 kDa. Molecular masses can be measured by gel filtration relative to dextran standards.

The saccharide may be chemically modified relative to the GBS carbohydrate as found in nature. For example, the saccharide may be de N acetylated (partially or fully), N propionated (partially or fully), etc. The effect of de acetylation etc., for example on immunogenicity, can be assessed by routine assays.

In some embodiments the GBS polysaccharide antigen is conjugated to a carrier, such as the mutated diphtheria toxin CRM197 and other carriers described below.

Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides:* Meningitides antigens may include proteins (such as those identified in References 1-7), saccharides (including a polysaccharide, oligosaccharide or lipopolysaccharide), or outer-membrane vesicles (References 8, 9, 10, 11) purified or derived from *N. meningitides* serogroup such as A, C, W135, Y, and/or B. Meningitides protein antigens may be selected from adhesions, autotransporters, toxins, Fe acquisition proteins, and membrane associated proteins (preferably integral outer membrane protein).

*Streptococcus pneumoniae:* Streptococcus pneumoniae antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. No. 6,699,703, U.S. Pat. No. 6,800,744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis:* Moraxella antigens include antigens identified in WO 02/18595 and WO 99/58562, outer membrane protein antigens (HMW-OMP), C-antigen, and/or LPS.

*Bordetella pertussis:* Pertussis antigens include petussis holotoxin (PT) and filamentous haemagglutinin (FHA) from *B. pertussis*, optionally also combination with pertactin and/or agglutinogens 2 and 3 antigen.

*Staphylococcus aureus:* Staphylococcus aureus antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis:* S. epidermidis antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as CRM197. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa: Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (Infect Immun. 2001 May; 69(5): 3510-3515).

*Legionella pneumophila.* Bacterial antigens may be derived from *Legionella pneumophila.*

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae:* Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis: Chlamydia trachomatis* antigens include antigens derived from serotypes A, B, Ba and C (agents of trachoma, a cause of blindness), serotypes L1, L2 & L3 (associated with Lymphogranuloma venereum), and serotypes, D-K. *Chlamydia* trachomas antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori: H. pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* antigens include LPS (Infect Immun. 2002 August; 70(8): 4414).

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (Infect Immun. 2003 January; 71(1)): 374-383, LPS (Infect Immun. 1999 October; 67(10): 5395), *Yersinia pestis* V antigen (Infect Immun. 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens (Proc Natl Acad Sci USA.

2004 Aug. 24; 101(34): 12652), and/or MPT51 antigens (Infect Immun. 2004 July; 72(7): 3829).

*Rickettsia*: Antigens include outer membrane proteins, including the outer membrane protein A and/or B (OmpB) (Biochim Biophys Acta. 2004 Nov. 1; 1702(2):145), LPS, and surface protein antigen (SPA) (J. Autoimmun. 1989 June; 2 Suppl:81).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (Infect Immun. 2003 October; 71(10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, OspC and OspD), other surface proteins such as OspE-related proteins (Erps), decorin-binding proteins (such as DbpA), and antigenically variable VI proteins, such as antigens associated with P39 and P13 (an integral membrane protein, Infect Immun. 2001 May; 69(5): 3323-3334), VlsE Antigenic Variation Protein (J Clin Microbiol. 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens useful in compositions of the invention may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens may be derived from gram-negative or gram-positive bacteria. The antigens may be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example CRM197). Such conjugation may be direct conjugation effected by reductive amination of carbonyl moieties on the saccharide to amino groups on the protein, as provided in U.S. Pat. No. 5,360,897 and Can J Biochem Cell Biol. 1984 May; 62(5):270-5. Alternatively, the saccharides can be conjugated through a linker, such as, with succinamide or other linkages provided in Bioconjugate Techniques, 1996 and CRC, Chemistry of Protein Conjugation and Cross-Linking, 1993.

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., J Gen Virol. 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (FIN), Fusion proteins F1 and F2, Nucleoprotein (NP), Phosphoprotein (P), Large protein (L), and Matrix protein (M). Preferred Paramyxovirus proteins include FIN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al., Hepatology (1991) 14:381).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae: Viral antigens may be derived from Calciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be derived from gag (p24gag and p55gag), env (gp160 and gp41), pol, tat, nef, rev vpu, miniproteins, (preferably p55 gag and gp140v delete). HIV antigens may be derived from one or more of the following strains: HIVIIIb, HIVSF2, HIVLAV, HIVLAI, HIVMN, HIV-1CM235, HIV-1US4.

Reovirus: Viral antigens may be derived from a Reovirus, such as an Orthoreovirus, a Rotavirus, an Orbivirus, or a Coltivirus. Reovirus antigens may be selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins ($\alpha$), early proteins ($\beta$), and late proteins ($\gamma$). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Further provided are antigens, compositions, methods, and microbes included in Vaccines, 4th Edition (Plotkin and Orenstein ed. 2004); Medical Microbiology 4th Edition (Murray et al. ed. 2002); Virology, 3rd Edition (W. K. Joklik ed. 1988); Fundamental Virology, 2nd Edition (B. N. Fields and D. M. Knipe, eds. 1991), which are contemplated in conjunction with the compositions of the present invention.

C. Fungal Antigens

Fungal antigens for use in the invention may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton*

*megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention may include one or more antigens derived from a sexually transmitted disease (STD). Such antigens may provide for prophylactic or therapy for STDs such as chlamydia, genital herpes, hepatits (such as HCV), genital warts, gonorrhoea, syphilis and/or chancroid (See, WO00/15255). Antigens may be derived from one or more viral or bacterial STDs. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli,* and *Streptococcus agalactiae.* Examples of specific antigens derived from these pathogens are described above.

E. Respiratory Antigens

The compositions of the invention may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus agalactiae* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific antigens derived from these pathogens are described above.

G. Antigens Suitable for Use in Elderly or Immunocompromised Individuals

The compositions of the invention may include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in Elderly or Immunocompromised individuals include antigens derived from one or more of the following pathogens: *Neisseria meningitides, Streptococcus pneumoniae, Streptococcus agalactiae* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention may include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly(α-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation.

Additional formulation methods and antigens (especially tumor antigens) are provided in U.S. Pat. No. 6,884,435.

J. Antigen References

The following references include antigens useful in conjunction with the compositions of the present invention:
1 International patent application WO99/24578
2 International patent application WO99/36544.
3 International patent application WO99/57280.
4 International patent application WO00/22430.
5 Tettelin et al. (2000) Science 287:1809-1815.
6 International patent application WO96/29412.
7 Pizza et al. (2000) Science 287:1816-1820.
8 PCT WO 01/52885.
9 Bjune et al. (1991) Lancet 338(8775).
10 Fuskasawa et al. (1999) Vaccine 17:2951-2958.
11 Rosenqist et al. (1998) Dev. Biol. Strand 92:323-333.
12 Constantino et al. (1992) Vaccine 10:691-698.
13 Constantino et al. (1999) Vaccine 17:1251-1263.
14 Watson (2000) Pediatr Infect Dis J 19:331-332.
15 Rubin (20000) Pediatr Clin North Am 47:269-285, v.
16 Jedrzejas (2001) Microbiol Mol Biol Rev 65:187-207.
17 International patent application filed on 3 Jul. 2001 claiming priority from GB-0016363.4; WO 02/02606; PCT IB/01/00166.
18 Kalman et al. (1999) Nature Genetics 21:385-389.
19 Read et al. (2000) Nucleic Acids Res 28:1397-406.
20 Shirai et al. (2000) J. Infect. Dis 181(Suppl 3):S524-S527.
21 International patent application WO99/27105.
22 International patent application WO00/27994.
23 International patent application WO00/37494.
24 International patent application WO99/28475.
25 Bell (2000) Pediatr Infect Dis J 19:1187-1188.
26 Iwarson (1995) APMIS 103:321-326.
27 Gerlich et al. (1990) Vaccine 8 Suppl:S63-68 & 79-80.
28 Hsu et al. (1999) Clin Liver Dis 3:901-915.
29 Gastofsson et al. (1996) N. Engl. J. Med. 334-:349-355.
30 Rappuoli et al. (1991) TIBTECH 9:232-238.
31 Vaccines (1988) eds. Plotkin & Mortimer. ISBN 0-7216-1946-0.
32 Del Guidice et al. (1998) Molecular Aspects of Medicine 19:1-70.
33 International patent application WO93/018150.
34 International patent application WO99/53310.
35 International patent application WO98/04702.
36 Ross et al. (2001) Vaccine 19:135-142.
37 Sutter et al. (2000) Pediatr Clin North Am 47:287-308.
38 Zimmerman & Spann (1999) Am Fan Physician 59:113-118, 125-126.
39 Dreensen (1997) Vaccine 15 Suppl" S2-6.
40 MMWR Morb Mortal Wkly rep 1998 Jan. 16:47(1):12, 9.
41 McMichael (2000) Vaccine 19 Suppl 1:S101-107.
42 Schuchat (1999) Lancer 353(9146):51-6.
43 GB patent applications 0026333.5, 0028727.6 & 0105640.7.
44 Dale (1999) Infect Disclin North Am 13:227-43, viii.
45 Ferretti et al. (2001) PNAS USA 98: 4658-4663.
46 Kuroda et al. (2001) Lancet 357(9264):1225-1240; see also pages 1218-1219.
47 Ramsay et al. (2001) Lancet 357(9251):195-196.
48 Lindberg (1999) Vaccine 17 Suppl 2:S28-36.
49 Buttery & Moxon (2000) J R Coil Physicians Long 34:163-168.
50 Ahmad & Chapnick (1999) Infect Dis Clin North Am 13:113-133, vii.
51 Goldblatt (1998) J. Med. Microbiol. 47:663-567.
52 European patent 0 477 508.
53 U.S. Pat. No. 5,306,492.
54 International patent application WO98/42721.
55 Conjugate Vaccines (eds. Cruse et al.) ISBN 3805549326, particularly vol. 10:48-114.
56 Hermanson (1996) Bioconjugate Techniques ISBN: 012323368 & 012342335X.
57 European patent application 0372501.
58 European patent application 58.
59 European patent application 0427347.
60 International patent application WO93/17712.
61 International patent application WO98/58668.
62 European patent application 0471177.
63 International patent application WO00/56360.
64 International patent application WO00/67161.

The contents of all of the above cited patents, patent applications and journal articles are incorporated by reference as if set forth fully herein.

Carrier Proteins

Where a saccharide or carbohydrate antigen is used, it is preferably conjugated to a carrier protein in order to enhance immunogenicity. See Ramsay et al. (2001) Lancet 357(9251): 195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X. Preferred carrier proteins are bacterial toxins or toxoids, such as diphtheria or tetanus toxoids. The CRM197 diphtheria toxoid is particularly preferred.

Other carrier polypeptides include the *N. meningitidis* outer membrane protein (EP-A-0372501), synthetic peptides (EP-A-0378881 and EP-A 0427347), heat shock proteins (WO 93/17712 and WO 94/03208), pertussis proteins (WO 98/58668 and EP A 0471177), protein D from *H. influenzae* (WO 00/56360), cytokines (WO 91/01146), lymphokines, hormones, growth factors, toxin A or B from *C. difficile* (WO 00/61761), iron-uptake proteins (WO 01/72337), etc. Where a mixture comprises capsular saccharide from both serigraphs A and C, it may be preferred that the ratio (w/w) of MenA saccharide:MenC saccharide is greater than 1 (e.g., 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g., detoxification of pertussis toxin by chemical and/or genetic means.

Pharmaceutically Acceptable Carriers

Compositions of the invention will typically, in addition to the components mentioned above, comprise one or more pharmaceutically acceptable carriers. These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Immunoregulatory Agents

Adjuvants

Vaccines of the invention may be administered in conjunction with other immunoregulatory agents. In particular, compositions will usually include an adjuvant. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of Vaccine Design . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2$/g. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (isoelectric point=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions suitable for use as adjuvants in the invention include squalene-water emulsions, such as 5% squalene, 0.5% polyoxyethylene (20) sorbitan monooleate (polysorbate 80, e.g., TWEEN® 80), and 0.5% sorbitan trioleate (e.g., SPAN® 85), such as MF59®, formulated into submicron particles using a microfluidizer). See WO90/14837. See also, Podda, Vaccine (2001) 19: 2673-2680; Frey et al., Vaccine (2003) 21:4234-4237. MF59® is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN™ 80 (polyoxyethylenesorbitan monooleate), and/or 0.25-1.0% SPAN 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)ethylamine (MTP-PE), for example, the submicron oil-in-water emulsion known as "MF59" (International Publication No. WO90/14837; U.S. Pat. Nos. 6,299,884 and 6,451,325, and Ott et al., in Vaccine Design: The Subunit and Adjuvant Approach (Powell, M. F. and Newman, M. J. eds.) Plenum Press, New York, 1995, pp. 277-296). MF59 contains 4-5% w/v Squalene (e.g. 4.3%), 0.25-0.5% w/v TWEEN™ 80, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v polyoxyethylene (20) sorbitan monooleate (polysorbate 80, e.g., TWEEN® 80), and 0.75% w/v sorbitan trioleate (e.g., SPAN® 85) and optionally MTP-PE. Yet another submicron oil-in-water emulsion is MF75, also known as SAF, containing 10% squalene, 0.4% polyoxyethylene (20) sorbitan monooleate (polysorbate 80, e.g., TWEEN® 80), 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria Molina* tree have been widely studied as adjuvants. Saponins can also be commercially obtained from Smilax ornata (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., Advanced Drug Delivery Reviews (1998) 32:247-271. See also Sjolander, et al., Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Q13-phage (such as coat proteins), GA-phage, fr-phage, AP205 phage, and Ty (such as retrotransposon Ty protein p1). VLPs are discussed further in WO03/024480, WO03/024481, and Niikura et al., Virology (2002) 293:273-280; Lenz et al., Journal of Immunology (2001) 5246-5355; Pinto, et al., Journal of Infectious Diseases (2003) 188:327-338; and Gerber et al., Journal of Virology (2001) 75(10):4752-4760. Virosomes are discussed further in, for example, Gluck et al., Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC 529. See Johnson et al. (1999) Bioorg Med Chem Lett 9:2273-2278.

(2) Lipid A Derivatives

Lipid A derivatives include derivatives of lipid A from *Escherichia coli* such as OM-174. OM-174 is described for example in Meraldi et al., Vaccine (2003) 21:2485-2491; and Pajak, et al., Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpGs can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., Nucleic Acids Research (2003) 31(9): 2393-2400; WO02/26757 and WO99/62923 for examples of possible analog substitutions. The adjuvant effect of CpG oligonucleotides is further discussed in Krieg, Nature Medicine (2003) 9(7): 831-835; McCluskie, et al., FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., J. Immunol. (2003) 170(8):4061-4068; Krieg, TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form immunomers. See, for example, Kandimalla, et al., BBRC (2003) 306:948-953; Kandimalla, et al., Biochemical Society Transactions (2003) 31(part 3):664-658; Bhagat et al., BBRC (2003) 300:853-861 and WO03/035836.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from E. coli (i.e., E. coli heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al., Infection and Immunity (2002) 70(6):3012-3019; Pizza, et al., Vaccine (2001) 19:2534-2541; Pizza, et al., Int. J. Med. Microbiol. (2000) 290(4-5):455-461; Scharton-Kersten et al., Infection and Immunity (2000) 68(9):5306-5313; Ryan et al., Infection and Immunity (1999) 67(12):6270-6280; Partidos et al., Immunol. Lett. (1999) 67(3):209-216; Peppoloni et al., Vaccines (2003) 2(2):285-293; and Pine et al., (2002) J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6): 1165-1167.

F. Bioadhesives and Mucoadhesives

Bioadhesives and mucoadhesives may also be used as adjuvants in the invention. Suitable bioadhesives include esterified hyaluronic acid microspheres (Singh et al. (2001) J. Cont. Rele. 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. See WO99/27960.

G. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non toxic (e.g. a poly(α-hydroxy acid), a polyhydroxybutyric acid, a polyorthoester, a polyanhydride, a polycaprolactone, etc.), with poly(lactide co glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N acetylmuramyl-1-alanyl-d-isoglutaminyl-1-alanine-2-(1'-2'-dipalmitoyl-sn glycero-3-hydroxyphosphoryloxy)ethylamine MTP-PE).

L. Imidazoquinoline Compounds

Examples of imidazoquinoline compounds suitable for use adjuvants in the invention include Imiquimod and its analogues, described further in Stanley, Clin Exp Dermatol (2002) 27(7):571-577; Jones, Curr Opin Investig Drugs (2003) 4(2):214-218; and U.S. Pat. Nos. 4,689,338, 5,389, 640, 5,268,376, 4,929,624, 5,266,575, 5,352,784, 5,494,916, 5,482,936, 5,346,905, 5,395,937, 5,238,944, and 5,525,612.

M. Thiosemicarbazone Compounds

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);
(2) a saponin (e.g., QS21)+a non-toxic LPS derivative (e.g. 3dMPL) (see WO94/00153);
(3) a saponin (e.g., QS21)+a non-toxic LPS derivative (e.g. 3dMPL)+a cholesterol;
(4) a saponin (e.g., QS21)+3dMPL+IL 12 (optionally+a sterol) (WO98/57659);
(5) combinations of 3dMPL with, for example, QS21 and/or oil-in-water emulsions (See European patent applications 0835318, 0735898 and 0761231);
(6) SAF, containing 10% Squalane, 0.4% Tween 80, 5% pluronic-block polymer L121, and thr-MDP, either microfluidized into a submicron emulsion or vortexed to generate a larger particle size emulsion.
(7) RIBI™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Therapeutic Methods

The invention provides methods for inducing or increasing an immune response to one or more gram positive (e.g., streptococcal and/or staphylococcal) bacteria (e.g., *S. agalactiae, S. pyogenes, S. pneumoniae*, and/or *S. aureus*) using the compositions described above. The immune response is preferably protective and can include antibodies and/or cell-mediated immunity (including systemic and mucosal immunity). Immune responses include booster responses.

Teenagers and children, including toddles and infants, can receive a vaccine for prophylactic use; therapeutic vaccines typically are administered to teenagers or adults. A vaccine intended for children may also be administered to adults e.g., to assess safety, dosage, immunogenicity, etc.

Diseases caused by *S. agalactiae* which can be prevented or treated according to the invention include, but are not limited to, newborn sepsis, meningitis and pneumonia and pregnant women infection such as in the womb, in the amniotic fluid, following cesarean sections, and in the urinary tract.

Diseases caused by *S. pneumoniae* which can be prevented or treated according to the invention include, but are not limited to, Pneumonia, bacteremia, otitis media, meningitis, sinusitis, peritonitis, and arthritis.

Diseases caused by *S. pyogenes* which can be prevented or treated according to the invention include, but are not limited to, erysipelas pharyngitis (such as streptococcal sore throat), scarlet fever, impetigo, cellulitis, septicemia, necrotizing fasciitis, myositis, toxic shock syndrome, and sequelae such as rheumatic fever and acute glomerulonephritis.

Diseases caused by *S. aureus* which can be prevented or treated according to the invention include, but are not limited to, minor skin infections, impetigo, boils, cellulitis folliculitis, furuncles, carbuncles, scalded skin syndrome, abscesses, pneumonia, meningitis, osteomyelitis, endocarditis, Toxic shock syndrome, and septicemia.

Diseases caused by *S. suis* which can be prevented or treated according to the invention include, but are not limited to, *S. suis* infections in swine and meningitis, septicemia, pneumonia, endocarditis, arthritis, and septic shock in humans exposed to swine or swine products.

Diseases caused by *S. equi* which can be prevented or treated according to the invention include, but are not limited to, "strangles" in equine, canine and Camelid patients (e.g., horses, donkeys, mules, dogs, camels and dromedaries) and metastatic strangles.

Diseases caused by *S. uberis* which can be prevented or treated according to the invention include, but are not limited to, mastitis in cattle.

Diseases caused by *S. dysgalactiae* which can be prevented or treated according to the invention include, but are not limited to, mastitis in, e.g., horses, cattle, and swine.

Diseases caused by *S. iniae* which can be prevented or treated according to the invention include, but are not limited to, *S. iniae* infection of fish and invasive infection in humans after skin injuries during the handling of infected fish.

Tests to Determine the Efficacy of the Immune Response

One way of assessing efficacy of therapeutic treatment involves monitoring bacterial infection after administration of the composition of the invention. One way of assessing efficacy of prophylactic treatment involves monitoring immune responses against the Cna_B domains in the compositions of the invention after administration of the composition.

Another way of assessing the immunogenicity of the component proteins of the immunogenic compositions of the present invention is to produce Cna_B domains recombinantly and to screen patient sera or mucosal secretions by immunoblot. A positive reaction between the protein and the patient serum indicates that the patient has previously mounted an immune response to the protein in question; i.e., the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against a Cna_B domain after administration of the composition. Typically, serum specific antibody responses are determined post-immunization but pre-challenge whereas mucosal specific antibody body responses are determined post-immunization and post-challenge.

The vaccine compositions of the present invention can be evaluated in in vitro and in vivo animal models prior to host, e.g., human, administration. Particularly useful mouse models include those in which intraperitoneal immunization is followed by either intraperitoneal challenge or intranasal challenge.

The efficacy of immunogenic compositions of the invention can also be determined in vivo by challenging animal models with gram positive (e.g., staphylococcal or streptococcal) bacteria, e.g., guinea pigs or mice, with the immunogenic compositions. The immunogenic compositions may or may not be derived from the same serotypes as the challenge serotypes.

In vivo efficacy models include but are not limited to: (i) a murine infection model using human gram positive (e.g., streptococcal and/or staphylococcal) bacteria serotypes; (ii) a murine disease model which is a murine model using a mouse-adapted streptococcal strain, such as the M23 strain of *S. pyogenes* which is particularly virulent in mice, and (iii) a primate model using human streptococcal isolates. Other in vivo models are disclosed in the Examples below.

The immune response may be one or both of a Th1 immune response and a Th2 response. The immune response may be an improved or an enhanced or an altered immune response. The immune response may be one or both of a systemic and a mucosal immune response. Preferably the immune response is an enhanced system and/or mucosal response.

An enhanced systemic and/or mucosal immunity is reflected in an enhanced Th1 and/or Th2 immune response. Preferably, the enhanced immune response includes an increase in the production of IgG1 and/or IgG2a and/or IgA.

Preferably the mucosal immune response is a Th2 immune response. Preferably, the mucosal immune response includes an increase in the production of IgA.

Activated Th2 cells enhance antibody production and are therefore of value in responding to extracellular infections. Activated Th2 cells may secrete one or more of IL-4, IL-5, IL-6, and IL-10. A Th2 immune response may result in the production of IgG1, IgE, IgA and memory B cells for future protection.

A Th2 immune response may include one or more of an increase in one or more of the cytokines associated with a Th2 immune response (such as IL-4, IL-5, IL-6 and IL-10), or an increase in the production of IgG1, IgE, IgA and memory B cells. Preferably, the enhanced Th2 immune response will include an increase in IgG1 production.

A Th1 immune response may include one or more of an increase in CTLs, an increase in one or more of the cytokines associated with a Th1 immune response (such as IL-2, IFNγ, and TNFβ), an increase in activated macrophages, an increase in NK activity, or an increase in the production of IgG2a. Preferably, the enhanced Th1 immune response will include an increase in IgG2a production.

Immunogenic compositions of the invention, in particular, immunogenic composition comprising one or more Cna_B domains of the present invention may be used either alone or in combination with other gram positive bacterial antigens (e.g., streptococcal or staphylococcal antigens), optionally with an immunoregulatory agent capable of eliciting a Th1 and/or Th2 response.

The invention also comprises an immunogenic composition comprising one or more immunoregulatory agent, such as a mineral salt, such as an aluminium salt and an oligonucleotide containing a CpG motif. Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, one or more of the immunoregulatory agents include an adjuvant. The adjuvant may be selected from one or more of the group consisting of a Th1 adjuvant and Th2 adjuvant.

The compositions of the invention will preferably elicit both a cell mediated immune response as well as a humoral immune response in order to effectively address a gram positive bacterial (e.g., streptococcal and/or staphylococcal) infection. This immune response will preferably induce long lasting (e.g., neutralizing) antibodies and a cell mediated immunity that can quickly respond upon exposure to one or more gram positive bacterial (e.g., streptococcal and/or staphylococcal) antigens.

In one particularly preferred embodiment, the immunogenic composition comprises one or more Cna_B domain antigen(s) which elicit(s) a neutralizing antibody response and one or more Cna_B domain antigen (s) which elicit(s) a cell mediated immune response. In this way, the neutralizing antibody response prevents or inhibits an initial gram positive bacterial (e.g., streptococcal and/or staphylococcal) infection while the cell-mediated immune response capable of eliciting an enhanced Th1 cellular response prevents further spreading of the gram positive bacterial (e.g., streptococcal and/or staphylococcal) infection.

Compositions of the invention will generally be administered directly to a patient. The compositions of the present invention may be administered, either alone or as part of a composition, via a variety of different routes. Certain routes may be favored for certain compositions, as resulting in the generation of a more effective immune response, preferably a CMI response, or as being less likely to induce side effects, or as being easier for administration.

Delivery methods include parenteral injection (e.g., subcutaneous, intraperitoneal, intravenous, intramuscular, or interstitial injection) and rectal, oral (e.g., tablet, spray), vaginal, topical, transdermal (e.g., see WO 99/27961), transcutaneous (e.g., see WO02/074244 and WO02/064162), intranasal (e.g., see WO03/028760), ocular, aural, and pulmonary or other mucosal administration.

By way of example, the compositions of the present invention may be administered via a systemic route or a mucosal route or a transdermal route or it may be administered directly into a specific tissue. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Preferably, the systemic, parenteral administration is intramuscular injection. As used herein, the term "mucosal administration" includes but is not limited to oral, intranasal, intravaginal, intrarectal, intratracheal, intestinal and ophthalmic administration.

Dosage treatment can be a single dose schedule or a multiple dose schedule. Multiple doses may be used in a primary immunization schedule and/or in a booster immunization schedule. In a multiple dose schedule the various doses may be given by the same or different routes e.g., a parenteral prime and mucosal boost, a mucosal prime and parenteral boost, etc.

The compositions of the invention may be prepared in various forms. For example, a composition can be prepared as an injectable, either as a liquid solution or a suspension. Solid forms suitable for solution in, or suspension in, liquid vehicles prior to injection can also be prepared (e.g., a lyophilized composition). A composition can be prepared for oral administration, such as a tablet or capsule, as a spray, or as a syrup (optionally flavored). A composition can be prepared for pulmonary administration, e.g., as an inhaler, using a fine powder or a spray. A composition can be prepared as a suppository or pessary. A composition can be prepared for nasal, aural or ocular administration e.g., as drops. A composition can be in kit form, designed such that a combined composition is reconstituted just prior to administration to a patient. Such kits may comprise one or more Cna_B domain antigens or other antigens in liquid form and one or more lyophilized antigens.

Immunogenic compositions used as vaccines comprise an immunologically effective amount of one or more Cna_B domain antigens (or nucleic acid molecules encoding the antigens), as well as any other components, as needed, such as antibiotics. An "immunologically effective amount" is an amount which, when administered to an individual, either in a single dose or as part of a series, increases a measurable immune response or prevents or reduces a clinical symptom.

The immunogenic compositions of the present invention may be administered in combination with an antibiotic treatment regime. In one embodiment, the antibiotic is administered prior to administration of the one or more Cna_B domain antigens (or nucleic acid molecules encoding the antigens) of the invention.

In another embodiment, the antibiotic is administered subsequent to the administration of a Cna_B domain antigen of the invention. Examples of antibiotics suitable for use in the treatment of a streptococcal infection include but are not limited to penicillin or a derivative thereof or clindamycin, cephalosporins, glycopeptides (e.g., vancomycin), and cycloserine.

The amount of active agent in a composition varies, however, depending upon the health and physical condition of the individual to be treated, age, the taxonomic group of individual to be treated (e.g., non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range which can be determined through routine trials.

Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other buffers, diluents, filters, needles, and syringes. The kit can also comprise a second or third container with another active agent, for example an antibiotic.

The kit can also comprise a package insert containing written instructions for methods of inducing immunity against streptoccal bacteria or for treating gram positive bacterial (e.g., streptococcal and/or staphylococcal) infections. The package insert can be an unapproved draft package insert or can be a package insert approved by the Food and Drug Administration (FDA) or other regulatory body.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Immunogenicity of a Cna_B Domain

The Cna_B domain of GAS protein Cpa_M18 was cloned together with a flanking domain (Fb-signal) in a PET21b vector. See FIGS. 1A-B. His-tagged recombinant protein was purified using activated chelating sepharose fast flow columns. See FIG. 2.

Figure 20:
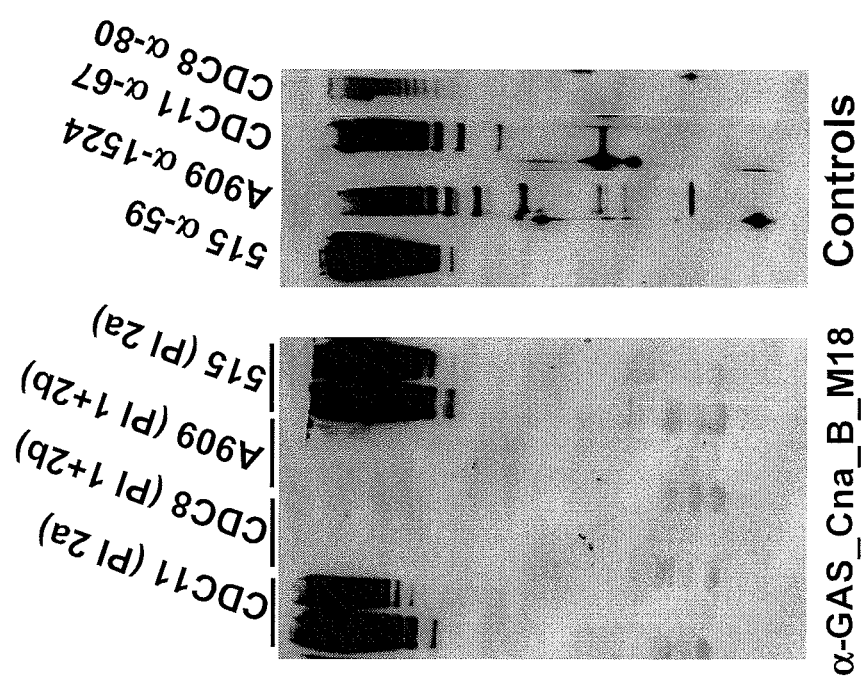
FIG. 20. Western blots demonstrating that antiserum against a Cna_B domain antigen recognizes GBS pili in a GBS protein extraction. "α-GAS_Cna_B_M18" is antiserum from mice immunized with Cna_B-Fb-M18, as described in Example 1.

Antiserum against the cloned Cna_B-Fb domain was obtained by immunizing 10 CD1 female mice three times each with 20 μg of the recombinant Cna_B-Fb protein. Cna_B-Fb serum was then probed by western blot experiments against a variety of purified His-tagged recombinant proteins from different human pathogens containing a Cna_B domain. The results are shown in FIGS. 3A-D. These experiments demonstrate that the Cna_B domain is immunogenic and that antiserum raised against it recognizes GAS_Cpa and F2 proteins as well as pili components of *S. agalactiae* and *S. pneumoniae*, which have been reported to be protective antigens (Maione et al., 2005 Science 309, 148-150; Rosini et al.,  2006 Mol. Micro. 61, 126-141 and Gianfaldoni et al., 2007, Infect. Immun. 75, 1059-1062). Example 5 reports experiments designed to address the possibility that antibodies in the sera reacted with the His tag; see also FIG. 20.

Reactivity of the Cna_B antiserum was compared to that of antiserum specific for the cpa_M18 protein using western blots. The results are shown in FIGS. 4A-B. Higher reactivity with all proteins tested was observed for the Cna_B antiserum. In particular, all the variants of GBS_59 (SAL 1486) tested were detected by the anti-Cna_B-Fb serum, but only one variant was detected by the anti-Cpa_M18 serum.

EXAMPLE 2

Opsonophagocytosis Assays

Opsonophagocytic killing of *S. agalactiae* (GBS) using specific sera and differentiated HL-60 cells was investigated in vitro to test whether the recombinant Cna_B-Fb domain elicited protective antibodies. GBS were grown in 5 ml of Todd Hewitt Broth (THB) to the mid exponential phase ($OD_{600}$=0.3), then centrifuged at 3000×g for 10 min at 4° C., washed with PBS 1×, suspended, and diluted in OP buffer (HBSS, 0.1% gelatin, 10% fetal calf serum) to a final concentration of approximately $2\times10^7$ CFU/ml). GBS cells (approximately $2\times10^5$ CFU) were mixed with heat-inactivated mouse serum (final concentration in the reaction 1:10) on wells of a chilled 96-well microtiter plate, then differentiated HL60 ($1-2\times10^6$ cells) and baby rabbit complement were added on ice with GBS cells (final reaction volume 125 μl). The mixtures were incubated for 60 min at 37° C. and mixed at 400-500×g. Phagocytosis was ended by returning the samples to ice at the end of the incubation period. Immediately before (time 0) and after 1 h incubation (time 1 h), a 25 μA aliquot was diluted in sterile distilled water (25 μl sample+ 225 μl water, then 1:10 and 1:100) and plated in Tryptic soy agar plates with 5% sheep blood. The plates were incubated overnight at 37° C.

The results are shown in FIG. 5. GAS_M18_Cna_B_Fb serum mediates the killing of GBS strain 515 (which expresses the Cna_B domain in pilin proteins SAL 1482, SAL 1486 and SAL 1487) and of strain JM10098 (which expressed the protective pilins SAN 1518 and SAN 1519).

Further opsonophagocytosis experiments pointed out that GAS_M18_cpa (the entire protein containing Cna_B-Fb domain) was equally able to kill bacteria, suggesting that antibodies raised against Cna_B-Fb domain are indeed responsible for bacterial killing.

Figure 6:
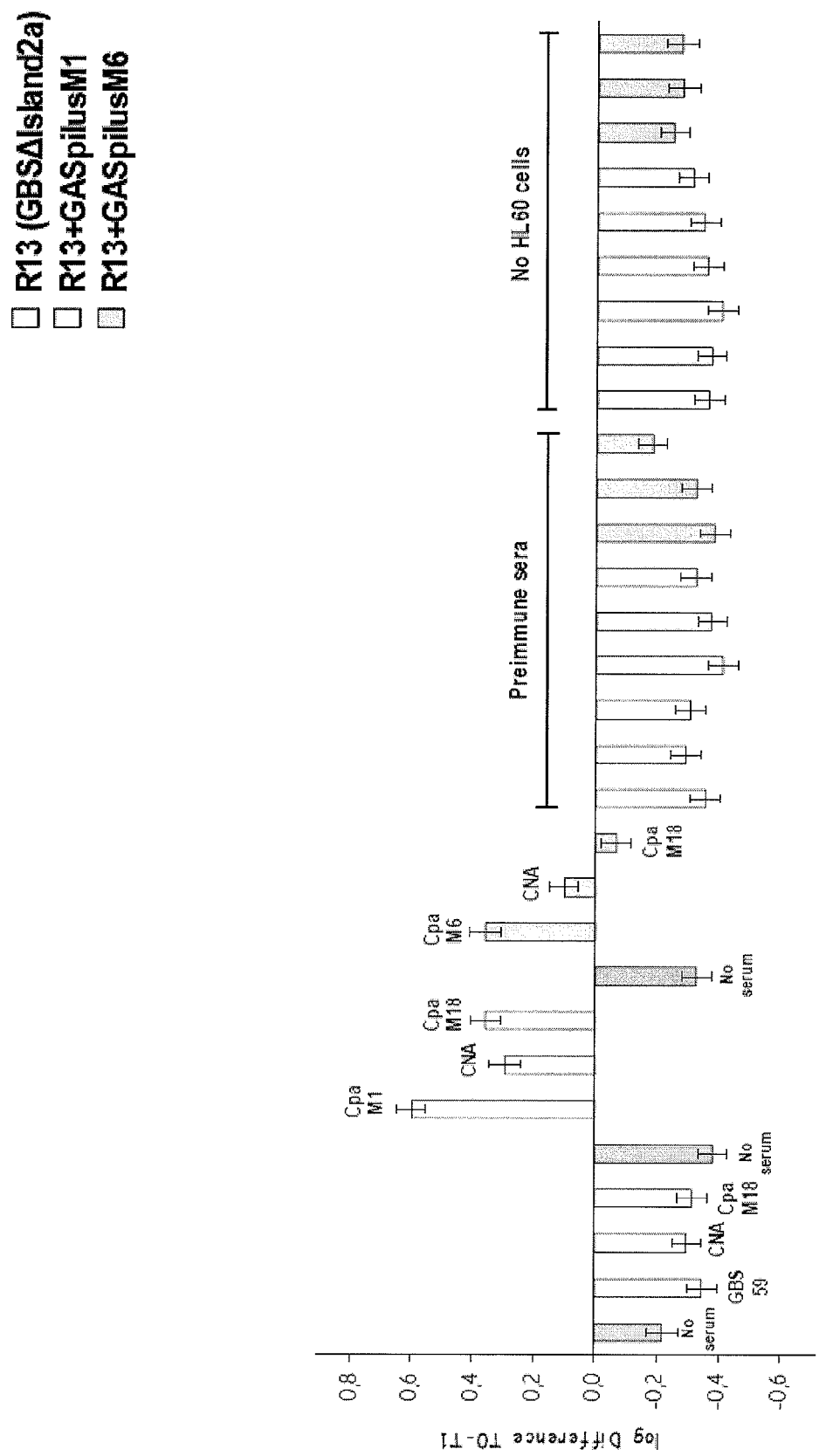
FIG. 6. Graph showing results of opsonophagocytosis assays for S. agalactiae mutant strain R13 (which lacks pili island 2) and its complemented strains containing S. pyogenes pilus M1 or S. pyogenes pilus M6. See Example 2.
Figure 10:
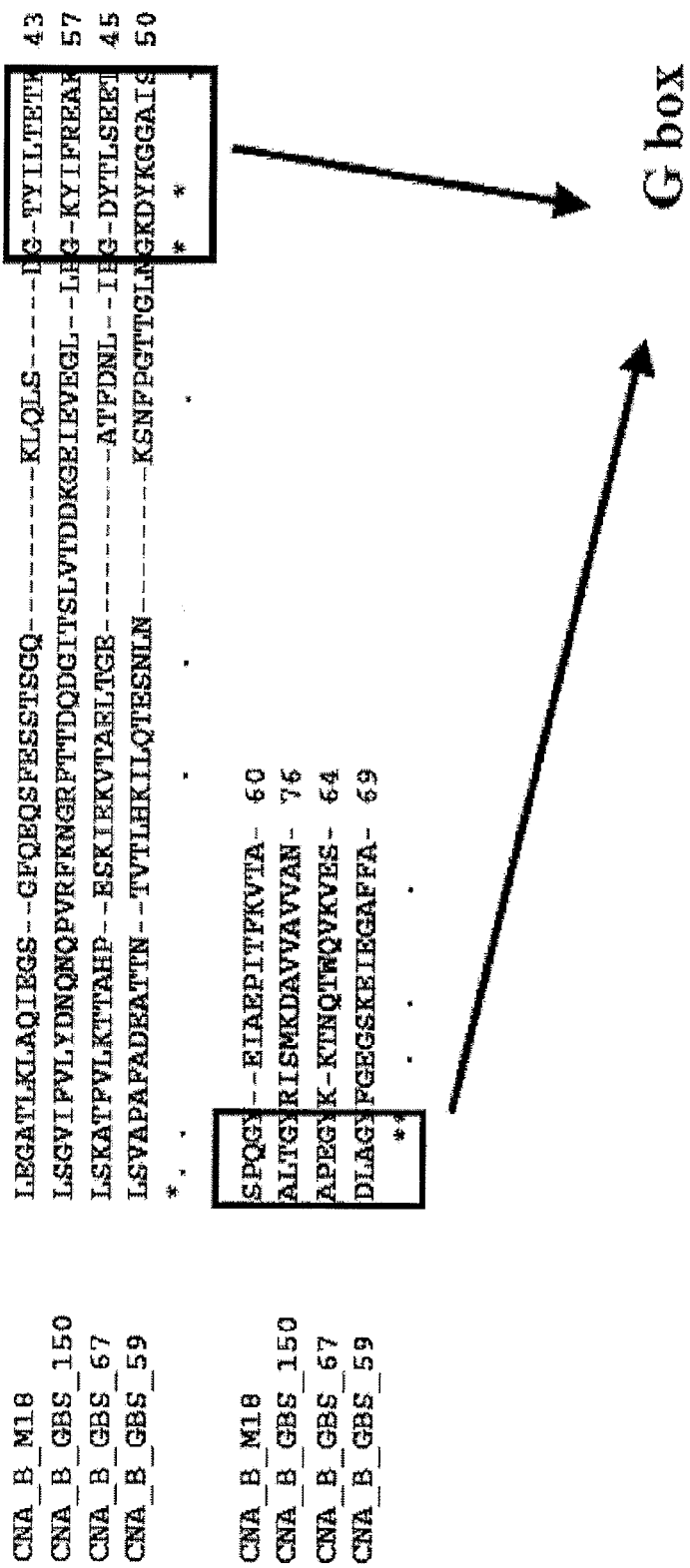
FIG. 10. Alignment of amino acid sequences of GBS island 2 pili components with a Cna_B domain of S. pyogenes Cpa protein from strain M18. Cna_B_CPA_M18 (Spy_M18_0126, SEQ ID NO:23), SEQ ID NO:7; Cna_B_GBS_150 (SAL 1482, SEQ ID NO:46), SEQ ID NO:28; Cna_B_GBS_67 (SAL 1487, SEQ ID NO:48), SEQ ID NO:30; and Cna_B_GBS_59 (SAL 1486, SEQ ID NO:102), SEQ ID NO:103.
Figure 14:
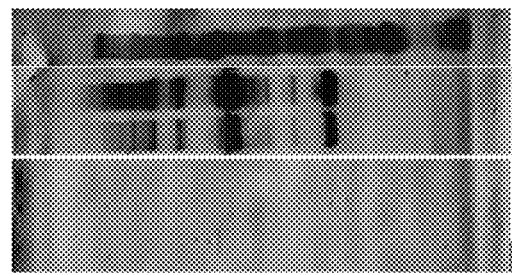
FIG. 14A. Western blot demonstrating that Cna_B antiserum recognized S. suis recombinant proteins.
FIG. 14B, amino acid sequences of Cna_B_CPA_M18 (Spy_M18_0126, SEQ ID NO:23), SEQ ID NO:14; Cna_B_Bkb3 (DUF 11) 89/1591 (SEQ ID NO:83), SEQ ID NO:75: Cna_B Bbk1 SSU05 0474 05AYH33 (SEQ ID NO:82), SEQ ID NO:76.
Figures 15, 15A, 15B:
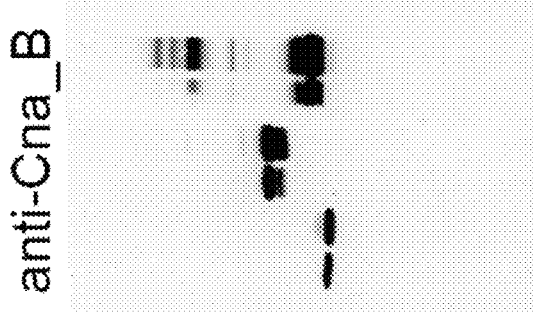
FIG. 15A. Western blot demonstrating that Cna_B antiserum recognizes S. equi recombinant proteins.
FIG. 15B, amino acid sequences of Cna_B_CPA_M18 (Spy_M18_0126, SEQ ID NO:23), SEQ ID NO:14; BKB SEQ0936 (SEQ ID NO:88), SEQ ID NO:77; ancillary protein SEQ 0935 (SEQ ID NO:87), SEQ ID NO:78.

In the absence of a suitable opsonophagocytosis system for *S. pyogenes* (GAS), R13, a mutant strain of GBS which lacks pili, and the same GBS R13 strain complemented with GAS pilus M1 and GAS pilus M6, were tested in opsonophagocytosis experiments. The results are shown in FIG. 6. These experiments demonstrate that GAS_M18_Cna_B_Fb antiserum mediates the killing of the GBS R13 strain which expresses GAS pili M1 and, to a lesser extent, the killing of the GBS R13 strain which expresses pili M6.

Because the Fb-signal domain is present only in GAS Cpa proteins, but not in the GBS pilins for which antibody-mediated killing was demonstrated, we focused on the Cna_B domain, which is present in all the proteins tested in Example 1. The amino acid sequences of these proteins were aligned to compare amino acid sequences of their Cna_B domains (FIGS. 7-13). These alignments identified a conserved region, termed herein the "G box," which has the consensus sequence GXYXLXEGXXXXXGY (SEQ ID NO:74).

EXAMPLE 3

Survival of Cna_B-Fb Immunized Mice after GBS Challenge

Thirty CD1 female mice were immunized on days 1, 20, and 34 with the recombinant Cna_B-Fb domain of the *S. pyogenes* Spy_M18_0126 protein prepared as described in Example 1. Ten mice were IP injected with 20 µg of the recombinant protein in 100 µl of _PBS+100 µl Freund's incomplete adjuvant. As positive controls, five mice were injected with 20 µg of *S. agalactiae* GBS59 (SAL_1486 protein in 100 µl of PBS+100 µl Freund's incomplete adjuvant, and five mice were injected with 20 µg of *S. agalactiae* GBS1523 (SAN 1518) protein in 100 µl of PBS+100 µl Freund's incomplete adjuvant. As negative controls, ten mice were injected with PBS plus Freund's incomplete adjuvant.

Mice were mated after the third injection, and newborns were challenged with a lethal dose of either GBS strain A909 or GBS strain 515. Eighty newborns from mothers immunized with the Cna_B-Fb and 80 with PBS, and forty newborns each from mothers immunized with *S. agalactiae* GBS59 (SAL_1486) or *S. agalactiae* GBS1523 (SAN 1518) were challenged. Newborn survival was monitored for four days. The survival rate for newborns immunized with the Cna_B-Fb domain was 42% and 44% after challenge with strains A909 and 515, respectively. The results are shown in Table 38, below.

TABLE 38

| | challenge strain | |
|---|---|---|
| injection with | A909 | 515 |
| Cna_B-Fb | 42% | 44% |
| PBS (negative) control | 15% | 12% |
| GBS1523 (SAN1518) (positive control) | 79% | nd |
| GBS59 (SAL1486) (positive control) | nd | 86% |

Figure 24:
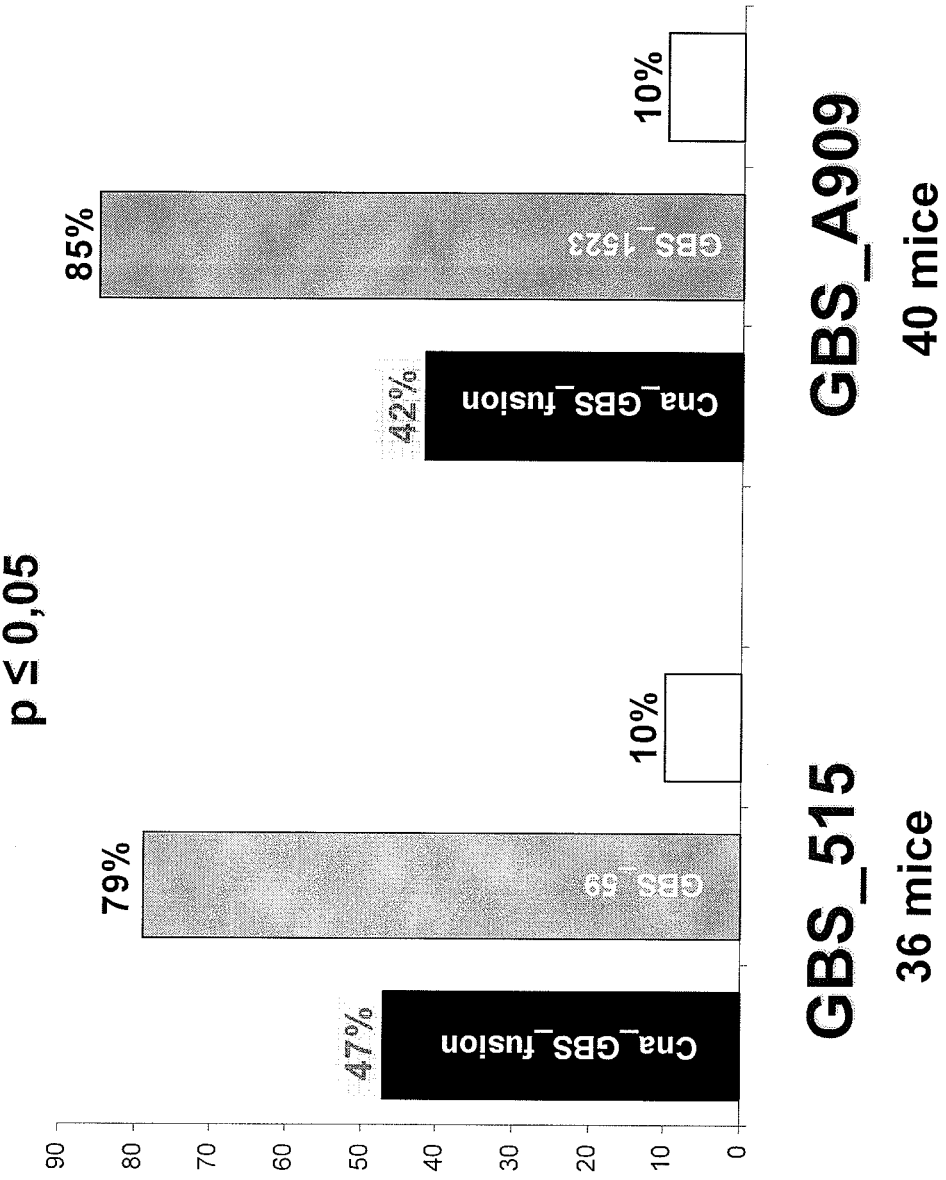
FIG. 24. Graphs demonstrating that mice born from mothers immunized with a chimeric Cna_B domain antigen show an increased survival rate over controls when immunized with a chimeric Cna_B domain antigen. See Example 1.

Results of a similar experiment are shown in FIG. 24.

EXAMPLE 4

ELISA Assays

Figure 19:
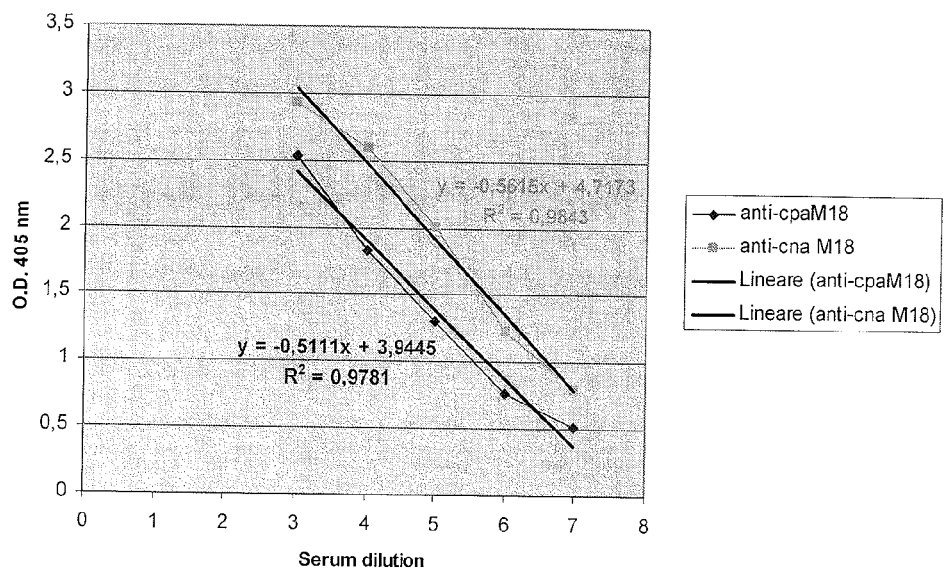
FIG. 19. Graph showing results of ELISA assays described in Example 4.

Evaluation of specific anti-Cna_B domain antibodies in GAS_Cpa_M18 serum was performed by coating both GAS_Cpa_M18 protein and Cna_B domain, which were successively challenged by serial dilutions of GAS_Cpa_M18 serum in an ELISA experiment (Tables 39 and 40). Dilutions corresponding to $OD_{540}=1$ indicated the ELISA titer for each protein (Table 40). FIG. 19 shows that when Y=1 ($OD_{540}$) for GAS_Cpa_M18 ELISA titer was 627.814. Similarly, when Y=1 ($OD_{540}$) for GAS_Cpa_M18 when challenging the coated Cna_B domain the ELISA titer resulted 318.061. This experiment showed that about half of the antibodies contained in GAS_Cpa_M18 protein serum were specific for the Cna_B domain.

TABLE 39

| | Cpa_M18_serum | |
|---|---|---|
| Coated protein | Cpa_M18 full length protein | Cna_B domain |
| ELISA titer | 627.814 | 318.061 |

TABLE 40

| serum dilution | $OD_{540}$ nm anti_cpa_M18_std | $OD_{450}$ nm anti_cna_B |
|---|---|---|
| 10000 | 3.407 | 3.136 |
| 20000 | 3.408 | 3.082 |
| 40000 | 3.282 | 2.553 |
| 80000 | 3.011 | 1.83 |
| 160000 | 2.576 | 1.305 |
| 320000 | 1.425 | 0.769 |
| 640000 | 0.815 | 0.508 |
| 1280000 | 0.505 | 0.295 |

EXAMPLE 5

FACS Analysis of Cross-Reactivity of GAS Cna_B_Fb Domain Serum with GAS and GBS Strains This example demonstrates that GAS Cna_B_Fb domain antiserum cross-reacts with strains of both GAS and GBS.

Antiserum against the cloned Cna_B-Fb domain and against the Cna_B domain only ("Cna_B_M6"; SEQ ID NO:145) was obtained by immunizing CD1 female mice three times each with 20 µg of the recombinant Cna_B-Fb protein or 20 µg of the recombinant M6_Cna_B domain.

Cross-hybridization specificity against various strains of GAS and GBS was confirmed using Fluorescence Activated Cell Sorting (FACS). A threshold of 80 channels was designated as a positive shift; 150 channels was designated as a very positive shift.

Figure 18A:
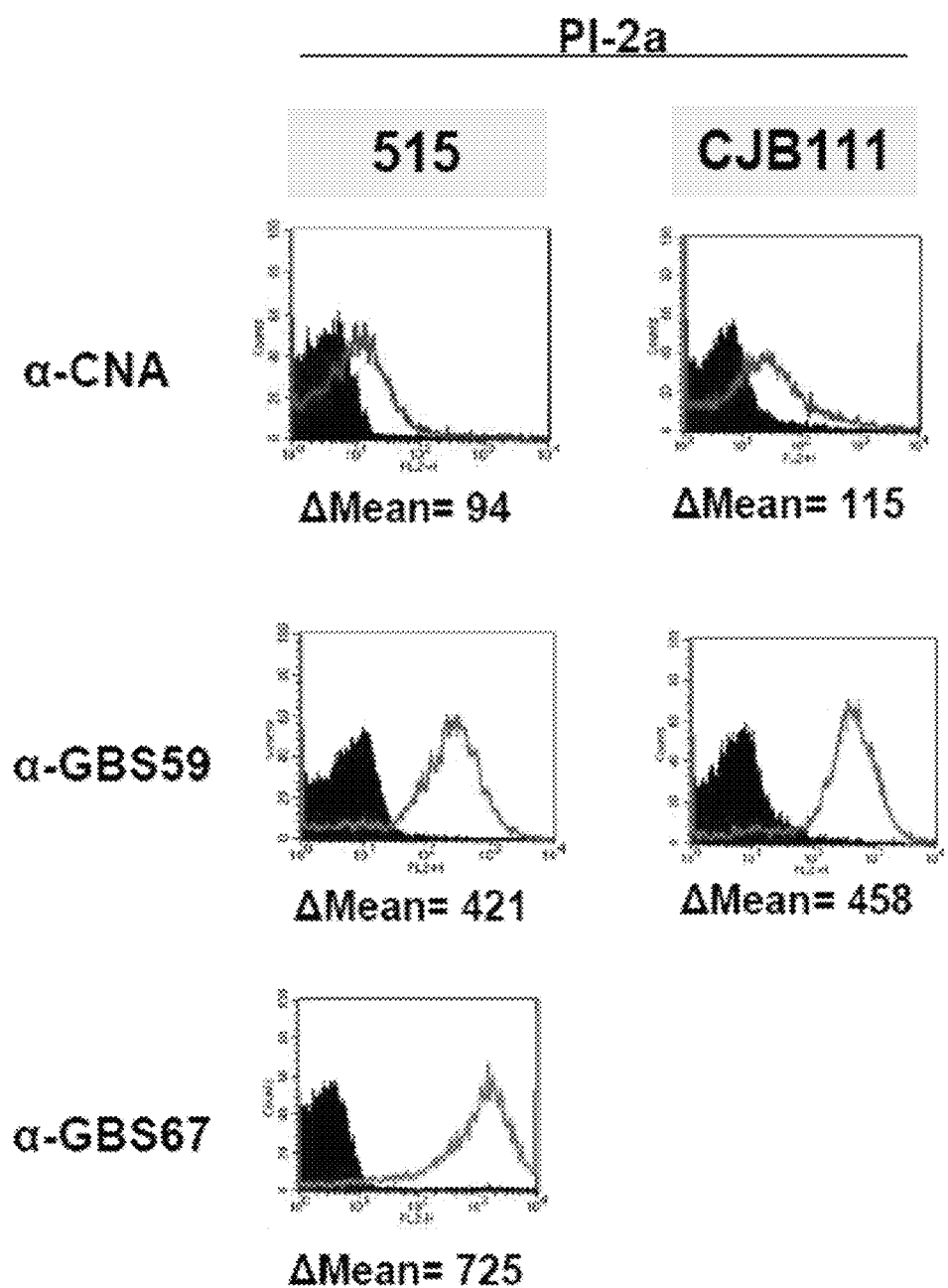
FIG. 18A. FACS analysis of GAS Cna_B serum cross-reaction with selected GBS strains.
Figure 18B:
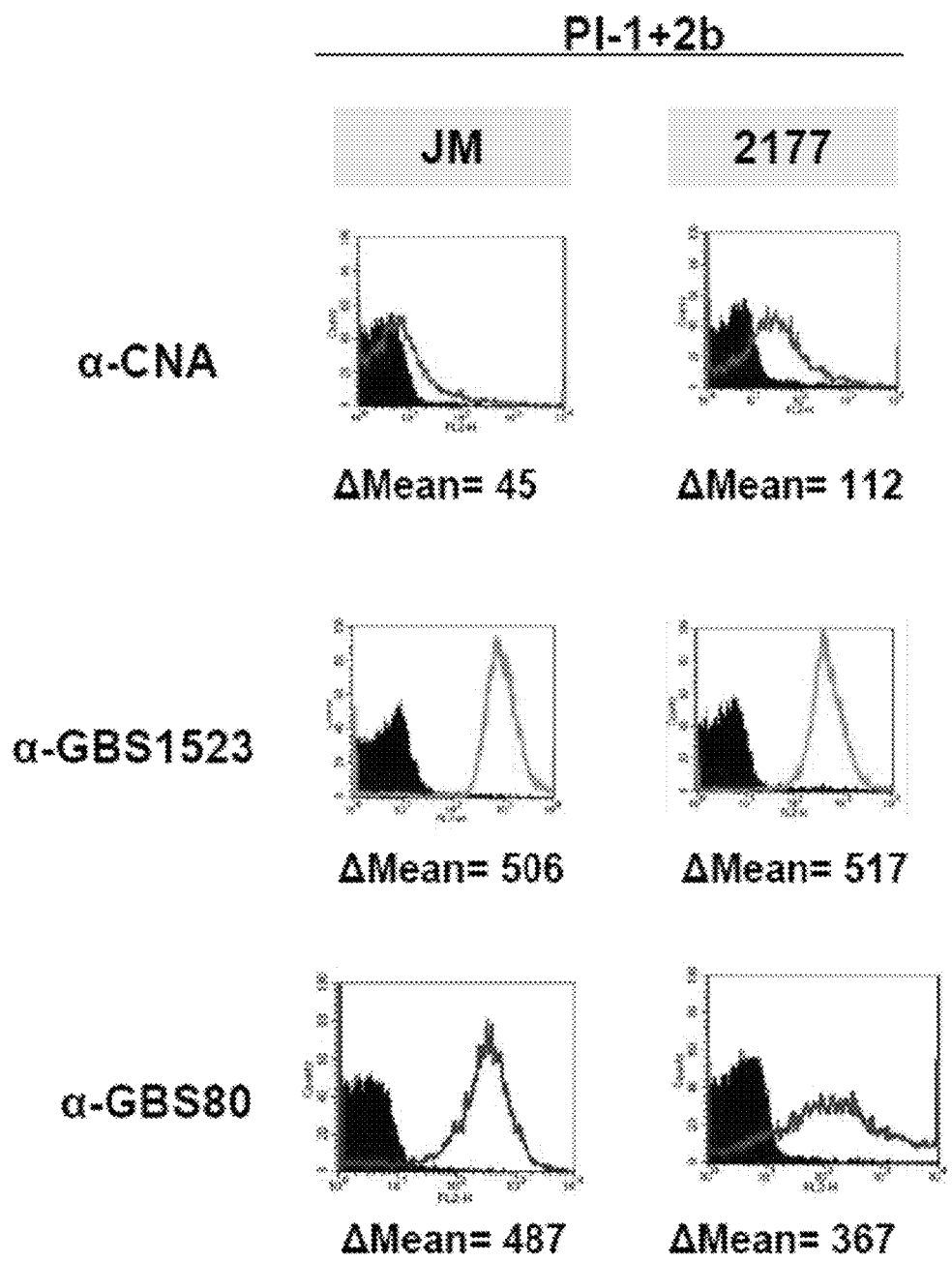
FIG. 18B. FACS analysis of GAS Cna_B serum cross-reaction with selected GBS strains.

The results are shown in Table 41. See also FIG. 18.

TABLE 41

| | MFI (Mean Fluorescence Intensity) | | | | | | | | | | |
|---|---|---|---|---|---|---|---|---|---|---|---|
| | Strains | | | | | | | | | | |
| Sera | M1Wessels | M3_44 | M3_43 | M6_16 | 27_M6 | 28_M6 | CJB111_GBS | 515_GBS | JM_GBS | 2177_GBS | CD_11GBS |
| α-CnaB_M18 | 220** | 96* | 64 | \ | \ | \ | 115* | 94* | 45 | 112* | 228** |
| α-CnaB_M6 | \ | \ | \ | 362** | 100* | 382** | \ | \ | \ | \ | \ |
| α-AP-1_M6 | \ | \ | \ | 520 | 390 | 300 | \ | \ | \ | \ | \ |
| α-GBS_59 | \ | \ | \ | \ | \ | \ | 458 | 421 | \ | \ | 480 |
| α-GBS_67 | \ | \ | \ | \ | \ | \ | \ | 725 | \ | \ | \ |
| α-GBS_80 | \ | \ | \ | \ | \ | \ | \ | \ | 487 | 367 | \ |
| α-GBS_1523 | \ | \ | \ | \ | \ | \ | \ | \ | 506 | 517 | \ |

*>80
**>150

EXAMPLE 6

In Vivo Protection from Subcutaneous Infection after Intraperitoneal Immunization This example demonstrates that mice immunized intraperitoneally with various Cna_B domain antigens show a reduced skin lesion area in a GAS subcutaneous infection model.

Figure 21:
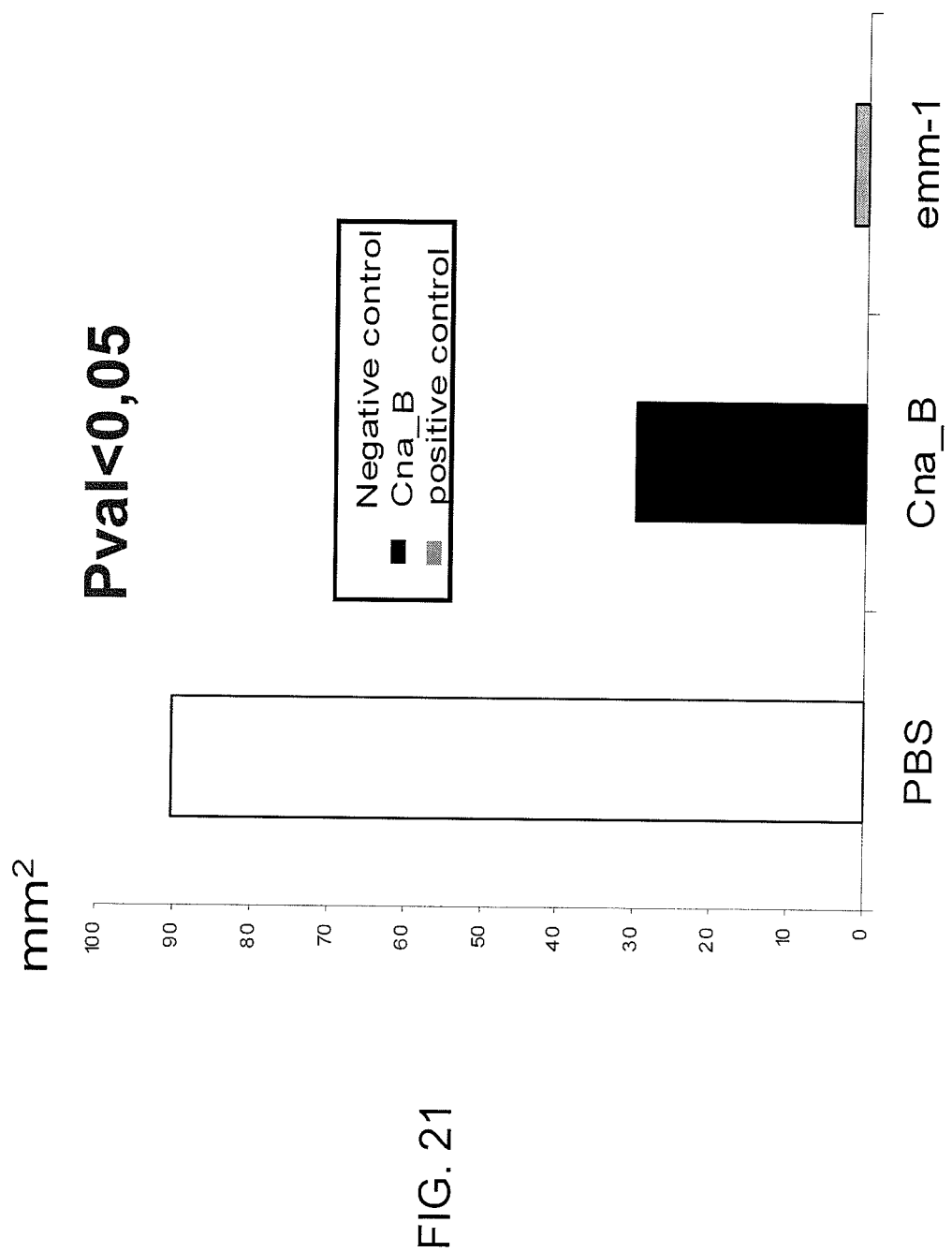
FIG. 21. Graph demonstrating that mice immunized with a Cna_B domain antigen show reduced skin lesion area in a GAS subcutaneous infection model. See Example 6.
Figure 25:
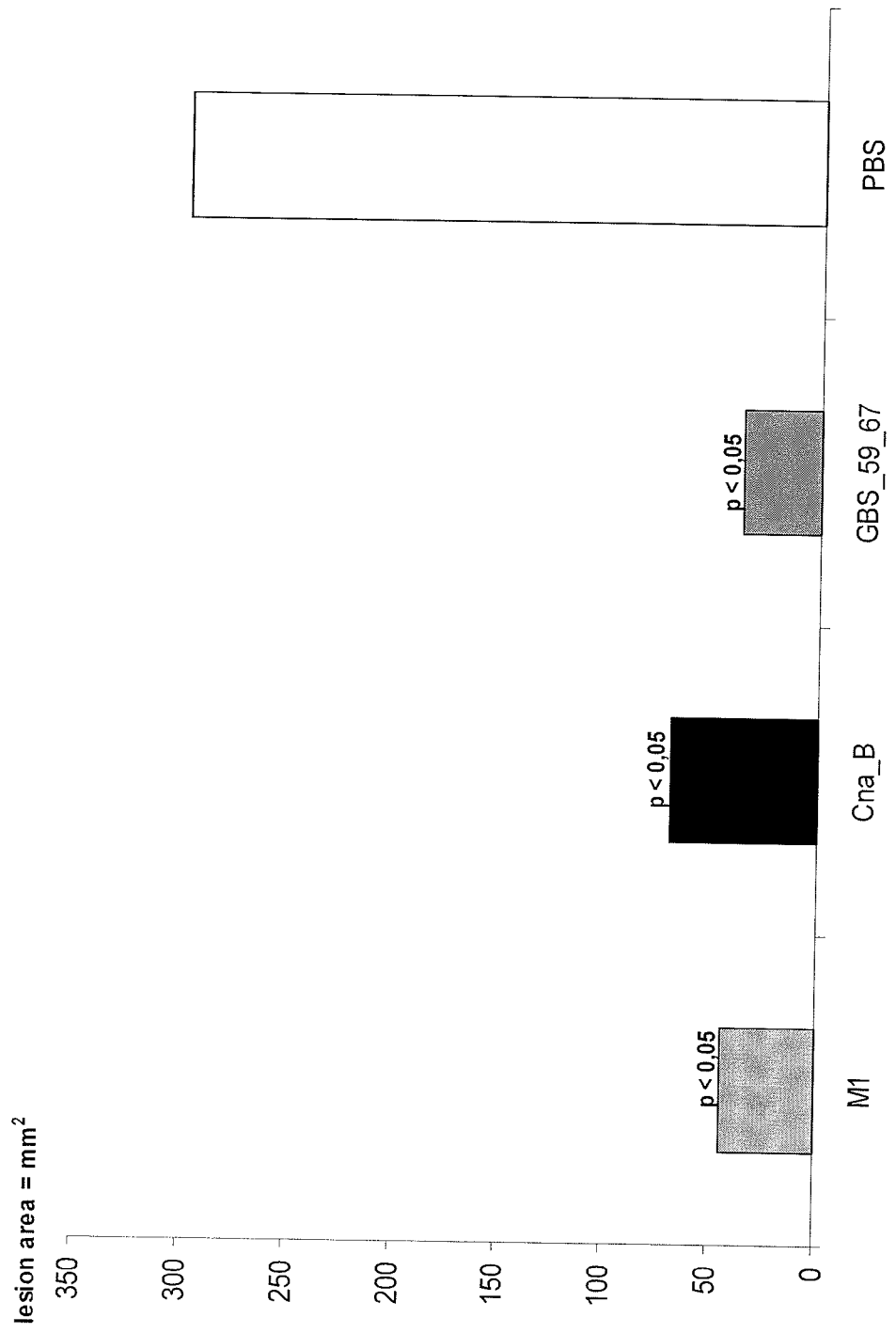
FIG. 25. Graph demonstrating that immunized with a chimeric Cna_B domain antigen show reduced skin lesion area in a GAS subcutaneous infection model. See Example 6.

Mice were immunized intraperitoneally with 20 μg of Cna_B-Fb_M18 domain three times on days 1, 21 and 35 and challenged two weeks after the third immunization by subcutaneous injection of $10^9$ cfu of S. pyogenes strain SF370_M1. Lesion areas were measured by evaluating the number of pixels in pictures of the lesions using the QUANTITY ONE® method (Bio-Rad). Phosphate buffered saline (PBS) was used as a negative control, and M1 protein ("emm-1") was used as a positive control. Results from immunizations with the GAS Cna_B domain antigen "Cna_B-Fb_M18" are shown in FIGS. 21 and 25. Results from immunizations with a GBS chimeric Cna_B domain antigen are shown in FIG. 25. The chimeric GBS Cna_B domain antigen was "GBS__59(515)-linker-GBS__67" (SEQ ID NO:129), which is described in Example 8.

EXAMPLE 7

Figure 22:
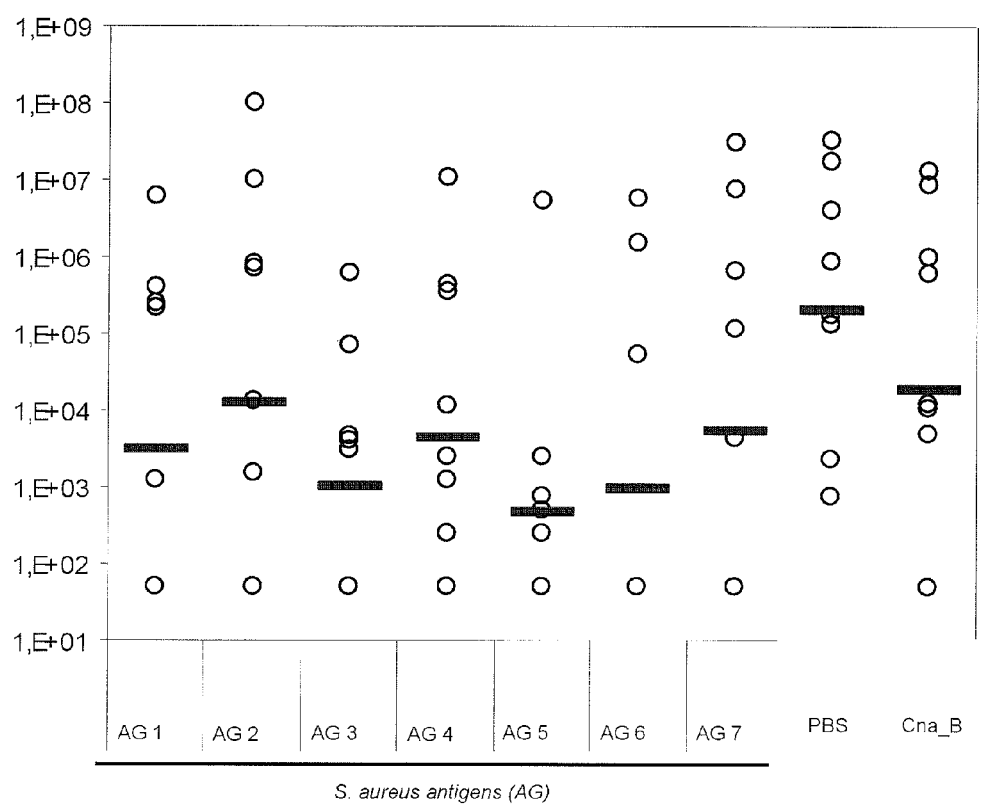
FIG. 22. Graph demonstrating that mice immunized with a Cna_B domain antigen show a reduced nasopharyngeal colonization rate when challenged with S. aureus. See Example 7.

In Vivo Protection from S. Aureus Challenge after Intraperitoneal Immunization This example demonstrates that intraperitoneal immunization with a Cna_B domain antigen protects against S. aureus colonization in a mouse renal abscess model Mice (10 mice for each experiment) were immunized with a Cna_B domain antigen (Cna_B-Fb_M18; 20 μg/mouse) or with various S. aureus antigens with the following schedule: at day 0 first immunization and at day 14 second immunization. Challenge was performed at day 24. Immunizations were done intraperitoneally. Immunized animals were challenged on day 24 by intravenous injection of a bacterial suspension of S. aureus Newman strain. Cultures of Newman strain were centrifuged, washed twice, and diluted in PBS before challenge. On day 28, mice were euthanized. Kidneys were removed and homogenized in 1% TRITON® X-100, aliquots diluted and plated on agar media for triplicate determination of CFU. PBS was used as a negative control. The results are shown in FIG. 22 ("Cna_B" is Cna_B-Fb_M18).

EXAMPLE 8

Cloning and Expression of Chimeric Cna_B Domain Antigens

The following chimeric Cna_B domain antigens were cloned and expressed in a pET15 expression vector using GBS59-Cna_B as first domain due to its high degree of solubility.

SEQ ID NO:127, shown below, is the amino acid sequence of a His-tagged Cna_B domain antigen ("GBS__59(515)-linker-GBS__80"; SEQ ID NO:140) containing the Cna_B domain of SAL 1486 ("GBS59") from GBS strain 515, a linker sequence, and the Cna_B domain of SAG 0645 ("GBS80") from GBS strain 2603V/R. The six histidine residues upstream from the chimeric sequence are bolded. The amino acid linker sequence is bolded. The underlined amino acids were added to encourage protein folding.

HHHHHHLAGATFLVKKDGKYLARKSGVATDAEKAAVDSTKSALDAAVKAYNDLTKEKQEG

QDGKSALATVSEKQKAYNDAFVKANYSYEWVEDKNAKNVVKLISNDKGQFEITGLTEGQY

SLEETQAPTGYAKLSGDVSFNVNATSYSKGSAQ<u>DIE</u>GSGGGGLGGAEFDLLASDGTAVKW

TDALIKANTNKNYIAGEAVTGQPIKLKSHTDGTFEIKGLAYAVDANAEGTAVTYKLKETK

APEGYVIPDKEIEFTVSQTSYNTKPTDIT<u>VDS</u>

SEQ ID NO:128, shown below, is the amino acid sequence of a His-tagged Cna_B domain antigen ("GBS__59(515)-linker-GBS__1523"; SEQ ID NO:141) containing the Cna_B domain of SAL 1486 ("GBS59") from GBS strain 515, a linker sequence, and the Cna_B domain of SAN 1518 ("GBS1523") from GBS strain COH1. The six histidine residues upstream from the chimeric sequence are bolded. The amino acid linker sequence is bolded. The underlined amino acids were added to encourage protein folding.

HHHHHHLAGATFLVKKDGKYLARKSGVATDAEKAAVDSTKSALDAAVKAYNDLTKEKQEG

QDGKSALATVSEKQKAYNDAFVKANYSYEWVEDKNAKNVVKLISNDKGQFEITGLTEGQY

SLEETQAPTGYAKLSGDVSFNVNATSYSKGSAQ<u>DIE</u>GSGGGGLQGAIFVLKNATGQFLNF

NDTNNVEWGTEANATEYTTGADGIITITGLKEGTYYLVEKKAPLGYNLLDNSQKVILGDG

ATDTTNSD

SEQ ID NO:129, shown below, is the amino acid sequence of a His-tagged Cna_B domain antigen ("GBS_59(515)-linker-GBS_67"; SEQ ID NO:142) containing the Cna_B domain of SAL 1486 ("GBS59") from GBS strain 515, a linker sequence, and the two Cna_B domains of SAL 1487 ("GBS67") from GBS strain 515 (the second domain is italicized). The six histidine residues upstream from the chimeric sequence are bolded. The amino acid linker sequence is bolded. The underlined amino acids were added to encourage protein folding.

HHHHHHLAGATFLVKKDGKYLARKSGVATDAEKAAVDSTKSALDAAVKAYNDLTKEKQEG

QDGKSALATVSEKQKAYNDAFVKANYSYEWVEDKNAKNVVKLISNDKGQFEITGLTEGQY

SLEETQAPTGYAKLSGDVSFNVNATSYSKGSAQDIEGSGGGGLSKATFVLKTTAHPESKI

EKVTAELTGEATFDNLIPGDYTLSEETAPEGYKKTNQTWQVKVESNGKTTIQNSGLKGAT

*FELQEFNEDYKLYLPIKNNNSKVVTGENGKISYKDLKDGKYQLIEAVSPEDYQKITNKPI*

*LTFEVVKGSIKNIIAVN*KQI

SEQ ID NO:130, shown below, is the amino acid sequence of a His-tagged Cna_B domain antigen ("GBS_59(515)-GBS_80-linker-GBS_1523-linker"; SEQ ID NO:143) containing the Cna_B domain of SAL 1486 ("GBS59") from GBS strain 515, the Cna_B domain of SAG 0645 from GBS strain 2603V/R, a linker sequence, the Cna_B domain of SAN 1518 from GBS strain COH1, and another linker sequence. The six histidine residues upstream from the chimeric sequence are bolded. The amino acid linker sequence is bolded. The underlined amino acids were added to encourage protein folding.

HHHHHHLAGATFLVKKDGKYLARKSGVATDAEKAAVDSTKSALDAAVKAYNDLTKEKQEG

QDGKSALATVSEKQKAYNDAFVKANYSYEWVEDKNAKNVVKLISNDKGQFEITGLTEGQY

SLEETQAPTGYAKLSGDVSFNVNATSYSKGSAQDIELGGAEFDLLASDGTAVKWTDALIK

ANTNKNYIAGEAVTGQPIKLKSHTDGTFEIKGLAYAVDANAEGTAVTYKLKETKAPEGYV

IPDKEIEFTVSQTSYNTKPTDITVDSGSGGGGLQGAIFVLKNATGQFLNFNDTNNVEWGT

EANATEYTTGADGIITITGLKEGTYYLVEKKAPLGYNLLDNSQKVILGDGATDTTNSDGS

GGGG

SEQ ID NO:131, shown below, is the amino acid sequence of a His-tagged Cna_B domain antigen ("SA Cna_B-SdrD"; SEQ ID NO:144) containing Cna_B domains of *S. aureus* SdrD protein and including "linker" amino acids (bolded) which occur naturally in the SdrD protein. The six histidine residues upstream from the chimeric sequence are bolded.

HHHHHHVGNVTVTVFDNNTNTKVGEAVTKEDGSYLIPNLPNGDYRVEFSNLPKGYEVTPS

KQGNNEELDSNGLSSVITVNGKDNLSADLGIYKPKYNLGDYVWEDTNKNGIQDQDEKGIS

GVTVTLKDENGNVLKTVTTDADGKYKFTDLDNGNYKVEFTTPEGYTPTTVTSGSDIEKDS

NGLTTTGVINGADNMTLDSGFYKTPKYNLGNYVWEDTNKDGKQDSTEKGISGVTVTLKNE

NGEVLQTTKTDKDGKYQFTGLENGTYKVEFETPSGYTPTQVGSGTDEGIDSNGTSTTGVI

KDKDNDTIDSGFYKPTYNLGDYVWEDTNKNGVQDKDEKGISGVTVTLKDENDKVLKTVTT

DENGKYQFTDLNNGTYKVEFETPSGYTPTSVTSGNDTEKDSNGLTTTGVIKDADNMTLDS

GFYKTPKYSLGDYVWYDSNKDGKQDSTEKGIKDVKVTLLNEKGEVIGTTKTDENGKYCFD

NLDSGKYKVIFEKPAGLTQTVTNTTEDDKDADGGEVDVTIT

EXAMPLE 9

Intraperitoneal Immunization with a Cna_B Domain Antigen Protects Against *S. Aureus* Colonization in a Mouse Renal Abscess Model This example demonstrates that intraperitoneal immunization with a Cna_B domain antigen protects against *S. aureus* colonization in a mouse renal abscess model.

Mice (10 mice for each experiment) were immunized with a Cna_B domain antigen (Cna_B-Fb_M18; 20 µg/mouse) with the following schedule: at day 0 first immunization and at day 14 second immunization. Challenge was performed at day 24. Immunizations were done intraperitoneally. Immunized animals were challenged on day 24 by intravenous injection of a bacterial suspension of *S. aureus* Newman strain. Cultures of Newman strain were centrifuged, washed twice, and diluted in PBS before challenge. On day 28, mice were euthanized. Kidneys were removed and homogenized in 1% TRITON® X-100, aliquots diluted and plated on agar media for triplicate determination of CFU. The *Staphylococcus* protein IsdB was used as a positive control, and alum was the negative control. Mice immunized with the Cna_B domain antigen showed reduced renal colonization rate after *S. aureus* challenge. The results are shown in FIG. 23.

EXAMPLE 10

Figure 26A:
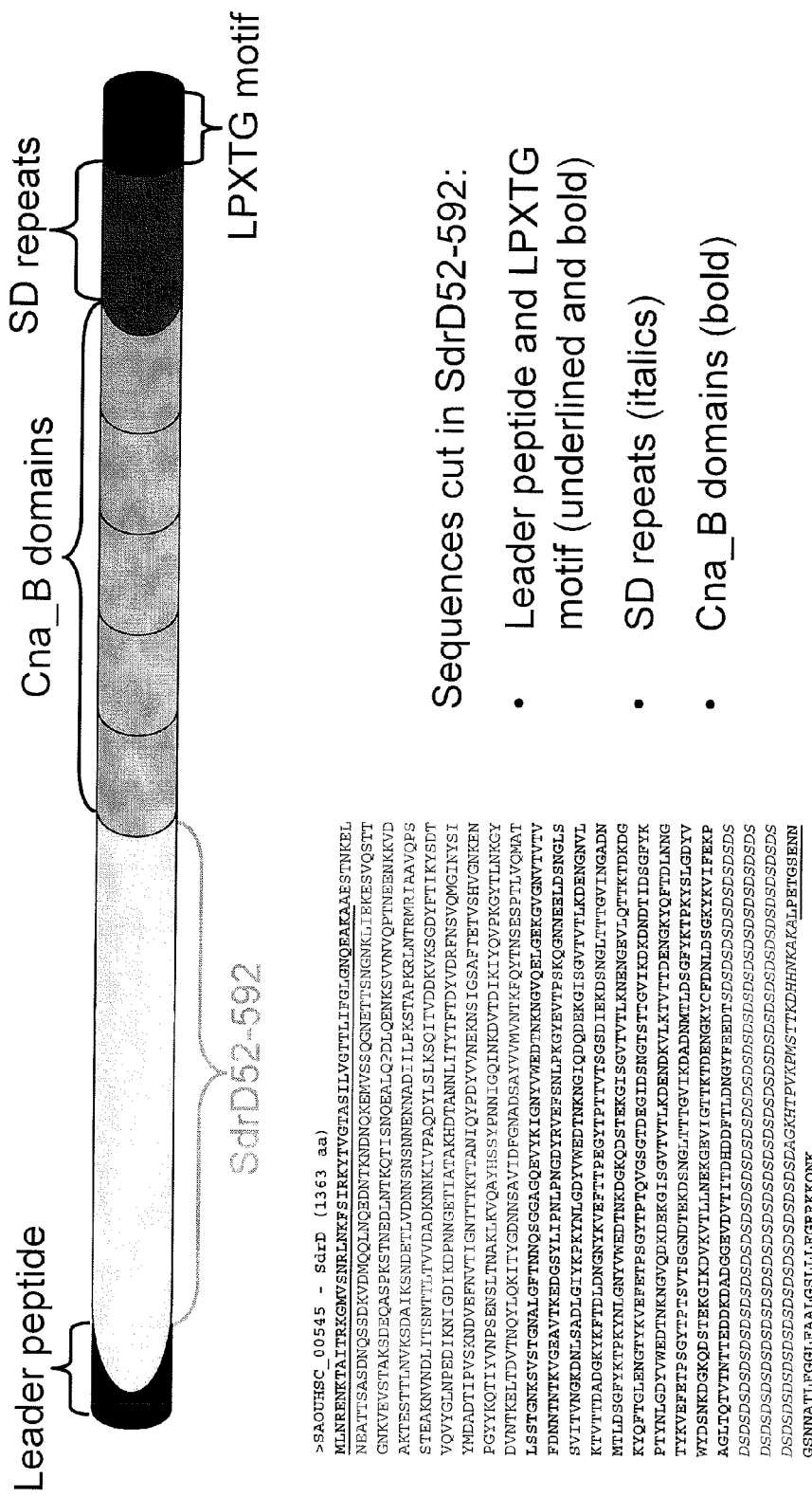
FIGS. 26A-B. Graphic representation and amino acid sequence (SEQ ID NO:132) of the SdrD protein of S. aureus subsp. aureus NCTC 8325 (FIG. 26A); graphic representation of the same Cna_B domain antigen and its amino acid sequence (SEQ ID NO:132), indicating the Cna_B domains (FIG. 26B).
Figure 26B:
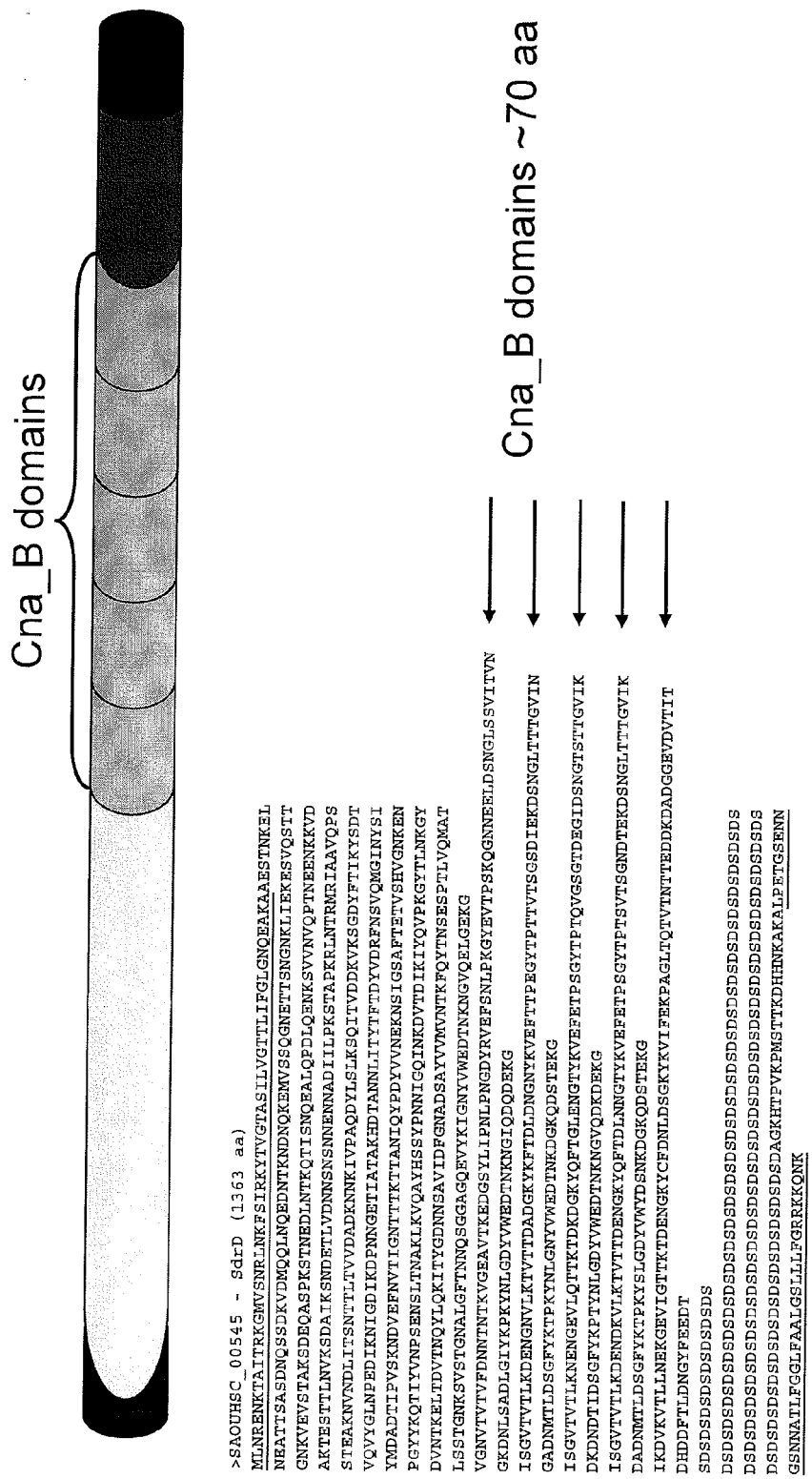

Cna_B_SdrD Confers Protection in a Sepsis Mouse Model Against *S. Aureus* Infection This example demonstrates that a Cna_B domain antigen (FIG. 27; SEQ ID NO:132) comprising Cna_B domains (SEQ ID NOS:134-138) of the *S. aureus* protein SdrD (FIGS. 26A, B) confers protection in a sepsis mouse model against *S. aureus* infection.

Groups of 14 mice each were immunized with the Cna_B_SdrD antigen (20 µg/mouse in alum) or a mutant form of *S. aureus* α-hemolysin (20 µg/mouse in alum) which cannot form pores (H1a$_{H35L}$; see, e.g., Wardenburg & Schneewind, "Vaccine protection against *Staphlococcus aureus* pneumonia," Exp Med. 2008 Feb. 18; 205(2): 287-294). Control mice were injected with alum.

Figure 28:
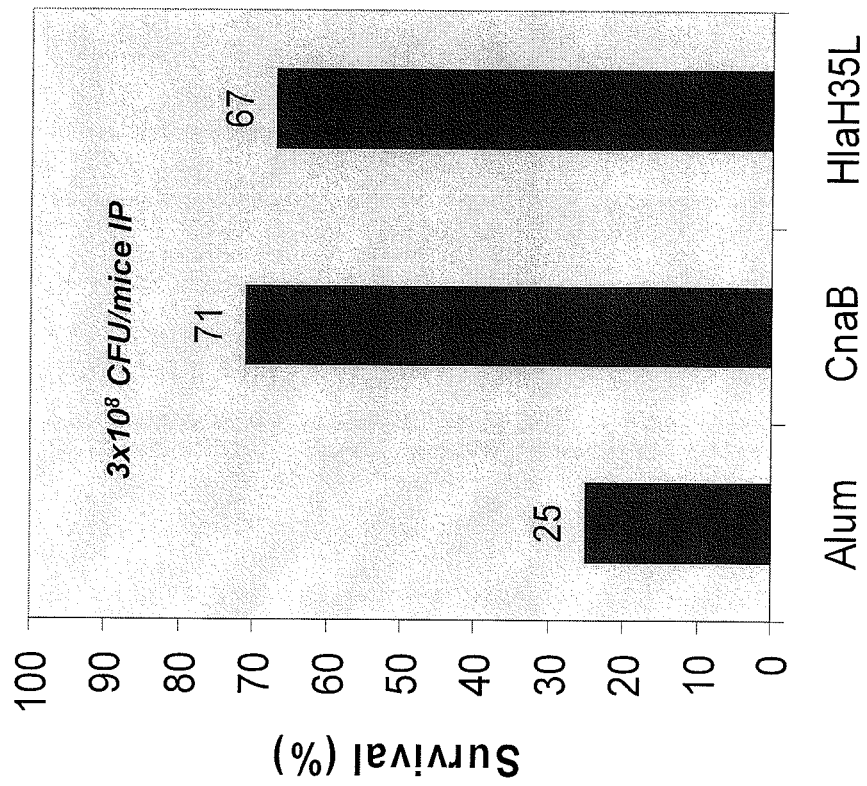
FIG. 28. Graph demonstrating that Cna_B_SdrD confers protection in a mouse model against infection with S. aureus strain USA300.

Mice were immunized with the following schedule: at day 0 first immunization and at day 14 second immunization. Challenge was performed at day 24. Immunizations were done intraperitoneally. Immunized animals were challenged on day 24 by intraperitoneal injection of a bacterial suspension of *S. aureus* strain USA300. Cultures of USA300 strain were centrifuged, washed twice and diluted in PBS before challenge. Mice were daily monitored for 14 days and euthanized at the appearance of humane endpoints, in agreement with Novartis Animal Welfare Policies. The percent survival two weeks after challenge with *S. aureus* strain USA300 is shown in FIG. 28. These results demonstrate that immunization with Cna_B_SdrD confers an high protection against *S. aureus* challenge suggesting this domain as a potential very good vaccine candidate.

TABLE 42

| Sequence identifiers | | |
|---|---|---|
| sequence of | SEQ ID NO: | FIG. |
| Cpa_M18 Cna_B and Fb | 1 | 1 |
| Cna_B_CPA_M5_MANFREDO (Spy_M5_0104) | 2 | 7 |
| Cna_B_CPA_M28 (M28_Spy0107) | 3 | 7 |
| Cna_B_CPA_M12 (MGAS2096_Spy0113) | 4 | 7 |
| Cna_B_CPA_M1 (M5005_Spy_0107) | 5 | 7 |
| Cna_B_CPA_M3 (SpyM3_0098) | 6 | 7 |
| Cna_B_CPA_M18 (Spy_M18_0126) | 7 | 7, 9, 10, 11, 12, 13, 16, 17 |
| Cna_B_CPA_M6 (M6_Spy0159) | 8 | 7 |
| Cna_B_CPA_M4_C (MGAS10750_Spy0115) | 9 | 7 |
| Cna_B_CPA_M28 (MGAS10270_Spy0113) | 10 | 7 |
| G box | 11 | 7 |
| G box | 12 | 7 |
| G box | 13 | 7 |
| G box | 14 | 7, 14, 15 |
| G box | 15 | 7 |
| G box | 16 | 7 |
| G box | 17 | 7 |
| Spy_M5_0104 | 18 | — |
| M28_Spy0107 | 19 | — |
| MGAS2096_Spy0113 | 20 | — |
| M5005_Spy_0107 | 21 | — |
| SpyM3_0098 | 22 | — |
| Spy_M18_0126 | 23 | — |
| M6_Spy0159 | 24 | — |
| MGAS10750_Spy0115 | 25 | — |
| MGAS10270_Spy0113 | 26 | — |
| Cna_B_GBS_52 (SAG_0646) | 27 | 8, 9 |
| Cna_B_GBS_150 (SAL 1482) | 28 | 8, 10 |
| Cna_B_GBS_104_1 (SAG 0649) | 29 | 8, 9 |
| Cna_B_GBS_67 (SAL 1487) | 30 | 8, 10 |
| Cna_B_GBS_1523 (SAN 1518) | 31 | 8, 11 |
| Cna_B_GBS_1524 (SAN 1519) | 32 | 8, 11 |
| Cna_B_GBS_80 (SAG 0645) | 33 | 8, 9 |
| Cna_B_GBS_104_2 (SAG 0649) | 34 | 8, 9 |
| Cna_B_GBS_1521 (SAN 1516) | 35 | 8 |
| G box | 36 | 8 |
| G box | 37 | 8 |
| G box | 38 | 8 |
| G box | 39 | 8 |
| G box | 40 | 8 |
| G box | 41 | 8 |
| G box | 42 | 8 |
| G box | 43 | 8 |
| G box | 44 | 8 |
| SAG_0646 | 45 | — |
| SAL 1482 | 46 | — |
| SAG 0649 | 47 | — |
| SAL 1487 | 48 | — |
| SAN 1518 | 49 | — |
| SAN 1519 | 50 | — |
| SAG 0645 | 51 | — |
| SAN 1516 | 52 | — |
| Cna_B domain RRGB (SP_0463) | 53 | 12 |
| Cna_B domain RRGA1 (SP_0462) | 54 | 12 |
| Cna_B domain RRGC2 (SP_0464) | 55 | 12 |
| Cna_B domain RRGA2 (SP_0462) | 56 | 12 |
| Cna_B domain RRGC1 (SP_0464) | 57 | 12 |
| G box | 58 | 12 |
| G box | 59 | 12 |
| G box | 60 | 12 |
| G box | 61 | 12 |
| G box | 62 | 12 |
| SP_0463 | 63 | — |
| SP_0462 | 64 | — |
| SP_0464 | 65 | — |
| Cna_B domain Ser-Asp rich2 (SdrD MW0517) | 66 | 13 |
| Cna_B domain Ser-Asp rich3 (SdrD MW0517) | 67 | 13 |
| Cna_B domain CBP (MW2612) | 68 | 13 |
| G box | 69 | 13 |
| G box | 70 | 13 |
| G box | 71 | 13 |

TABLE 42-continued

Sequence identifiers

| sequence of | SEQ ID NO: | FIG. |
|---|---|---|
| SdrD MW0517 | 72 | — |
| MW2612 | 73 | — |
| G box consensus sequence | 74 | — |
| Cna_B_Bkb3 (DUF 11) 89/1591 | 75 | 14 |
| Cna_B_Bkb1 SSU05_0474 05ZYH33 | 76 | 14 |
| BKB SEQ0936 | 77 | 15 |
| G box | 78 | 15 |
| linker | 79 | — |
| Cna_B_autotransporter (SSU05_0474[*Streptococcus suis* 05ZYH33] | 80 | 16 |
| Cna_B (Protein of unknown function DUF11: Surface protein from Gram-positive cocci, anchor region [*Streptococcus suis* 89/1591] | 81 | 16 |
| SSU05_0474[*Streptococcus suis* 05ZYH33 | 82 | — |
| Protein of unknown function DUF11: Surface protein from Gram-positive cocci, anchor region [*Streptococcus suis* 89/1591] | 83 | — |
| Cna_B_ap1 (SEQ0935*) | 84 | 17 |
| Cna_B_ap2 (SEQ0935*) | 85 | 17 |
| Cna_B_bkb (SEQ0936**) | 86 | 17 |
| * SEQ0935 ancillary protein SEQ0935 undefined product 914186:916159 forward MW: 73872 67 | 87 | — |
| ** SEQ0936 BKB SEQ0936 undefined product 916183:917625 forward MW: 51902 46.3 | 88 | — |
| *S. suis* strain 05ZYH33 | 89 | — |
| *S. suis* strain 05ZYH33 | 90 | — |
| *S. suis* strain 05ZYH33 | 91 | — |
| *S. suis* strain 05ZYH33 | 92 | — |
| *S. suis* strain 98HAH33 | 93 | — |
| *S. suis* strain 98HAH33 | 94 | — |
| *S. suis* strain 98HAH33 | 95 | — |
| *Streptococcus suis* 89/1591 | 96 | — |
| *S. suis* strain 05ZYH33 | 97 | — |
| *S. equi* FszE: Sez_1828 | 98 | — |
| *S. equi* FszD: Sez_1822 | 99 | — |
| *S. equi* FszC: Sez_1821 | 100 | — |
| *S. equi* FbpZ: Sez_1825 | 101 | — |
| GBS59 (SAL 1486) | 102 | — |
| SAL 1486 Cna_B | 103 | 13 |
| SAL 1486 G Box | 104 | 13 |
| Cpa_M6 *S. pyogenes* vWFA (M6_Spy0159) | 105 | — |
| SAL_1487 cell wall surface anchor family protein vWFA | 106 | — |
| Ancillary pilus subunit *S. pneumoniae* vWFA RrgA (SP_0462) | 107 | — |
| multi-Cna_B domain antigen | 108 | — |
| multi-Cna_B domain antigen | 109 | — |
| Cna_B domain of SAL_1487 | 110 | — |
| Cna_B domain of SAL_1487 | 111 | — |
| Cna_B domain of SAG 0645 | 112 | — |
| Cna_B domain of SAL_1518 | 113 | — |
| Cna_B domain of SAL_1486 | 114 | — |
| Cna_B domain of SAL_1486 | 115 | — |
| Cna_B domain of SAG_1407 | 116 | — |
| Cna_B domain of SAG_1407 | 117 | — |
| SAG_1407 | 118 | — |
| nucleotide sequence encoding GAS protein F2 Spy0119 | 119 | — |
| Cna_B_M6 Spy_0159 | 120 | — |
| GAS protein F2 Spy0119 | 121 | — |
| Cna_B domain 1 of NO: 121 | 122 | — |
| Cna_B domain 2 of NO: 121 | 123 | — |
| Cna_B domain 3 of NO: 121 | 124 | — |
| Cna_B domain 4 of NO: 121 | 125 | — |
| Cna_B domain 5 of NO: 121 | 126 | — |
| His-tagged GBS_59(515)-linker-GBS_80 | 127 | — |
| His-tagged GBS_59(515)-linker-GBS_1523 | 128 | — |
| His-tagged GBS_59(515)-linker_GBS_67 | 129 | — |
| His-tagged GBS_59(515)-GBS_80-linker-GBS_1523-linker | 130 | — |
| His-tagged SA Cna_B-SdrD | 131 | — |
| SA SdrD protein | 132 | 27 |
| Cna_B_SdrD antigen (Example 10) | 133 | 28 |
| Cna_B domain of SdrD | 134 | 27B |
| Cna_B domain of SdrD | 135 | 27B |
| Cna_B domain of SdrD | 136 | 27B |
| Cna_B domain of SdrD | 137 | 27B |
| Cna_B domain of SdrD | 138 | 27B |
| Cna_B_SdrD antigen (Example 10) | 139 | 28 |
| GBS_59(515)-linker-GBS_80 | 140 | — |
| GBS_59(515)-linker-GBS_1523 | 141 | — |
| GBS_59(515)-linker_GBS_67 | 142 | — |
| GBS_59(515)-GBS_80-linker-GBS_1523-linker | 143 | — |
| SA Cna_B-SdrD | 144 | — |
| Cna_B_M6 | 145 | — |

The invention claimed is:

1. An expression vector comprising a nucleic acid molecule which encodes:

(1) a Cna_B domain antigen selected from the group consisting of:

(a) a Cna_B domain antigen comprising the amino acid sequence SEQ ID NO:5, wherein amino acid 1 of SEQ ID NO:5 is not linked by a peptide bond to amino acid 311 of SEQ ID NO:21 and/or amino acid 70 of SEQ ID NO:5 is not linked by a peptide bond to amino acid 382 of SEQ ID NO:21;

(b) a Cna_B domain antigen which consists of the amino acid sequence SEQ ID NO:5 and 307, 308, 309, or 310 additional contiguous amino acids of SEQ ID NO:21 at the N terminus of SEQ ID NO:5;

(c) a Cna_B domain antigen which consists of the amino acid sequence SEQ ID NO:5 and 307, 308, 309, or 310 additional contiguous amino acids of SEQ ID NO:21 at the N terminus of SEQ ID NO:5 and 0-380 additional contiguous amino acids of SEQ ID NO:21 at the C terminus of SEQ ID NO:5; and (d) a Cna_B domain antigen which consists of the amino acid sequence SEQ ID NO:5, and wherein the Cna_B domain antigen is not a native gram positive bacterial protein; or (2) a fusion polypeptide comprising the Cna_B domain antigen of (a), (b), (c), or (d) and another bacterial antigen.

2. A host cell comprising the expression vector of claim 1.

3. A method of producing a polypeptide, comprising:
culturing a host cell comprising the expression vector of claim 1 under conditions under which the expression vector expresses the polypeptide; and
recovering the polypeptide.

* * * * *

SEQUENCE LISTING

```
<160> NUMBER OF SEQ ID NOS: 145

<210> SEQ ID NO 1
<211> LENGTH: 170
<212> TYPE: PRT
<213> ORGANISM: S. pyogenes

<400> SEQUENCE: 1

Leu Glu Gly Ala Thr Leu Lys Leu Ala Gln Ile Glu Gly Ser Gly Phe
 1               5                  10                  15

Gln Glu Gln Ser Phe Glu Ser Ser Thr Ser Gly Gln Lys Leu Gln Leu
                20                  25                  30

Ser Asp Gly Thr Tyr Ile Leu Thr Glu Thr Lys Ser Pro Gln Gly Tyr
            35                  40                  45

Glu Ile Ala Glu Pro Ile Thr Phe Lys Val Thr Ala Gly Lys Val Phe
```

```
                 50                  55                  60

Ile Lys Gly Lys Asp Gly Gln Phe Val Glu Asn Gln Asn Lys Glu Val
 65                  70                  75                  80

Ala Glu Pro Tyr Ser Val Thr Ala Tyr Asn Asp Phe Asp Asp Ser Gly
                 85                  90                  95

Phe Ile Asn Pro Lys Thr Phe Thr Pro Tyr Gly Lys Phe Tyr Tyr Ala
                100                 105                 110

Lys Asn Ala Asn Gly Thr Ser Gln Val Val Tyr Cys Phe Asn Val Asp
                115                 120                 125

Leu His Ser Pro Pro Asp Ser Leu Asp Lys Gly Glu Thr Ile Asp Pro
                130                 135                 140

Asp Phe Asn Glu Gly Lys Glu Ile Lys Tyr Thr His Ile Leu Gly Ala
145                 150                 155                 160

Asp Leu Phe Ser Tyr Ala Asn Asn Pro Arg
                165                 170

<210> SEQ ID NO 2
<211> LENGTH: 61
<212> TYPE: PRT
<213> ORGANISM: S. pyogenes

<400> SEQUENCE: 2

Leu Glu Gly Ala Thr Leu Arg Leu Thr Gly Glu Asp Ile Pro Asp Phe
  1               5                  10                  15

Gln Glu Lys Val Phe Gln Ser Asn Gly Thr Gly Glu Lys Ile Glu Leu
                 20                  25                  30

Ser Asn Gly Thr Tyr Thr Leu Thr Glu Thr Ser Ser Pro Asp Gly Tyr
                 35                  40                  45

Lys Ile Thr Glu Pro Ile Lys Phe Arg Val Val Asn Lys
             50                  55                  60

<210> SEQ ID NO 3
<211> LENGTH: 61
<212> TYPE: PRT
<213> ORGANISM: S. pyogenes

<400> SEQUENCE: 3

Leu Glu Gly Ala Thr Leu Arg Leu Thr Gly Glu Asp Ile Pro Asp Phe
  1               5                  10                  15

Gln Glu Lys Val Phe Gln Ser Asn Gly Thr Gly Glu Lys Ile Glu Leu
                 20                  25                  30

Ser Asn Gly Thr Tyr Thr Leu Thr Glu Thr Ser Ser Pro Asp Gly Tyr
                 35                  40                  45

Lys Ile Ala Glu Pro Ile Lys Phe Arg Val Val Asn Lys
             50                  55                  60

<210> SEQ ID NO 4
<211> LENGTH: 61
<212> TYPE: PRT
<213> ORGANISM: S. pyogenes

<400> SEQUENCE: 4

Leu Glu Gly Ala Thr Leu Arg Leu Thr Gly Glu Asp Ile Leu Asp Phe
  1               5                  10                  15

Gln Glu Lys Val Phe Gln Ser Asn Gly Thr Gly Glu Lys Ile Glu Leu
                 20                  25                  30

Ser Asn Gly Thr Tyr Thr Leu Thr Glu Thr Ser Ser Pro Asp Gly Tyr
                 35                  40                  45
```

```
Lys Ile Ala Glu Pro Ile Lys Phe Arg Val Val Asn Lys
 50                  55                  60

<210> SEQ ID NO 5
<211> LENGTH: 70
<212> TYPE: PRT
<213> ORGANISM: S. pyogenes

<400> SEQUENCE: 5

Leu Glu Gly Ala Thr Leu Gln Leu Thr Gly Asp Asn Val Asn Ser Phe
  1               5                  10                  15

Gln Ala Arg Val Phe Ser Ser Asn Asp Ile Gly Glu Arg Ile Glu Leu
                 20                  25                  30

Ser Asp Gly Thr Tyr Thr Leu Thr Glu Leu Asn Ser Pro Ala Gly Tyr
             35                  40                  45

Ser Ile Ala Glu Pro Ile Thr Phe Lys Val Glu Ala Gly Lys Val Tyr
 50                  55                  60

Thr Ile Ile Asp Gly Lys
 65                  70

<210> SEQ ID NO 6
<211> LENGTH: 61
<212> TYPE: PRT
<213> ORGANISM: S. pyogenes

<400> SEQUENCE: 6

Leu Glu Gly Ala Thr Leu Lys Leu Ala Gln Ile Glu Gly Ser Gly Phe
  1               5                  10                  15

Gln Glu Lys Ile Phe Asp Ser Asn Lys Ser Gly Glu Lys Val Glu Leu
                 20                  25                  30

Pro Asn Gly Thr Tyr Val Leu Ser Glu Leu Lys Pro Pro Gln Gly Tyr
             35                  40                  45

Gly Val Ala Thr Pro Ile Thr Phe Lys Val Ala Ala Glu
 50                  55                  60

<210> SEQ ID NO 7
<211> LENGTH: 60
<212> TYPE: PRT
<213> ORGANISM: S. pyogenes

<400> SEQUENCE: 7

Leu Glu Gly Ala Thr Leu Lys Leu Ala Gln Ile Glu Gly Ser Gly Phe
  1               5                  10                  15

Gln Glu Gln Ser Phe Glu Ser Ser Thr Ser Gly Gln Lys Leu Gln Leu
                 20                  25                  30

Ser Asp Gly Thr Tyr Ile Leu Thr Glu Thr Lys Ser Pro Gln Gly Tyr
             35                  40                  45

Glu Ile Ala Glu Pro Ile Thr Phe Lys Val Thr Ala
 50                  55                  60

<210> SEQ ID NO 8
<211> LENGTH: 70
<212> TYPE: PRT
<213> ORGANISM: S. pyogenes

<400> SEQUENCE: 8

Leu Ala Gly Val Glu Phe Glu Leu Arg Lys Glu Asp Lys Lys Ile Val
  1               5                  10                  15

Trp Glu Lys Gly Thr Thr Gly Ser Asn Gly Gln Leu Asn Phe Lys Tyr
```

```
                20                  25                  30
Leu Gln Lys Gly Lys Thr Tyr Tyr Leu Tyr Glu Thr Lys Ala Lys Leu
         35                  40                  45
Gly Tyr Thr Leu Pro Glu Asn Pro Trp Glu Val Ala Val Ala Asn Asn
     50                  55                  60
Gly Asp Ile Lys Val Lys
 65                  70
```

<210> SEQ ID NO 9
<211> LENGTH: 65
<212> TYPE: PRT
<213> ORGANISM: S. pyogenes

<400> SEQUENCE: 9

```
Leu Ala Gly Ala Lys Phe Gln Leu Glu Ser Asn Lys Gly Val Val Leu
  1               5                  10                  15
Thr Gly Glu Thr Asp Gly Lys Gly Glu Tyr Thr Phe Thr Asn Leu Pro
                 20                  25                  30
Phe Gly Asp Tyr Ile Leu Thr Glu Ile Ala Ala Pro Lys Gly Tyr Ile
             35                  40                  45
Leu Asp Lys Thr Pro Arg Ser Ile Ala Ile Gly Asp Thr Val Asp Lys
     50                  55                  60
Glu
 65
```

<210> SEQ ID NO 10
<211> LENGTH: 84
<212> TYPE: PRT
<213> ORGANISM: S. pyogenes

<400> SEQUENCE: 10

```
Leu Gly Lys Val Ile Val Lys Lys Thr Gly Glu Asn Ala Met Pro Leu
  1               5                  10                  15
Gly Lys Ala Thr Phe Val Leu Lys Asn Asp His Asp Lys Ser Glu Ile
                 20                  25                  30
Ser His Glu Thr Val Glu Gly Ser Gly Glu Ala Ala Phe Glu Asn Ile
             35                  40                  45
Lys Pro Gly Asn Tyr Thr Leu Thr Glu Lys Thr Ala Pro Ile Gly Tyr
     50                  55                  60
Lys Lys Thr Asp Lys Thr Trp Lys Val Lys Val Ala Asp Asn Gly Ala
 65                  70                  75                  80
Thr Thr Ile Glu
```

<210> SEQ ID NO 11
<211> LENGTH: 14
<212> TYPE: PRT
<213> ORGANISM: S. pyogenes

<400> SEQUENCE: 11

```
Gly Thr Tyr Thr Leu Thr Glu Thr Ser Ser Pro Asp Gly Tyr
  1               5                  10
```

<210> SEQ ID NO 12
<211> LENGTH: 14
<212> TYPE: PRT
<213> ORGANISM: S. pyogenes

<400> SEQUENCE: 12

```
Gly Thr Tyr Thr Leu Thr Glu Leu Asn Ser Pro Ala Gly Tyr
```

```
<210> SEQ ID NO 13
<211> LENGTH: 14
<212> TYPE: PRT
<213> ORGANISM: S. pyogenes

<400> SEQUENCE: 13

Gly Thr Tyr Val Leu Ser Glu Leu Lys Pro Pro Gln Gly Tyr
1               5                   10

<210> SEQ ID NO 14
<211> LENGTH: 14
<212> TYPE: PRT
<213> ORGANISM: S. pyogenes

<400> SEQUENCE: 14

Gly Thr Tyr Ile Leu Thr Glu Thr Lys Ser Pro Gln Gly Tyr
1               5                   10

<210> SEQ ID NO 15
<211> LENGTH: 15
<212> TYPE: PRT
<213> ORGANISM: S. pyogenes

<400> SEQUENCE: 15

Gly Lys Thr Tyr Tyr Leu Tyr Glu Thr Lys Ala Lys Leu Gly Tyr
1               5                   10                  15

<210> SEQ ID NO 16
<211> LENGTH: 14
<212> TYPE: PRT
<213> ORGANISM: S. pyogenes

<400> SEQUENCE: 16

Gly Asp Tyr Ile Leu Thr Glu Ile Ala Ala Pro Lys Gly Tyr
1               5                   10

<210> SEQ ID NO 17
<211> LENGTH: 14
<212> TYPE: PRT
<213> ORGANISM: S. pyogenes

<400> SEQUENCE: 17

Gly Asn Tyr Thr Leu Thr Glu Lys Thr Ala Pro Ile Gly Tyr
1               5                   10

<210> SEQ ID NO 18
<211> LENGTH: 523
<212> TYPE: PRT
<213> ORGANISM: S. pyogenes

<400> SEQUENCE: 18

Met Gln Lys Arg Asp Lys Thr Asn Tyr Gly Ser Ala Asn Asn Lys Arg
1               5                   10                  15

Arg Gln Thr Thr Ile Gly Leu Leu Lys Val Phe Leu Thr Phe Val Ala
                20                  25                  30

Leu Ile Gly Ile Val Gly Phe Ser Ile Arg Ala Phe Gly Ala Glu Glu
            35                  40                  45

Lys Ser Thr Glu Thr Lys Lys Thr Ser Val Ile Ile Arg Lys Tyr Ala
        50                  55                  60

Glu Gly Asp Tyr Ser Lys Leu Leu Glu Gly Ala Thr Leu Arg Leu Thr
65                  70                  75                  80
```

```
Gly Glu Asp Ile Pro Asp Phe Gln Glu Lys Val Phe Gln Ser Asn Gly
                85                  90                  95

Thr Gly Glu Lys Ile Glu Leu Ser Asn Gly Thr Tyr Thr Leu Thr Glu
                100                 105                 110

Thr Ser Ser Pro Asp Gly Tyr Lys Ile Thr Glu Pro Ile Lys Phe Arg
        115                 120                 125

Val Val Asn Lys Lys Val Phe Ile Val Gln Lys Asp Gly Ser Gln Val
    130                 135                 140

Glu Asn Pro Asn Lys Glu Leu Gly Ser Pro Tyr Thr Ile Glu Ala Tyr
145                 150                 155                 160

Asn Asp Phe Asp Glu Phe Gly Leu Leu Ser Thr Gln Asn Tyr Ala Lys
                165                 170                 175

Phe Tyr Tyr Gly Lys Asn Tyr Asp Gly Ser Ser Gln Ile Val Tyr Cys
            180                 185                 190

Phe Asn Ala Asn Leu Lys Ser Pro Pro Asp Ser Glu Asp His Gly Ala
        195                 200                 205

Thr Ile Asn Pro Asp Phe Thr Thr Gly Asp Ile Arg Tyr Ser His Ile
    210                 215                 220

Ala Gly Ser Asp Leu Ile Lys Tyr Ala Asn Thr Ala Arg Asp Glu Asp
225                 230                 235                 240

Pro Gln Leu Phe Leu Lys His Val Lys Lys Val Ile Glu Asn Gly Tyr
                245                 250                 255

His Lys Lys Gly Gln Ala Ile Pro Tyr Asn Gly Leu Thr Glu Ala Gln
            260                 265                 270

Phe Arg Ala Ala Thr Gln Leu Ala Ile Tyr Tyr Phe Thr Asp Ser Val
        275                 280                 285

Asp Leu Thr Lys Asp Arg Leu Lys Asp Phe His Gly Phe Gly Asp Met
    290                 295                 300

Asn Asp Gln Thr Leu Gly Val Ala Lys Lys Ile Val Glu Tyr Ala Leu
305                 310                 315                 320

Ser Asp Glu Asp Ser Lys Leu Thr Asn Leu Asp Phe Phe Val Pro Asn
                325                 330                 335

Asn Ser Lys Tyr Gln Ser Leu Ile Gly Thr Glu Tyr His Pro Asp Asp
            340                 345                 350

Leu Val Asp Val Ile Arg Met Glu Asp Lys Lys Gln Glu Val Ile Pro
        355                 360                 365

Val Thr His Ser Leu Thr Val Gln Lys Thr Val Val Gly Glu Leu Gly
    370                 375                 380

Asp Lys Thr Lys Gly Phe Gln Phe Glu Leu Glu Leu Lys Asp Lys Thr
385                 390                 395                 400

Gly Gln Pro Ile Val Asn Thr Leu Lys Thr Asn Asn Gln Asp Leu Val
                405                 410                 415

Ala Lys Asp Gly Lys Tyr Ser Phe Asn Leu Lys His Gly Asp Thr Ile
            420                 425                 430

Arg Ile Glu Gly Leu Pro Thr Gly Tyr Ser Tyr Thr Leu Lys Glu Thr
        435                 440                 445

Glu Ala Lys Asp Tyr Ile Val Thr Val Asp Asn Lys Val Ser Gln Glu
    450                 455                 460

Ala Gln Ser Ala Ser Glu Asn Val Thr Ala Asp Lys Glu Val Thr Phe
465                 470                 475                 480

Glu Asn Arg Lys Asp Leu Val Pro Pro Thr Gly Leu Thr Thr Asp Gly
                485                 490                 495
```

Ala Ile Tyr Leu Trp Leu Leu Leu Val Pro Phe Gly Leu Val
            500                 505                 510

Trp Leu Phe Gly Arg Lys Gly Leu Lys Asn Asp
        515                 520

<210> SEQ ID NO 19
<211> LENGTH: 747
<212> TYPE: PRT
<213> ORGANISM: S. pyogenes

<400> SEQUENCE: 19

Met Asn Asn Lys Lys Leu Gln Lys Gln Asp Ala Pro Arg Val Ser
 1               5                  10                  15

Asn Arg Lys Pro Lys Gln Leu Thr Val Thr Leu Val Gly Val Phe Leu
                20                  25                  30

Met Leu Leu Val Leu Ile Gly Phe Glu Gly Lys Val Arg Ala Ala His
            35                  40                  45

Glu Leu Val Glu Val Pro Val Pro Ile Phe His Asn Pro Asp Pro Gln
    50                  55                  60

Ser Asp Tyr Gln Trp Tyr Gly Tyr Glu Ala Tyr Thr Gly Gly Tyr Pro
65                  70                  75                  80

Lys Tyr Asp Leu Phe Lys Thr Tyr Tyr His Asp Leu Arg Val Asn Leu
                85                  90                  95

His Gly Ser Lys Ser Tyr Gln Val Tyr Cys Phe Asn Val His Lys His
            100                 105                 110

Tyr Pro Arg Ser Ser Gln Ser Phe Asp Arg Lys Trp Tyr Lys Lys Leu
        115                 120                 125

Asp Gly Thr Ala Glu Asn Phe Asp Ser Leu Ala Met Glu Pro Arg Val
    130                 135                 140

Arg Lys Glu Glu Leu Thr Lys Lys Leu Arg Ala Val Met Tyr Asn Ala
145                 150                 155                 160

Tyr Pro Asn Asp Ala Asn Gly Ile Met Lys Asp Leu Glu Pro Leu Asn
                165                 170                 175

Ala Ile Lys Val Thr Gln Glu Ala Val Trp Tyr Tyr Ser Asp Ser Ala
            180                 185                 190

Gln Ile Asn Pro Asp Glu Ser Phe Lys Thr Glu Ala Gln Ser Asn Gly
        195                 200                 205

Ile Asn Asp Gln Gln Leu Gly Leu Met Arg Lys Ala Leu Lys Glu Leu
    210                 215                 220

Ile Asp Pro Asn Leu Gly Ser Lys Tyr Ser Asn Lys Thr Pro Ser Gly
225                 230                 235                 240

Tyr Arg Leu Asn Val Phe Glu Ser His Asp Lys Thr Phe Gln Asn Leu
                245                 250                 255

Leu Ser Ala Glu Tyr Val Pro Asp Thr Pro Lys Pro Gly Glu Glu
            260                 265                 270

Pro Pro Ala Lys Thr Glu Lys Thr Ser Val Ile Ile Arg Lys Tyr Ala
        275                 280                 285

Glu Gly Asp Tyr Ser Lys Leu Leu Glu Gly Ala Thr Leu Arg Leu Thr
    290                 295                 300

Gly Glu Asp Ile Pro Asp Phe Gln Glu Lys Val Phe Gln Ser Asn Gly
305                 310                 315                 320

Thr Gly Glu Lys Ile Glu Leu Ser Asn Gly Thr Tyr Thr Leu Thr Glu
                325                 330                 335

Thr Ser Ser Pro Asp Gly Tyr Lys Ile Ala Glu Pro Ile Lys Phe Arg
            340                 345                 350

Val Val Asn Lys Lys Val Phe Ile Val Gln Lys Asp Gly Ser Gln Val
            355                 360                 365

Glu Asn Pro Asn Lys Glu Val Gly Ser Pro Tyr Thr Ile Glu Ala Tyr
    370                 375                 380

Asn Asp Phe Asp Glu Phe Gly Leu Leu Ser Thr Gln Asn Tyr Ala Lys
385                 390                 395                 400

Phe Tyr Tyr Gly Lys Asn Tyr Asp Gly Ser Ser Gln Ile Val Tyr Cys
                405                 410                 415

Phe Asn Ala Asn Leu Lys Ser Pro Pro Asp Ser Glu Asp His Gly Ala
            420                 425                 430

Thr Ile Asn Pro Asp Phe Thr Thr Gly Asp Ile Arg Tyr Ser His Ile
            435                 440                 445

Ala Gly Ser Asp Leu Ile Lys Tyr Ala Asn Thr Ala Arg Asp Glu Asp
            450                 455                 460

Pro Gln Leu Phe Leu Lys His Val Lys Val Ile Glu Asn Gly Tyr
465                 470                 475                 480

His Lys Lys Gly Gln Ala Ile Pro Tyr Asn Gly Leu Thr Glu Ala Gln
                485                 490                 495

Phe Arg Ala Ala Thr Gln Leu Ala Ile Tyr Tyr Phe Thr Asp Ser Val
            500                 505                 510

Asp Leu Thr Lys Asp Arg Leu Lys Asp Phe His Gly Phe Gly Asp Met
            515                 520                 525

Asn Asp Gln Thr Leu Gly Val Ala Lys Lys Ile Val Glu Tyr Ala Leu
            530                 535                 540

Ser Asp Glu Asp Ser Lys Leu Thr Asn Leu Asp Phe Phe Val Pro Asn
545                 550                 555                 560

Asn Ser Lys Tyr Gln Ser Leu Ile Gly Thr Glu Tyr His Pro Asp Asp
                565                 570                 575

Leu Val Asp Val Ile Arg Met Glu Asp Lys Lys Gln Glu Val Ile Pro
            580                 585                 590

Val Ile His Ser Leu Thr Val Lys Lys Thr Val Gly Glu Leu Gly
            595                 600                 605

Asp Lys Thr Lys Gly Phe Gln Phe Glu Leu Glu Leu Lys Asp Lys Thr
            610                 615                 620

Gly Gln Pro Ile Val Asp Ala Leu Lys Thr Asn Asn Gln Asp Leu Val
625                 630                 635                 640

Ala Lys Asp Gly Lys Tyr Ser Phe Asn Leu Lys His Gly Asp Thr Ile
                645                 650                 655

Arg Ile Glu Gly Leu Pro Thr Gly Tyr Ser Tyr Thr Leu Lys Glu Thr
            660                 665                 670

Glu Ala Lys Asp Tyr Ile Val Thr Val Asp Asn Lys Val Ser Gln Glu
            675                 680                 685

Ala Gln Ser Ala Ser Glu Asn Val Thr Ala Asp Lys Glu Val Thr Phe
            690                 695                 700

Glu Asn Arg Lys Asp Leu Val Pro Pro Thr Gly Phe Thr Thr Asp Gly
705                 710                 715                 720

Gly Thr Tyr Leu Trp Leu Leu Leu Val Pro Phe Gly Leu Leu Val
                725                 730                 735

Trp Phe Phe Gly Arg Lys Gly Leu Lys Asn Asp
            740                 745

<210> SEQ ID NO 20
<211> LENGTH: 756

```
<212> TYPE: PRT
<213> ORGANISM: S. pyogenes

<400> SEQUENCE: 20

Met Asn Asn Lys Lys Leu Gln Lys Lys Gln Asp Ala Pro Arg Val Ser
 1               5                  10                  15

Asn Arg Lys Pro Lys Gln Leu Thr Val Thr Leu Val Gly Val Phe Leu
                20                  25                  30

Met Phe Leu Thr Leu Val Ser Ser Met Arg Gly Ala Gln Ser Ile Phe
            35                  40                  45

Gly Glu Glu Lys Arg Ile Glu Val Ser Val Pro Lys Ile Lys Ser
        50                  55                  60

Pro Asp Asp Ala Tyr Pro Trp Tyr Gly Tyr Asp Ser Tyr Asp Ser Ser
65                  70                  75                  80

His Pro Tyr Tyr Glu Arg Phe Lys Val Ala His Asp Leu Arg Val Asn
                85                  90                  95

Leu Asn Gly Ser Lys Ser Tyr Gln Val Tyr Cys Phe Asn Ile Asn Ser
                100                 105                 110

His Tyr Pro Asn Arg Lys Asn Ala Phe Ser Lys Gln Trp Phe Lys Arg
            115                 120                 125

Val Asp Gly Thr Gly Asp Val Phe Thr Asn Tyr Ala Gln Thr Pro Lys
        130                 135                 140

Ile Arg Gly Glu Ser Leu Asn Asn Lys Leu Leu Ser Ile Met Tyr Asn
145                 150                 155                 160

Ala Tyr Pro Lys Asn Ala Asn Gly Tyr Met Asp Lys Ile Glu Pro Leu
                165                 170                 175

Asn Ala Ile Leu Val Thr Gln Gln Ala Val Trp Tyr Tyr Ser Asp Ser
                180                 185                 190

Ser Tyr Gly Asn Ile Lys Thr Leu Trp Ala Ser Glu Leu Lys Asp Gly
            195                 200                 205

Lys Ile Asp Phe Glu Gln Val Lys Leu Met Arg Glu Ala Tyr Ser Lys
        210                 215                 220

Leu Ile Ser Asp Asp Leu Glu Glu Thr Ser Lys Asn Lys Leu Pro Gln
225                 230                 235                 240

Gly Ser Lys Leu Asn Ile Phe Val Pro Gln Asp Lys Ser Val Gln Asn
                245                 250                 255

Leu Leu Ser Ala Glu Tyr Val Pro Glu Ser Pro Ala Pro Gly Gln
                260                 265                 270

Ser Pro Glu Pro Pro Val Gln Thr Lys Lys Thr Ser Val Ile Ile Arg
            275                 280                 285

Lys Tyr Ala Glu Gly Asp Tyr Ser Lys Leu Leu Glu Gly Ala Thr Leu
        290                 295                 300

Arg Leu Thr Gly Glu Asp Ile Leu Asp Phe Gln Glu Lys Val Phe Gln
305                 310                 315                 320

Ser Asn Gly Thr Gly Glu Lys Ile Glu Leu Ser Asn Gly Thr Tyr Thr
                325                 330                 335

Leu Thr Glu Thr Ser Ser Pro Asp Gly Tyr Lys Ile Ala Glu Pro Ile
            340                 345                 350

Lys Phe Arg Val Val Asn Lys Lys Val Phe Ile Val Gln Lys Asp Gly
        355                 360                 365

Ser Gln Val Glu Asn Pro Asn Lys Gly Val Ala Glu Pro Tyr Ser Val
        370                 375                 380

Glu Ala Tyr Ser Asp Met Gln Asp Ser Asn Tyr Ile Asn Pro Glu Thr
385                 390                 395                 400
```

Phe Thr Pro Tyr Gly Lys Phe Tyr Tyr Ala Lys Asn Lys Asp Lys Ser
                405                 410                 415

Ser Gln Val Val Tyr Cys Phe Asn Ala Asp Leu His Ser Pro Pro Glu
            420                 425                 430

Ser Glu Asp Gly Gly Gly Thr Ile Asp Pro Asp Ile Ser Thr Met Lys
        435                 440                 445

Glu Val Lys Tyr Thr His Thr Ala Gly Ser Asp Leu Phe Lys Tyr Ala
    450                 455                 460

Leu Arg Pro Arg Asp Thr Asn Pro Glu Asp Phe Leu Lys His Ile Lys
465                 470                 475                 480

Lys Val Ile Glu Lys Gly Tyr Asn Lys Lys Gly Asp Ser Tyr Asn Gly
                485                 490                 495

Leu Thr Glu Thr Gln Phe Arg Ala Ala Thr Gln Leu Ala Ile Tyr Tyr
            500                 505                 510

Phe Thr Asp Ser Thr Asp Leu Lys Thr Leu Lys Thr Tyr Asn Asn Gly
        515                 520                 525

Lys Gly Tyr His Gly Phe Glu Ser Met Asp Glu Lys Thr Leu Ala Val
    530                 535                 540

Thr Lys Glu Leu Ile Asn Tyr Ala Gln Asp Asn Ser Ala Pro Gln Leu
545                 550                 555                 560

Thr Asn Leu Asp Phe Phe Val Pro Asn Asn Ser Lys Tyr Gln Ser Leu
                565                 570                 575

Ile Gly Thr Glu Tyr His Pro Asp Asp Leu Val Asp Val Ile Arg Met
            580                 585                 590

Glu Asp Lys Lys Gln Glu Val Ile Pro Val Thr His Ser Leu Thr Val
        595                 600                 605

Lys Lys Thr Val Val Gly Glu Leu Gly Asp Lys Thr Lys Gly Phe Gln
    610                 615                 620

Phe Glu Leu Glu Leu Lys Asp Lys Thr Gly Gln Pro Ile Val Asn Thr
625                 630                 635                 640

Leu Lys Thr Asn Asn Gln Asp Leu Val Ala Lys Asp Gly Lys Tyr Ser
                645                 650                 655

Phe Asn Leu Lys His Gly Asp Thr Ile Arg Ile Glu Gly Leu Pro Thr
            660                 665                 670

Gly Tyr Ser Tyr Thr Leu Lys Glu Thr Glu Ala Lys Asp Tyr Ile Val
        675                 680                 685

Thr Val Asp Asn Lys Val Ser Gln Glu Ala Gln Ser Ala Ser Glu Asn
    690                 695                 700

Val Thr Ala Asp Lys Glu Val Thr Phe Glu Asn Arg Lys Asp Leu Val
705                 710                 715                 720

Pro Pro Thr Gly Phe Ile Thr Asp Gly Gly Thr Tyr Leu Trp Leu Leu
                725                 730                 735

Leu Leu Val Pro Phe Gly Leu Leu Val Trp Phe Phe Gly Arg Lys Gly
            740                 745                 750

Leu Lys Asn Asp
        755

<210> SEQ ID NO 21
<211> LENGTH: 762
<212> TYPE: PRT
<213> ORGANISM: S. pyogenes

<400> SEQUENCE: 21

Met Arg Gly Glu Lys Met Lys Lys Thr Arg Phe Pro Asn Lys Leu Asn

-continued

```
  1               5                  10                 15
Thr Leu Asn Thr Gln Arg Val Leu Ser Lys Asn Ser Lys Arg Phe Thr
             20                  25                 30
Val Thr Leu Val Gly Val Phe Leu Met Ile Phe Ala Leu Val Thr Ser
             35                  40                 45
Met Val Gly Ala Lys Thr Val Phe Gly Leu Val Glu Ser Ser Thr Pro
 50                      55                 60
Asn Ala Ile Asn Pro Asp Ser Ser Glu Tyr Arg Trp Tyr Gly Tyr
 65              70                  75              80
Glu Ser Tyr Val Arg Gly His Pro Tyr Lys Gln Phe Arg Val Ala
             85                  90                 95
His Asp Leu Arg Val Asn Leu Glu Gly Ser Arg Ser Tyr Gln Val Tyr
            100                 105                110
Cys Phe Asn Leu Lys Lys Ala Phe Pro Leu Gly Ser Asp Ser Ser Val
            115                 120                125
Lys Lys Trp Tyr Lys Lys His Asp Gly Ile Ser Thr Lys Phe Glu Asp
            130                 135                140
Tyr Ala Ile Ser Pro Arg Ile Thr Gly Asp Glu Leu Asn Gln Lys Leu
145                 150                 155                160
Arg Ala Val Met Tyr Asn Gly His Pro Gln Asn Ala Asn Gly Ile Met
                165                 170                175
Glu Gly Leu Glu Pro Leu Asn Ala Ile Arg Val Thr Gln Glu Ala Val
            180                 185                190
Trp Tyr Tyr Ser Asp Asn Ala Pro Ile Ser Asn Pro Asp Glu Ser Phe
                195                 200                205
Lys Arg Glu Ser Glu Ser Asn Leu Val Ser Thr Ser Gln Leu Ser Leu
            210                 215                220
Met Arg Gln Ala Leu Lys Gln Leu Ile Asp Pro Asn Leu Ala Thr Lys
225                 230                 235                240
Met Pro Lys Gln Val Pro Asp Asp Phe Gln Leu Ser Ile Phe Glu Ser
                245                 250                255
Glu Asp Lys Gly Asp Lys Tyr Asn Lys Gly Tyr Gln Asn Leu Leu Ser
            260                 265                270
Gly Gly Leu Val Pro Thr Lys Pro Thr Pro Gly Asp Pro Pro Met
            275                 280                285
Pro Pro Asn Gln Pro Gln Thr Thr Ser Val Leu Ile Arg Lys Tyr Ala
290                 295                 300
Ile Gly Asp Tyr Ser Lys Leu Leu Glu Gly Ala Thr Leu Gln Leu Thr
305             310                 315                320
Gly Asp Asn Val Asn Ser Phe Gln Ala Arg Val Phe Ser Ser Asn Asp
                325                 330                335
Ile Gly Glu Arg Ile Glu Leu Ser Asp Gly Thr Tyr Thr Leu Thr Glu
                340                 345                350
Leu Asn Ser Pro Ala Gly Tyr Ser Ile Ala Glu Pro Ile Thr Phe Lys
                355                 360                365
Val Glu Ala Gly Lys Val Tyr Thr Ile Ile Asp Gly Lys Gln Ile Glu
            370                 375                380
Asn Pro Asn Lys Glu Ile Val Glu Pro Tyr Ser Val Glu Ala Tyr Asn
385                 390                 395                400
Asp Phe Glu Glu Phe Ser Val Leu Thr Thr Gln Asn Tyr Ala Lys Phe
                405                 410                415
Tyr Tyr Ala Lys Asn Lys Asn Gly Ser Ser Gln Val Val Tyr Cys Phe
            420                 425                430
```

```
Asn Ala Asp Leu Lys Ser Pro Pro Asp Ser Glu Asp Gly Gly Lys Thr
        435                 440                 445

Met Thr Pro Asp Phe Thr Thr Gly Glu Val Lys Tyr Thr His Ile Ala
    450                 455                 460

Gly Arg Asp Leu Phe Lys Tyr Thr Val Lys Pro Arg Asp Thr Asp Pro
465                 470                 475                 480

Asp Thr Phe Leu Lys His Ile Lys Lys Val Ile Glu Lys Gly Tyr Arg
                485                 490                 495

Glu Lys Gly Gln Ala Ile Glu Tyr Ser Gly Leu Thr Glu Thr Gln Leu
                500                 505                 510

Arg Ala Ala Thr Gln Leu Ala Ile Tyr Tyr Phe Thr Asp Ser Ala Glu
            515                 520                 525

Leu Asp Lys Asp Lys Leu Lys Asp Tyr His Gly Phe Gly Asp Met Asn
    530                 535                 540

Asp Ser Thr Leu Ala Val Ala Lys Ile Leu Val Glu Tyr Ala Gln Asp
545                 550                 555                 560

Ser Asn Pro Pro Gln Leu Thr Asp Leu Asp Phe Phe Ile Pro Asn Asn
                565                 570                 575

Asn Lys Tyr Gln Ser Leu Ile Gly Thr Gln Trp His Pro Glu Asp Leu
                580                 585                 590

Val Asp Ile Ile Arg Met Glu Asp Lys Lys Glu Val Ile Pro Val Thr
            595                 600                 605

His Asn Leu Thr Leu Arg Lys Thr Val Thr Gly Leu Ala Gly Asp Arg
    610                 615                 620

Thr Lys Asp Phe His Phe Glu Ile Glu Leu Lys Asn Asn Lys Gln Glu
625                 630                 635                 640

Leu Leu Ser Gln Thr Val Lys Thr Asp Lys Thr Asn Leu Glu Phe Lys
                645                 650                 655

Asp Gly Lys Ala Thr Ile Asn Leu Lys His Gly Glu Ser Leu Thr Leu
                660                 665                 670

Gln Gly Leu Pro Glu Gly Tyr Ser Tyr Leu Val Lys Glu Thr Asp Ser
            675                 680                 685

Glu Gly Tyr Lys Val Lys Val Asn Ser Gln Glu Val Ala Asn Ala Thr
    690                 695                 700

Val Ser Lys Thr Gly Ile Thr Ser Asp Glu Thr Leu Ala Phe Glu Asn
705                 710                 715                 720

Asn Lys Glu Pro Val Val Pro Thr Gly Val Asp Gln Lys Ile Asn Gly
                725                 730                 735

Tyr Leu Ala Leu Ile Val Ile Ala Gly Ile Ser Leu Gly Ile Trp Gly
                740                 745                 750

Ile His Thr Ile Arg Ile Arg Lys His Asp
        755                 760

<210> SEQ ID NO 22
<211> LENGTH: 744
<212> TYPE: PRT
<213> ORGANISM: S. pyogenes

<400> SEQUENCE: 22

Met Gln Lys Arg Asp Lys Thr Asn Tyr Gly Ser Ala Asn Asn Lys Arg
  1               5                  10                  15

Arg Gln Thr Thr Ile Gly Leu Leu Lys Val Phe Leu Thr Phe Val Ala
                20                  25                  30

Leu Ile Gly Ile Val Gly Phe Ser Ile Arg Ala Phe Gly Ala Glu Glu
```

-continued

```
                35                  40                  45
Gln Ser Val Pro Asn Lys Gln Ser Ser Val Gln Asp Tyr Pro Trp Tyr
 50                  55                  60
Gly Tyr Asp Ser Tyr Ser Lys Gly Tyr Pro Asp Tyr Ser Pro Leu Lys
 65                  70                  75                  80
Thr Tyr His Asn Leu Lys Val Asn Leu Asp Gly Ser Lys Glu Tyr Gln
                 85                  90                  95
Ala Tyr Cys Phe Asn Leu Thr Lys His Phe Pro Ser Lys Ser Asp Ser
                100                 105                 110
Val Arg Ser Gln Trp Tyr Lys Lys Leu Glu Gly Thr Asn Glu Asn Phe
                115                 120                 125
Ile Lys Leu Ala Asp Lys Pro Arg Ile Glu Asp Gly Gln Leu Gln Gln
                130                 135                 140
Asn Ile Leu Arg Ile Leu Tyr Asn Gly Tyr Pro Asn Asp Arg Asn Gly
145                 150                 155                 160
Ile Met Lys Gly Ile Asp Pro Leu Asn Ala Ile Leu Val Thr Gln Asn
                165                 170                 175
Ala Ile Trp Tyr Tyr Thr Asp Ser Ser Tyr Ile Ser Asp Thr Ser Lys
                180                 185                 190
Ala Phe Gln Gln Glu Thr Asp Leu Lys Leu Asp Ser Gln Gln Leu
                195                 200                 205
Gln Leu Met Arg Asn Ala Leu Lys Arg Leu Ile Asn Pro Lys Glu Val
210                 215                 220
Glu Ser Leu Pro Asn Gln Val Pro Ala Asn Tyr Gln Leu Ser Ile Phe
225                 230                 235                 240
Gln Ser Ser Asp Lys Thr Phe Gln Asn Leu Leu Ser Ala Glu Tyr Val
                245                 250                 255
Pro Asp Thr Pro Lys Pro Gly Glu Glu Pro Ala Lys Thr Glu
                260                 265                 270
Lys Thr Ser Val Ile Ile Arg Lys Tyr Ala Glu Gly Asp Tyr Ser Lys
                275                 280                 285
Leu Leu Glu Gly Ala Thr Leu Lys Leu Ala Gln Ile Glu Gly Ser Gly
290                 295                 300
Phe Gln Glu Lys Ile Phe Asp Ser Asn Lys Ser Gly Glu Lys Val Glu
305                 310                 315                 320
Leu Pro Asn Gly Thr Tyr Val Leu Ser Glu Leu Lys Pro Pro Gln Gly
                325                 330                 335
Tyr Gly Val Ala Thr Pro Ile Thr Phe Lys Val Ala Ala Glu Lys Val
                340                 345                 350
Leu Ile Lys Asn Lys Glu Gly Gln Phe Val Glu Asn Gln Asn Lys Glu
                355                 360                 365
Ile Ala Glu Pro Tyr Ser Val Thr Ala Phe Asn Asp Phe Glu Glu Ile
                370                 375                 380
Gly Tyr Leu Ser Asp Phe Asn Asn Tyr Gly Lys Phe Tyr Tyr Ala Lys
385                 390                 395                 400
Asn Thr Asn Gly Thr Asn Gln Val Val Tyr Cys Phe Asn Ala Asp Leu
                405                 410                 415
His Ser Pro Pro Asp Ser Tyr Asp His Gly Ala Asn Ile Asp Pro Asp
                420                 425                 430
Val Ser Glu Ser Lys Glu Ile Lys Tyr Thr His Val Ser Gly Tyr Asp
                435                 440                 445
Leu Tyr Lys Tyr Ala Ala Thr Pro Arg Asp Lys Asp Ala Asp Phe Phe
                450                 455                 460
```

```
Leu Lys His Ile Lys Lys Ile Leu Asp Lys Gly Tyr Lys Lys Gly
465                 470                 475                 480

Asp Thr Tyr Lys Thr Leu Thr Glu Ala Gln Phe Arg Ala Ala Thr Gln
                485                 490                 495

Leu Ala Ile Tyr Tyr Tyr Thr Asp Ser Ala Asp Leu Thr Thr Leu Lys
            500                 505                 510

Thr Tyr Asn Asp Asn Lys Gly Tyr His Gly Phe Asp Lys Leu Asp Asp
                515                 520                 525

Ala Thr Leu Ala Val Val His Glu Leu Ile Thr Tyr Ala Glu Asp Val
            530                 535                 540

Thr Leu Pro Met Thr Gln Asn Leu Asp Phe Phe Val Pro Asn Ser Ser
545                 550                 555                 560

Arg Tyr Gln Ala Leu Ile Gly Thr Gln Tyr His Pro Asn Glu Leu Ile
                565                 570                 575

Asp Val Ile Ser Met Glu Asp Lys Gln Ala Pro Ile Ile Pro Ile Thr
            580                 585                 590

His Lys Leu Thr Ile Ser Lys Thr Val Thr Gly Thr Ile Ala Asp Lys
            595                 600                 605

Lys Lys Glu Phe Asn Phe Glu Ile His Leu Lys Ser Ser Asp Gly Gln
610                 615                 620

Ala Ile Ser Gly Thr Tyr Pro Thr Asn Ser Gly Glu Leu Thr Val Thr
625                 630                 635                 640

Asp Gly Lys Ala Thr Phe Thr Leu Lys Asp Gly Glu Ser Leu Ile Val
                645                 650                 655

Glu Gly Leu Pro Ser Gly Tyr Ser Tyr Glu Ile Thr Glu Thr Gly Ala
                660                 665                 670

Ser Asp Tyr Glu Val Ser Val Asn Gly Lys Asn Ala Pro Asp Gly Lys
            675                 680                 685

Ala Thr Lys Ala Ser Val Lys Glu Asp Glu Thr Val Ala Phe Glu Asn
            690                 695                 700

Arg Lys Asp Leu Val Pro Pro Thr Gly Leu Thr Thr Asp Gly Ala Ile
705                 710                 715                 720

Tyr Leu Trp Leu Leu Leu Val Pro Phe Gly Leu Leu Val Trp Leu
                725                 730                 735

Phe Gly Arg Lys Gly Thr Lys Lys
                740

<210> SEQ ID NO 23
<211> LENGTH: 524
<212> TYPE: PRT
<213> ORGANISM: S. pyogenes

<400> SEQUENCE: 23

Met Gln Lys Arg Asp Lys Thr Asn Tyr Gly Ser Ala Asn Asn Lys Arg
1               5                   10                  15

Arg Gln Thr Thr Ile Gly Leu Leu Lys Val Phe Leu Thr Phe Val Ala
                20                  25                  30

Leu Ile Gly Ile Val Gly Phe Ser Ile Arg Ala Phe Gly Ala Glu Glu
            35                  40                  45

Gln Ser Thr Glu Thr Lys Lys Thr Ser Val Ile Ile Arg Lys Tyr Ala
        50                  55                  60

Glu Gly Asp Tyr Ser Lys Leu Leu Glu Gly Ala Thr Leu Lys Leu Ala
65                  70                  75                  80

Gln Ile Glu Gly Ser Gly Phe Gln Glu Gln Ser Phe Glu Ser Ser Thr
```

```
                        85                  90                  95
Ser Gly Gln Lys Leu Gln Leu Ser Asp Gly Thr Tyr Ile Leu Thr Glu
                100                 105                 110

Thr Lys Ser Pro Gln Gly Tyr Glu Ile Ala Glu Pro Ile Thr Phe Lys
            115                 120                 125

Val Thr Ala Gly Lys Val Phe Ile Lys Gly Lys Asp Gly Gln Phe Val
        130                 135                 140

Glu Asn Gln Asn Lys Glu Val Ala Glu Pro Tyr Ser Val Thr Ala Tyr
145                 150                 155                 160

Asn Asp Phe Asp Asp Ser Gly Phe Ile Asn Pro Lys Thr Phe Thr Pro
                165                 170                 175

Tyr Gly Lys Phe Tyr Tyr Ala Lys Asn Ala Asn Gly Thr Ser Gln Val
            180                 185                 190

Val Tyr Cys Phe Asn Val Asp Leu His Ser Pro Asp Ser Leu Asp
        195                 200                 205

Lys Gly Glu Thr Ile Asp Pro Asp Phe Asn Glu Gly Lys Glu Ile Lys
    210                 215                 220

Tyr Thr His Ile Leu Gly Ala Asp Leu Phe Ser Tyr Ala Asn Asn Pro
225                 230                 235                 240

Arg Ala Ser Thr Asn Asp Glu Leu Leu Ser Gln Val Lys Lys Val Leu
                245                 250                 255

Glu Lys Gly Tyr Arg Asp Asp Ser Thr Thr Tyr Ala Asn Leu Thr Ser
            260                 265                 270

Val Glu Phe Arg Ala Ala Thr Gln Leu Ala Ile Tyr Tyr Phe Thr Asp
        275                 280                 285

Ser Val Asp Leu Asp Asn Leu Ala Asp Tyr His Gly Phe Gly Ala Leu
    290                 295                 300

Thr Thr Glu Ala Leu Asn Ala Thr Lys Glu Ile Val Ala Tyr Ala Glu
305                 310                 315                 320

Asp Arg Ala Asn Leu Pro Asn Ile Ser Asn Leu Asp Phe Tyr Val Pro
                325                 330                 335

Asn Ser Asn Lys Tyr Gln Ser Leu Ile Gly Thr Gln Tyr His Pro Glu
            340                 345                 350

Ser Leu Val Asp Ile Ile Arg Met Glu Asp Lys Gln Ala Pro Ile Ile
        355                 360                 365

Pro Ile Thr His Lys Leu Thr Ile Ser Lys Thr Val Thr Gly Thr Ile
    370                 375                 380

Ala Asp Lys Lys Lys Glu Phe Asn Phe Glu Ile His Leu Lys Ser Ser
385                 390                 395                 400

Asp Gly Gln Ala Ile Ser Gly Thr Tyr Pro Thr Asn Ser Gly Glu Leu
                405                 410                 415

Thr Val Thr Asp Gly Lys Ala Thr Phe Thr Leu Lys Asp Gly Glu Ser
            420                 425                 430

Leu Ile Val Glu Gly Leu Pro Ser Gly Tyr Ser Tyr Glu Ile Thr Glu
        435                 440                 445

Thr Gly Ala Ser Asp Tyr Glu Val Ser Val Asn Gly Lys Asn Ala Pro
    450                 455                 460

Asp Gly Lys Ala Thr Lys Ala Ser Val Lys Asp Gly Thr Ile Thr
465                 470                 475                 480

Phe Glu Asn Arg Lys Asp Leu Val Pro Pro Thr Gly Leu Thr Thr Asp
                485                 490                 495

Gly Ala Ile Tyr Leu Trp Leu Leu Leu Leu Val Leu Leu Gly Leu Trp
            500                 505                 510
```

```
Val Trp Leu Ile Gly Arg Lys Gly Leu Lys Asn Asp
        515                 520

<210> SEQ ID NO 24
<211> LENGTH: 1036
<212> TYPE: PRT
<213> ORGANISM: S. pyogenes

<400> SEQUENCE: 24

Met Tyr Ser Arg Leu Lys Arg Glu Leu Val Ile Val Ile Asn Arg Lys
  1               5                  10                  15

Lys Lys Tyr Lys Leu Ile Arg Leu Met Val Thr Val Gly Leu Ile Phe
             20                  25                  30

Ser Gln Leu Val Leu Pro Ile Arg Arg Leu Gly Leu Gln Met Ile Ser
             35                  40                  45

Thr Gln Thr Lys Val Ile Pro Gln Glu Ile Val Thr Gln Thr Glu Thr
         50                  55                  60

Gly Gly Thr Gln Val Val Ala Thr Lys Gln Lys Leu Glu Ser Glu Asn
 65                  70                  75                  80

Ser Ser Leu Lys Val Ala Leu Lys Arg Glu Ser Gly Phe Glu His Asn
                 85                  90                  95

Ala Thr Ile Asp Ala Ser Leu Asp Thr Glu Ser Gln Gly Asp Asn Ser
                100                 105                 110

Gln Arg Ser Val Thr Gln Ala Ile Val Thr Met Ala Leu Glu Leu Arg
            115                 120                 125

Lys Gln Gly Leu Ser Ile Val Asp Thr Lys Ile Val Arg Ile Gln Ser
130                 135                 140

Ser Thr Asn Gln Arg Asn Asp Ile Thr Thr Leu Thr Phe Lys Asn
145                 150                 155                 160

Gly Leu Ser Leu Glu Gly Ala Ser Thr Glu Ala Asn Asp Pro Asn Val
                165                 170                 175

Arg Val Gly Ile Val Asn Pro Asn Asp Thr Val Gln Thr Ile Thr Pro
                180                 185                 190

Thr Ile Lys Gln Asp Ala Asp Gly Lys Val Lys Asn Leu Val Phe Thr
            195                 200                 205

Gly Arg Leu Gly Lys Gln Val Ile Ile Val Ser Thr Thr Arg Leu Lys
210                 215                 220

Glu Glu Gln Thr Ile Ser Leu Asp Ser Tyr Gly Glu Leu Val Ile Asp
225                 230                 235                 240

Gly Ala Val Gly Leu Ser Gln Lys Asp Arg Pro Pro Tyr Ser Lys Pro
                245                 250                 255

Ile Thr Val Asn Ile Leu Lys Pro Lys Leu Ser Ser Ile Glu Ser Ser
                260                 265                 270

Leu Asp Ser Lys Asp Phe Glu Ile Val Lys Thr Ile Asp Asn Leu Tyr
            275                 280                 285

Thr Trp Asp Asp Gln Phe Tyr Leu Leu Asp Phe Ile Ser Lys Gln Tyr
        290                 295                 300

Glu Val Leu Lys Thr Asp Tyr Gln Ser Ala Lys Asp Ser Thr Pro Gln
305                 310                 315                 320

Thr Arg Asp Ile Leu Phe Gly Glu Tyr Thr Val Glu Pro Leu Val Met
                325                 330                 335

Asn Lys Gly His Asn Asn Thr Ile Asn Ile Tyr Ile Arg Ser Thr Arg
                340                 345                 350

Pro Leu Gly Leu Lys Pro Ile Gly Ala Ala Pro Ala Leu Ile Gln Pro
```

```
            355                 360                 365
Arg Ser Phe Arg Ser Leu Thr Pro Arg Ser Thr Arg Met Lys Arg Ser
370                 375                 380

Ala Pro Val Glu Lys Phe Glu Gly Glu Leu Glu His His Lys Arg Ile
385                 390                 395                 400

Asp Tyr Leu Gly Asp Asn Gln Asn Asn Pro Asp Thr Thr Ile Asp Asp
                405                 410                 415

Lys Glu Asp Glu His Asp Thr Ser Asp Leu Tyr Arg Leu Tyr Leu Asp
                420                 425                 430

Met Thr Gly Lys Lys Asn Pro Leu Asp Ile Leu Val Val Asp Lys
            435                 440                 445

Ser Gly Ser Met Gln Glu Gly Ile Gly Ser Val Gln Arg Tyr Arg Tyr
        450                 455                 460

Tyr Ala Gln Arg Trp Asp Tyr Tyr Ser Gln Trp Val Tyr His Gly
465                 470                 475                 480

Thr Phe Asp Tyr Ser Ser Tyr Gln Gly Glu Ser Phe Asn Arg Gly Gln
                485                 490                 495

Ile His Tyr Arg Tyr Arg Gly Ile Val Ser Val Ser Asp Gly Ile Arg
                500                 505                 510

Arg Asp Asp Ala Val Lys Asn Ser Leu Leu Gly Val Asn Gly Leu Leu
            515                 520                 525

Gln Arg Phe Val Asn Ile Asn Pro Glu Asn Lys Leu Ser Val Ile Gly
        530                 535                 540

Phe Gln Gly Ser Ala Asp Tyr His Ala Gly Lys Trp Tyr Pro Asp Gln
545                 550                 555                 560

Ser Pro Arg Gly Gly Phe Tyr Gln Pro Asn Leu Asn Asn Ser Arg Asp
                565                 570                 575

Ala Glu Leu Leu Lys Gly Trp Ser Thr Asn Ser Leu Leu Asp Pro Asn
            580                 585                 590

Thr Leu Thr Ala Leu His Asn Asn Gly Thr Asn Tyr His Ala Ala Leu
        595                 600                 605

Leu Lys Ala Lys Glu Ile Leu Asn Glu Val Lys Asp Asp Gly Arg Arg
610                 615                 620

Lys Ile Met Ile Phe Ile Ser Asp Gly Val Pro Thr Phe Tyr Phe Gly
625                 630                 635                 640

Glu Asp Gly Tyr Arg Ser Gly Asn Gly Ser Ser Asn Asp Arg Asn Asn
                645                 650                 655

Val Thr Arg Ser Gln Glu Gly Ser Lys Leu Ala Ile Asp Glu Phe Lys
            660                 665                 670

Ala Arg Tyr Pro Asn Leu Ser Ile Tyr Ser Leu Gly Val Ser Lys Asp
        675                 680                 685

Ile Asn Ser Asp Thr Ala Ser Ser Pro Val Val Leu Lys Tyr Leu
690                 695                 700

Ser Gly Glu Glu His Tyr Tyr Gly Ile Thr Asp Thr Ala Glu Leu Glu
705                 710                 715                 720

Lys Thr Leu Asn Lys Ile Val Glu Asp Ser Lys Leu Ser Gln Leu Gly
                725                 730                 735

Ile Ser Asp Ser Leu Ser Gln Tyr Val Asp Tyr Asp Lys Gln Pro
            740                 745                 750

Asp Val Leu Val Thr Arg Lys Ser Lys Val Asn Asp Glu Thr Glu Ile
        755                 760                 765

Leu Tyr Gln Lys Asp Gln Val Gln Glu Ala Gly Lys Asp Ile Ile Asp
770                 775                 780
```

```
Lys Val Val Phe Thr Pro Lys Thr Thr Ser Gln Pro Lys Gly Lys Val
785                 790                 795                 800

Thr Leu Thr Phe Lys Ser Asp Tyr Lys Val Asp Asp Glu Tyr Thr Tyr
                805                 810                 815

Thr Leu Ser Phe Asn Val Lys Ala Ser Asp Glu Ala Tyr Glu Lys Tyr
                820                 825                 830

Lys Asp Asn Glu Gly Arg Tyr Ser Glu Met Gly Asp Ser Asp Thr Asp
                835                 840                 845

Tyr Gly Thr Asn Gln Thr Ser Ser Gly Lys Gly Leu Pro Ser Asn
850                 855                 860

Ser Asp Ala Ser Val Asn Tyr Met Ala Asp Gly Arg Glu Gln Lys Leu
865                 870                 875                 880

Pro Tyr Lys His Pro Val Ile Gln Val Lys Thr Val Pro Ile Thr Phe
                885                 890                 895

Thr Lys Val Asp Ala Asp Asn Asn Gln Lys Lys Leu Ala Gly Val Glu
                900                 905                 910

Phe Glu Leu Arg Lys Glu Asp Lys Lys Ile Val Trp Glu Lys Gly Thr
                915                 920                 925

Thr Gly Ser Asn Gly Gln Leu Asn Phe Lys Tyr Leu Gln Lys Gly Lys
                930                 935                 940

Thr Tyr Tyr Leu Tyr Glu Thr Lys Ala Lys Leu Gly Tyr Thr Leu Pro
945                 950                 955                 960

Glu Asn Pro Trp Glu Val Ala Val Ala Asn Asn Gly Asp Ile Lys Val
                965                 970                 975

Lys His Pro Ile Glu Gly Glu Leu Lys Ser Lys Asp Gly Ser Tyr Met
                980                 985                 990

Ile Lys Asn Tyr Lys Ile Tyr Gln Leu Pro Ser Ser Gly Gly Arg Gly
                995                 1000                1005

Ser Gln Ile Phe Ile Ile Val Gly Ser Met Thr Ala Thr Val Ala Leu
    1010                1015                1020

Leu Phe Tyr Arg Arg Gln His Arg Lys Lys Gln Tyr
1025                1030                1035

<210> SEQ ID NO 25
<211> LENGTH: 1367
<212> TYPE: PRT
<213> ORGANISM: S. pyogenes

<400> SEQUENCE: 25

Met Tyr Ser Arg Leu Lys Arg Glu Leu Val Ile Val Ile Asn Arg Lys
1               5                   10                  15

Lys Lys Tyr Lys Leu Ile Arg Leu Met Val Thr Leu Gly Leu Ile Phe
                20                  25                  30

Ser Gln Leu Ala Pro Pro Phe Gly Thr Leu Met Ala Leu Ser Gly His
            35                  40                  45

Ser Arg Ser Lys Ser Pro Val Thr Glu Val Lys Ala Asp Asn Val Ser
        50                  55                  60

Thr Leu Lys Thr Gly Ser Phe Lys Leu Lys Phe Asp Glu Asp Gly
65                  70                  75                  80

Lys Thr Pro Ile Lys Asp Val Thr Phe Gln Leu Thr Ser Glu Thr Asn
                85                  90                  95

Pro Ser Asn Tyr Lys Ile Glu Gln Ile Thr Ser Gly Ala Gly Asp Ala
                100                 105                 110

Ser Phe Ala Asn Ile Pro Pro Gly Thr Tyr Leu Leu Lys Glu Val Ala
```

```
            115                 120                 125
Pro Pro Ser Gly Tyr Gln Val Met Ala Asp Tyr Tyr Arg Ile Thr Val
        130                 135                 140

Ser Pro Asp Gly Tyr Thr Gln Tyr Thr Tyr Val Lys Val Gly Thr Thr
145                 150                 155                 160

Thr Ser Ser Pro Thr Thr Ser Leu Pro Ser Thr Ser Gly Gly Gly Thr
                165                 170                 175

Gly Gly Thr Val Phe Arg Thr Ser Lys Thr Ser Gly Val Val Thr Val
            180                 185                 190

Thr Asp Tyr Asn Phe Thr Thr Lys Asn Lys Ala Gln Gly Asn Thr Asp
        195                 200                 205

Tyr Thr Thr Leu Trp Ala Thr Ser Gly Glu Phe Phe Asp Met Ser Phe
    210                 215                 220

Lys Leu Lys Val Asn Glu Gly Thr Gln Ala Gly Asp Ser Phe Thr Ile
225                 230                 235                 240

Lys Leu Ser Asp Tyr Leu Ser Pro Asn Gly Ile Arg Glu Lys Phe Ile
                245                 250                 255

Ser Ala Pro Pro Leu Met Leu Asp Lys Lys Val Val Ala Thr Gly Ile
            260                 265                 270

Tyr Asp Glu Ser Thr Asn Ser Tyr Ile Tyr Thr Phe Asn Asp Leu Ile
        275                 280                 285

Asn His Lys Gln Asn Ala Glu Ile Thr Val Asn Tyr Thr Phe Ser Pro
290                 295                 300

Glu Ala Lys Lys Val Asp Arg Asp Trp Tyr Val Asn Thr Tyr Asn Ile
305                 310                 315                 320

Thr Asn Ile Ile Asp Gly Gln Lys Gln Asp Ser Gly Asn Phe Thr Ile
                325                 330                 335

Asp Tyr Gly Gln Gly Gln Tyr Met Thr Gly Thr Leu Asn Ser Gly Leu
            340                 345                 350

Arg Leu Arg Asn Asn Ile Thr Tyr Leu Asn Arg Thr Thr Gly Glu Val
        355                 360                 365

Glu Tyr Thr Ile Tyr Leu Asn Asn Gly Ala Ser Pro Arg Asp Lys Asp
    370                 375                 380

Phe Thr Val Lys Asn Pro Val Thr Gly Arg His Phe Leu Asn Leu Glu
385                 390                 395                 400

Asp Lys Ser Ala Ser Val Ala Phe Thr Gln Lys Asn Ile Thr Val Tyr
                405                 410                 415

Arg Val Pro Leu Ser Gln Lys Thr Ser Lys Met Pro Tyr Ser Met Ser
            420                 425                 430

Gly Glu Thr Asp Gly Leu Glu Ser Ile Pro Phe Asp Tyr Ser Ser Lys
        435                 440                 445

Gly Ile Thr Phe Thr Lys Glu Ser Phe His Asp Asn Glu Thr Asn Ser
    450                 455                 460

Asn Thr Ala Gly Leu Leu Ile Lys Ile Lys Ala Tyr Ile Thr Ala Asp
465                 470                 475                 480

Asn Lys Arg Ser Ala Asp Val Ser Leu Ser Ala Gly Trp Thr Tyr Thr
                485                 490                 495

Asn Leu Ile Arg Ser Arg Ser Asp Ala Lys Ala Ser Ala Phe Glu Leu
            500                 505                 510

Gly Asn Thr Ser Ser Gly Val Ala Asn Asn Ile Glu Pro Thr Val Thr
        515                 520                 525

Ile Arg Asn Tyr Lys Ile Lys Lys Gly Ser Ile Val Phe Thr Lys Gln
    530                 535                 540
```

```
Asp Val Glu Thr Lys Met Thr Leu Ser Gly Val Ala Phe Arg Leu Glu
545                 550                 555                 560

Lys Lys Glu Glu Asn Asp Trp Gln Ile Val Glu Lys Tyr Lys Asp Val
                565                 570                 575

Gln Thr Gly Thr Glu Gly Lys Leu Ile Leu Ser Asp Leu Asp Pro Gly
            580                 585                 590

Glu Tyr Gln Leu Ile Glu Thr Lys Pro Leu Asp Gly Tyr Leu Val Ser
        595                 600                 605

Ser Gly Pro Val Val Thr Phe Thr Ile Thr Asp Gln Gly Thr Glu Gly
    610                 615                 620

Thr Val Lys Pro Ser Asp Lys Ile Ile Pro Asn Thr Lys Pro Gly Lys
625                 630                 635                 640

Gln Lys Ile Lys Val Ile Lys Lys Asp Glu Gln Ser Arg Val Pro Leu
                645                 650                 655

Ala Gly Ala Lys Phe Gln Leu Glu Ser Asn Lys Gly Val Val Leu Thr
            660                 665                 670

Gly Glu Thr Asp Gly Lys Gly Glu Tyr Thr Phe Thr Asn Leu Pro Phe
        675                 680                 685

Gly Asp Tyr Ile Leu Thr Glu Ile Ala Ala Pro Lys Gly Tyr Ile Leu
    690                 695                 700

Asp Lys Thr Pro Arg Ser Ile Ala Ile Gly Asp Thr Val Asp Lys Glu
705                 710                 715                 720

Pro Glu Pro Thr Val Val Glu Ala Ala Thr Pro Arg Thr Val Arg Ser
                725                 730                 735

Val Ser Pro Ser Ala Thr Val Ser Lys Asp Val Ser Arg Asn Ile
            740                 745                 750

Leu Val Lys Lys Val Glu Phe Thr Thr Thr Asn Gly Gln Thr Pro Leu
            755                 760                 765

Gln Val Lys Pro Asn Gln Gly Glu Asn Leu Ile Ala Arg Ser Glu Phe
    770                 775                 780

Glu Leu Lys Lys Glu Ile Asp Ile Lys Lys Gly Asp Tyr Phe Ala Val
785                 790                 795                 800

Lys Leu Ser Asp Asn Ile Asp Pro Phe Gly Val Ser Thr Gly Glu Thr
                805                 810                 815

Thr Thr Phe Asn Ile Thr Gly Pro Tyr Gly Thr Leu Ala Val Gly Lys
            820                 825                 830

Tyr Asp Ser Lys Ser Arg Ser Ile Ile Tyr Thr Phe Thr Asp Tyr Val
        835                 840                 845

Glu Lys Tyr Glu Val Ser Asn Phe Ser Thr Ile Leu Pro Tyr Phe Ile
    850                 855                 860

Asp Arg Tyr Ala Val Thr Arg Asp Ala Asp Ile Asn Ile Ser Thr Ser
865                 870                 875                 880

Val Gly Ser Gln Thr Asn Thr Ala Arg Val Arg Val Leu Tyr Thr Pro
                885                 890                 895

Tyr Tyr Gly Ala Thr Asp Ser Tyr Ser Pro Val Asn Ile Gly Ser Met
            900                 905                 910

Ile Thr Lys Leu Asp Glu Lys Asn Gly Thr Phe Thr Asn Tyr Ile Tyr
        915                 920                 925

Ile Asn Pro Met Gln Gln Phe Ile Arg Asn Gly Lys Leu Thr Phe Gln
    930                 935                 940

Gly Gly Gly Ser Ala Ile Ile Asp Asn Glu Thr Gln Val Thr Leu Phe
945                 950                 955                 960
```

-continued

```
Lys Val Asn Asn Ser Thr Asp Met Pro Pro Ser Trp Gly Ile Thr Asp
                965                 970                 975
Ser Thr Leu Arg Val Glu Asn Asp Ile Leu Val Asn Lys Lys Gln Gly
            980                 985                 990
Glu Ile Ser Val Asp Phe Glu Asn Ile Leu Glu Ala Arg Asn Ser Phe
        995                1000                1005
Ile Met Lys Val Val Gly Lys Ile Ala Ser Ser Gly Thr Ser Val Arg
    1010                1015                1020
Thr Ser Ala Thr Leu Ser Gln Lys Tyr Asp Asn Thr Tyr Gly Tyr Tyr
1025                1030                1035                1040
Ser Thr Asn Gly Arg Trp Ile Pro Lys Gly Pro Tyr Ser Glu Tyr Tyr
            1045                1050                1055
Arg Tyr Asp Thr Thr Ala Ile Leu His Ser Gly Asp Ser Asn Val Asp
        1060                1065                1070
Gly Ala Ile Arg Ile Ser Val Thr Asn Arg Lys Asn Ser Val Ala Phe
    1075                1080                1085
Thr Lys Thr Asn Gly Leu Glu Lys Pro Leu Glu Ala Thr Phe Glu Leu
1090                1095                1100
Arg Arg Leu Asn Ser Asn Lys Thr Phe Thr Ser Val Lys Thr Thr Lys
1105                1110                1115                1120
Ser Thr Lys Asp Thr Gly Lys Phe Ser Phe Glu Gly Met Glu Ser Gly
            1125                1130                1135
Ser Tyr Glu Val Trp Glu Thr Gln Ser Pro Glu Gly Tyr Leu Lys Pro
            1140                1145                1150
Asp Lys Ala Val Ala Thr Phe Lys Val Asp Lys Asp Gly Thr Ile Lys
            1155                1160                1165
Asp Leu Thr Pro Asp Asn Gly Lys Ile Ile Asn Tyr Pro Asn Thr Ala
    1170                1175                1180
Lys Ile Ile Phe Thr Lys Met Leu Ala Ser Glu Lys Glu Leu Ser
1185                1190                1195                1200
Pro Ala Thr Lys Glu Lys Ser Ala Thr Phe Ser Leu Trp Arg Leu Lys
            1205                1210                1215
Glu Glu Ser Leu Lys Glu Thr Asn Thr Val Ser Gln Ala Tyr Asp Glu
            1220                1225                1230
Gln Tyr Tyr Glu Pro Val Met Glu Asn Asn Ser Val Arg Thr Val Thr
    1235                1240                1245
Ser Asp Ser Ser Gly Asn Val Leu Phe Asp Lys Leu Ser Pro Gly Phe
    1250                1255                1260
Tyr Ala Ile Lys Glu Glu Lys Ala Pro Asp Gly Tyr Val Lys Gln Gln
1265                1270                1275                1280
Gly Ile Val Arg Ile Phe Gln Val Asp Ser Ser Gly Lys Val Ile Lys
            1285                1290                1295
Tyr Gln Tyr Phe Lys Asp Lys Ser Ile Ala Gly Lys Leu Thr Glu Ile
            1300                1305                1310
Thr Asp Leu Glu Thr Gln Leu Lys Gln Phe Asn Glu Ile Ile Asn
    1315                1320                1325
Lys Lys Phe Val Phe Pro Met Thr Gly Gly Gln Gly Ile Ala Leu Leu
    1330                1335                1340
Met Ile Ile Gly Gly Thr Met Met Gly Ile Ala Tyr Phe Gly His Arg
1345                1350                1355                1360
Arg Lys Gln Arg Leu Asn Asp
            1365
```

```
<210> SEQ ID NO 26
<211> LENGTH: 890
<212> TYPE: PRT
<213> ORGANISM: S. pyogenes

<400> SEQUENCE: 26
```

| | | | | | | | | | | | | | | |
|---|---|---|---|---|---|---|---|---|---|---|---|---|---|---|
| Met | Lys | Lys | Gln | Lys | Leu | Trp | Arg | Gly | Leu | Ser | Val | Thr | Leu | Leu |
| 1 | | | | 5 | | | | | 10 | | | | | 15 |
| Ile | Leu | Ser | Gln | Ile | Pro | Phe | Gly | Ile | Leu | Val | Gln | Gly | Glu | Thr | Gln |
| | | | 20 | | | | | 25 | | | | | 30 | | |
| Asp | Asn | Asn | Pro | Ala | Leu | Gly | Lys | Val | Ile | Val | Lys | Lys | Thr | Gly | Glu |
| | | 35 | | | | | 40 | | | | | 45 | | | |
| Asn | Ala | Met | Pro | Leu | Gly | Lys | Ala | Thr | Phe | Val | Leu | Lys | Asn | Asp | His |
| | 50 | | | | | 55 | | | | | 60 | | | | |
| Asp | Lys | Ser | Glu | Ile | Ser | His | Glu | Thr | Val | Glu | Gly | Ser | Gly | Glu | Ala |
| 65 | | | | | 70 | | | | | 75 | | | | | 80 |
| Ala | Phe | Glu | Asn | Ile | Lys | Pro | Gly | Asn | Tyr | Thr | Leu | Thr | Glu | Lys | Thr |
| | | | | 85 | | | | | 90 | | | | | 95 | |
| Ala | Pro | Ile | Gly | Tyr | Lys | Lys | Thr | Asp | Lys | Thr | Trp | Lys | Val | Lys | Val |
| | | | 100 | | | | | 105 | | | | | 110 | | |
| Ala | Asp | Asn | Gly | Ala | Thr | Thr | Ile | Glu | Asp | Ile | Asp | Pro | Asp | Lys | Val |
| | | | 115 | | | | | 120 | | | | | 125 | | |
| Glu | Lys | Arg | Lys | Glu | Ala | Leu | Asn | Gly | Gln | Tyr | Pro | Glu | Ser | Ala | Ile |
| | 130 | | | | | 135 | | | | | 140 | | | | |
| Tyr | Glu | Asp | Thr | Lys | Glu | Ser | Tyr | Pro | Leu | Val | Lys | Val | Glu | Asp | Ser |
| 145 | | | | | 150 | | | | | 155 | | | | | 160 |
| Lys | Val | Gly | Asn | Gln | Tyr | Lys | Ala | Leu | Asn | Pro | Ile | Asn | Gly | Glu | Asp |
| | | | | 165 | | | | | 170 | | | | | 175 | |
| Gly | Arg | Arg | Glu | Ile | Thr | Glu | Gly | Trp | Leu | Ser | Lys | Lys | Ile | Lys | Lys |
| | | | 180 | | | | | 185 | | | | | 190 | | |
| Val | Asn | Glu | Leu | Asp | Lys | Asn | Lys | Tyr | Lys | Ile | Glu | Leu | Thr | Val | Glu |
| | | | 195 | | | | | 200 | | | | | 205 | | |
| Gly | Lys | Thr | Ile | Val | Glu | Thr | Lys | Glu | Leu | Asn | Gln | Pro | Leu | Asp | Val |
| | 210 | | | | | 215 | | | | | 220 | | | | |
| Val | Leu | Leu | Leu | Asp | Asn | Ser | Asn | Ser | Met | Asn | Asn | Glu | Arg | Ala | His |
| 225 | | | | | 230 | | | | | 235 | | | | | 240 |
| Asn | Ser | Gln | Arg | Ala | Leu | Lys | Ala | Gly | Glu | Ala | Val | Glu | Lys | Leu | Ile |
| | | | | 245 | | | | | 250 | | | | | 255 | |
| Asp | Lys | Ile | Thr | Ser | Asn | Lys | Asp | Asn | Arg | Val | Ala | Leu | Val | Thr | Tyr |
| | | | 260 | | | | | 265 | | | | | 270 | | |
| Ala | Ser | Thr | Ile | Phe | Asp | Gly | Thr | Glu | Ala | Thr | Val | Ser | Lys | Gly | Val |
| | | | 275 | | | | | 280 | | | | | 285 | | |
| Ala | Asp | Arg | Asn | Gly | Lys | Ala | Leu | Asn | Asp | Ser | Val | Ser | Trp | Asp | Tyr |
| | 290 | | | | | 295 | | | | | 300 | | | | |
| His | Lys | Thr | Thr | Phe | Thr | Ala | Thr | Thr | His | Asn | Tyr | Ser | Tyr | Leu | Asn |
| 305 | | | | | 310 | | | | | 315 | | | | | 320 |
| Leu | Thr | Asn | Asp | Ala | Asn | Glu | Val | Asn | Ile | Leu | Lys | Ser | Arg | Ile | Pro |
| | | | | 325 | | | | | 330 | | | | | 335 | |
| Lys | Glu | Ala | Glu | His | Ile | Asn | Gly | Asn | Arg | Thr | Leu | Tyr | Gln | Phe | Gly |
| | | | 340 | | | | | 345 | | | | | 350 | | |
| Ala | Thr | Phe | Thr | Gln | Lys | Ala | Leu | Met | Lys | Ala | Asn | Glu | Ile | Leu | Glu |
| | | | 355 | | | | | 360 | | | | | 365 | | |
| Thr | Gln | Ser | Ser | Asn | Asp | Arg | Lys | Lys | Val | Ile | Phe | His | Val | Thr | Asp |
| | 370 | | | | | 375 | | | | | 380 | | | | |

```
Gly Val Pro Thr Met Ser Tyr Ala Ile Asn Phe Asn Pro Tyr Ile Ser
385                 390                 395                 400

Thr Ser Tyr Gln Asn Gln Phe Lys Ser Phe Leu Asn Lys Thr Pro Asp
            405                 410                 415

Arg Ser Gly Ile Leu Gln Glu Asp Phe Ile Ile Asn Gly Asp Asp Tyr
        420                 425                 430

Gln Ile Val Lys Gly Asp Gly Glu Ser Phe Lys Leu Phe Ser Asp Arg
        435                 440                 445

Lys Val Pro Val Pro Gly Gly Thr Thr Gln Ala Ala Tyr Gln Val Pro
    450                 455                 460

Gln Asn Gln Leu Ser Val Met Ser Asn Glu Gly Tyr Ala Ile Asn Arg
465                 470                 475                 480

Gly Tyr Ile Tyr Leu Tyr Trp Arg Asp Tyr Asn Trp Val Tyr Pro Phe
            485                 490                 495

Asp Pro Lys Thr Lys Thr Val Ser Ala Thr Lys Gln Ile Lys Thr His
        500                 505                 510

Gly Glu Pro Thr Thr Leu Tyr Phe Asn Gly Asn Ile Lys Pro Lys Gly
        515                 520                 525

Tyr Asp Ile Phe Thr Val Gly Ile Gly Val Asn Gly Asp Pro Gly Ala
    530                 535                 540

Thr Pro Leu Glu Ala Lys Glu Phe Met Gln Ser Ile Ser Ser Lys Thr
545                 550                 555                 560

Glu Asn Tyr Thr Asn Val Asp Asp Thr Asn Lys Ile Tyr Asp Glu Leu
            565                 570                 575

Asn Lys Tyr Phe Lys Thr Ile Val Glu Glu Lys His Ser Ile Val Asp
        580                 585                 590

Gly Asn Val Thr Asp Pro Met Gly Glu Met Ile Glu Phe Gln Leu Lys
        595                 600                 605

Asp Gly Gln Ser Phe Thr His Asp Asp Tyr Val Leu Val Gly Asn Asp
    610                 615                 620

Gly Ser Gln Leu Lys Asn Gly Val Ala Leu Gly Gly Pro Asn Ser Asp
625                 630                 635                 640

Gly Gly Ile Leu Lys Asp Val Thr Val Thr Tyr Asp Lys Thr Ser Gln
            645                 650                 655

Thr Ile Lys Ile Asn His Leu Asn Leu Gly Ser Gly Gln Lys Val Val
        660                 665                 670

Leu Thr Tyr Asp Val Arg Leu Lys Glu Asn Tyr Ile Ser Asn Lys Phe
        675                 680                 685

Tyr Asn Thr Asn Asn Arg Thr Thr Leu Ser Pro Lys Ser Glu Lys Glu
    690                 695                 700

Pro Asn Thr Ile Arg Asp Phe Pro Ile Pro Lys Ile Arg Asp Val Arg
705                 710                 715                 720

Glu Phe Pro Val Leu Thr Ile Ser Asn Gln Lys Lys Met Gly Glu Val
            725                 730                 735

Glu Phe Ile Lys Val Asn Lys Asp Lys His Ser Glu Ser Leu Leu Gly
        740                 745                 750

Ala Lys Phe Gln Leu Gln Ile Glu Lys Asp Phe Ser Gly Tyr Lys Gln
        755                 760                 765

Phe Val Pro Glu Gly Ser Asp Val Thr Thr Lys Asn Asp Gly Lys Ile
    770                 775                 780

Tyr Phe Lys Ala Leu Gln Asp Gly Asn Tyr Lys Leu Tyr Glu Ile Ser
785                 790                 795                 800

Ser Pro Asp Gly Tyr Ile Glu Val Lys Thr Lys Pro Val Val Thr Phe
```

```
                805                 810                 815
Thr Ile Gln Asn Gly Glu Val Thr Asn Leu Lys Gln Asp Pro Asn Ala
        820                 825                 830

Asn Lys Asn Gln Ile Gly Tyr Phe Glu Glu Asp Gly Lys His Leu Ile
        835                 840                 845

Thr Asn Thr Pro Lys Arg Pro Pro Ser Val Phe Pro Lys Thr Gly Gly
        850                 855                 860

Ile Gly Thr Ile Val Tyr Ile Leu Val Gly Cys Thr Leu Met Ile Val
865                 870                 875                 880

Ala Thr Gly Ser Phe Arg Arg Asn Gln Gln
                885                 890

<210> SEQ ID NO 27
<211> LENGTH: 84
<212> TYPE: PRT
<213> ORGANISM: S. agalactiae

<400> SEQUENCE: 27

Leu Ala Gly Val Val Phe Glu Leu Tyr Glu Lys Asn Gly Arg Thr Pro
1               5                   10                  15

Ile Arg Val Lys Asn Gly Val His Ser Gln Asp Ile Asp Ala Ala Lys
            20                  25                  30

His Leu Glu Thr Asp Ser Ser Gly His Ile Arg Ile Ser Gly Leu Ile
        35                  40                  45

His Gly Asp Tyr Val Leu Lys Glu Ile Glu Thr Gln Ser Gly Tyr Gln
    50                  55                  60

Ile Gly Gln Ala Glu Thr Ala Val Thr Ile Glu Lys Ser Lys Thr Val
65                  70                  75                  80

Thr Val Thr Ile

<210> SEQ ID NO 28
<211> LENGTH: 71
<212> TYPE: PRT
<213> ORGANISM: S. agalactiae

<400> SEQUENCE: 28

Leu Ser Gly Val Ile Phe Val Leu Tyr Asp Asn Gln Asn Gln Pro Val
1               5                   10                  15

Arg Phe Lys Asn Gly Arg Phe Thr Thr Asp Gln Asp Gly Ile Thr Ser
            20                  25                  30

Leu Val Thr Asp Asp Lys Gly Glu Ile Glu Val Glu Gly Leu Leu Pro
        35                  40                  45

Gly Lys Tyr Ile Phe Arg Glu Val Lys Ala Leu Thr Gly Tyr Arg Ile
    50                  55                  60

Ser Met Lys Asp Ala Val Val
65                  70

<210> SEQ ID NO 29
<211> LENGTH: 74
<212> TYPE: PRT
<213> ORGANISM: S. agalactiae

<400> SEQUENCE: 29

Leu Gly Lys Val Ile Val Lys Lys Thr Gly Asp Asn Ala Thr Pro Leu
1               5                   10                  15

Gly Lys Ala Thr Phe Val Leu Lys Asn Asp Asn Asp Lys Ser Glu Thr
            20                  25                  30
```

```
Ser His Glu Thr Val Glu Gly Ser Gly Glu Ala Thr Phe Glu Asn Ile
         35                  40                  45

Lys Pro Gly Asp Tyr Thr Leu Arg Glu Glu Thr Ala Pro Ile Gly Tyr
 50                  55                  60

Lys Lys Thr Asp Lys Thr Trp Lys Val Lys
 65                  70
```

<210> SEQ ID NO 30
<211> LENGTH: 61
<212> TYPE: PRT
<213> ORGANISM: S. agalactiae

<400> SEQUENCE: 30

```
Leu Ser Lys Ala Thr Phe Val Leu Lys Thr Thr Ala His Pro Glu Ser
 1               5                  10                  15

Lys Ile Glu Lys Val Thr Ala Glu Leu Thr Gly Glu Ala Thr Phe Asp
                 20                  25                  30

Asn Leu Ile Pro Gly Asp Tyr Thr Leu Ser Glu Glu Thr Ala Pro Glu
         35                  40                  45

Gly Tyr Lys Lys Thr Asn Gln Thr Trp Gln Val Lys Val
 50                  55                  60
```

<210> SEQ ID NO 31
<211> LENGTH: 85
<212> TYPE: PRT
<213> ORGANISM: S. agalactiae

<400> SEQUENCE: 31

```
Leu Gln Gly Ala Ile Phe Val Leu Lys Asn Ala Thr Gly Gln Phe Leu
 1               5                  10                  15

Asn Phe Asn Asp Thr Asn Asn Val Glu Trp Gly Thr Glu Ala Asn Ala
                 20                  25                  30

Thr Glu Tyr Thr Thr Gly Ala Asp Gly Ile Ile Thr Ile Thr Gly Leu
         35                  40                  45

Lys Glu Gly Thr Tyr Tyr Leu Val Glu Lys Lys Ala Pro Leu Gly Tyr
 50                  55                  60

Asn Leu Leu Asp Asn Ser Gln Lys Val Ile Leu Gly Asp Gly Ala Thr
 65                  70                  75                  80

Asp Thr Thr Asn Ser
                 85
```

<210> SEQ ID NO 32
<211> LENGTH: 80
<212> TYPE: PRT
<213> ORGANISM: S. agalactiae

<400> SEQUENCE: 32

```
Leu Ala Gly Ala Val Phe Asp Ile Tyr Glu Ser Asp Ala Asn Gly Asn
 1               5                  10                  15

Lys Ala Ser His Pro Met Tyr Ser Gly Leu Val Thr Asn Asp Lys Gly
                 20                  25                  30

Leu Leu Leu Val Asp Ala Asn Asn Tyr Leu Ser Leu Pro Val Gly Lys
         35                  40                  45

Tyr Tyr Leu Thr Glu Thr Lys Ala Pro Pro Gly Tyr Leu Leu Pro Lys
 50                  55                  60

Asn Asp Ile Ser Val Leu Val Ile Ser Thr Gly Val Thr Phe Glu Gln
 65                  70                  75                  80
```

<210> SEQ ID NO 33
<211> LENGTH: 93
<212> TYPE: PRT
<213> ORGANISM: S. agalactiae

<400> SEQUENCE: 33

Leu Gly Gly Ala Glu Phe Asp Leu Leu Ala Ser Asp Gly Thr Ala Val
1               5                   10                  15

Lys Trp Thr Asp Ala Leu Ile Lys Ala Asn Thr Asn Lys Asn Tyr Ile
            20                  25                  30

Ala Gly Glu Ala Val Thr Gly Gln Pro Ile Lys Leu Lys Ser His Thr
        35                  40                  45

Asp Gly Thr Phe Glu Ile Lys Gly Leu Ala Tyr Ala Val Asp Ala Asn
    50                  55                  60

Ala Glu Gly Thr Ala Val Thr Tyr Lys Leu Lys Glu Thr Lys Ala Pro
65                  70                  75                  80

Glu Gly Tyr Val Ile Pro Asp Lys Glu Ile Glu Phe Thr
                85                  90

<210> SEQ ID NO 34
<211> LENGTH: 78
<212> TYPE: PRT
<213> ORGANISM: S. agalactiae

<400> SEQUENCE: 34

Leu Leu Gly Ala Lys Phe Gln Leu Gln Ile Glu Lys Asp Phe Ser Gly
1               5                   10                  15

Tyr Lys Gln Phe Val Pro Glu Gly Ser Asp Val Thr Thr Lys Asn Asp
            20                  25                  30

Gly Lys Ile Tyr Phe Lys Ala Leu Gln Asp Gly Asn Tyr Lys Leu Tyr
        35                  40                  45

Glu Ile Ser Ser Pro Asp Gly Tyr Ile Glu Val Lys Thr Lys Pro Val
    50                  55                  60

Val Thr Phe Thr Ile Gln Asn Gly Glu Val Thr Asn Leu Lys
65                  70                  75

<210> SEQ ID NO 35
<211> LENGTH: 87
<212> TYPE: PRT
<213> ORGANISM: S. agalactiae

<400> SEQUENCE: 35

Leu Thr Lys Ala Val His Lys Thr Gln Pro Leu Gln Thr Phe Asp Asn
1               5                   10                  15

Leu Pro Ala Glu Gly Ile Val Ala Asn Asn Leu Pro Gln Gly Ile Tyr
            20                  25                  30

Leu Phe Ile Gln Thr Lys Thr Ala Gln Gly Tyr Glu Leu Met Ser Pro
        35                  40                  45

Phe Ile Leu Ser Ile Pro Lys Asp Gly Lys Tyr Asp Ile Thr Ala Phe
    50                  55                  60

Glu Lys Met Ser Pro Leu Asn Ala Lys Pro Lys Lys Glu Glu Thr Ile
65                  70                  75                  80

Thr Pro Thr Val Thr His Gln
                85

<210> SEQ ID NO 36
<211> LENGTH: 14
<212> TYPE: PRT
<213> ORGANISM: S. agalactiae

```
<400> SEQUENCE: 36

Gly Asp Tyr Val Leu Lys Glu Ile Glu Thr Gln Ser Gly Tyr
1               5                   10

<210> SEQ ID NO 37
<211> LENGTH: 14
<212> TYPE: PRT
<213> ORGANISM: S. agalactiae

<400> SEQUENCE: 37

Gly Lys Tyr Ile Phe Arg Glu Ala Lys Ala Leu Thr Gly Tyr
1               5                   10

<210> SEQ ID NO 38
<211> LENGTH: 14
<212> TYPE: PRT
<213> ORGANISM: S. agalactiae

<400> SEQUENCE: 38

Gly Asp Tyr Thr Leu Arg Glu Glu Thr Ala Pro Ile Gly Tyr
1               5                   10

<210> SEQ ID NO 39
<211> LENGTH: 14
<212> TYPE: PRT
<213> ORGANISM: S. agalactiae

<400> SEQUENCE: 39

Gly Asp Tyr Thr Leu Ser Glu Glu Thr Ala Pro Glu Gly Tyr
1               5                   10

<210> SEQ ID NO 40
<211> LENGTH: 14
<212> TYPE: PRT
<213> ORGANISM: S. agalactiae

<400> SEQUENCE: 40

Gly Thr Tyr Tyr Leu Val Glu Lys Lys Ala Pro Leu Gly Tyr
1               5                   10

<210> SEQ ID NO 41
<211> LENGTH: 14
<212> TYPE: PRT
<213> ORGANISM: S. agalactiae

<400> SEQUENCE: 41

Gly Lys Tyr Tyr Leu Thr Glu Thr Lys Ala Pro Pro Gly Tyr
1               5                   10

<210> SEQ ID NO 42
<211> LENGTH: 17
<212> TYPE: PRT
<213> ORGANISM: S. agalactiae

<400> SEQUENCE: 42

Gly Thr Ala Val Thr Tyr Lys Leu Lys Glu Thr Lys Ala Pro Glu Gly
1               5                   10                  15

Tyr

<210> SEQ ID NO 43
<211> LENGTH: 14
<212> TYPE: PRT
<213> ORGANISM: S. agalactiae
```

-continued

<400> SEQUENCE: 43

Gly Asn Tyr Lys Leu Tyr Glu Ile Ser Ser Pro Asp Gly Tyr
1               5                   10

<210> SEQ ID NO 44
<211> LENGTH: 14
<212> TYPE: PRT
<213> ORGANISM: S. agalactiae

<400> SEQUENCE: 44

Gly Ile Tyr Leu Phe Ile Gln Thr Lys Thr Ala Gln Gly Tyr
1               5                   10

<210> SEQ ID NO 45
<211> LENGTH: 307
<212> TYPE: PRT
<213> ORGANISM: S. agalactiae

<400> SEQUENCE: 45

Met Lys Gln Thr Leu Lys Leu Met Phe Ser Phe Leu Leu Met Leu Gly
1               5                   10                  15

Thr Met Phe Gly Ile Ser Gln Thr Val Leu Ala Gln Glu Thr His Gln
            20                  25                  30

Leu Thr Ile Val His Leu Glu Ala Arg Asp Ile Asp Arg Pro Asn Pro
        35                  40                  45

Gln Leu Glu Ile Ala Pro Lys Glu Gly Thr Pro Ile Glu Gly Val Leu
    50                  55                  60

Tyr Gln Leu Tyr Gln Leu Lys Ser Thr Glu Asp Gly Asp Leu Leu Ala
65                  70                  75                  80

His Trp Asn Ser Leu Thr Ile Thr Glu Leu Lys Lys Gln Ala Gln Gln
                85                  90                  95

Val Phe Glu Ala Thr Thr Asn Gln Gln Gly Lys Ala Thr Phe Asn Gln
            100                 105                 110

Leu Pro Asp Gly Ile Tyr Tyr Gly Leu Ala Val Lys Ala Gly Glu Lys
        115                 120                 125

Asn Arg Asn Val Ser Ala Phe Leu Val Asp Leu Ser Glu Asp Lys Val
    130                 135                 140

Ile Tyr Pro Lys Ile Ile Trp Ser Thr Gly Glu Leu Asp Leu Leu Lys
145                 150                 155                 160

Val Gly Val Asp Gly Asp Thr Lys Lys Pro Leu Ala Gly Val Val Phe
                165                 170                 175

Glu Leu Tyr Glu Lys Asn Gly Arg Thr Pro Ile Arg Val Lys Asn Gly
            180                 185                 190

Val His Ser Gln Asp Ile Asp Ala Ala Lys His Leu Glu Thr Asp Ser
        195                 200                 205

Ser Gly His Ile Arg Ile Ser Gly Leu Ile His Gly Asp Tyr Val Leu
    210                 215                 220

Lys Glu Ile Glu Thr Gln Ser Gly Tyr Gln Ile Gly Gln Ala Glu Thr
225                 230                 235                 240

Ala Val Thr Ile Glu Lys Ser Lys Thr Val Thr Val Thr Ile Glu Asn
                245                 250                 255

Lys Lys Val Pro Thr Pro Lys Val Pro Ser Arg Gly Gly Leu Ile Pro
            260                 265                 270

Lys Thr Gly Glu Gln Gln Ala Met Ala Leu Val Ile Ile Gly Gly Ile
        275                 280                 285

```
Leu Ile Ala Leu Ala Leu Arg Leu Leu Ser Lys His Arg Lys His Gln
            290                 295                 300
Asn Lys Asp
305

<210> SEQ ID NO 46
<211> LENGTH: 308
<212> TYPE: PRT
<213> ORGANISM: S. agalactiae

<400> SEQUENCE: 46

Met Lys Lys Ile Arg Lys Ser Leu Gly Leu Leu Cys Cys Phe Leu
 1               5                  10                  15

Gly Leu Val Gln Leu Ala Phe Phe Ser Val Ala Ser Val Asn Ala Asp
                20                  25                  30

Thr Pro Asn Gln Leu Thr Ile Thr Gln Ile Gly Leu Gln Pro Asn Thr
            35                  40                  45

Thr Glu Glu Gly Ile Ser Tyr Arg Leu Trp Thr Val Thr Asp Asn Leu
        50                  55                  60

Lys Val Asp Leu Leu Ser Gln Met Thr Asp Ser Glu Leu Asn Gln Lys
 65                 70                  75                  80

Tyr Lys Ser Ile Leu Thr Ser Pro Thr Asp Thr Asn Gly Gln Thr Lys
                85                  90                  95

Ile Ala Leu Pro Asn Gly Ser Tyr Phe Gly Arg Ala Tyr Lys Ala Asp
            100                 105                 110

Gln Ser Val Ser Thr Ile Val Pro Phe Tyr Ile Glu Leu Pro Asp Asp
        115                 120                 125

Lys Leu Ser Asn Gln Leu Gln Ile Asn Pro Lys Arg Lys Val Glu Thr
130                 135                 140

Gly Arg Leu Lys Leu Ile Lys Tyr Thr Lys Glu Gly Lys Ile Lys Lys
145                 150                 155                 160

Arg Leu Ser Gly Val Ile Phe Val Leu Tyr Asp Asn Gln Asn Gln Pro
                165                 170                 175

Val Arg Phe Lys Asn Gly Arg Phe Thr Thr Asp Gln Asp Gly Ile Thr
            180                 185                 190

Ser Leu Val Thr Asp Asp Lys Gly Glu Ile Glu Val Glu Gly Leu Leu
        195                 200                 205

Pro Gly Lys Tyr Ile Phe Arg Glu Val Lys Ala Leu Thr Gly Tyr Arg
    210                 215                 220

Ile Ser Met Lys Asp Ala Val Val Ala Val Ala Asn Lys Thr Gln
225                 230                 235                 240

Glu Val Glu Val Glu Asn Glu Lys Glu Thr Pro Pro Thr Asn Pro
                245                 250                 255

Lys Pro Ser Gln Pro Leu Phe Pro Gln Ser Phe Leu Pro Lys Thr Gly
            260                 265                 270

Met Ile Ile Gly Gly Gly Leu Thr Ile Leu Gly Cys Ile Ile Leu Gly
        275                 280                 285

Ile Leu Phe Ile Phe Leu Arg Lys Thr Lys Asn Ser Lys Ser Glu Arg
    290                 295                 300

Asn Asp Thr Val
305

<210> SEQ ID NO 47
<211> LENGTH: 890
<212> TYPE: PRT
<213> ORGANISM: S. agalactiae
```

<400> SEQUENCE: 47

```
Met Lys Lys Arg Gln Lys Ile Trp Arg Gly Leu Ser Val Thr Leu Leu
 1               5                  10                  15
Ile Leu Ser Gln Ile Pro Phe Gly Ile Leu Val Gln Gly Glu Thr Gln
             20                  25                  30
Asp Thr Asn Gln Ala Leu Gly Lys Val Ile Val Lys Lys Thr Gly Asp
         35                  40                  45
Asn Ala Thr Pro Leu Gly Lys Ala Thr Phe Val Leu Lys Asn Asp Asn
 50                  55                  60
Asp Lys Ser Glu Thr Ser His Glu Thr Val Glu Gly Ser Gly Glu Ala
 65                  70                  75                  80
Thr Phe Glu Asn Ile Lys Pro Gly Asp Tyr Thr Leu Arg Glu Glu Thr
                 85                  90                  95
Ala Pro Ile Gly Tyr Lys Lys Thr Asp Lys Thr Trp Lys Val Lys Val
                100                 105                 110
Ala Asp Asn Gly Ala Thr Ile Ile Glu Gly Met Asp Ala Asp Lys Ala
            115                 120                 125
Glu Lys Arg Lys Glu Val Leu Asn Ala Gln Tyr Pro Lys Ser Ala Ile
130                 135                 140
Tyr Glu Asp Thr Lys Glu Asn Tyr Pro Leu Val Asn Val Glu Gly Ser
145                 150                 155                 160
Lys Val Gly Glu Gln Tyr Lys Ala Leu Asn Pro Ile Asn Gly Lys Asp
                165                 170                 175
Gly Arg Arg Glu Ile Ala Glu Gly Trp Leu Ser Lys Lys Ile Thr Gly
            180                 185                 190
Val Asn Asp Leu Asp Lys Asn Lys Tyr Lys Ile Glu Leu Thr Val Glu
        195                 200                 205
Gly Lys Thr Thr Val Glu Thr Lys Glu Leu Asn Gln Pro Leu Asp Val
210                 215                 220
Val Val Leu Leu Asp Asn Ser Asn Ser Met Asn Asn Glu Arg Ala Asn
225                 230                 235                 240
Asn Ser Gln Arg Ala Leu Lys Ala Gly Glu Ala Val Glu Lys Leu Ile
                245                 250                 255
Asp Lys Ile Thr Ser Asn Lys Asp Asn Arg Val Ala Leu Val Thr Tyr
            260                 265                 270
Ala Ser Thr Ile Phe Asp Gly Thr Glu Ala Thr Val Ser Lys Gly Val
        275                 280                 285
Ala Asp Gln Asn Gly Lys Ala Leu Asn Asp Ser Val Ser Trp Asp Tyr
290                 295                 300
His Lys Thr Thr Phe Thr Ala Thr Thr His Asn Tyr Ser Tyr Leu Asn
305                 310                 315                 320
Leu Thr Asn Asp Ala Asn Glu Val Asn Ile Leu Lys Ser Arg Ile Pro
                325                 330                 335
Lys Glu Ala Glu His Ile Asn Gly Asp Arg Thr Leu Tyr Gln Phe Gly
            340                 345                 350
Ala Thr Phe Thr Gln Lys Ala Leu Met Lys Ala Asn Glu Ile Leu Glu
        355                 360                 365
Thr Gln Ser Ser Asn Ala Arg Lys Lys Leu Ile Phe His Val Thr Asp
370                 375                 380
Gly Val Pro Thr Met Ser Tyr Ala Ile Asn Phe Asn Pro Tyr Ile Ser
385                 390                 395                 400
Thr Ser Tyr Gln Asn Gln Phe Asn Ser Phe Leu Asn Lys Ile Pro Asp
```

```
                    405                 410                 415
    Arg Ser Gly Ile Leu Gln Glu Asp Phe Ile Ile Asn Gly Asp Asp Tyr
                420                 425                 430

Gln Ile Val Lys Gly Asp Gly Glu Ser Phe Lys Leu Phe Ser Asp Arg
                435                 440                 445

Lys Val Pro Val Thr Gly Thr Thr Gln Ala Ala Tyr Arg Val Pro
    450                 455                 460

Gln Asn Gln Leu Ser Val Met Ser Asn Glu Gly Tyr Ala Ile Asn Ser
    465                 470                 475                 480

Gly Tyr Ile Tyr Leu Tyr Trp Arg Asp Tyr Asn Trp Val Tyr Pro Phe
                485                 490                 495

Asp Pro Lys Thr Lys Val Ser Ala Thr Lys Gln Ile Lys Thr His
                500                 505                 510

Gly Glu Pro Thr Thr Leu Tyr Phe Asn Gly Asn Ile Arg Pro Lys Gly
                515                 520                 525

Tyr Asp Ile Phe Thr Val Gly Ile Gly Val Asn Gly Asp Pro Gly Ala
                530                 535                 540

Thr Pro Leu Glu Ala Glu Lys Phe Met Gln Ser Ile Ser Ser Lys Thr
    545                 550                 555                 560

Glu Asn Tyr Thr Asn Val Asp Asp Thr Asn Lys Ile Tyr Asp Glu Leu
                565                 570                 575

Asn Lys Tyr Phe Lys Thr Ile Val Glu Lys His Ser Ile Val Asp
                580                 585                 590

Gly Asn Val Thr Asp Pro Met Gly Glu Met Ile Glu Phe Gln Leu Lys
                595                 600                 605

Asn Gly Gln Ser Phe Thr His Asp Asp Tyr Val Leu Val Gly Asn Asp
                610                 615                 620

Gly Ser Gln Leu Lys Asn Gly Val Ala Leu Gly Pro Asn Ser Asp
    625                 630                 635                 640

Gly Gly Ile Leu Lys Asp Val Thr Val Thr Tyr Asp Lys Thr Ser Gln
                645                 650                 655

Thr Ile Lys Ile Asn His Leu Asn Leu Gly Ser Gly Gln Lys Val Val
                660                 665                 670

Leu Thr Tyr Asp Val Arg Leu Lys Asp Asn Tyr Ile Ser Asn Lys Phe
                675                 680                 685

Tyr Asn Thr Asn Asn Arg Thr Thr Leu Ser Pro Lys Ser Glu Lys Glu
                690                 695                 700

Pro Asn Thr Ile Arg Asp Phe Pro Ile Pro Lys Ile Arg Asp Val Arg
    705                 710                 715                 720

Glu Phe Pro Val Leu Thr Ile Ser Asn Gln Lys Lys Met Gly Glu Val
                725                 730                 735

Glu Phe Ile Lys Val Asn Lys Asp Lys His Ser Glu Ser Leu Leu Gly
                740                 745                 750

Ala Lys Phe Gln Leu Gln Ile Glu Lys Asp Phe Ser Gly Tyr Lys Gln
                755                 760                 765

Phe Val Pro Glu Gly Ser Asp Val Thr Thr Lys Asn Asp Gly Lys Ile
    770                 775                 780

Tyr Phe Lys Ala Leu Gln Asp Gly Asn Tyr Lys Leu Tyr Glu Ile Ser
    785                 790                 795                 800

Ser Pro Asp Gly Tyr Ile Glu Val Lys Thr Lys Pro Val Val Thr Phe
                805                 810                 815

Thr Ile Gln Asn Gly Glu Val Thr Asn Leu Lys Ala Asp Pro Asn Ala
                820                 825                 830
```

Asn Lys Asn Gln Ile Gly Tyr Leu Glu Gly Asn Gly Lys His Leu Ile
    835                 840                 845

Thr Asn Thr Pro Lys Arg Pro Pro Gly Val Phe Pro Lys Thr Gly Gly
    850                 855                 860

Ile Gly Thr Ile Val Tyr Ile Leu Val Gly Ser Thr Phe Met Ile Leu
865                 870                 875                 880

Thr Ile Cys Ser Phe Arg Arg Lys Gln Leu
            885                 890

<210> SEQ ID NO 48
<211> LENGTH: 901
<212> TYPE: PRT
<213> ORGANISM: S. agalactiae

<400> SEQUENCE: 48

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Val Lys Lys Thr Asp
        35                  40                  45

Asp Gln Asn Lys Pro Leu Ser Lys Ala Thr Phe Val Leu Lys Thr Thr
    50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn Gln Glu Glu Leu Asp Lys Gln Tyr Pro
    130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
        195                 200                 205

Lys Ile Glu Leu Thr Val Ser Gly Lys Thr Ile Val Lys Pro Val Asp
    210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
            260                 265                 270

Ser Asp Asn Arg Val Ala Leu Val Thr Tyr Gly Ser Asp Ile Phe Asp
        275                 280                 285

Gly Arg Ser Val Asp Val Val Lys Gly Phe Lys Glu Asp Asp Lys Tyr
    290                 295                 300

Tyr Gly Leu Gln Thr Lys Phe Thr Ile Gln Thr Glu Asn Tyr Ser His

```
             305                 310                 315                 320
Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
                340                 345                 350

Glu Gln Gln Lys Glu Tyr Tyr Leu Ser Lys Val Gly Glu Thr Phe Thr
                355                 360                 365

Met Lys Ala Phe Met Glu Ala Asp Asp Ile Leu Ser Gln Val Asn Arg
                370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
                405                 410                 415

Phe Glu Gln Met Lys Lys Asn Gly Tyr Leu Asn Lys Ser Asn Phe Leu
                420                 425                 430

Leu Thr Asp Lys Pro Asp Asp Ile Lys Gly Asn Gly Glu Ser Tyr Phe
                435                 440                 445

Leu Phe Pro Leu Asp Ser Tyr Gln Thr Gln Ile Ile Ser Gly Asn Leu
                450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
                485                 490                 495

Tyr Ile Asn Ser Leu Lys Gln Lys Asn Tyr Asp Ile Phe Asn Phe Gly
                500                 505                 510

Ile Asp Ile Ser Gly Phe Arg Gln Val Tyr Asn Glu Glu Tyr Lys Lys
                515                 520                 525

Asn Gln Asp Gly Thr Phe Gln Lys Leu Lys Glu Ala Phe Lys Leu
                530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Phe Glu Thr Ile Leu Thr Lys Glu
                580                 585                 590

Asn Ser Ile Val Asn Gly Thr Ile Glu Asp Pro Met Gly Asp Lys Ile
                595                 600                 605

Asn Leu Gln Leu Gly Asn Gly Gln Ile Leu Gln Pro Ser Asp Tyr Thr
                610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
                645                 650                 655

Ile Gly Asn Lys Leu Tyr Val Arg Gly Leu Asn Leu Gly Glu Gly Gln
                660                 665                 670

Lys Val Thr Leu Thr Tyr Asp Val Lys Leu Asp Asp Ser Phe Ile Ser
                675                 680                 685

Asn Lys Phe Tyr Asp Thr Asn Gly Arg Thr Thr Leu Asn Pro Lys Ser
                690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735
```

-continued

Glu Ile Glu Phe Ile Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
            755                 760                 765

Tyr Leu Pro Ile Lys Asn Asn Asn Ser Lys Val Val Thr Gly Glu Asn
            770                 775                 780

Gly Lys Ile Ser Tyr Lys Asp Leu Lys Asp Gly Lys Tyr Gln Leu Ile
785                 790                 795                 800

Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
            820                 825                 830

Asn Lys Gln Ile Ser Glu Tyr His Glu Glu Gly Asp Lys His Leu Ile
            835                 840                 845

Thr Asn Thr His Ile Pro Pro Lys Gly Ile Ile Pro Lys Thr Gly Gly
            850                 855                 860

Lys Gly Ile Leu Ser Phe Ile Leu Ile Gly Gly Ala Met Met Ser Ile
865                 870                 875                 880

Ala Gly Gly Ile Tyr Ile Trp Lys Arg Tyr Lys Lys Ser Ser Asp Met
                885                 890                 895

Ser Ile Lys Lys Asp
                900

<210> SEQ ID NO 49
<211> LENGTH: 502
<212> TYPE: PRT
<213> ORGANISM: S. agalactiae

<400> SEQUENCE: 49

Met Lys Lys Lys Met Ile Gln Ser Leu Leu Val Ala Ser Leu Ala Phe
1               5                   10                  15

Gly Met Ala Val Ser Pro Val Thr Pro Ile Ala Phe Ala Ala Glu Thr
            20                  25                  30

Gly Thr Ile Thr Val Gln Asp Thr Gln Lys Gly Ala Thr Tyr Lys Ala
            35                  40                  45

Tyr Lys Val Phe Asp Ala Glu Ile Asp Asn Ala Asn Val Ser Asp Ser
        50                  55                  60

Asn Lys Asp Gly Ala Ser Tyr Leu Ile Pro Gln Gly Lys Glu Ala Glu
65                  70                  75                  80

Tyr Lys Ala Ser Thr Asp Phe Asn Ser Leu Phe Thr Thr Thr Thr Asn
                85                  90                  95

Gly Gly Arg Thr Tyr Val Thr Lys Lys Asp Thr Ala Ser Ala Asn Glu
            100                 105                 110

Ile Ala Thr Trp Ala Lys Ser Ile Ser Ala Asn Thr Thr Pro Val Ser
            115                 120                 125

Thr Val Thr Glu Ser Asn Asn Asp Gly Thr Glu Val Ile Asn Val Ser
        130                 135                 140

Gln Tyr Gly Tyr Tyr Val Ser Ser Thr Val Asn Asn Gly Ala Val
145                 150                 155                 160

Ile Met Val Thr Ser Val Thr Pro Asn Ala Thr Ile His Glu Lys Asn
                165                 170                 175

Thr Asp Ala Thr Trp Gly Asp Gly Gly Lys Thr Val Asp Gln Lys
            180                 185                 190

Thr Tyr Ser Val Gly Asp Thr Val Lys Tyr Thr Ile Thr Tyr Lys Asn

```
                195                 200                 205
Ala Val Asn Tyr His Gly Thr Glu Lys Val Gln Tyr Val Ile Lys
    210                 215                 220

Asp Thr Met Pro Ser Ala Ser Val Val Asp Leu Asn Glu Gly Ser Tyr
225                 230                 235                 240

Glu Val Thr Ile Thr Asp Gly Ser Gly Asn Ile Thr Thr Leu Thr Gln
                245                 250                 255

Gly Ser Glu Lys Ala Thr Gly Lys Tyr Asn Leu Leu Glu Glu Asn Asn
            260                 265                 270

Asn Phe Thr Ile Thr Ile Pro Trp Ala Ala Thr Asn Thr Pro Thr Gly
        275                 280                 285

Asn Thr Gln Asn Gly Ala Asn Asp Asp Phe Phe Tyr Lys Gly Ile Asn
    290                 295                 300

Thr Ile Thr Val Thr Tyr Thr Gly Val Leu Lys Ser Gly Ala Lys Pro
305                 310                 315                 320

Gly Ser Ala Asp Leu Pro Glu Asn Thr Asn Ile Ala Thr Ile Asn Pro
                325                 330                 335

Asn Thr Ser Asn Asp Asp Pro Gly Gln Lys Val Thr Val Arg Asp Gly
            340                 345                 350

Gln Ile Thr Ile Lys Lys Ile Asp Gly Ser Thr Lys Ala Ser Leu Gln
        355                 360                 365

Gly Ala Ile Phe Val Leu Lys Asn Ala Thr Gly Gln Phe Leu Asn Phe
    370                 375                 380

Asn Asp Thr Asn Asn Val Glu Trp Gly Thr Glu Ala Asn Ala Thr Glu
385                 390                 395                 400

Tyr Thr Thr Gly Ala Asp Gly Ile Ile Thr Ile Thr Gly Leu Lys Glu
                405                 410                 415

Gly Thr Tyr Tyr Leu Val Glu Lys Lys Ala Pro Leu Gly Tyr Asn Leu
            420                 425                 430

Leu Asp Asn Ser Gln Lys Val Ile Leu Gly Asp Gly Ala Thr Asp Thr
        435                 440                 445

Thr Asn Ser Asp Asn Leu Leu Val Asn Pro Thr Val Glu Asn Asn Lys
    450                 455                 460

Gly Thr Glu Leu Pro Ser Thr Gly Gly Ile Gly Thr Thr Ile Phe Tyr
465                 470                 475                 480

Ile Ile Gly Ala Ile Leu Val Ile Gly Ala Gly Ile Val Leu Val Ala
                485                 490                 495

Arg Arg Arg Leu Arg Ser
            500

<210> SEQ ID NO 50
<211> LENGTH: 1434
<212> TYPE: PRT
<213> ORGANISM: S. agalactiae

<400> SEQUENCE: 50

Met Leu Lys Lys Cys Gln Thr Phe Ile Ile Glu Ser Leu Lys Lys Lys
1               5                   10                  15

Lys His Pro Lys Glu Trp Lys Ile Ile Met Trp Ser Leu Met Ile Leu
            20                  25                  30

Thr Thr Phe Leu Thr Thr Tyr Phe Leu Ile Leu Pro Ala Ile Thr Val
        35                  40                  45

Glu Glu Thr Lys Thr Asp Asp Val Gly Ile Thr Leu Glu Asn Lys Asn
    50                  55                  60
```

```
Ser Ser Gln Val Thr Ser Thr Ser Ser Ser Gln Ser Ser Val Glu
 65                  70                  75                  80

Gln Ser Lys Pro Gln Thr Pro Ala Ser Ser Val Thr Glu Thr Ser Ser
                 85                  90                  95

Ser Glu Glu Ala Ala Tyr Arg Glu Pro Leu Met Phe Arg Gly Ala
                100                 105                 110

Asp Tyr Thr Val Thr Val Thr Leu Thr Lys Glu Ala Lys Ile Pro Lys
                115                 120                 125

Asn Ala Asp Leu Lys Val Thr Glu Leu Lys Asp Asn Ser Ala Thr Phe
130                 135                 140

Lys Asp Tyr Lys Lys Ala Leu Thr Glu Val Ala Lys Gln Asp Ser
145                 150                 155                 160

Glu Ile Lys Asn Phe Lys Leu Tyr Asp Ile Thr Ile Glu Ser Asn Gly
                165                 170                 175

Lys Glu Ala Glu Pro Gln Ala Pro Val Lys Val Glu Val Asn Tyr Asp
                180                 185                 190

Lys Pro Leu Glu Ala Ser Asp Glu Asn Leu Lys Val Val His Phe Lys
            195                 200                 205

Asp Asp Gly Gln Thr Glu Val Leu Lys Ser Lys Asp Thr Ala Glu Thr
210                 215                 220

Lys Asn Thr Ser Ser Asp Val Ala Phe Lys Thr Asp Ser Phe Ser Ile
225                 230                 235                 240

Tyr Ala Ile Val Gln Glu Asp Asn Thr Glu Val Pro Arg Leu Thr Tyr
                245                 250                 255

His Phe Gln Asn Asn Asp Gly Thr Asp Tyr Asp Phe Leu Thr Ala Ser
                260                 265                 270

Gly Met Gln Val His His Gln Ile Ile Lys Asp Gly Glu Ser Leu Gly
            275                 280                 285

Glu Val Gly Ile Pro Thr Ile Lys Ala Gly Glu His Phe Asn Gly Trp
            290                 295                 300

Tyr Thr Tyr Asp Pro Thr Thr Gly Lys Tyr Gly Asp Pro Val Lys Phe
305                 310                 315                 320

Gly Glu Pro Ile Thr Val Thr Glu Thr Lys Glu Ile Cys Val Arg Pro
                325                 330                 335

Phe Met Ser Lys Val Ala Thr Val Thr Leu Tyr Asp Asp Ser Ala Gly
                340                 345                 350

Lys Ser Ile Leu Glu Arg Tyr Gln Val Pro Leu Asp Ser Ser Gly Asn
            355                 360                 365

Gly Thr Ala Asp Leu Ser Ser Phe Lys Val Ser Pro Pro Thr Ser Thr
370                 375                 380

Leu Leu Phe Val Gly Trp Ser Lys Thr Gln Asn Gly Ala Pro Leu Ser
385                 390                 395                 400

Glu Ser Glu Ile Gln Ala Leu Pro Val Ser Ser Asp Ile Ser Leu Tyr
                405                 410                 415

Pro Val Phe Lys Glu Ser Tyr Gly Val Glu Phe Asn Thr Gly Asp Leu
            420                 425                 430

Ser Thr Gly Val Thr Tyr Ile Ala Pro Arg Arg Val Leu Thr Gly Gln
            435                 440                 445

Pro Ala Ser Thr Ile Lys Pro Asn Asp Pro Thr Arg Pro Gly Tyr Thr
            450                 455                 460

Phe Ala Gly Trp Tyr Thr Ala Ala Ser Gly Gly Ala Ala Phe Asp Phe
465                 470                 475                 480

Asn Gln Val Leu Thr Lys Asp Thr Thr Leu Tyr Ala His Trp Ser Pro
```

```
            485                 490                 495
Ala Gln Thr Thr Tyr Thr Ile Asn Tyr Trp Gln Gln Ser Ala Thr Asp
                500                 505                 510

Asn Lys Asn Ala Thr Asp Ala Gln Lys Thr Tyr Glu Tyr Ala Gly Gln
            515                 520                 525

Val Thr Arg Ser Gly Leu Ser Leu Ser Asn Gln Thr Leu Thr Gln Gln
        530                 535                 540

Asp Ile Asn Asp Lys Leu Pro Thr Gly Phe Lys Val Asn Asn Thr Arg
545                 550                 555                 560

Thr Glu Thr Ser Val Met Ile Lys Asp Asp Gly Ser Ser Val Val Asn
                565                 570                 575

Val Tyr Tyr Asp Arg Lys Leu Ile Thr Ile Lys Phe Ala Lys Tyr Gly
            580                 585                 590

Gly Tyr Ser Leu Pro Glu Tyr Tyr Ser Tyr Asn Trp Ser Ser Asp
        595                 600                 605

Ala Asp Thr Tyr Thr Gly Leu Tyr Gly Thr Thr Leu Ala Ala Asn Gly
610                 615                 620

Tyr Gln Trp Lys Thr Gly Ala Trp Gly Tyr Leu Ala Asn Val Gly Asn
625                 630                 635                 640

Asn Gln Val Gly Thr Gly Met Ser Tyr Leu Gly Glu Phe Ile Leu
                645                 650                 655

Pro Asn Asp Thr Val Asp Ser Asp Val Ile Lys Leu Phe Pro Lys Gly
            660                 665                 670

Asn Ile Val Gln Thr Tyr Arg Phe Phe Lys Gln Gly Leu Asp Gly Thr
        675                 680                 685

Tyr Ser Leu Ala Asp Thr Gly Gly Ala Gly Ala Asp Glu Phe Thr
    690                 695                 700

Phe Thr Glu Lys Tyr Leu Gly Phe Asn Val Lys Tyr Tyr Gln Arg Leu
705                 710                 715                 720

Tyr Pro Asp Asn Tyr Leu Phe Asp Gln Tyr Ala Ser Gln Thr Ser Ala
                725                 730                 735

Gly Val Lys Val Pro Ile Ser Asp Glu Tyr Tyr Asp Arg Tyr Gly Ala
            740                 745                 750

Tyr His Lys Asp Tyr Leu Asn Leu Val Val Trp Tyr Glu Arg Asn Ser
        755                 760                 765

Tyr Lys Ile Lys Tyr Leu Asp Pro Leu Asp Asn Thr Glu Leu Pro Asn
    770                 775                 780

Phe Pro Val Lys Asp Val Leu Tyr Glu Gln Asn Leu Ser Ser Tyr Ala
785                 790                 795                 800

Pro Asp Thr Thr Thr Val Gln Pro Lys Pro Ser Arg Pro Gly Tyr Val
                805                 810                 815

Trp Asp Gly Lys Trp Tyr Lys Asp Gln Ala Gln Thr Val Phe Asp
            820                 825                 830

Phe Asn Thr Thr Met Pro Pro His Asp Val Lys Val Tyr Ala Gly Trp
        835                 840                 845

Gln Lys Val Thr Tyr Arg Val Asn Ile Asp Pro Asn Gly Gly Arg Leu
    850                 855                 860

Ser Lys Thr Asp Asp Thr Tyr Leu Asp Leu His Tyr Gly Asp Arg Ile
865                 870                 875                 880

Pro Asp Tyr Thr Asp Ile Thr Arg Asp Tyr Ile Gln Asp Pro Ser Gly
                885                 890                 895

Thr Tyr Tyr Tyr Lys Tyr Asp Ser Arg Asp Lys Asp Pro Asp Ser Thr
            900                 905                 910
```

```
Lys Asp Ala Tyr Tyr Thr Thr Asp Thr Ser Leu Ser Asn Val Asp Thr
    915                 920                 925

Thr Thr Lys Tyr Lys Tyr Val Lys Asp Ala Tyr Lys Leu Val Gly Trp
    930                 935                 940

Tyr Tyr Val Asn Pro Asp Gly Ser Ile Arg Pro Tyr Asn Phe Ser Gly
945                 950                 955                 960

Ala Val Thr Gln Asp Ile Asn Leu Arg Ala Ile Trp Arg Lys Ala Gly
                965                 970                 975

Asp Tyr His Ile Ile Tyr Ser Asn Asp Ala Val Gly Thr Asp Gly Lys
            980                 985                 990

Pro Ala Leu Asp Ala Ser Gly Gln Gln Leu Gln Thr Ser Asn Glu Pro
    995                 1000                1005

Thr Asp Pro Asp Ser Tyr Asp Asp Gly Ser His Ser Ala Leu Leu Arg
    1010                1015                1020

Arg Pro Thr Met Pro Asp Gly Tyr Arg Phe Arg Gly Trp Trp Tyr Asn
1025                1030                1035                1040

Gly Lys Ile Tyr Asn Pro Tyr Asp Ser Ile Asp Ala His Leu
                1045                1050                1055

Ala Asp Ala Asn Lys Asn Ile Thr Ile Lys Pro Val Ile Ile Pro Val
                1060                1065                1070

Gly Asp Ile Lys Leu Glu Asp Thr Ser Ile Lys Tyr Asn Gly Asn Gly
                1075                1080                1085

Gly Thr Arg Val Glu Asn Gly Asn Val Val Thr Gln Val Glu Thr Pro
                1090                1095                1100

Arg Met Glu Leu Asn Ser Thr Thr Ile Pro Glu Asn Gln Tyr Phe
1105                1110                1115                1120

Thr Arg Thr Gly Tyr Asn Leu Ile Gly Trp His His Asp Lys Asp Leu
                1125                1130                1135

Ala Asp Thr Gly Arg Val Glu Phe Thr Ala Gly Gln Ser Ile Gly Ile
                1140                1145                1150

Asp Asn Asn Pro Asp Ala Thr Asn Thr Leu Tyr Ala Val Trp Gln Pro
    1155                1160                1165

Lys Glu Tyr Thr Val Arg Val Ser Lys Thr Val Val Gly Leu Asp Glu
    1170                1175                1180

Asp Lys Thr Lys Asp Phe Leu Phe Asn Pro Ser Glu Thr Leu Gln Gln
1185                1190                1195                1200

Glu Asn Phe Pro Leu Arg Asp Gly Gln Thr Lys Glu Phe Lys Val Pro
                1205                1210                1215

Tyr Gly Thr Ser Ile Ser Ile Asp Glu Gln Ala Tyr Asp Glu Phe Lys
                1220                1225                1230

Val Ser Glu Ser Ile Thr Glu Lys Asn Leu Ala Thr Gly Glu Ala Asp
    1235                1240                1245

Lys Thr Tyr Asp Ala Thr Gly Leu Gln Ser Leu Thr Val Ser Gly Asp
    1250                1255                1260

Val Asp Ile Ser Phe Thr Asn Thr Arg Ile Lys Gln Lys Val Arg Leu
1265                1270                1275                1280

Gln Lys Val Asn Val Glu Asn Asp Asn Asn Phe Leu Ala Gly Ala Val
                1285                1290                1295

Phe Asp Ile Tyr Glu Ser Asp Ala Asn Gly Asn Lys Ala Ser His Pro
                1300                1305                1310

Met Tyr Ser Gly Leu Val Thr Asn Asp Lys Gly Leu Leu Leu Val Asp
                1315                1320                1325
```

-continued

```
Ala Asn Asn Tyr Leu Ser Leu Pro Val Gly Lys Tyr Tyr Leu Thr Glu
    1330                1335                1340

Thr Lys Ala Pro Pro Gly Tyr Leu Leu Pro Lys Asn Asp Ile Ser Val
1345                1350                1355                1360

Leu Val Ile Ser Thr Gly Val Thr Phe Glu Gln Asn Gly Asn Asn Ala
                1365                1370                1375

Thr Pro Ile Lys Glu Asn Leu Val Asp Gly Ser Thr Val Tyr Thr Phe
            1380                1385                1390

Lys Ile Thr Asn Ser Lys Gly Thr Glu Leu Pro Ser Thr Gly Gly Ile
                1395                1400                1405

Gly Thr His Ile Tyr Ile Leu Val Gly Leu Ala Leu Ala Leu Pro Ser
    1410                1415                1420

Gly Leu Ile Leu Tyr Tyr Arg Lys Lys Ile
1425                1430

<210> SEQ ID NO 51
<211> LENGTH: 554
<212> TYPE: PRT
<213> ORGANISM: S. agalactiae

<400> SEQUENCE: 51

Met Lys Leu Ser Lys Lys Leu Leu Phe Ser Ala Ala Val Leu Thr Met
1               5                   10                  15

Val Ala Gly Ser Thr Val Glu Pro Val Ala Gln Phe Ala Thr Gly Met
            20                  25                  30

Ser Ile Val Arg Ala Ala Glu Val Ser Gln Glu Arg Pro Ala Lys Thr
        35                  40                  45

Thr Val Asn Ile Tyr Lys Leu Gln Ala Asp Ser Tyr Lys Ser Glu Ile
50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
                85                  90                  95

Lys Arg Tyr Lys Val Lys Thr Asp Ile Ser Val Asp Glu Leu Lys Lys
            100                 105                 110

Leu Thr Thr Val Glu Ala Ala Asp Ala Lys Val Gly Thr Ile Leu Glu
        115                 120                 125

Glu Gly Val Ser Leu Pro Gln Lys Thr Asn Ala Gln Gly Leu Val Val
    130                 135                 140

Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
            180                 185                 190

Glu Ile Asn Ile Tyr Pro Lys Asn Val Val Thr Asp Glu Pro Lys Thr
        195                 200                 205

Asp Lys Asp Val Lys Lys Leu Gly Gln Asp Ala Gly Tyr Thr Ile
    210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
            260                 265                 270
```

-continued

```
Arg Asp Glu His Tyr Thr Ile Asp Glu Pro Thr Val Asp Asn Gln Asn
            275                 280                 285
Thr Leu Lys Ile Thr Phe Lys Pro Glu Lys Phe Lys Glu Ile Ala Glu
        290                 295                 300
Leu Leu Lys Gly Met Thr Leu Val Lys Asn Gln Asp Ala Leu Asp Lys
305                 310                 315                 320
Ala Thr Ala Asn Thr Asp Asp Ala Ala Phe Leu Glu Ile Pro Val Ala
                325                 330                 335
Ser Thr Ile Asn Glu Lys Ala Val Leu Gly Lys Ala Ile Glu Asn Thr
            340                 345                 350
Phe Glu Leu Gln Tyr Asp His Thr Pro Asp Lys Ala Asp Asn Pro Lys
        355                 360                 365
Pro Ser Asn Pro Pro Arg Lys Pro Glu Val His Thr Gly Gly Lys Arg
370                 375                 380
Phe Val Lys Lys Asp Ser Thr Glu Thr Gln Thr Leu Gly Gly Ala Glu
385                 390                 395                 400
Phe Asp Leu Leu Ala Ser Asp Gly Thr Ala Val Lys Trp Thr Asp Ala
                405                 410                 415
Leu Ile Lys Ala Asn Thr Asn Lys Asn Tyr Ile Ala Gly Glu Ala Val
            420                 425                 430
Thr Gly Gln Pro Ile Lys Leu Lys Ser His Thr Asp Gly Thr Phe Glu
        435                 440                 445
Ile Lys Gly Leu Ala Tyr Ala Val Asp Ala Asn Ala Glu Gly Thr Ala
450                 455                 460
Val Thr Tyr Lys Leu Lys Glu Thr Lys Ala Pro Glu Gly Tyr Val Ile
465                 470                 475                 480
Pro Asp Lys Glu Ile Glu Phe Thr Val Ser Gln Thr Ser Tyr Asn Thr
                485                 490                 495
Lys Pro Thr Asp Ile Thr Val Asp Ser Ala Asp Ala Thr Pro Asp Thr
            500                 505                 510
Ile Lys Asn Asn Lys Arg Pro Ser Ile Pro Asn Thr Gly Gly Ile Gly
        515                 520                 525
Thr Ala Ile Phe Val Ala Ile Gly Ala Ala Val Met Ala Phe Ala Val
530                 535                 540
Lys Gly Met Lys Arg Arg Thr Lys Asp Asn
545                 550
```

<210> SEQ ID NO 52
<211> LENGTH: 223
<212> TYPE: PRT
<213> ORGANISM: S. agalactiae

<400> SEQUENCE: 52

```
Met Ile Tyr Lys Lys Ile Leu Lys Ile Thr Leu Leu Leu Leu Phe Ser
1               5                   10                  15
Leu Ser Thr Gln Leu Val Ser Ala Asp Thr Asn Asp Gln Met Lys Thr
            20                  25                  30
Gly Ser Ile Thr Ile Gln Asn Lys Tyr Asn Asn Gln Gly Ile Ala Gly
        35                  40                  45
Gly Asn Leu Leu Val Tyr Gln Val Ala Gln Ala Lys Asp Val Asp Gly
    50                  55                  60
Asn Gln Val Phe Thr Leu Thr Thr Pro Phe Gln Gly Ile Gly Ile Lys
65                  70                  75                  80
Asp Asp Asp Leu Thr Gln Val Asn Leu Asp Ser Asn Gln Ala Lys Tyr
```

```
                        85                  90                  95
Val Asn Leu Leu Thr Lys Ala Val His Lys Thr Gln Pro Leu Gln Thr
                100                 105                 110

Phe Asp Asn Leu Pro Ala Glu Gly Ile Val Ala Asn Leu Pro Gln
            115                 120                 125

Gly Ile Tyr Leu Phe Ile Gln Thr Lys Thr Ala Gln Gly Tyr Glu Leu
        130                 135                 140

Met Ser Pro Phe Ile Leu Ser Ile Pro Lys Asp Gly Lys Tyr Asp Ile
145                 150                 155                 160

Thr Ala Phe Glu Lys Met Ser Pro Leu Asn Ala Lys Pro Lys Lys Glu
                165                 170                 175

Glu Thr Ile Thr Pro Thr Val Thr His Gln Thr Lys Gly Lys Leu Pro
                180                 185                 190

Phe Thr Gly Gln Val Trp Trp Pro Ile Pro Ile Leu Ile Met Ser Gly
            195                 200                 205

Leu Leu Cys Leu Ile Ile Ala Leu Lys Trp Arg Arg Arg Arg Asp
        210                 215                 220

<210> SEQ ID NO 53
<211> LENGTH: 136
<212> TYPE: PRT
<213> ORGANISM: S. pneumoniae

<400> SEQUENCE: 53

Leu Ala Gly Ala Glu Phe Val Ile Ala Asn Ala Asp Asn Ala Gly Gln
1               5                   10                  15

Tyr Leu Ala Arg Lys Ala Asp Lys Val Ser Gln Glu Glu Lys Gln Leu
            20                  25                  30

Val Val Thr Thr Lys Asp Ala Leu Asp Arg Ala Val Ala Ala Tyr Asn
        35                  40                  45

Ala Leu Thr Ala Gln Gln Gln Thr Gln Gln Glu Lys Glu Lys Val Asp
    50                  55                  60

Lys Ala Gln Ala Ala Tyr Asn Ala Val Ile Ala Ala Asn Asn Ala
65                  70                  75                  80

Phe Glu Trp Val Ala Asp Lys Asp Asn Glu Asn Val Val Lys Leu Val
                85                  90                  95

Ser Asp Ala Gln Gly Arg Phe Glu Ile Thr Gly Leu Leu Ala Gly Thr
            100                 105                 110

Tyr Tyr Leu Glu Glu Thr Lys Gln Pro Ala Gly Tyr Ala Leu Leu Thr
        115                 120                 125

Ser Arg Gln Lys Phe Glu Val Thr
    130                 135

<210> SEQ ID NO 54
<211> LENGTH: 69
<212> TYPE: PRT
<213> ORGANISM: S. pneumoniae

<400> SEQUENCE: 54

Leu Gly Asp Ala Val Phe Glu Leu Lys Asn Asn Thr Asp Gly Thr Thr
1               5                   10                  15

Val Ser Gln Arg Thr Glu Ala Gln Thr Gly Glu Ala Ile Phe Ser Asn
            20                  25                  30

Ile Lys Pro Gly Thr Tyr Thr Leu Thr Glu Ala Gln Pro Pro Val Gly
        35                  40                  45

Tyr Lys Pro Ser Thr Lys Gln Trp Thr Val Glu Val Glu Lys Asn Gly
```

```
                    50                  55                  60

Arg Thr Thr Val Gln
 65

<210> SEQ ID NO 55
<211> LENGTH: 79
<212> TYPE: PRT
<213> ORGANISM: S. pneumoniae

<400> SEQUENCE: 55

Leu Gln Gly Ala Met Phe Lys Val Met Lys Glu Ser Gly His Tyr
  1               5                  10                  15

Thr Pro Val Leu Gln Asn Gly Lys Glu Val Val Thr Ser Gly Lys
                 20                  25                  30

Asp Gly Arg Phe Arg Val Glu Gly Leu Glu Tyr Gly Thr Tyr Leu
                 35                  40                  45

Trp Glu Leu Gln Ala Pro Thr Gly Tyr Val Gln Leu Thr Ser Pro Val
             50                  55                  60

Ser Phe Thr Ile Gly Lys Asp Thr Arg Lys Glu Leu Val Thr Val
 65                  70                  75

<210> SEQ ID NO 56
<211> LENGTH: 82
<212> TYPE: PRT
<213> ORGANISM: S. pneumoniae

<400> SEQUENCE: 56

Leu Arg Gly Ala Val Phe Ser Leu Gln Lys Gln His Pro Asp Tyr Pro
  1               5                  10                  15

Asp Ile Tyr Gly Ala Ile Asp Gln Asn Gly Thr Tyr Gln Asn Val Arg
                 20                  25                  30

Thr Gly Glu Asp Gly Lys Leu Thr Phe Lys Asn Leu Ser Asp Gly Lys
                 35                  40                  45

Tyr Arg Leu Phe Glu Asn Ser Glu Pro Ala Gly Tyr Lys Pro Val Gln
             50                  55                  60

Asn Lys Pro Ile Val Ala Phe Gln Ile Val Asn Gly Glu Val Arg Asp
 65                  70                  75                  80

Val Thr

<210> SEQ ID NO 57
<211> LENGTH: 89
<212> TYPE: PRT
<213> ORGANISM: S. pneumoniae

<400> SEQUENCE: 57

Leu Glu Gly Val Gly Phe Lys Leu Val Ser Val Ala Arg Asp Val Ser
  1               5                  10                  15

Glu Lys Glu Val Pro Leu Ile Gly Glu Tyr Arg Tyr Ser Ser Ser Gly
                 20                  25                  30

Gln Val Gly Arg Thr Leu Tyr Thr Asp Lys Asn Gly Glu Ile Phe Val
                 35                  40                  45

Thr Asn Leu Pro Ile Gly Asn Tyr Arg Phe Lys Glu Val Glu Pro Leu
             50                  55                  60

Ala Gly Tyr Ala Val Thr Thr Leu Asp Thr Asp Val Gln Leu Val Asp
 65                  70                  75                  80

His Gln Leu Val Thr Ile Thr Val Val
                 85
```

```
<210> SEQ ID NO 58
<211> LENGTH: 14
<212> TYPE: PRT
<213> ORGANISM: S. pneumoniae

<400> SEQUENCE: 58

Gly Thr Tyr Ile Leu Thr Glu Thr Lys Ser Pro Gln Gly Tyr
 1               5                  10

<210> SEQ ID NO 59
<211> LENGTH: 14
<212> TYPE: PRT
<213> ORGANISM: S. pneumoniae

<400> SEQUENCE: 59

Gly Thr Tyr Tyr Leu Glu Glu Thr Lys Gln Pro Ala Gly Tyr
 1               5                  10

<210> SEQ ID NO 60
<211> LENGTH: 14
<212> TYPE: PRT
<213> ORGANISM: S. pneumoniae

<400> SEQUENCE: 60

Gly Thr Tyr Thr Leu Thr Glu Ala Gln Pro Pro Val Gly Tyr
 1               5                  10

<210> SEQ ID NO 61
<211> LENGTH: 14
<212> TYPE: PRT
<213> ORGANISM: S. pneumoniae

<400> SEQUENCE: 61

Gly Lys Tyr Arg Leu Phe Glu Asn Ser Glu Pro Ala Gly Tyr
 1               5                  10

<210> SEQ ID NO 62
<211> LENGTH: 14
<212> TYPE: PRT
<213> ORGANISM: S. pneumoniae

<400> SEQUENCE: 62

Gly Asn Tyr Arg Phe Lys Glu Val Glu Pro Leu Ala Gly Tyr
 1               5                  10

<210> SEQ ID NO 63
<211> LENGTH: 665
<212> TYPE: PRT
<213> ORGANISM: S. pneumoniae

<400> SEQUENCE: 63

Met Lys Ser Ile Asn Lys Phe Leu Thr Met Leu Ala Ala Leu Leu Leu
 1               5                  10                  15

Thr Ala Ser Ser Leu Phe Ser Ala Ala Thr Val Phe Ala Ala Gly Thr
             20                  25                  30

Thr Thr Thr Ser Val Thr Val His Lys Leu Leu Ala Thr Asp Gly Asp
         35                  40                  45

Met Asp Lys Ile Ala Asn Glu Leu Glu Thr Gly Asn Tyr Ala Gly Asn
     50                  55                  60

Lys Val Gly Val Leu Pro Ala Asn Ala Lys Glu Ile Ala Gly Val Met
 65                  70                  75                  80

Phe Val Trp Thr Asn Thr Asn Asn Glu Ile Ile Asp Glu Asn Gly Gln
```

```
                        85                  90                  95
Thr Leu Gly Val Asn Ile Asp Pro Gln Thr Phe Lys Leu Ser Gly Ala
                100                 105                 110

Met Pro Ala Thr Ala Met Lys Lys Leu Thr Glu Ala Glu Gly Ala Lys
                115                 120                 125

Phe Asn Thr Ala Asn Leu Pro Ala Ala Lys Tyr Lys Ile Tyr Glu Ile
                135                 140
            130

His Ser Leu Ser Thr Tyr Val Gly Glu Asp Gly Ala Thr Leu Thr Gly
145                 150                 155                 160

Ser Lys Ala Val Pro Ile Glu Ile Glu Leu Pro Leu Asn Asp Val Val
                165                 170                 175

Asp Ala His Val Tyr Pro Lys Asn Thr Glu Ala Lys Pro Lys Ile Asp
                180                 185                 190

Lys Asp Phe Lys Gly Lys Ala Asn Pro Asp Thr Pro Arg Val Asp Lys
                195                 200                 205

Asp Thr Pro Val Asn His Gln Val Gly Asp Val Val Glu Tyr Glu Ile
            210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255

Thr Val Asp Asp Val Ala Leu Glu Ala Gly Asp Tyr Ala Leu Thr Glu
                260                 265                 270

Val Ala Thr Gly Phe Asp Leu Lys Leu Thr Asp Ala Gly Leu Ala Lys
            275                 280                 285

Val Asn Asp Gln Asn Ala Glu Lys Thr Val Lys Ile Thr Tyr Ser Ala
            290                 295                 300

Thr Leu Asn Asp Lys Ala Ile Val Glu Val Pro Glu Ser Asn Asp Val
305                 310                 315                 320

Thr Phe Asn Tyr Gly Asn Asn Pro Asp His Gly Asn Thr Pro Lys Pro
                325                 330                 335

Asn Lys Pro Asn Glu Asn Gly Asp Leu Thr Leu Thr Lys Thr Trp Val
                340                 345                 350

Asp Ala Thr Gly Ala Pro Ile Pro Ala Gly Ala Glu Ala Thr Phe Asp
            355                 360                 365

Leu Val Asn Ala Gln Thr Gly Lys Val Val Gln Thr Val Thr Leu Thr
            370                 375                 380

Thr Asp Lys Asn Thr Val Thr Val Asn Gly Leu Asp Lys Asn Thr Glu
385                 390                 395                 400

Tyr Lys Phe Val Glu Arg Ser Ile Lys Gly Tyr Ser Ala Asp Tyr Gln
                405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
            435                 440                 445

Lys Lys Phe Val Lys Val Asn Asp Lys Asp Asn Arg Leu Ala Gly Ala
            450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gln Leu Val Val Thr Thr
                485                 490                 495

Lys Asp Ala Leu Asp Arg Ala Val Ala Ala Tyr Asn Ala Leu Thr Ala
            500                 505                 510
```

```
Gln Gln Gln Thr Gln Gln Glu Lys Glu Lys Val Asp Lys Ala Gln Ala
            515                 520                 525

Ala Tyr Asn Ala Ala Val Ile Ala Ala Asn Asn Ala Phe Glu Trp Val
            530                 535                 540

Ala Asp Lys Asp Asn Glu Asn Val Val Lys Leu Val Ser Asp Ala Gln
545                 550                 555                 560

Gly Arg Phe Glu Ile Thr Gly Leu Leu Ala Gly Thr Tyr Tyr Leu Glu
                565                 570                 575

Glu Thr Lys Gln Pro Ala Gly Tyr Ala Leu Leu Thr Ser Arg Gln Lys
            580                 585                 590

Phe Glu Val Thr Ala Thr Ser Tyr Ser Ala Thr Gly Gln Gly Ile Glu
            595                 600                 605

Tyr Thr Ala Gly Ser Gly Lys Asp Asp Ala Thr Lys Val Val Asn Lys
            610                 615                 620

Lys Ile Thr Ile Pro Gln Thr Gly Gly Ile Gly Thr Ile Ile Phe Ala
625                 630                 635                 640

Val Ala Gly Ala Ala Ile Met Gly Ile Ala Val Tyr Ala Tyr Val Lys
                645                 650                 655

Asn Asn Lys Asp Glu Asp Gln Leu Ala
                660                 665

<210> SEQ ID NO 64
<211> LENGTH: 893
<212> TYPE: PRT
<213> ORGANISM: S. pneumoniae

<400> SEQUENCE: 64

Met Leu Asn Arg Glu Thr His Met Lys Lys Val Arg Lys Ile Phe Gln
 1               5                  10                  15

Lys Ala Val Ala Gly Leu Cys Cys Ile Ser Gln Leu Thr Ala Phe Ser
             20                  25                  30

Ser Ile Val Ala Leu Ala Glu Thr Pro Glu Thr Ser Pro Ala Ile Gly
         35                  40                  45

Lys Val Val Ile Lys Glu Thr Gly Glu Gly Ala Leu Leu Gly Asp
     50                  55                  60

Ala Val Phe Glu Leu Lys Asn Asn Thr Asp Gly Thr Thr Val Ser Gln
65                  70                  75                  80

Arg Thr Glu Ala Gln Thr Gly Glu Ala Ile Phe Ser Asn Ile Lys Pro
                 85                  90                  95

Gly Thr Tyr Thr Leu Thr Glu Ala Gln Pro Pro Val Gly Tyr Lys Pro
            100                 105                 110

Ser Thr Lys Gln Trp Thr Val Glu Val Glu Lys Asn Gly Arg Thr Thr
        115                 120                 125

Val Gln Gly Glu Gln Val Glu Asn Arg Glu Glu Ala Leu Ser Asp Gln
    130                 135                 140

Tyr Pro Gln Thr Gly Thr Tyr Pro Asp Val Gln Thr Pro Tyr Gln Ile
145                 150                 155                 160

Ile Lys Val Asp Gly Ser Glu Lys Asn Gly Gln His Lys Ala Leu Asn
                165                 170                 175

Pro Asn Pro Tyr Glu Arg Val Ile Pro Glu Gly Thr Leu Ser Lys Arg
            180                 185                 190

Ile Tyr Gln Val Asn Asn Leu Asp Asp Asn Gln Tyr Gly Ile Glu Leu
        195                 200                 205

Thr Val Ser Gly Lys Thr Val Tyr Glu Gln Lys Asp Lys Ser Val Pro
```

```
            210                 215                 220
Leu Asp Val Val Ile Leu Asp Asn Ser Asn Ser Met Ser Asn Ile
225                 230                 235                 240

Arg Asn Lys Asn Ala Arg Ala Glu Arg Ala Gly Glu Ala Thr Arg
                    245                 250                 255

Ser Leu Ile Asp Lys Ile Thr Ser Asp Ser Glu Asn Arg Val Ala Leu
                260                 265                 270

Val Thr Tyr Ala Ser Thr Ile Phe Asp Gly Thr Glu Phe Thr Val Glu
            275                 280                 285

Lys Gly Val Ala Asp Lys Asn Gly Lys Arg Leu Asn Asp Ser Leu Phe
        290                 295                 300

Trp Asn Tyr Asp Gln Thr Ser Phe Thr Thr Asn Thr Lys Asp Tyr Ser
305                 310                 315                 320

Tyr Leu Lys Leu Thr Asn Asp Lys Asn Asp Ile Val Glu Leu Lys Asn
                325                 330                 335

Lys Val Pro Thr Glu Ala Glu Asp His Asp Gly Asn Arg Leu Met Tyr
                340                 345                 350

Gln Phe Gly Ala Thr Phe Thr Gln Lys Ala Leu Met Lys Ala Asp Glu
            355                 360                 365

Ile Leu Thr Gln Gln Ala Arg Gln Asn Ser Gln Lys Val Ile Phe His
        370                 375                 380

Ile Thr Asp Gly Val Pro Thr Met Ser Tyr Pro Ile Asn Phe Asn His
385                 390                 395                 400

Ala Thr Phe Ala Pro Ser Tyr Gln Asn Gln Leu Asn Ala Phe Phe Ser
                405                 410                 415

Lys Ser Pro Asn Lys Asp Gly Ile Leu Leu Ser Asp Phe Ile Thr Gln
                420                 425                 430

Ala Thr Ser Gly Glu His Thr Ile Val Arg Gly Asp Gly Gln Ser Tyr
            435                 440                 445

Gln Met Phe Thr Asp Lys Thr Val Tyr Glu Lys Gly Ala Pro Ala Ala
        450                 455                 460

Phe Pro Val Lys Pro Glu Lys Tyr Ser Glu Met Lys Ala Ala Gly Tyr
465                 470                 475                 480

Ala Val Ile Gly Asp Pro Ile Asn Gly Gly Tyr Ile Trp Leu Asn Trp
                485                 490                 495

Arg Glu Ser Ile Leu Ala Tyr Pro Phe Asn Ser Asn Thr Ala Lys Ile
                500                 505                 510

Thr Asn His Gly Asp Pro Thr Arg Trp Tyr Tyr Asn Gly Asn Ile Ala
            515                 520                 525

Pro Asp Gly Tyr Asp Val Phe Thr Val Gly Ile Gly Ile Asn Gly Asp
        530                 535                 540

Pro Gly Thr Asp Glu Ala Thr Ala Thr Ser Phe Met Gln Ser Ile Ser
545                 550                 555                 560

Ser Lys Pro Glu Asn Tyr Thr Asn Val Thr Asp Thr Thr Lys Ile Leu
                565                 570                 575

Glu Gln Leu Asn Arg Tyr Phe His Thr Ile Val Thr Glu Lys Lys Ser
            580                 585                 590

Ile Glu Asn Gly Thr Ile Thr Asp Pro Met Gly Glu Leu Ile Asp Leu
        595                 600                 605

Gln Leu Gly Thr Asp Gly Arg Phe Asp Pro Ala Asp Tyr Thr Leu Thr
        610                 615                 620

Ala Asn Asp Gly Ser Arg Leu Glu Asn Gly Gln Ala Val Gly Gly Pro
625                 630                 635                 640
```

```
Gln Asn Asp Gly Gly Leu Leu Lys Asn Ala Lys Val Leu Tyr Asp Thr
                645                 650                 655

Thr Glu Lys Arg Ile Arg Val Thr Gly Leu Tyr Leu Gly Thr Asp Glu
            660                 665                 670

Lys Val Thr Leu Thr Tyr Asn Val Arg Leu Asn Asp Glu Phe Val Ser
        675                 680                 685

Asn Lys Phe Tyr Asp Thr Asn Gly Arg Thr Thr Leu His Pro Lys Glu
    690                 695                 700

Val Glu Gln Asn Thr Val Arg Asp Phe Pro Ile Pro Lys Ile Arg Asp
705                 710                 715                 720

Val Arg Lys Tyr Pro Glu Ile Thr Ile Ser Lys Glu Lys Lys Leu Gly
                725                 730                 735

Asp Ile Glu Phe Ile Lys Val Asn Lys Asn Asp Lys Lys Pro Leu Arg
            740                 745                 750

Gly Ala Val Phe Ser Leu Gln Lys Gln His Pro Asp Tyr Pro Asp Ile
        755                 760                 765

Tyr Gly Ala Ile Asp Gln Asn Gly Thr Tyr Gln Asn Val Arg Thr Gly
    770                 775                 780

Glu Asp Gly Lys Leu Thr Phe Lys Asn Leu Ser Asp Gly Lys Tyr Arg
785                 790                 795                 800

Leu Phe Glu Asn Ser Glu Pro Ala Gly Tyr Lys Pro Val Gln Asn Lys
                805                 810                 815

Pro Ile Val Ala Phe Gln Ile Val Asn Gly Glu Val Arg Asp Val Thr
            820                 825                 830

Ser Ile Val Pro Gln Asp Ile Pro Ala Gly Tyr Glu Phe Thr Asn Asp
        835                 840                 845

Lys His Tyr Ile Thr Asn Glu Pro Ile Pro Lys Arg Glu Tyr Pro
    850                 855                 860

Arg Thr Gly Gly Ile Gly Met Leu Pro Phe Tyr Leu Ile Gly Cys Met
865                 870                 875                 880

Met Met Gly Gly Val Leu Leu Tyr Thr Arg Lys His Pro
                885                 890

<210> SEQ ID NO 65
<211> LENGTH: 393
<212> TYPE: PRT
<213> ORGANISM: S. pneumoniae

<400> SEQUENCE: 65

Met Ile Ser Arg Ile Phe Phe Val Met Ala Leu Cys Phe Ser Leu Val
 1               5                  10                  15

Trp Gly Ala His Ala Val Gln Ala Gln Glu Asp His Thr Leu Val Leu
                20                  25                  30

Gln Leu Glu Asn Tyr Gln Glu Val Val Ser Gln Leu Pro Ser Arg Asp
            35                  40                  45

Gly His Arg Leu Gln Val Trp Lys Leu Asp Asp Ser Tyr Ser Tyr Asp
        50                  55                  60

Asp Arg Val Gln Ile Val Arg Asp Leu His Ser Trp Asp Glu Asn Lys
65                  70                  75                  80

Leu Ser Ser Phe Lys Lys Thr Ser Phe Glu Met Thr Phe Leu Glu Asn
                85                  90                  95

Gln Ile Glu Val Ser His Ile Pro Asn Gly Leu Tyr Tyr Val Arg Ser
            100                 105                 110

Ile Ile Gln Thr Asp Ala Val Ser Tyr Pro Ala Glu Phe Leu Phe Glu
```

```
                    115                 120                 125
Met Thr Asp Gln Thr Val Glu Pro Leu Val Ile Val Ala Lys Lys Thr
    130                 135                 140

Asp Thr Met Thr Thr Lys Val Lys Leu Ile Lys Val Asp Gln Asp His
145                 150                 155                 160

Asn Arg Leu Glu Gly Val Gly Phe Lys Leu Val Ser Val Ala Arg Asp
                165                 170                 175

Val Ser Glu Lys Glu Val Pro Leu Ile Gly Glu Tyr Arg Tyr Ser Ser
                180                 185                 190

Ser Gly Gln Val Gly Arg Thr Leu Tyr Thr Asp Lys Asn Gly Glu Ile
                195                 200                 205

Phe Val Thr Asn Leu Pro Leu Gly Asn Tyr Arg Phe Lys Glu Val Glu
    210                 215                 220

Pro Leu Ala Gly Tyr Ala Val Thr Thr Leu Asp Thr Asp Val Gln Leu
225                 230                 235                 240

Val Asp His Gln Leu Val Thr Ile Thr Val Val Asn Gln Lys Leu Pro
                245                 250                 255

Arg Gly Asn Val Asp Phe Met Lys Val Asp Gly Arg Thr Asn Thr Ser
                260                 265                 270

Leu Gln Gly Ala Met Phe Lys Val Met Lys Glu Ser Gly His Tyr
                275                 280                 285

Thr Pro Val Leu Gln Asn Gly Lys Glu Val Val Thr Ser Gly Lys
    290                 295                 300

Asp Gly Arg Phe Arg Val Glu Gly Leu Glu Tyr Gly Thr Tyr Tyr Leu
305                 310                 315                 320

Trp Glu Leu Gln Ala Pro Thr Gly Tyr Val Gln Leu Thr Ser Pro Val
                325                 330                 335

Ser Phe Thr Ile Gly Lys Asp Thr Arg Lys Glu Leu Val Thr Val Val
                340                 345                 350

Lys Asn Asn Lys Arg Pro Arg Ile Asp Val Pro Asp Thr Gly Glu Glu
                355                 360                 365

Thr Leu Tyr Ile Leu Met Leu Val Ala Ile Leu Leu Phe Gly Ser Gly
    370                 375                 380

Tyr Tyr Leu Thr Lys Lys Pro Asn Asn
385                 390

<210> SEQ ID NO 66
<211> LENGTH: 169
<212> TYPE: PRT
<213> ORGANISM: S. aureus

<400> SEQUENCE: 66

Ile Ser Gly Val Thr Val Thr Leu Lys Asp Glu Asn Gly Asn Val Leu
1               5                   10                  15

Lys Thr Val Thr Thr Asp Ala Asp Gly Lys Tyr Lys Phe Thr Asp Leu
                20                  25                  30

Asp Asn Gly Asn Tyr Lys Val Glu Phe Thr Thr Pro Glu Gly Tyr Thr
            35                  40                  45

Pro Thr Thr Val Thr Ser Gly Ser Asp Ile Glu Lys Asp Ser Asn Gly
        50                  55                  60

Leu Thr Thr Thr Gly Val Ile Asn Gly Ala Asp Asn Met Thr Leu Asp
65                  70                  75                  80

Ser Gly Phe Tyr Lys Thr Pro Lys Tyr Asn Leu Gly Asn Tyr Val Trp
                85                  90                  95
```

```
Glu Asp Thr Asn Lys Asp Gly Lys Gln Asp Ser Thr Glu Lys Gly Ile
            100                 105                 110

Ser Gly Val Thr Val Thr Leu Lys Asn Glu Asn Gly Glu Val Leu Gln
        115                 120                 125

Thr Thr Lys Thr Asp Lys Asp Gly Lys Tyr Gln Phe Thr Gly Leu Glu
        130                 135                 140

Asn Gly Thr Tyr Lys Val Glu Phe Glu Thr Pro Ser Gly Tyr Thr Pro
145                 150                 155                 160

Thr Gln Val Gly Ser Gly Thr Asp Glu
                165
```

<210> SEQ ID NO 67
<211> LENGTH: 68
<212> TYPE: PRT
<213> ORGANISM: S. aureus

<400> SEQUENCE: 67

```
Ile Ser Gly Val Thr Val Thr Leu Lys Asp Glu Asn Asp Lys Val Leu
1               5                   10                  15

Lys Thr Val Thr Thr Asp Glu Asn Gly Lys Tyr Gln Phe Thr Asp Leu
            20                  25                  30

Asn Asn Gly Thr Tyr Lys Val Glu Phe Glu Thr Pro Ser Gly Tyr Thr
        35                  40                  45

Pro Thr Ser Val Thr Ser Gly Asn Asp Thr Glu Lys Asp Ser Asn Gly
    50                  55                  60

Leu Thr Thr Thr
65
```

<210> SEQ ID NO 68
<211> LENGTH: 76
<212> TYPE: PRT
<213> ORGANISM: S. aureus

<400> SEQUENCE: 68

```
Ile Ala Asn Val Lys Phe Lys Leu Ser Lys Lys Asp Gly Ser Val Val
1               5                   10                  15

Lys Asp Asn Gln Lys Glu Ile Glu Ile Thr Asp Ala Asn Gly Ile
            20                  25                  30

Ala Asn Ile Lys Ala Leu Pro Ser Gly Asp Tyr Ile Leu Lys Glu Ile
        35                  40                  45

Glu Ala Pro Ala Pro Tyr Thr Phe Asp Lys Lys Glu Tyr Pro Phe
    50                  55                  60

Thr Met Lys Asp Thr Asp Asn Gln Gly Tyr Phe Thr
65                  70                  75
```

<210> SEQ ID NO 69
<211> LENGTH: 13
<212> TYPE: PRT
<213> ORGANISM: S. aureus

<400> SEQUENCE: 69

```
Gly Thr Tyr Lys Val Glu Phe Glu Thr Pro Ser Gly Tyr
1               5                   10
```

<210> SEQ ID NO 70
<211> LENGTH: 14
<212> TYPE: PRT
<213> ORGANISM: S. aureus

<400> SEQUENCE: 70

```
Gly Asp Tyr Ile Leu Lys Glu Ile Glu Ala Pro Ala Pro Tyr
1               5                   10

<210> SEQ ID NO 71
<211> LENGTH: 14
<212> TYPE: PRT
<213> ORGANISM: S. aureus

<400> SEQUENCE: 71

Gly Thr Tyr Ile Leu Thr Glu Thr Lys Ser Pro Gln Gly Tyr
1               5                   10

<210> SEQ ID NO 72
<211> LENGTH: 1347
<212> TYPE: PRT
<213> ORGANISM: S. aureus

<400> SEQUENCE: 72

Met Leu Asn Arg Glu Asn Lys Thr Ala Ile Thr Arg Lys Gly Met Val
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Gln Lys Glu Met Val
                85                  90                  95

Ser Ser Gln Gly Asn Glu Thr Thr Ser Asn Gly Asn Lys Ser Ile Glu
                100                 105                 110

Lys Glu Ser Val Gln Ser Thr Thr Gly Asn Lys Val Glu Val Ser Thr
            115                 120                 125

Ala Lys Ser Asp Glu Gln Ala Ser Pro Lys Ser Thr Asn Glu Asp Leu
        130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Ala Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Ala Glu Thr Leu Val Asp Asn Asn Ser Asn
        195                 200                 205

Ser Asn Asn Glu Asn Asn Ala Asp Ile Ile Leu Pro Lys Ser Thr Ala
    210                 215                 220

Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255

Leu Thr Val Val Asp Ala Asp Lys Asn Asn Lys Ile Val Pro Ala Gln
            260                 265                 270

Asp Tyr Leu Glu Leu Lys Ser Gln Ile Lys Val Asp Lys Val Lys
        275                 280                 285

Ser Gly Asp Tyr Phe Thr Ile Lys Tyr Ser Asp Thr Val Gln Val Tyr
    290                 295                 300
```

```
Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Gln Met Gly Ile Asn Tyr Ser Ile Tyr Met Asp Ala Asp Thr Ile Pro
                355                 360                 365

Val Ser Lys Asn Asp Val Glu Phe Asn Val Thr Ile Gly Asn Thr Thr
        370                 375                 380

Thr Lys Thr Thr Ala Asn Ile Gln Tyr Pro Asp Tyr Val Val Asn Glu
385                 390                 395                 400

Lys Asn Ser Ile Gly Ser Ala Phe Thr Glu Thr Val Ser His Val Gly
                405                 410                 415

Asn Lys Glu Asn Pro Gly Tyr Tyr Lys Gln Thr Ile Tyr Ile Asn Pro
            420                 425                 430

Ser Glu Asn Ser Leu Thr Asn Ala Lys Leu Lys Val Gln Ala Tyr His
        435                 440                 445

Ser Ser Tyr Pro Asn Asn Ile Gly Gln Ile Asn Lys Glu Val Thr Asp
    450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
                485                 490                 495

Lys Ile Thr Tyr Gly Asp Asn Asn Ser Ala Val Ile Asp Phe Gly Asn
            500                 505                 510

Ala Asp Ser Ala Tyr Val Val Met Val Asn Thr Lys Phe Gln Tyr Thr
        515                 520                 525

Thr Ser Glu Ser Pro Thr Leu Val Gln Met Val Thr Leu Ser Ser Asp
    530                 535                 540

Asn Ser Lys Ser Ala Ser Met Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590

Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
    610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
            660                 665                 670

Ala Asp Leu Gly Ile Tyr Lys Pro Lys Tyr Asn Leu Gly Asp Tyr Val
        675                 680                 685

Trp Glu Asp Thr Asn Lys Asn Gly Ile Gln Asp Gln Asp Glu Lys Gly
    690                 695                 700

Ile Ser Gly Val Thr Val Thr Leu Lys Asp Glu Asn Gly Asn Val Leu
705                 710                 715                 720
```

```
Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
            740                 745                 750

Pro Thr Thr Val Thr Ser Gly Ser Asp Ile Glu Lys Asp Ser Asn Gly
                755                 760                 765

Leu Thr Thr Thr Gly Val Ile Asn Gly Ala Asp Asn Met Thr Leu Asp
                770             775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
                835                 840                 845

Asn Gly Thr Tyr Lys Val Glu Phe Glu Thr Pro Ser Gly Tyr Thr Pro
                850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
                915                 920                 925

Val Thr Val Thr Leu Lys Asp Glu Asn Asp Lys Val Leu Lys Thr Val
                930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
                980                 985                 990

Thr Gly Val Ile Lys Asp Ala Asp Asn Met Thr Leu Asp Ser Gly Phe
                995                 1000                1005

Tyr Lys Thr Ser Lys Tyr Ser Leu Gly Asp Tyr Val Trp Tyr Asp Ser
                1010                1015                1020

Asn Lys Asp Gly Lys Gln Asp Ser Thr Glu Lys Gly Ile Lys Asp Val
1025                1030                1035                1040

Lys Val Thr Leu Leu Asn Glu Lys Gly Glu Val Ile Gly Thr Thr Lys
                1045                1050                1055

Thr Asp Glu Asn Gly Lys Tyr Arg Phe Asp Asn Leu Asp Ser Gly Lys
                1060                1065                1070

Tyr Lys Val Ile Phe Glu Lys Pro Ala Gly Leu Thr Gln Thr Gly Thr
                1075                1080                1085

Asn Thr Thr Glu Asp Asp Lys Asp Ala Asp Gly Gly Glu Val Asp Val
                1090                1095                1100

Thr Ile Thr Asp His Asp Asp Phe Thr Leu Asp Asn Gly Tyr Phe Glu
1105                1110                1115                1120

Glu Asp Thr Ser Asp Ser Asp Ser Asp Ser Asp Ser Asp Ser Asp Ser
                1125                1130                1135

Asp Ser Asp Ser Asp Ser Asp Ser Asp Ser Asp Ser Asp Ser Asp Ser
```

-continued

```
                1140                1145                1150
Asp Ser Asp Ser Asp Ser Asp Ser Asp Ser Asp Ser Asp Ser
            1155                1160                1165
Asp Ser Asp Ser Asp Ser Asp Ser Asp Ser Asp Ser Asp Ser
            1170                1175                1180
Asp Ser Asp Ser Asp Ser Asp Ser Asp Ser Asp Ser Asp Ser
1185                1190                1195                1200
Asp Ser Asp Ser Asp Ser Asp Ser Asp Ser Asp Ser Asp Ser
                1205                1210                1215
Asp Ser Asp Ser Asp Ser Asp Ser Asp Ser Asp Ser Glu Ser
            1220                1225                1230
Asp Ser Asp Ser Asp Ser Asp Ser Asp Ser Asp Ser Asp Ser
            1235                1240                1245
Asp Ser Asp Ser Asp Ser Asp Ser Asp Ser Asp Ser Asp Ser
            1250                1255                1260
Asp Ser Asp Ser Asp Ser Asp Ser Asp Ser Asp Ser Asp Ser
1265                1270                1275                1280
Asp Ser Asp Ser Asp Ser Asp Ala Gly Lys His Thr Pro Val Lys Pro
                1285                1290                1295
Met Ser Thr Thr Lys Asp His His Asn Lys Ala Lys Ala Leu Pro Glu
            1300                1305                1310
Thr Gly Asn Glu Asn Ser Gly Ser Asn Asn Ala Thr Leu Phe Gly Gly
            1315                1320                1325
Leu Phe Ala Ala Leu Gly Ser Leu Leu Leu Phe Gly Arg Arg Lys Lys
            1330                1335                1340
Gln Asn Lys
1345

<210> SEQ ID NO 73
<211> LENGTH: 1183
<212> TYPE: PRT
<213> ORGANISM: S. aureus

<400> SEQUENCE: 73

Met Asn Lys Asn Val Leu Lys Phe Met Val Phe Ile Met Leu Leu Asn
  1               5                  10                  15
Ile Ile Thr Pro Leu Phe Asn Lys Asn Glu Ala Leu Ala Ala Arg Asp
                 20                  25                  30
Ile Ser Ser Thr Asn Val Thr Asp Leu Thr Val Ser Pro Thr Lys Ile
             35                  40                  45
Glu Asp Gly Gly Lys Thr Thr Val Lys Met Thr Phe Asp Asp Lys Ser
 50                  55                  60
Val Lys Ile Gln Asn Gly Asp Thr Ile Lys Val Ala Trp Pro Thr Ser
 65                  70                  75                  80
Gly Thr Val Lys Ile Glu Gly Tyr Ser Lys Thr Val Pro Leu Thr Val
                 85                  90                  95
Lys Gly Glu Gln Val Gly Gln Ala Val Ile Thr Pro Asp Gly Ala Thr
                100                 105                 110
Ile Thr Phe Asn Asp Lys Val Glu Lys Leu Ser Asp Val Ser Gly Phe
            115                 120                 125
Ala Glu Phe Glu Val Gln Gly Arg Asn Leu Thr Gln Thr Asn Thr Ser
        130                 135                 140
Asp Asp Lys Val Ala Thr Ile Thr Ser Gly Asn Lys Ser Thr Asn Val
145                 150                 155                 160
```

Thr Val His Lys Ser Glu Ala Gly Thr Ser Val Phe Tyr Lys
        165                 170                 175

Thr Gly Asp Met Leu Pro Glu Asp Thr Thr His Val Arg Trp Phe Leu
            180                 185                 190

Asn Ile Asn Asn Glu Lys Arg Tyr Val Ser Lys Asp Ile Thr Ile Lys
        195                 200                 205

Asp Gln Ile Gln Gly Gly Gln Gln Leu Asp Leu Ser Thr Leu Asn Ile
        210                 215                 220

Asn Val Thr Gly Thr His Ser Asn Tyr Tyr Ser Gly Ser Asn Ala Ile
225                 230                 235                 240

Thr Asp Phe Glu Lys Ala Phe Pro Gly Ser Lys Ile Thr Val Asp Asn
            245                 250                 255

Thr Lys Asn Thr Ile Asp Val Thr Ile Pro Gln Gly Tyr Gly Ser Tyr
            260                 265                 270

Asn Ser Phe Ser Ile Asn Tyr Lys Thr Lys Ile Thr Asn Glu Gln Gln
        275                 280                 285

Lys Glu Phe Val Asn Asn Ser Gln Ala Trp Tyr Gln Glu His Gly Lys
        290                 295                 300

Glu Glu Val Asn Gly Lys Ser Phe Asn His Thr Val His Asn Ile Asn
305                 310                 315                 320

Ala Asn Ala Gly Ile Glu Gly Thr Val Lys Gly Glu Leu Lys Val Leu
            325                 330                 335

Lys Gln Asp Lys Asp Thr Lys Ala Pro Ile Ala Asn Val Lys Phe Lys
            340                 345                 350

Leu Ser Lys Lys Asp Gly Ser Val Val Lys Asp Asn Gln Lys Glu Ile
        355                 360                 365

Glu Ile Ile Thr Asp Ala Asn Gly Ile Ala Asn Ile Lys Ala Leu Pro
        370                 375                 380

Ser Gly Asp Tyr Ile Leu Lys Glu Ile Glu Ala Pro Ala Pro Tyr Thr
385                 390                 395                 400

Phe Asp Lys Asp Lys Glu Tyr Pro Phe Thr Met Lys Asp Thr Asp Asn
            405                 410                 415

Gln Gly Tyr Phe Thr Thr Ile Glu Asn Ala Lys Glu Ile Glu Lys Thr
        420                 425                 430

Lys Asp Val Ser Ala Gln Lys Val Trp Glu Gly Thr Gln Lys Val Lys
        435                 440                 445

Pro Thr Ile Tyr Phe Lys Leu Tyr Lys Gln Asp Asp Asn Gln Asn Thr
        450                 455                 460

Thr Pro Val Asp Lys Ala Glu Ile Lys Lys Leu Glu Asp Gly Thr Thr
465                 470                 475                 480

Lys Val Thr Trp Ser Asn Leu Pro Glu Asn Asp Lys Asn Gly Lys Thr
            485                 490                 495

Ile Lys Tyr Leu Val Lys Glu Val Asn Ala Gln Gly Glu Asp Thr Thr
        500                 505                 510

Pro Glu Gly Tyr Thr Lys Glu Asn Gly Leu Val Val Thr Asn Thr
        515                 520                 525

Glu Lys Pro Ile Glu Thr Thr Ser Ile Ser Gly Glu Lys Val Trp Asp
530                 535                 540

Asp Lys Asp Asn Gln Asp Gly Lys Arg Pro Glu Lys Val Ser Val Asn
545                 550                 555                 560

Leu Leu Ala Asn Gly Glu Lys Val Lys Ala Val Asp Val Thr Ser Glu
            565                 570                 575

Thr Asn Trp Lys Tyr Glu Phe Lys Asp Leu Pro Lys Tyr Asp Glu Gly

-continued

```
              580                 585                 590
Lys Lys Ile Glu Tyr Thr Val Thr Glu Asp His Val Lys Asp Tyr Thr
            595                 600                 605

Thr Asp Ile Asn Gly Thr Thr Ile Thr Asn Lys Tyr Thr Pro Gly Glu
        610                 615                 620

Thr Ser Ala Thr Val Thr Lys Asn Trp Asp Asp Asn Asn Gln Asp
625                 630                 635                 640

Gly Lys Arg Pro Thr Glu Ile Lys Val Glu Leu Tyr Gln Asp Gly Lys
                645                 650                 655

Ala Thr Gly Lys Thr Ala Lys Leu Asn Glu Ser Asn Asn Trp Thr His
            660                 665                 670

Thr Trp Thr Gly Leu Asp Glu Lys Ala Lys Gly Gln Gln Val Lys Tyr
        675                 680                 685

Thr Val Glu Glu Leu Thr Lys Val Lys Gly Tyr Thr Thr His Val Asp
    690                 695                 700

Asn Asn Asp Met Gly Asn Leu Ile Val Thr Asn Lys Tyr Thr Pro Glu
705                 710                 715                 720

Thr Thr Ser Ile Asn Gly Glu Lys Val Trp Asp Asp Lys Asp Asn Gln
                725                 730                 735

Asp Gly Lys Arg Pro Glu Lys Val Ser Ile Asn Leu Leu Ala Asn Gly
            740                 745                 750

Glu Lys Val Lys Thr Leu Asp Val Thr Ser Glu Thr Asn Trp Lys Tyr
        755                 760                 765

Glu Phe Lys Asp Leu Pro Lys Tyr Asp Glu Gly Lys Lys Ile Glu Tyr
    770                 775                 780

Thr Val Thr Glu Asp His Val Lys Asp Tyr Thr Thr Asp Ile Asn Gly
785                 790                 795                 800

Thr Thr Ile Thr Asn Lys Tyr Thr Pro Gly Glu Thr Ser Ala Thr Val
                805                 810                 815

Thr Lys Asn Trp Asp Asp Asn Asn Gln Asp Gly Lys Arg Pro Thr
            820                 825                 830

Glu Ile Lys Val Glu Leu Tyr Gln Asp Gly Lys Ala Thr Gly Lys Thr
        835                 840                 845

Ala Thr Leu Asn Glu Ser Asn Asn Trp Thr His Thr Trp Ala Gly Leu
850                 855                 860

Asp Glu Lys Ala Lys Gly Gln Gln Val Lys Tyr Thr Val Glu Glu Leu
865                 870                 875                 880

Thr Lys Val Lys Gly Tyr Thr Thr His Val Asp Asn Asn Asp Met Gly
                885                 890                 895

Asn Leu Ile Val Thr Asn Lys Tyr Thr Pro Glu Thr Thr Ser Ile Ser
            900                 905                 910

Gly Glu Lys Val Trp Asp Asp Lys Asp Asn Gln Asp Gly Lys Arg Pro
        915                 920                 925

Glu Lys Val Ser Val Asn Leu Leu Ala Asn Gly Glu Lys Val Lys Ala
    930                 935                 940

Val Asp Val Thr Ser Glu Thr Asn Trp Lys Tyr Glu Phe Lys Asp Leu
945                 950                 955                 960

Pro Lys Tyr Asp Glu Gly Lys Lys Ile Glu Tyr Thr Val Thr Glu Asp
                965                 970                 975

His Val Lys Asp Tyr Thr Thr Asp Ile Asn Gly Thr Thr Ile Thr Asn
            980                 985                 990

Lys Tyr Thr Pro Gly Glu Thr Ser Ala Thr Val Thr Lys Asn Trp Asp
        995                 1000                1005
```

-continued

Asp Asn Asn Asn Gln Asp Gly Lys Arg Pro Thr Glu Ile Lys Val Glu
    1010                1015                1020

Leu Tyr Gln Asp Gly Lys Ala Thr Gly Lys Thr Ala Thr Leu Asn Glu
1025                1030                1035                1040

Ser Asn Asn Trp Thr His Thr Trp Ala Gly Leu Asp Glu Lys Ala Lys
            1045                1050                1055

Gly Gln Gln Val Lys Tyr Thr Val Glu Glu Leu Thr Lys Val Lys Gly
        1060                1065                1070

Tyr Thr Thr His Val Asp Asn Asn Asp Met Gly Asn Leu Ile Val Thr
            1075                1080            1085

Asn Lys Tyr Thr Pro Glu Lys Pro Asn Lys Pro Ile Tyr Pro Glu Lys
        1090                1095                1100

Pro Lys Asp Lys Thr Pro Pro Thr Lys Pro Asp His Ser Asn Lys Val
1105                1110                1115                1120

Lys Pro Thr Pro Pro Asp Lys Pro Ser Lys Val Asp Lys Asp Gln
            1125                1130                1135

Pro Lys Asp Asn Lys Thr Lys Pro Glu Asn Pro Leu Lys Glu Leu Pro
            1140                1145                1150

Lys Thr Gly Met Lys Ile Ile Thr Ser Trp Ile Thr Trp Val Phe Ile
            1155                1160                1165

Gly Ile Leu Gly Leu Tyr Leu Ile Leu Arg Lys Arg Phe Asn Ser
            1170                1175                1180

<210> SEQ ID NO 74
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(14)
<223> OTHER INFORMATION: Xaa = Any Amino Acid
<223> OTHER INFORMATION: consensus sequence

<400> SEQUENCE: 74

Gly Xaa Tyr Xaa Leu Xaa Glu Xaa Xaa Xaa Xaa Xaa Gly Tyr
1               5                   10

<210> SEQ ID NO 75
<211> LENGTH: 14
<212> TYPE: PRT
<213> ORGANISM: S. suis

<400> SEQUENCE: 75

Gly Thr Tyr Tyr Leu Lys Glu Ile Thr Ala Pro Thr Gly Tyr
1               5                   10

<210> SEQ ID NO 76
<211> LENGTH: 14
<212> TYPE: PRT
<213> ORGANISM: S. suis

<400> SEQUENCE: 76

Thr Thr Tyr Tyr Leu Glu Glu Met Lys Ala Pro Asn Gly Tyr
1               5                   10

<210> SEQ ID NO 77
<211> LENGTH: 14
<212> TYPE: PRT
<213> ORGANISM: S. equi

```
<400> SEQUENCE: 77

Gly Asp Tyr Lys Leu Ser Glu Thr Thr Thr Pro Gly Gly Tyr
1               5                   10

<210> SEQ ID NO 78
<211> LENGTH: 14
<212> TYPE: PRT
<213> ORGANISM: S. equi

<400> SEQUENCE: 78

Ile Thr Tyr Ser Val Lys Glu Val Met Val Pro Val Gly Tyr
1               5                   10

<210> SEQ ID NO 79
<211> LENGTH: 6
<212> TYPE: PRT
<213> ORGANISM: Artificial Sequence
<220> FEATURE:
<223> OTHER INFORMATION: amino acid linker

<400> SEQUENCE: 79

Gly Ser Gly Gly Gly Gly
1               5

<210> SEQ ID NO 80
<211> LENGTH: 77
<212> TYPE: PRT
<213> ORGANISM: S. suis

<400> SEQUENCE: 80

Leu Thr Gly Ala Glu Phe Lys Leu Tyr Asp Ala Ala Asn Asn Gly Thr
1               5                   10                  15

Glu Ile Lys Val Val Lys Glu Ser Asp Gly Val Tyr Arg Val Ala Gln
            20                  25                  30

Ala Asp Glu Gln Gly Val Val Ile Glu Ala Gly Glu Val Val Ile Lys
        35                  40                  45

Gly Leu Lys His Ser Thr Thr Tyr Tyr Leu Glu Glu Met Lys Ala Pro
    50                  55                  60

Asn Gly Tyr Asn Ile Leu Thr Glu Arg Gln Ser Ile Glu
65                  70                  75

<210> SEQ ID NO 81
<211> LENGTH: 62
<212> TYPE: PRT
<213> ORGANISM: S. suis

<400> SEQUENCE: 81

Leu Ala Gly Ala Val Phe Gly Ile Tyr Ser Asp Ala Glu Thr Lys Gln
1               5                   10                  15

Leu Val Asp Ile Val Thr Thr Asn Ala Asp Gly Tyr Ala Ile Ser Thr
            20                  25                  30

Lys Val Gly Lys Gly Thr Tyr Tyr Leu Lys Glu Ile Thr Ala Pro Thr
        35                  40                  45

Gly Tyr Ser Leu Asn Thr Asn Val Tyr Thr Ala Glu Ala Ser
    50                  55                  60

<210> SEQ ID NO 82
<211> LENGTH: 480
<212> TYPE: PRT
<213> ORGANISM: S. suis
```

```
<400> SEQUENCE: 82

Met Lys Lys Leu Gln Gln Phe Phe Thr Ser Leu Val Ala Val Leu Thr
  1               5                  10                  15

Val Phe Ala Phe Gly Ser Thr Ala Leu Ala Gln Thr Val Asp Ser Gly
              20                  25                  30

Lys Ser Gly Ala Gly Thr Ile Thr Val Ser Asn Ala Ser Gln Gly Gln
              35                  40                  45

Thr Tyr Thr Ala Tyr Lys Leu Phe Asp Ala Thr Val Thr Thr Asp Gly
  50                  55                  60

Ser Gly Ile Ser Tyr Lys Leu Pro Ala Gly Lys Ile Ala Thr Asn Phe
 65                  70                  75                  80

Gly Gly Asp Thr Trp Phe Glu Val Asp Ser Lys Gly Asn Ile Thr Ala
              85                  90                  95

Lys Glu Gly Ala Thr Val Ser Ser Glu Ala Phe Ala Ala Trp Ala Lys
             100                 105                 110

Asn Phe Gly Thr Glu Val Thr Ser Ala Thr Ala Asn Asp Asn Ser Leu
             115                 120                 125

Val Phe Thr His Leu Thr Phe Gly Tyr Tyr Phe Val Thr Ser Ser Leu
130                 135                 140

Gly Ala Val Leu Thr Val Asp Ser Thr Thr Pro Asn Ala Thr Val Ile
145                 150                 155                 160

Asp Lys Asn Thr Thr Asn Pro Thr Ile Pro Asp Ser Asn Asn Gly Gly
                165                 170                 175

Gly Lys Lys Ile Leu Ser Asn Gly Ala Thr Thr Ser Glu Thr Thr Ala
             180                 185                 190

Lys Ile Gly Asp Thr Ile Asn Phe Gln Ile Lys Phe Asn Ala Thr Asn
             195                 200                 205

Tyr Val Thr Lys Asp Arg Gln Thr Lys Gln Ile Val Ser Tyr Thr Ile
210                 215                 220

Glu Asp Ser Pro Thr Ala Leu Ala Ile Asp Gln Asn Ser Val Asn Val
225                 230                 235                 240

Lys Val Asp Gly Val Asp Ile Thr Ala Lys Ile Ser Lys Thr Phe Asp
                245                 250                 255

Ala Thr Gly Lys Met Asn Leu Val Ile Thr Trp Ala Asp Ala Ala Ala
             260                 265                 270

Ser Asn Lys Thr Ile Tyr Asn Ser Pro Ala Glu Val Ile Ile Thr Tyr
             275                 280                 285

Ser Ala Val Val Thr Lys Asp Ala Lys Glu Gly Ala Thr Asn Ser
290                 295                 300

Ala Thr Ile Gly Tyr Asn Thr Ile Asp Asn Pro Thr Pro Pro Thr
305                 310                 315                 320

Pro Val Asp Pro Asp Lys Pro Thr Glu Thr Thr Lys Val Thr Thr His
                325                 330                 335

Arg Phe Thr Leu Lys Lys Thr Asn Asn Val Gly Glu Thr Leu Thr Gly
             340                 345                 350

Ala Glu Phe Lys Leu Tyr Asp Ala Ala Asn Asn Gly Thr Glu Ile Lys
             355                 360                 365

Val Val Lys Glu Ser Asp Gly Val Tyr Arg Val Ala Gln Ala Asp Glu
370                 375                 380

Gln Gly Val Val Ile Glu Ala Gly Glu Val Val Ile Lys Gly Leu Lys
385                 390                 395                 400

His Ser Thr Thr Tyr Tyr Leu Glu Glu Met Lys Ala Pro Asn Gly Tyr
             405                 410                 415
```

```
Asn Ile Leu Thr Glu Arg Gln Ser Ile Glu Val Lys Glu Asn Asn Thr
                420                 425                 430

Ala Gln Ala Asn Ile Val Asn Lys Lys Gly Val Leu Pro Ser Thr
            435                 440                 445

Gly Ala Ile Gly Thr Thr Leu Phe Tyr Leu Val Gly Ser Ile Leu Leu
450                 455                 460

Leu Val Ala Leu Val Tyr Thr Ile Ser Lys Arg Arg Met Asn Asn Ile
465                 470                 475                 480

<210> SEQ ID NO 83
<211> LENGTH: 546
<212> TYPE: PRT
<213> ORGANISM: S. suis

<400> SEQUENCE: 83

Met Lys Arg Ile Phe Thr Leu Leu Thr Val Leu Leu Thr Val Leu Gly
1               5                   10                  15

Met Asn Ala Arg Pro Val Phe Ala Ala Ser Asn Thr Asp Gln Ala Glu
            20                  25                  30

Leu Lys Ile Thr Asn Ile Glu Gly Asn Pro Thr Val Thr Leu Tyr Lys
        35                  40                  45

Ile Gly Glu Gly Val Tyr Asn Ala Thr Asn Asp Ser Phe Ile Arg Phe
50                  55                  60

Asp Tyr Ala Ser Gly Val Lys Leu Thr Glu Thr Gly Pro Thr Ala Glu
65                  70                  75                  80

Glu Ile Thr Asn Ile Ala Asn Gly Ile Leu Asp Asn Thr Ile Gln Ala
                85                  90                  95

Lys Ala Ser Lys Val Leu Gln Val Thr Asn Gly Thr Ala Thr Tyr Arg
            100                 105                 110

Ala Thr Gly Ala Gly Val Tyr Ile Ala Ile Leu Thr Gly Ala Thr Asp
        115                 120                 125

Gly Arg Ser Phe Asn Pro Ile Leu Leu Ala Ala Ser Tyr Asn Gly Glu
130                 135                 140

Gly Lys Leu Thr Gly Gly Ser Val Asp Ser Lys Ala Lys Tyr Leu Tyr
145                 150                 155                 160

Gly Gln Thr Ser Val Ala Lys Ser Thr Leu Pro Ser Ile Asp Lys Thr
                165                 170                 175

Val Ser Gly Val Thr Ala Asp Ala Asp Lys Asn Ser Ala Ser Leu Gly
            180                 185                 190

Gln Val Leu Thr Tyr Ser Leu Asn Val Thr Leu Pro Ser Tyr Pro Thr
        195                 200                 205

Gln Ala Lys Asn Lys Thr Ile Phe Ile Ser Asp Thr Met Ser Glu Gly
210                 215                 220

Leu Thr Phe Asp Tyr Ala Ser Leu Thr Ile Ser Trp Asn Gly Gln Thr
225                 230                 235                 240

Leu Ile Ala Asp Thr Thr Gly Gln Phe Lys Thr Gln Gly Asp Ile Leu
                245                 250                 255

Ile Ala Lys Ala Val Lys Val Gly Asn Gly Phe Asn Leu Ala Phe Val
            260                 265                 270

Tyr Asp Asn Leu Asn Glu Ile Ala Pro Val Val Thr Tyr Lys Gly Ile
        275                 280                 285

Ile Asn Asp Lys Ala Val Val Gly Gly Thr Gly Asn Ala Asn Lys Ala
290                 295                 300

Glu Phe Phe Tyr Ala Arg Asn Pro Asn Ser Gly Asn Thr Tyr Glu Asp
```

```
            305                 310                 315                 320
    Pro Asn Asn Lys Pro Asn Pro Gln Asn Asp Asn Thr Ile Val Asn Lys
                    325                 330                 335

Glu Asp Ser Glu Thr Val Tyr Thr Tyr Gln Ile Ala Phe Lys Lys Val
                    340                 345                 350

Asp Ser Ile Thr Lys Ala Pro Leu Ala Gly Ala Val Phe Gly Ile Tyr
                    355                 360                 365

Ser Asp Ala Glu Thr Lys Gln Leu Val Asp Ile Val Thr Thr Asn Ala
                370                 375                 380

Asp Gly Tyr Ala Ile Ser Thr Lys Val Gly Lys Gly Thr Tyr Tyr Leu
    385                 390                 395                 400

Lys Glu Ile Thr Ala Pro Thr Gly Tyr Ser Leu Asn Thr Asn Val Tyr
                    405                 410                 415

Thr Ala Glu Ala Ser Trp Thr Ser Ala Thr Thr Thr Ser Ser Ala Ser
                    420                 425                 430

Ser Thr Arg Ser Glu Tyr Thr Ser Val Val Gly Glu Ala Lys Asp Ser
                    435                 440                 445

Thr Gln Val Gly Trp Leu Lys His Asn Val Phe Tyr Lys Leu Asp Asn
                    450                 455                 460

Lys Pro Glu Gly Thr Asp Val Gln Ala Ala Tyr Leu Lys Ala Thr Thr
    465                 470                 475                 480

Thr Thr Ala Gln Asn Thr Thr Val Thr Thr Asn Pro Thr Ala Gly
                    485                 490                 495

Ala Gly Thr Val Ser Ile Ala Asp Val Pro Asn Thr Lys Leu Gly Glu
                    500                 505                 510

Leu Pro Ser Thr Gly Gly Met Gly Thr Tyr Leu Phe Thr Phe Ile Gly
                    515                 520                 525

Val Leu Val Leu Thr Val Gly Leu Gly Leu Tyr Phe Thr Lys Asn Lys
                    530                 535                 540

Lys Ala
    545

<210> SEQ ID NO 84
<211> LENGTH: 61
<212> TYPE: PRT
<213> ORGANISM: S. equi

<400> SEQUENCE: 84

Leu Tyr Ala Asn Asp Gln Lys Val Asn Asp Lys Thr Ile Glu Leu Ser
    1               5                   10                  15

Asp Thr Asn Ser Trp Gln Ala Ser Phe Gly Lys Leu Asp Lys Tyr Asp
                    20                  25                  30

Ser Gln Asn Gln Lys Ile Thr Tyr Ser Val Lys Glu Val Met Val Pro
                    35                  40                  45

Val Gly Tyr Gln Ser Gln Val Glu Gly Asp Ser Gly Val
                50                  55                  60

<210> SEQ ID NO 85
<211> LENGTH: 61
<212> TYPE: PRT
<213> ORGANISM: S. equi

<400> SEQUENCE: 85

Leu Leu Lys Ala Asp Gly Lys Val Ile Arg Glu His Gln Met Thr Pro
    1               5                   10                  15

Asp Gln Gln Gly Lys Trp Glu Tyr Thr Phe Asp Gln Leu Pro Val Tyr
```

```
                20                  25                  30
Gln Thr Gly Lys Lys Ile Ser Tyr Ser Ile Glu Glu Lys Gln Val Ala
            35                  40                  45
Gly Tyr Gln Ala Pro Val Tyr Glu Val Asp Glu Gly Leu
        50                  55                  60

<210> SEQ ID NO 86
<211> LENGTH: 68
<212> TYPE: PRT
<213> ORGANISM: S. equi

<400> SEQUENCE: 86

Leu Lys Gly Ala Gly Phe Thr Leu Tyr Lys Leu Val Lys Gly Asp Asn
1               5                  10                  15

Gly Glu Glu Lys Tyr Gln Ile Val Gln Glu Ile Lys Ala Gly Asp Thr
            20                  25                  30

Thr Ser Phe Glu Phe Val Gly Leu Asp Ala Gly Asp Tyr Lys Leu Ser
        35                  40                  45

Glu Thr Thr Pro Gly Gly Tyr Asn Thr Ile Ala Asp Val Met Phe
    50                  55                  60

Ser Ile Val Ala
65

<210> SEQ ID NO 87
<211> LENGTH: 657
<212> TYPE: PRT
<213> ORGANISM: S. equi

<400> SEQUENCE: 87

Leu Lys Gln Leu Thr Lys Ile Val Ser Val Val Leu Leu Leu Val Phe
1               5                  10                  15

Thr Leu Ser Ala Ser Leu His Lys Val Arg Ala Thr Asn Leu Ser Asp
            20                  25                  30

Asn Ile Thr Ser Leu Thr Val Ala Ser Ser Leu Arg Asp Gly Glu
        35                  40                  45

Arg Thr Thr Val Lys Val Ala Phe Asp Asp Lys Lys Gln Lys Ile Lys
    50                  55                  60

Ala Gly Asp Thr Ile Glu Val Thr Trp Pro Thr Ser Gly Asn Val Tyr
65                  70                  75                  80

Ile Gln Gly Phe Asn Lys Thr Ile Pro Leu Asn Ile Arg Gly Val Asp
                85                  90                  95

Val Gly Thr Leu Glu Val Thr Leu Asp Lys Ala Val Phe Thr Phe Asn
            100                 105                 110

Gln Asn Ile Glu Thr Met His Asp Val Ser Gly Trp Gly Glu Phe Asp
        115                 120                 125

Ile Thr Val Arg Asn Val Thr Gln Thr Thr Ala Glu Thr Ser Gly Thr
    130                 135                 140

Thr Thr Val Lys Val Gly Asn Arg Thr Ala Thr Ile Val Thr Lys
145                 150                 155                 160

Pro Glu Ala Gly Thr Gly Thr Ser Ser Phe Tyr Tyr Lys Thr Gly Asp
                165                 170                 175

Met Gln Pro Asn Asp Thr Glu Arg Val Arg Trp Phe Leu Leu Ile Asn
            180                 185                 190

Asn Asn Lys Glu Trp Val Ala Asn Thr Val Thr Val Glu Asp Asp Ile
        195                 200                 205

Gln Gly Gly Gln Thr Leu Asp Met Ser Ser Phe Asp Ile Thr Val Ser
```

-continued

```
                210                 215                 220
Gly Tyr Arg Asn Glu Arg Phe Val Gly Glu Asn Ala Leu Thr Glu Phe
225                 230                 235                 240

His Thr Thr Phe Pro Asn Ser Val Ile Thr Ala Thr Asp Asn His Ile
                245                 250                 255

Ser Val Arg Leu Asp Gln Tyr Asp Ala Ser Gln Asn Thr Val Asn Ile
                260                 265                 270

Ala Tyr Lys Thr Lys Ile Thr Asp Phe Asp Gln Lys Glu Phe Ala Asn
                275                 280                 285

Asn Ser Lys Ile Trp Tyr Gln Ile Leu Tyr Lys Asp Gln Val Ser Gly
290                 295                 300

Gln Glu Ser Asn His Gln Val Ala Asn Ile Asn Ala Asn Gly Gly Val
305                 310                 315                 320

Asp Gly Ser Arg Tyr Thr Ser Phe Thr Val Lys Lys Ile Trp Asn Asp
                325                 330                 335

Lys Glu Asn Gln Asp Gly Lys Arg Pro Lys Thr Ile Thr Val Gln Leu
                340                 345                 350

Tyr Ala Asn Asp Gln Lys Val Asn Asp Lys Thr Ile Glu Leu Ser Asp
                355                 360                 365

Thr Asn Ser Trp Gln Ala Ser Phe Gly Lys Leu Asp Lys Tyr Asp Ser
370                 375                 380

Gln Asn Gln Lys Ile Thr Tyr Ser Val Lys Glu Val Met Val Pro Val
385                 390                 395                 400

Gly Tyr Gln Ser Gln Val Glu Gly Asp Ser Gly Val Gly Phe Thr Ile
                405                 410                 415

Thr Asn Thr Tyr Thr Pro Glu Val Ile Ser Ile Thr Gly Gln Lys Thr
                420                 425                 430

Trp Asp Asp Arg Glu Asn Gln Asp Gly Lys Arg Pro Lys Glu Ile Thr
                435                 440                 445

Val Arg Leu Leu Ala Asn Asp Ala Ala Thr Asp Lys Val Ala Thr Ala
450                 455                 460

Ser Glu Gln Thr Gly Trp Lys Tyr Thr Phe Thr Asn Leu Pro Lys Tyr
465                 470                 475                 480

Lys Asp Gly Lys Gln Ile Thr Tyr Thr Ile Gln Glu Asp Pro Val Ala
                485                 490                 495

Asp Tyr Thr Thr Thr Ile Gln Gly Phe Asp Ile Thr Asn His His Glu
                500                 505                 510

Val Ala Leu Thr Ser Leu Lys Val Ile Lys Val Trp Asn Asp Lys Asp
                515                 520                 525

Asp Tyr Tyr His Lys Arg Pro Lys Glu Ile Thr Ile Leu Leu Lys Ala
                530                 535                 540

Asp Gly Lys Val Ile Arg Glu His Gln Met Thr Pro Asp Gln Gln Gly
545                 550                 555                 560

Lys Trp Glu Tyr Thr Phe Asp Gln Leu Pro Val Tyr Gln Thr Gly Lys
                565                 570                 575

Lys Ile Ser Tyr Ser Ile Glu Glu Lys Gln Val Ala Gly Tyr Gln Ala
                580                 585                 590

Pro Val Tyr Glu Val Asp Glu Gly Leu Lys Gln Val Thr Val Thr Asn
                595                 600                 605

Thr Leu Asn Pro Ser Tyr Lys Leu Pro Asp Thr Gly Gly Gln Gly Val
                610                 615                 620

Lys Trp Tyr Leu Leu Ile Gly Gly Gly Phe Ile Ile Val Ala Ile Leu
625                 630                 635                 640
```

```
Val Leu Ile Ser Leu Tyr Gln Lys His Lys Arg His Asn Met Ser Lys
                645                 650                 655
Pro

<210> SEQ ID NO 88
<211> LENGTH: 480
<212> TYPE: PRT
<213> ORGANISM: S. equi

<400> SEQUENCE: 88

Met Lys Thr Ile Lys Leu Ile Leu Thr Ser Leu Leu Val Thr Phe Leu
  1               5                  10                  15

Thr Met Leu Ser Gly Lys Ala Phe Ala Asp Thr Ala Ser Tyr Thr Ile
             20                  25                  30

Thr Val Glu Gly Ala Thr Ala Gly His Thr Tyr Glu Ala Tyr Gln Ile
         35                  40                  45

Phe Lys Gly Asp Leu Phe Asp Ser Thr Leu Ser Asn Ile Thr Trp Gly
 50                  55                  60

Gly Gly Val Thr Pro Phe Glu Phe Asp Gly Ser Lys Asp Ala Ala Lys
 65                  70                  75                  80

Ile Ala Glu Gly Leu Lys Glu Ala Asn Ala Ala Phe Ala Lys Glu
                 85                  90                  95

Ala Gly Lys His Leu Thr Ala Thr Ile Ala Gly Thr Gly Thr His Ala
            100                 105                 110

Ile Thr Val Asn Glu Ala Gly Tyr Tyr Leu Ile Lys Asp Lys Asn Asp
        115                 120                 125

Ser Gln Thr Gly Lys His Asp Ala Tyr Thr Ser Phe Val Leu Lys Val
    130                 135                 140

Val Lys Asn Thr Ser Phe Lys Pro Lys Ser Ala Ile Pro Thr Val Leu
145                 150                 155                 160

Lys Lys Val Lys Asp Arg Asn Asp Lys Thr Gly Leu Glu Thr Gly Trp
                165                 170                 175

Gln Asp Ser Ala Asp Tyr Asp Lys Asn Asp Lys Val Pro Phe Gln Leu
            180                 185                 190

Thr Ala Thr Leu Pro Ser Asn Tyr Asp Ala Phe Gln Glu Tyr Tyr Leu
        195                 200                 205

Glu Phe Val Asp Thr Leu Ser Lys Gly Leu Ser Tyr Asn Lys Asp Ala
    210                 215                 220

Lys Val Tyr Val Val Asn Gly Asp Thr Arg Gln Asp Ile Thr Asn Ser
225                 230                 235                 240

Phe Thr Val Ser Glu Asp Gly Ser Ser Phe Lys Ile Asn Asn Leu Lys
                245                 250                 255

Ala Val Gln Gly Val Thr Ile Thr Ala Thr Ser Lys Ile Val Val Glu
            260                 265                 270

Tyr Thr Ala Thr Leu Asn Asp Gln Ala Ala Ile Gly Lys Lys Gly Asn
        275                 280                 285

Pro Asn Glu Val Ala Leu Lys Tyr Ser Asn Asp Pro Asn Ala Leu Gly
    290                 295                 300

Lys Gly Glu Glu Ser Pro Lys Gly Glu Thr Pro Lys Asp Lys Val Ile
305                 310                 315                 320

Val Phe Thr Tyr Lys Thr Ile Ile Asn Lys Val Asp Gln Asp Gln Lys
                325                 330                 335

Ala Leu Lys Gly Ala Gly Phe Thr Leu Tyr Lys Leu Val Lys Gly Asp
            340                 345                 350
```

```
Asn Gly Glu Glu Lys Tyr Gln Ile Val Gln Glu Ile Lys Ala Gly Asp
        355                 360                 365

Thr Thr Ser Phe Glu Phe Val Gly Leu Asp Ala Gly Asp Tyr Lys Leu
370                 375                 380

Ser Glu Thr Thr Thr Pro Gly Gly Tyr Asn Thr Ile Ala Asp Val Met
385                 390                 395                 400

Phe Ser Ile Val Ala Gln His Glu Thr Glu Ser Asp Asp Pro Gln Leu
                405                 410                 415

Thr Ser Leu Thr Val Asp Lys Ala Thr Gly Phe Thr Ala Asp Thr Glu
                420                 425                 430

Ala Gly Thr Val Ser Ala Thr Ile Val Asn Lys Lys Gly Ser Ile Leu
                435                 440                 445

Pro Ser Thr Gly Ser Ile Gly Thr Thr Met Leu Tyr Val Phe Gly Val
                450                 455                 460

Met Leu Met Thr Ile Ser Thr Leu Phe Ile Phe Arg Gln Lys Gln Gln
465                 470                 475                 480

<210> SEQ ID NO 89
<211> LENGTH: 1364
<212> TYPE: PRT
<213> ORGANISM: S. suis

<400> SEQUENCE: 89

Met Phe Pro Asn Gly Asn Val Ala Asn Ser Ile Pro Gln Ser Ile Glu
1               5                   10                  15

Leu Tyr Val Ala Asp Gly Thr Lys Ala Met Ser Tyr Ser Lys Asp Ser
                20                  25                  30

Leu Glu Lys Leu Thr Tyr Lys Gly Thr Ser Asn Asn Gly Asn Ile His
                35                  40                  45

His Tyr Tyr Leu Pro Gly Thr Asp Ile Gly Ile Ser Val Arg Val Tyr
        50                  55                  60

Ser Glu Arg Asn Ser Tyr Pro Ala Phe Asp Gly Phe Glu Ser Thr His
65              70                  75                  80

Thr Ile Glu Phe Tyr Gln Glu Gly Trp Lys Leu Gly Asn Lys Ala Ile
                85                  90                  95

Val Val Arg Leu Lys Glu Arg Lys Phe Gln Lys Asn Gly Leu Tyr
                100                 105                 110

Tyr Asn Gly Met Ser Val Pro Trp Asn Ser Pro Val Met Gly Gly Gly
                115                 120                 125

Arg Thr Thr Asn Ile Tyr Arg Arg Glu Gly Asp Thr Val Ser Gln Gly
130                 135                 140

Gly Ala Tyr Pro Val Asp Trp Tyr Gly Phe Lys Leu Lys Lys Val Gly
145                 150                 155                 160

Ile Lys Asn Gly Gln Lys Ile Pro Leu Ser Gly Ala Ile Phe Thr Leu
                165                 170                 175

Tyr Lys Gly Asn Glu Pro Tyr Arg Thr Ala Val Ser Asp Asp Asn Gly
                180                 185                 190

Asp Ile Gln Phe Ser Glu Ile Ile Gly Gly Thr Tyr Thr Phe Lys Glu
                195                 200                 205

Thr Ser Ala Pro Ser Gly Tyr Ile Leu Asp Pro Thr Glu His Thr Ile
                210                 215                 220

Val Val Thr Asp Asn Gln Asn Ile Thr Ile Asp Gly Lys Lys Tyr Asp
225                 230                 235                 240

Val Asn Lys Pro Thr Glu Val Val Asn Thr Lys Ser Thr Thr Leu Gln
```

```
              245                 250                 255
Ile Asn Lys Phe Glu Phe Gly Glu Ser Lys Pro Leu Lys Gly Ala Val
            260                 265                 270
Phe Arg Leu Gln Ser Lys Asn Gly Asn Tyr Asp Val Thr Ile Gly
            275                 280             285
Asp Val Leu Pro Ala Ser Gln Phe Ile Phe Ser Asn Leu Ala Lys Gly
            290                 295                 300
Ile Tyr Thr Leu Thr Glu Thr Lys Ala Pro Ala Gly Tyr Lys Thr Ile
305                 310                 315                 320
Pro Pro Leu Asp Ile Glu Val Tyr Glu Glu Asn Gly Glu Leu Lys Val
                325                 330                 335
Arg Lys Leu Thr Asp Thr Ser Asn Thr Gln Thr Gly Ala Val Glu Val
                340                 345                 350
Val Asn Gly Asn Phe Ser Ile Asn Val Val Asp Glu Asp Phe Ser Thr
                355                 360                 365
Glu Phe Thr Lys Val Asn Glu Gln Gly Gln Pro Leu Ala Asp Ala Val
            370                 375                 380
Phe Glu Leu Arg Gln Ile Thr Gln Thr Gly Tyr Lys Arg Val Leu Thr
385                 390                 395                 400
Gly Leu Thr Ser Asn Ser Gln Gly Lys Leu Arg Val Asp His Leu Gln
                405                 410                 415
Gly Gly Ile Thr Tyr Glu Leu Trp Glu Thr Ser Ala Pro Ala Gly Tyr
                420                 425                 430
Ser Lys Leu Thr Thr Ala Ala Ala Arg Phe Thr Val Ser Glu Thr Gly
                435                 440                 445
Thr Ile Ser Phe Glu Ser Gly Thr Ser Glu Arg Ile Ile Asn Arg Pro
            450                 455                 460
Pro Thr Tyr Lys Val Lys Val Gln Lys Ile Asp Ala Leu Thr Gly Gln
465                 470                 475                 480
Lys Val Thr Val Gln Thr Arg Ile Gly Ile Thr Asp Ser Gln Gly Asn
                485                 490                 495
Val Ile Asp Gly Gln Ile Ala Asn Phe Asp Asn Gly Glu Phe Ser Phe
            500                 505                 510
Pro Lys Asn Phe Thr Pro Gly Thr Tyr Tyr Ile Lys Glu Glu Lys Thr
            515                 520                 525
Pro Ser Gly Tyr Ile Gly Leu Ser Gly Leu Val Pro Phe Thr Ile Arg
            530                 535                 540
Ala Asp Gly Ile Val Glu Val Asn Ser Asp Tyr Leu Glu Gly Ile Asp
545                 550                 555                 560
Val Thr Thr Ser Ser Pro Asp Thr Ile Thr Ile Lys Val Lys Asn Tyr
                565                 570                 575
Pro Leu Gly Lys Phe Lys Val Ser Lys Arg Val Lys Gly Ile Ser Asp
            580                 585                 590
Leu Thr Asn Leu Ile Thr Gly Gln Met Thr Phe Thr Leu Thr Lys Asn
                595                 600                 605
Asp Asp Val Asn Phe Ala Pro Ile Val Lys Gln Gln Ala Ala Asn Gln
            610                 615                 620
Asp Phe Val Phe Glu Asn Leu Gln Pro Gly Val Tyr Thr Leu Thr Glu
625                 630                 635                 640
Thr Gln Ala Pro Ser Gly Tyr Val Lys Ser Thr Glu Asn Tyr Thr Ile
                645                 650                 655
Tyr Val Asn Arg Asp Gly Ser Val Arg Phe Tyr Ser Ser Asp Ile
                660                 665                 670
```

```
Ser Ser His Ile Ala Arg Gly Leu His Val Ile Lys Ser Ala Glu Ile
        675                 680                 685

Ala Met Ala Ser Thr Tyr Gly Ser Ser Thr Glu Asp Lys Ala Leu Asp
        690                 695                 700

Gly Asp Leu Thr Thr Gly Ala Leu Tyr Gln Leu Pro Ser Ser Thr Leu
705                 710                 715                 720

Asn Glu Gly Gln Trp Trp Gly Val Asn Leu Gly Ser Pro Gln Arg Val
                725                 730                 735

Thr Gln Ile Arg Phe Ala Gln Gly Lys Asn Thr Thr Asn Gly Ser Asp
                740                 745                 750

His Asp Lys Met Asp Ser Tyr Ala Leu Glu Tyr Ser Pro Asp Gly Ile
                755                 760                 765

Thr Tyr Gln Ser Ile Gly Asn Phe Thr Glu Thr Asp Leu Thr Gln Thr
        770                 775                 780

Val Asp Ile Tyr Ala Gln Tyr Ile Arg Val Arg Asn Leu Gln Thr Gly
785                 790                 795                 800

Thr Asn Arg Trp Leu Gly Ile Arg Glu Leu Gln Val Ser Val Arg Asp
                805                 810                 815

Ala Thr Gln Thr Ile Glu Ala Gly Gly Ser Asp Ala Ala Asn Val
                820                 825                 830

Ile Lys Ile Gly Asn Ile Glu Asn Pro Glu Phe Lys Ile Glu Lys Val
        835                 840                 845

Asp Ala Asn Asn Lys Gln Ile Ser Lys Pro Val Thr Phe Lys Leu Tyr
        850                 855                 860

Lys Val Asp Asp Ser Thr Thr Glu Ala Thr Val Ser Ser Thr Ser Leu
865                 870                 875                 880

Asp Asp Thr Asn Leu Val Gln Thr Leu Thr Phe Thr Gly Gln Ser Ser
                885                 890                 895

Leu Thr Arg Leu Thr Ala Thr Ala Leu Gly Lys Tyr Val Leu Val Glu
        900                 905                 910

Thr Gln Ala Pro Glu Gly Tyr Asp Gly Leu Ser Ala Pro Val Leu Leu
        915                 920                 925

Glu Leu Tyr Glu Thr Thr Gln Ala Tyr Ala Val Thr Gln Gln Lys Ala
        930                 935                 940

Val Thr Arg Phe Arg Val Leu Ser Gln Thr Asn Ser Val Ser Val Thr
945                 950                 955                 960

Asp Leu Pro Gly Val Ser Gly Ala Leu Ala Asn Ala Ile Ser Ile Lys
                965                 970                 975

Val Lys Asn Asn Glu Arg Arg Tyr Asn Leu Lys Ile Lys Lys Arg Asp
                980                 985                 990

Tyr His His Pro Thr Leu Gly Leu Asn Ala Arg Phe Glu Leu Val Thr
                995                 1000                1005

Glu Ala Gly His Pro Val Val Ile Asp Gly Val Asn Met Lys Gly Asp
        1010                1015                1020

Thr Asn Ser Ala Asp Asn Ser Ile Thr Phe Ser Asn Leu Pro Val Gly
1025                1030                1035                1040

Val Tyr Ile Leu Lys Glu Thr Val Val Pro Thr Gly Gly Tyr Arg Pro
                1045                1050                1055

Val Asn Gln Leu Gln Asp Thr Lys Phe Glu Ile Arg Pro Asp Gly Ser
                1060                1065                1070

Leu Gln Ile Leu Glu Ser Asp Ser Asn Met Val Thr Val Asp Thr Ser
                1075                1080                1085
```

Gln Gly Ala Thr Phe Glu Ile Thr Ile Lys Asn Phe Lys Gln Phe Lys
            1090                1095                1100

Phe Arg Leu Gln Lys Thr Asp Asn Arg Asp Glu Asn His Leu Leu Asn
1105                1110                1115                1120

Gly Ala Thr Phe Lys Ile Tyr Ser Asp Pro Asn Asn Asp Gly Val Glu
            1125                1130                1135

Asp Thr Glu Val Ala Ser Gly Val Thr Thr Asn Gly Leu Phe Glu Thr
            1140                1145                1150

Ser Leu Ser Phe Gly Tyr Tyr Ile Leu Glu Glu Thr Val Ala Pro Thr
            1155                1160                1165

Gly Tyr Gln Leu Asn Pro Lys Lys Tyr Arg Phe Gln Ile Asn His Asp
            1170                1175                1180

Gly Thr Thr Lys Leu His Asn Gly Asp Asn Gln Val Thr Leu Ala Glu
1185                1190                1195                1200

Arg Val Asp Gly Asp Asn Val Ile Leu Phe Asn Met Lys Asn Thr Lys
            1205                1210                1215

Gln Thr Thr His Ile Lys Leu Ala Lys Arg Ser Tyr Ser Asp Pro Thr
            1220                1225                1230

Gln Arg Leu Val Ala Thr Phe Glu Leu Arg Glu Ser Asp Asn Pro Gln
            1235                1240                1245

Ala Thr Ala Val Val Lys Thr Thr Thr Thr Gly Asp Glu Val Leu
            1250                1255                1260

Phe Asp Asn Leu Ala Val Gly Lys Thr Tyr Ile Leu Lys Glu Ile Val
1265                1270                1275                1280

Ala Pro Asp Gly Tyr Gln Lys Ile Glu Lys Glu Phe His Ile Asn Ile
            1285                1290                1295

Gly Ala Asp Gly Ala Ile Ser Ile Gln Asp Gly Glu Asp Leu Val Ser
            1300                1305                1310

Leu Asp Asn Met Asp Asn His Leu Ile Ile Val Lys Asn Leu Arg Lys
            1315                1320                1325

Gly Glu Tyr Pro Lys Thr Gly Gly Met Gly Ile Ile Pro Tyr Ile Ala
            1330                1335                1340

Leu Gly Gly Val Met Met Phe Ile Ala Phe Ala Val Glu Gln Arg Arg
1345                1350                1355                1360

Lys Tyr Thr Arg

<210> SEQ ID NO 90
<211> LENGTH: 284
<212> TYPE: PRT
<213> ORGANISM: S. suis

<400> SEQUENCE: 90

Met Lys Thr Val Arg Gln Ile Ile Cys Cys Leu Val Ala Ile Cys
1               5                   10                  15

Val Leu Ser Leu Pro Ser Leu Ser Leu Gln Ala Gln Asp Ser Phe Asp
            20                  25                  30

Val Gln Val His Ile Pro Phe Pro Asn Gly Ile Asp Ala Ser Gln Val
            35                  40                  45

Ser Thr Gly Leu Glu Ala Trp Tyr Ile Ala Ser Glu Glu Pro Val Ser
            50                  55                  60

Ser Glu Gln Leu Ala Asp Ser Leu Tyr Gln Lys Ser Arg Ser Glu Leu
65                  70                  75                  80

Thr Ser Leu Tyr Gly Glu Pro Ile Ser Ser Gln Ala Leu Ser Pro Glu
            85                  90                  95

```
Gly Gln Ala Thr Phe Arg Gly Leu Thr Lys Gly Trp Tyr Tyr Val Arg
                100                 105                 110

Gln Val Gly Lys Pro Thr Ser Leu Glu Val Ile Pro Phe Leu Met Asn
        115                 120                 125

Val Gly Arg Gly Val Thr Lys Ile Glu Ala Lys Val Arg Arg Pro Ser
    130                 135                 140

Glu Glu Lys Gly Ser Lys Pro Phe Leu Lys Val Ser Thr Ser Thr Ala
145                 150                 155                 160

Pro Leu Ser Gly Ala Glu Phe Ala Val Leu Glu Glu Val Gly Gly Glu
                165                 170                 175

Leu Lys Glu Val Ile Val Asp Gly Asn Ser Tyr His Val Thr Ser Ser
            180                 185                 190

Ser Asn Gly Gln Phe Val Val Gly Pro Leu Pro Tyr Gly Thr Tyr Tyr
        195                 200                 205

Leu Lys Glu Val Lys Ala Pro Thr Gly Tyr Ile Leu Ser Gln Asp Thr
    210                 215                 220

Ile Pro Phe Glu Ile Thr Ser Asp Ser His Val Ser Glu Ile Ile Lys
225                 230                 235                 240

Ile Lys Asn Lys Pro Val Thr Pro Pro Gly Ile Glu Ile Pro Tyr Thr
                245                 250                 255

Gly Asn Val Val Val Ile Ala Val Leu Ser Thr Gly Ile Leu Leu Phe
            260                 265                 270

Leu Leu Gly Tyr Arg Leu Val Thr Tyr Thr Lys Arg
        275                 280

<210> SEQ ID NO 91
<211> LENGTH: 376
<212> TYPE: PRT
<213> ORGANISM: S. suis

<400> SEQUENCE: 91

Met Thr Gln Thr Val Arg Gly Phe Met Val Lys Leu Asn Asn Asn Gly
1               5                   10                  15

Leu Ala Lys Leu Glu Glu Lys Ala Arg Glu Gly Glu Val Asn Phe Thr
            20                  25                  30

Leu Thr Tyr Lys Ala Thr Leu Asn Asp Ser Ala Lys Val Glu Thr Glu
        35                  40                  45

Ile Pro Asn Gln Val Lys Leu Ile Tyr Gly Asn Arg Pro Ser Glu Phe
    50                  55                  60

Ser Glu Pro Lys Ser Thr Thr Pro Lys Asp Gly Glu Ile Ile Val Asn
65                  70                  75                  80

Lys Thr Trp Asp Thr Gly Val Asn Gln Thr Glu Val Val Phe Gly Val
                85                  90                  95

Tyr Glu Lys Gly Thr Gly Val Arg Val Gly Glu Ile Lys Leu Ala Ala
            100                 105                 110

Gly Val Asn Thr Gly Lys Leu Thr Gly Leu Asp Gly Ala Lys Glu Tyr
        115                 120                 125

Ile Val Ile Glu Glu Thr Ile Val Ser Gly Ser Leu Pro Ser Tyr Ser
    130                 135                 140

Asn Gly Asp Thr Gly Thr Ile Arg Ile Glu Asn Lys Lys Asn Pro Asn
145                 150                 155                 160

Pro Thr Pro Leu Thr Pro Glu Asp Pro Lys Val Val Thr Tyr Gly Lys
                165                 170                 175

Arg Phe Val Lys Thr Asp Asp Lys Asp Leu Asp Ser Ser Glu Lys Leu
            180                 185                 190
```

Leu Gly Ala Glu Phe Ile Val Arg Lys Asp Gly Glu Ser Tyr Leu
              195                 200                 205

Ala Leu Lys Asp Thr Val Thr Gln Ala Lys Glu Ile Ala Asp Tyr Lys
210                 215                 220

Ala Ala Glu Ala Asp Tyr Leu Ala Thr Val Lys Ser Ala Thr Thr Asp
225                 230                 235                 240

Asn Pro Lys Ile Asp Glu Ile Lys Gln Lys Asp Ala Arg Asp Thr
              245                 250                 255

Ala Tyr Glu Lys Met Asn Met Gln Trp Thr Trp Val Gly Thr Lys Glu
              260                 265                 270

Gly Ala Phe Thr Phe Val Ser Ser Thr Asp Gly Lys Phe Glu Val Lys
              275                 280                 285

Gly Leu Lys Glu Gly Lys Tyr Glu Leu Ile Glu Thr Lys Ala Pro Glu
              290                 295                 300

Gly Phe Ala Leu Pro Thr Ser Pro Val Glu Phe Thr Val Gly Ala His
305                 310                 315                 320

Thr Trp Gly Thr Ile Asp Ala Leu Thr Ala Asp Asn Phe Gln Gln Ile
              325                 330                 335

Lys Asn Lys Lys Val Thr Ile Pro Gln Thr Gly Gly Ile Gly Thr Leu
              340                 345                 350

Val Phe Thr Ile Val Gly Leu Ser Thr Met Val Phe Ala Phe Ile Ala
              355                 360                 365

Met Lys Lys Arg Gln Ser Glu Glu
              370                 375

<210> SEQ ID NO 92
<211> LENGTH: 999
<212> TYPE: PRT
<213> ORGANISM: S. suis

<400> SEQUENCE: 92

Met Ile Glu Phe Arg Lys Lys Ala Val Gln Leu Ala Ser Leu Met Ser
1               5                   10                  15

Val Phe Phe Leu Cys Thr Tyr Ser Phe Thr Asp Ala Met Tyr Ile Met
                20                  25                  30

Ala Glu Ser Leu Ser Thr Asp Gly Ala Ser Thr Ile Arg Arg Thr Tyr
            35                  40                  45

Ile Glu Asp Lys Lys Glu Asp Lys Asp Arg Leu Asn Ile Glu Leu Val
        50                  55                  60

Glu Ser Leu Ser Ser Pro Lys Thr Ile Gly Gln Lys Ile Thr Ile Asp
65                  70                  75                  80

Lys Gln Ser Leu Ala Thr Gln Asn Phe Asn Glu Lys Gly Ile Val Val
                85                  90                  95

Ile Thr Gln Lys Gly Leu Glu Leu Lys Lys Asp Asp Leu Glu Lys Gly
                100                 105                 110

Trp Lys Leu Asp Glu Ser Tyr Asn Glu Lys Asp Leu Ala Ile Thr Lys
            115                 120                 125

Ser Glu Thr Glu Lys Arg Ser Leu Ser Asn Glu Leu Asp Val Leu Ser
130                 135                 140

Lys Thr Val Glu Glu Leu Pro Val Tyr Gly Glu Asn Tyr His Ser Tyr
145                 150                 155                 160

Arg Leu Leu Pro Thr Thr Glu Leu Asp Tyr Ser Ala Asp Asn Val Ser
                165                 170                 175

Leu Thr Leu Ser Phe Thr Lys Val Ser Glu Val Ile Lys Gly Glu Leu

-continued

```
            180                 185                 190
Val Ala Val Val Asp Ala Glu His Ile Ala Tyr Phe Lys Ala Glu Pro
        195                 200                 205
Ser Val Phe Lys Glu Tyr Ser Gln Val Asn Glu Lys Pro Ser Ser Thr
        210                 215                 220
Glu Asp Val Asn Val Val Ser Pro Ser Gln Asp Pro Pro Val Ser Glu
225                 230                 235                 240
Thr Lys Glu Asn Val Pro Asp Asn Pro Glu Ser Gln Gly Ser Ser Thr
                245                 250                 255
Val Pro Glu Ser Glu Gln Ala Val Asp Ala Leu Val Glu Gln Arg Gly
            260                 265                 270
Val Ile Cys Ile Lys Leu Thr Lys Ser Ser Glu Gln Glu Glu Gly
        275                 280                 285
Ile Glu Asp Thr Glu Asn Glu Ala Ile Glu Gly Ala Thr Phe Glu Val
        290                 295                 300
Arg Asn Val Glu Ser Glu Asn Leu Val Tyr Thr Gly Gln Thr Asp Lys
305                 310                 315                 320
Asp Gly Leu Leu Thr Ile Ser Asn Leu Pro Leu Gly Asn Tyr Ala Val
                325                 330                 335
Ile Gln Lys Ser Thr Ile Asp Gly Tyr Glu Ile Ser Ala Thr Lys Glu
            340                 345                 350
Val Val Glu Leu Thr Val Ala Gln Ser Arg Gln Thr Val Ser Ile Ser
        355                 360                 365
Asn Ser Pro Lys Asn Pro Leu Glu Gly Leu Met Leu Asn Ser Ile Leu
        370                 375                 380
Asp Ser Ser Leu Ile Pro Arg Ser Ala Arg Val Ala Arg Ser Leu Leu
385                 390                 395                 400
Asp Thr Ser Leu Leu Asp Asn Pro Thr Val Thr Gly Asn Ala Asn Ala
                405                 410                 415
Thr Thr Thr Thr Thr Val Phe Gly Asn Lys Thr Thr Thr Ile Thr Arg
            420                 425                 430
Glu Glu Ser Asn Ile Lys Tyr Ile Phe Lys Pro Ile Thr Ile Ser Ile
        435                 440                 445
Pro Gly Val Tyr Gln Ser Tyr Ser Gln Asp Gly Val Leu Lys Lys Lys
        450                 455                 460
Glu Val Val Val Asp Ser Asn Thr Asn Thr Thr Lys Ile Ile Trp Glu
465                 470                 475                 480
Tyr Thr Thr Thr Val Gly Gly Val Asn Ser Asn Ile Thr Ser Ile Arg
                485                 490                 495
Asn Ala Phe Ser Thr Thr Thr Asp Ser Gly Leu Gly Glu Pro Lys Ile
            500                 505                 510
Thr Ser Ile Met Lys Asp Gly Val Ala Ile Thr Pro Asn Thr Thr Tyr
        515                 520                 525
Tyr Gly Asn Phe Asp Asn Phe Lys Ser Ala Thr Asp Asn Leu Pro Val
        530                 535                 540
Gly Asn Gly Thr Tyr Val Tyr Thr Ile Glu Thr Pro Val Val Ile Pro
545                 550                 555                 560
Ser Asp Asn Tyr Ser Leu Asp Tyr Arg Ser Glu Val Thr Val Asp Ala
                565                 570                 575
Pro Lys Gly Ser Lys Leu Thr Tyr Asn Gly Thr Ser Val Thr Leu Thr
            580                 585                 590
Gln Lys Glu Thr Arg Thr Leu Ser Thr Ala Asp Thr Ile Thr Leu Pro
        595                 600                 605
```

```
Ala Lys Asn Asp Gly Gly Pro Leu Gly Asp Leu Lys Val Asp Thr Val
610                 615                 620

Asn Thr Ser Asn Thr Asn Arg Thr Ile Gly Lys Tyr Arg Asp Asn Asp
625                 630                 635                 640

Asp Lys Val Ile Glu Trp Thr Ser Ser Gln Leu Asn Asp Thr Ser Thr
                645                 650                 655

Thr Gln Ser Phe Thr Phe Asp Val Ala Leu Asp Ser Ser Gln Ala Ala
                660                 665                 670

His Glu Tyr Lys Val Tyr Ile Tyr Glu Pro Ser Asn Gly Thr Tyr Thr
            675                 680                 685

Glu Thr Lys Ala Glu Lys Val Ala Thr Pro Gly Asn Gln Ile Thr Val
690                 695                 700

Asp Asn Val Pro Ala Gly Ala Val Ala Leu Val Lys Thr Val Thr Asn
705                 710                 715                 720

Val Lys Asp Glu Lys Val Asn His Thr Ile Ser Gly Ala Gln Leu Glu
                725                 730                 735

Ala Leu Lys Gly Asp Ile Lys Ile Gln Lys Asn Trp Glu Ala Asp Ser
                740                 745                 750

Asp Lys Val Asp Val Thr Phe Thr Val Asn Gly Gly Ser Leu Thr Asn
                755                 760                 765

Arg Lys Glu Thr Leu Ser Ala Asn Asn Thr Gln Ile Thr Ile Ala Asn
770                 775                 780

Val Asp Lys Phe Ser Gly Met Arg Ser Thr Ala Thr Lys Lys Arg Ile
785                 790                 795                 800

Tyr Tyr Asp Val Thr Glu Ala Val Pro Ser Gly Tyr Ile Leu Ser Ser
                805                 810                 815

Ala Gln Thr Asp Trp Glu Asn Leu Tyr Tyr Val Phe Thr Asn Lys Lys
                820                 825                 830

Asp Asn Thr Thr Thr Pro Val Phe Pro Pro Asp Thr Cys Gly Asn Tyr
                835                 840                 845

Gly Val Ser Ser Ile Asp Leu Val Ser Ile Asn Tyr Val Met Tyr Lys
                850                 855                 860

Ser Gly Ser Lys Ile Trp Gly Gly Phe Asp Gly Ser Met Lys Met Asn
865                 870                 875                 880

Leu Lys Ile Pro Ala Phe Ala Arg Ala Gly Asp Ser Phe Thr Leu Glu
                885                 890                 895

Leu Pro Pro Glu Leu Lys Leu Ser His Val Ala Asn Pro Asn Val Ala
                900                 905                 910

Trp Ser Thr Val Ser Ala Asn Gly Lys Val Ile Ala Lys Val Tyr His
                915                 920                 925

Glu Lys Asp Asn Leu Ile Arg Phe Val Leu Thr Thr Glu Ala Tyr Ser
930                 935                 940

Val Gln Glu Tyr Asn Gly Trp Phe Glu Ile Gly Val Pro Thr Ser Asn
945                 950                 955                 960

Val Ile Lys Ile Asn Asn Arg Glu Thr Thr Glu Leu Tyr Lys Thr Gly
                965                 970                 975

Val Leu Pro Asn Leu Pro Glu Trp Tyr Thr Thr Thr Arg Asn Gln
                980                 985                 990

Thr Leu Ile Lys Arg Ser Arg
                995
```

<210> SEQ ID NO 93
<211> LENGTH: 299

<212> TYPE: PRT
<213> ORGANISM: S. suis

<400> SEQUENCE: 93

```
Met His Phe Thr Leu Thr Tyr Lys Ala Thr Ile His Asp Ser Ala Lys
1               5                   10                  15
Val Glu Thr Glu Ile Pro Asn Gln Val Lys Leu Ile Tyr Gly Asn Arg
            20                  25                  30
Pro Ser Glu Phe Tyr Glu Pro Lys Ser Thr Thr Pro Lys Asp Gly Glu
        35                  40                  45
Ile Ile Val Asn Lys Thr Trp Asp Thr Gly Val Asn Gln Thr Glu Val
50                  55                  60
Val Phe Gly Val Tyr Glu Lys Gly Thr Gly Val Arg Val Gly Glu Ile
65                  70                  75                  80
Lys Leu Ala Ala Gly Val Asn Thr Gly Lys Leu Thr Gly Leu Asp Gly
                85                  90                  95
Ala Lys Glu Tyr Ile Val Ile Glu Glu Thr Ile Val Ser Gly Ser Leu
            100                 105                 110
Pro Ser Tyr Ser Asn Gly Asp Thr Gly Thr Ile Arg Ile Glu Asn Lys
        115                 120                 125
Lys Asn Pro Asn Pro Thr Pro Leu Thr Pro Glu Asp Pro Lys Val Val
130                 135                 140
Thr Tyr Gly Lys Arg Phe Val Lys Thr Asp Asp Lys Asp Leu Asp Ser
145                 150                 155                 160
Ser Glu Lys Leu Leu Gly Ala Glu Phe Ile Val Arg Lys Asp Gly Glu
                165                 170                 175
Glu Ser Tyr Leu Ala Leu Lys Asp Thr Val Thr Gln Ala Lys Glu Ile
            180                 185                 190
Ala Asp Tyr Lys Ala Ala Glu Ala Asp Tyr Leu Ala Thr Val Lys Ser
        195                 200                 205
Ala Thr Thr Asp Asn Pro Lys Ile Asp Glu Ile Lys Gln Lys Lys Asp
210                 215                 220
Ala Arg Asp Thr Ala Tyr Glu Lys Met Asn Met Gln Trp Thr Trp Val
225                 230                 235                 240
Gly Thr Lys Glu Gly Ala Phe Thr Phe Val Ser Ser Thr Asp Gly Lys
                245                 250                 255
Phe Glu Val Lys Gly Leu Lys Glu Gly Lys Tyr Glu Leu Ile Glu Thr
            260                 265                 270
Lys Ala Pro Glu Gly Phe Ala Leu Pro Thr Ser Pro Val Glu Phe Thr
        275                 280                 285
Val Gly Ala His Thr Trp Gly Thr Ile Asp Ala
290                 295
```

<210> SEQ ID NO 94
<211> LENGTH: 1097
<212> TYPE: PRT
<213> ORGANISM: S. suis

<400> SEQUENCE: 94

```
Met Lys Gly Ala Val Phe Arg Leu Gln Ser Lys Asn Gly Gly Asn Tyr
1               5                   10                  15
Asp Val Thr Ile Gly Asp Val Leu Pro Ala Ser Gln Phe Ile Phe Ser
            20                  25                  30
Asn Leu Ala Lys Gly Ile Tyr Thr Leu Thr Glu Thr Lys Ala Pro Ala
        35                  40                  45
```

```
Gly Tyr Lys Thr Ile Pro Pro Leu Asp Ile Glu Val Tyr Glu Asn
 50              55                  60

Gly Glu Leu Lys Val Arg Lys Leu Thr Asp Thr Ser Asn Thr Gln Thr
 65                  70                  75                  80

Gly Ala Val Glu Val Val Asn Gly Asn Phe Ser Ile Asn Val Val Asp
                 85                  90                  95

Glu Asp Phe Ser Thr Glu Phe Thr Lys Val Asn Glu Gln Gly Gln Pro
             100                 105                 110

Leu Ala Asp Ala Val Phe Glu Leu Arg Gln Ile Thr Gln Thr Gly Tyr
         115                 120                 125

Lys Arg Val Leu Thr Gly Leu Thr Ser Asn Ser Gln Gly Lys Leu Arg
130                 135                 140

Val Asp His Leu Gln Gly Gly Ile Thr Tyr Glu Leu Trp Glu Thr Ser
145                 150                 155                 160

Ala Pro Ala Gly Tyr Ser Lys Leu Thr Thr Ala Ala Arg Phe Thr
                165                 170                 175

Val Ser Glu Thr Gly Thr Ile Ser Phe Glu Ser Gly Thr Ser Glu Arg
             180                 185                 190

Ile Ile Asn Arg Pro Pro Thr Tyr Lys Val Lys Val Gln Lys Ile Asp
         195                 200                 205

Ala Leu Thr Gly Gln Lys Val Thr Val Gln Thr Arg Ile Gly Ile Thr
210                 215                 220

Asp Ser Gln Gly Asn Val Ile Asp Gly Gln Ile Ala Asn Phe Asp Asn
225                 230                 235                 240

Gly Glu Phe Ser Phe Pro Lys Asn Phe Thr Pro Gly Thr Tyr Tyr Ile
                245                 250                 255

Lys Glu Glu Lys Thr Pro Ser Gly Tyr Ile Gly Leu Ser Gly Leu Val
             260                 265                 270

Pro Phe Thr Ile Arg Ala Asp Gly Ile Val Glu Val Asn Ser Asp Tyr
         275                 280                 285

Leu Glu Gly Ile Asp Val Thr Thr Ser Ser Pro Asp Thr Ile Thr Ile
290                 295                 300

Lys Val Lys Asn Tyr Pro Leu Gly Lys Phe Lys Val Ser Lys Arg Val
305                 310                 315                 320

Lys Gly Ile Ser Asp Leu Thr Asn Leu Ile Thr Gly Gln Met Thr Phe
                325                 330                 335

Thr Leu Thr Lys Asn Asp Asp Val Asn Phe Ala Pro Ile Val Lys Gln
             340                 345                 350

Gln Ala Ala Asn Gln Asp Phe Val Phe Glu Asn Leu Gln Pro Gly Val
         355                 360                 365

Tyr Thr Leu Thr Glu Thr Gln Ala Pro Ser Gly Tyr Val Lys Ser Thr
370                 375                 380

Glu Asn Tyr Thr Ile Tyr Val Asn Arg Asp Gly Ser Val Arg Phe Tyr
385                 390                 395                 400

Ser Asp Ser Asp Ile Ser Ser His Ile Ala Arg Gly Leu His Val Ile
                405                 410                 415

Lys Ser Ala Glu Ile Ala Met Ala Ser Thr Tyr Gly Ser Ser Thr Glu
             420                 425                 430

Asp Lys Ala Leu Asp Gly Asp Leu Thr Thr Gly Ala Leu Tyr Gln Leu
         435                 440                 445

Pro Ser Ser Thr Leu Asn Glu Gly Gln Trp Trp Gly Val Asn Leu Gly
450                 455                 460

Ser Pro Gln Arg Val Thr Gln Ile Arg Phe Ala Gln Gly Lys Asn Thr
```

```
465                 470                 475                 480
Thr Asn Gly Ser Asp His Asp Lys Met Asp Ser Tyr Ala Leu Glu Tyr
                485                 490                 495
Ser Pro Asp Gly Ile Thr Tyr Gln Ser Ile Gly Asn Phe Thr Glu Thr
            500                 505                 510
Asp Leu Thr Gln Thr Val Asp Ile Tyr Ala Gln Tyr Ile Arg Val Arg
            515                 520                 525
Asn Leu Gln Thr Gly Thr Asn Arg Trp Leu Gly Ile Arg Glu Leu Gln
530                 535                 540
Val Ser Val Arg Asp Ala Thr Gln Thr Ile Glu Ala Gly Gly Ser Asp
545                 550                 555                 560
Ala Ala Ala Asn Val Ile Lys Ile Gly Asn Ile Glu Asn Pro Glu Phe
                565                 570                 575
Lys Ile Glu Lys Val Asp Ala Asn Asn Lys Gln Ile Ser Lys Pro Val
            580                 585                 590
Thr Phe Lys Leu Tyr Lys Val Asp Asp Ser Thr Thr Glu Ala Thr Val
            595                 600                 605
Ser Ser Thr Ser Leu Asp Asp Thr Asn Leu Val Gln Thr Leu Thr Phe
610                 615                 620
Thr Gly Gln Ser Ser Leu Thr Arg Leu Thr Ala Thr Ala Leu Gly Lys
625                 630                 635                 640
Tyr Val Leu Val Glu Thr Gln Ala Pro Glu Gly Tyr Asp Gly Leu Ser
                645                 650                 655
Ala Pro Val Leu Leu Glu Leu Tyr Glu Thr Thr Gln Ala Tyr Ala Val
            660                 665                 670
Thr Gln Gln Lys Ala Val Thr Arg Phe Arg Val Leu Ser Gln Thr Asn
            675                 680                 685
Ser Val Ser Val Thr Asp Leu Pro Gly Val Ser Gly Ala Leu Ala Asn
            690                 695                 700
Ala Ile Ser Ile Lys Val Lys Asn Asn Glu Arg Arg Tyr Asn Leu Lys
705                 710                 715                 720
Ile Lys Lys Arg Asp Tyr His His Pro Thr Leu Gly Leu Asn Ala Arg
                725                 730                 735
Phe Glu Leu Val Thr Glu Ala Gly His Pro Val Val Ile Asp Gly Val
            740                 745                 750
Asn Met Lys Gly Asp Thr Asn Ser Ala Asp Asn Ser Ile Thr Phe Ser
            755                 760                 765
Asn Leu Pro Val Gly Val Tyr Ile Leu Lys Glu Thr Val Val Pro Thr
            770                 775                 780
Gly Gly Tyr Arg Pro Val Asn Gln Leu Gln Asp Thr Lys Phe Glu Ile
785                 790                 795                 800
Arg Pro Asp Gly Ser Leu Gln Ile Leu Glu Ser Asp Ser Asn Met Val
                805                 810                 815
Thr Val Asp Thr Ser Gln Gly Ala Thr Phe Glu Ile Thr Ile Lys Asn
            820                 825                 830
Phe Lys Gln Phe Lys Phe Arg Leu Gln Lys Thr Asp Asn Arg Asp Glu
            835                 840                 845
Asn His Leu Leu Asn Gly Ala Thr Phe Lys Ile Tyr Ser Asp Pro Asn
            850                 855                 860
Asn Asp Gly Val Glu Asp Thr Glu Val Ala Ser Gly Val Thr Thr Asn
865                 870                 875                 880
Gly Leu Phe Glu Thr Ser Leu Ser Phe Gly Tyr Tyr Ile Leu Glu Glu
                885                 890                 895
```

```
Thr Val Ala Pro Thr Gly Tyr Gln Leu Asn Pro Lys Lys Tyr Arg Phe
            900                 905                 910

Gln Ile Asn His Asp Gly Thr Lys Leu His Asn Gly Asp Asn Gln
            915                 920                 925

Val Thr Leu Ala Glu Arg Val Asp Gly Asp Asn Val Ile Leu Phe Asn
            930                 935                 940

Met Lys Asn Thr Lys Gln Thr Thr His Ile Lys Leu Ala Lys Arg Ser
945                 950                 955                 960

Tyr Ser Asp Pro Thr Gln Arg Leu Val Ala Thr Phe Glu Leu Arg Glu
            965                 970                 975

Ser Asp Asn Pro Gln Ala Thr Ala Val Lys Thr Thr Thr Thr
            980                 985                 990

Gly Asp Glu Val Leu Phe Asp Asn Leu Ala Val Gly Lys Thr Tyr Ile
            995                 1000                1005

Leu Lys Glu Ile Val Ala Pro Asp Gly Tyr Gln Lys Ile Glu Lys Glu
            1010                1015                1020

Phe His Ile Asn Ile Gly Ala Asp Gly Ala Ile Ser Ile Gln Asp Gly
1025                1030                1035                1040

Glu Asp Leu Val Ser Leu Asp Asn Met Asp Asn His Leu Ile Ile Val
            1045                1050                1055

Lys Asn Leu Arg Lys Gly Glu Tyr Pro Lys Thr Gly Met Gly Ile
            1060                1065                1070

Ile Pro Tyr Ile Ala Leu Gly Gly Val Met Met Phe Ile Ala Phe Ala
            1075                1080                1085

Val Glu Gln Arg Arg Lys Tyr Thr Arg
            1090                1095

<210> SEQ ID NO 95
<211> LENGTH: 752
<212> TYPE: PRT
<213> ORGANISM: S. suis

<400> SEQUENCE: 95

Met Ser Lys Thr Val Glu Glu Leu Pro Val Tyr Gly Glu Asn Tyr His
1               5                   10                  15

Ser Tyr Arg Leu Leu Pro Thr Thr Glu Leu Asp Tyr Ser Ala Asp Asn
            20                  25                  30

Val Ser Leu Thr Leu Ser Phe Thr Lys Val Ser Glu Val Ile Lys Gly
            35                  40                  45

Glu Leu Val Ala Val Val Asp Ala Glu His Ile Ala Tyr Phe Lys Ala
            50                  55                  60

Glu Pro Ser Val Phe Lys Glu Tyr Ser Gln Val Asn Glu Lys Pro Ser
65                  70                  75                  80

Ser Thr Glu Asp Val Asn Val Ser Pro Ser Gln Asp Pro Pro Val
            85                  90                  95

Ser Glu Thr Lys Glu Asn Val Pro Asp Asn Pro Glu Ser Gln Gly Ser
            100                 105                 110

Ser Thr Val Pro Glu Ser Glu Gln Ala Val Asp Ala Leu Val Glu Gln
            115                 120                 125

Arg Gly Val Ile Cys Ile Lys Leu Thr Lys Ser Ser Glu Gln Glu
            130                 135                 140

Glu Gly Ile Glu Asp Thr Glu Asn Glu Ala Ile Glu Gly Ala Thr Phe
145                 150                 155                 160

Glu Val Arg Asn Val Glu Ser Glu Asn Leu Val Tyr Thr Gly Gln Thr
```

```
            165                 170                 175
Asp Lys Asp Gly Leu Leu Thr Ile Ser Asn Leu Pro Leu Gly Asn Tyr
            180                 185                 190

Ala Val Ile Gln Lys Ser Thr Ile Asp Gly Tyr Glu Ile Ser Ala Thr
            195                 200                 205

Lys Glu Val Val Glu Leu Thr Val Ala Gln Ser Arg Gln Thr Val Ser
            210                 215                 220

Ile Ser Asn Ser Pro Lys Asn Pro Leu Glu Gly Leu Met Leu Asn Ser
225                 230                 235                 240

Ile Leu Asp Ser Ser Leu Ile Pro Arg Ser Ala Arg Val Ala Arg Ser
            245                 250                 255

Leu Leu Asp Thr Ser Leu Leu Asp Asn Pro Thr Val Thr Gly Asn Ala
            260                 265                 270

Asn Ala Thr Thr Thr Thr Val Phe Gly Asn Lys Thr Thr Thr Ile
            275                 280                 285

Thr Arg Glu Glu Ser Asn Ile Lys Tyr Ile Phe Lys Pro Ile Thr Ile
            290                 295                 300

Ser Ile Pro Gly Val Tyr Gln Ser Tyr Ser Gln Asp Gly Val Leu Lys
305                 310                 315                 320

Lys Lys Glu Val Val Asp Ser Asn Thr Asn Thr Thr Lys Ile Ile
            325                 330                 335

Trp Glu Tyr Thr Thr Thr Val Gly Gly Val Asn Ser Asn Ile Thr Ser
            340                 345                 350

Ile Arg Asn Ala Phe Ser Thr Thr Thr Asp Ser Gly Leu Gly Glu Pro
            355                 360                 365

Lys Ile Thr Ser Ile Met Lys Asp Gly Val Ala Ile Thr Pro Asn Thr
            370                 375                 380

Thr Tyr Tyr Gly Asn Phe Asp Asn Phe Lys Ser Ala Thr Asp Asn Leu
385                 390                 395                 400

Pro Val Gly Asn Gly Thr Tyr Val Tyr Thr Ile Glu Thr Pro Val Val
            405                 410                 415

Ile Pro Ser Asp Asn Tyr Ser Leu Asp Tyr Arg Ser Glu Val Thr Val
            420                 425                 430

Asp Ala Pro Lys Gly Ser Lys Leu Thr Tyr Asn Gly Thr Ser Val Thr
            435                 440                 445

Leu Thr Gln Lys Glu Thr Arg Thr Leu Ser Thr Ala Asp Thr Ile Thr
            450                 455                 460

Leu Pro Ala Lys Asn Asp Gly Pro Leu Gly Asp Leu Lys Val Asp
465                 470                 475                 480

Thr Val Asn Thr Ser Asn Thr Asn Arg Thr Ile Gly Lys Tyr Arg Asp
            485                 490                 495

Asn Asp Asp Lys Val Ile Glu Trp Thr Ser Ser Gln Leu Asn Asp Thr
            500                 505                 510

Ser Thr Thr Gln Ser Phe Thr Phe Asp Val Ala Leu Asp Ser Ser Gln
            515                 520                 525

Ala Ala His Glu Tyr Lys Val Tyr Ile Tyr Glu Pro Ser Asn Gly Thr
            530                 535                 540

Tyr Thr Glu Thr Lys Ala Glu Lys Val Ala Thr Pro Gly Asn Gln Ile
545                 550                 555                 560

Thr Val Asp Asn Val Pro Ala Gly Ala Val Ala Leu Val Lys Thr Val
            565                 570                 575

Thr Asn Val Lys Asp Glu Lys Val Asn His Thr Ile Ser Gly Ala Gln
            580                 585                 590
```

-continued

```
Leu Glu Ala Leu Lys Gly Asp Ile Lys Ile Gln Lys Asn Trp Glu Ala
            595                 600                 605
Asp Ser Asp Lys Val Asp Val Thr Phe Thr Val Asn Gly Gly Ser Leu
610                 615                 620
Thr Asn Arg Lys Glu Thr Leu Ser Ala Asn Asn Thr Gln Ile Thr Ile
625                 630                 635                 640
Ala Asn Val Asp Lys Phe Ser Gly Met Arg Ser Thr Ala Thr Lys Lys
            645                 650                 655
Arg Ile Tyr Tyr Asp Val Thr Glu Ala Val Pro Ser Gly Tyr Ile Leu
            660                 665                 670
Ser Ser Ala Gln Thr Asp Trp Glu Asn Leu Tyr Tyr Val Phe Thr Asn
            675                 680                 685
Lys Lys Asp Asn Thr Thr Thr Pro Val Phe Pro Pro Asp Thr Cys Gly
            690                 695                 700
Asn Tyr Gly Val Ser Ser Ile Asp Leu Val Ser Ile Asn Tyr Val Met
705                 710                 715                 720
Tyr Lys Ser Gly Ser Lys Ile Trp Gly Gly Phe Asp Gly Ser Met Lys
            725                 730                 735
Met Asn Leu Lys Ile Pro Ala Phe Ala Arg Ala Gly Asp Ser Leu Leu
            740                 745                 750

<210> SEQ ID NO 96
<211> LENGTH: 546
<212> TYPE: PRT
<213> ORGANISM: S. suis

<400> SEQUENCE: 96

Met Lys Arg Ile Phe Thr Leu Leu Thr Val Leu Leu Thr Val Leu Gly
  1               5                  10                  15
Met Asn Ala Arg Pro Val Phe Ala Ala Ser Asn Thr Asp Gln Ala Glu
            20                  25                  30
Leu Lys Ile Thr Asn Ile Glu Gly Asn Pro Thr Val Thr Leu Tyr Lys
            35                  40                  45
Ile Gly Glu Gly Val Tyr Asn Ala Thr Asn Asp Ser Phe Ile Arg Phe
 50                  55                  60
Asp Tyr Ala Ser Gly Val Lys Leu Thr Glu Thr Gly Pro Thr Ala Glu
 65                  70                  75                  80
Glu Ile Thr Asn Ile Ala Asn Gly Ile Leu Asp Asn Thr Ile Gln Ala
            85                  90                  95
Lys Ala Ser Lys Val Leu Gln Val Thr Asn Gly Thr Ala Thr Tyr Arg
            100                 105                 110
Ala Thr Gly Ala Gly Val Tyr Ile Ala Ile Leu Thr Gly Ala Thr Asp
            115                 120                 125
Gly Arg Ser Phe Asn Pro Ile Leu Leu Ala Ala Ser Tyr Asn Gly Glu
            130                 135                 140
Gly Lys Leu Thr Gly Gly Ser Val Asp Ser Lys Ala Lys Tyr Leu Tyr
145                 150                 155                 160
Gly Gln Thr Ser Val Ala Lys Ser Thr Leu Pro Ser Ile Asp Lys Thr
            165                 170                 175
Val Ser Gly Val Thr Ala Asp Ala Asp Lys Asn Ser Ala Ser Leu Gly
            180                 185                 190
Gln Val Leu Thr Tyr Ser Leu Asn Val Thr Leu Pro Ser Tyr Pro Thr
            195                 200                 205
Gln Ala Lys Asn Lys Thr Ile Phe Ile Ser Asp Thr Met Ser Glu Gly
```

```
                        210                 215                 220
Leu Thr Phe Asp Tyr Ala Ser Leu Thr Ile Ser Trp Asn Gly Gln Thr
225                 230                 235                 240

Leu Ile Ala Asp Thr Thr Gly Gln Phe Lys Thr Gln Gly Asp Ile Leu
                245                 250                 255

Ile Ala Lys Ala Val Lys Val Gly Asn Gly Phe Asn Leu Ala Phe Val
            260                 265                 270

Tyr Asp Asn Leu Asn Glu Ile Ala Pro Val Val Thr Tyr Lys Gly Ile
        275                 280                 285

Ile Asn Asp Lys Ala Val Val Gly Gly Thr Gly Asn Ala Asn Lys Ala
    290                 295                 300

Glu Phe Phe Tyr Ala Arg Asn Pro Asn Ser Gly Asn Thr Tyr Glu Asp
305                 310                 315                 320

Pro Asn Asn Lys Pro Asn Pro Gln Asn Asp Asn Thr Ile Val Asn Lys
                325                 330                 335

Glu Asp Ser Glu Thr Val Tyr Thr Tyr Gln Ile Ala Phe Lys Lys Val
            340                 345                 350

Asp Ser Ile Thr Lys Ala Pro Leu Ala Gly Ala Val Phe Gly Ile Tyr
        355                 360                 365

Ser Asp Ala Glu Thr Lys Gln Leu Val Asp Ile Val Thr Asn Ala
    370                 375                 380

Asp Gly Tyr Ala Ile Ser Thr Lys Val Gly Lys Gly Thr Tyr Tyr Leu
385                 390                 395                 400

Lys Glu Ile Thr Ala Pro Thr Gly Tyr Ser Leu Asn Thr Asn Val Tyr
                405                 410                 415

Thr Ala Glu Ala Ser Trp Thr Ser Ala Thr Thr Ser Ser Ala Ser
            420                 425                 430

Ser Thr Arg Ser Glu Tyr Thr Ser Val Val Gly Glu Ala Lys Asp Ser
        435                 440                 445

Thr Gln Val Gly Trp Leu Lys His Asn Val Phe Tyr Lys Leu Asp Asn
    450                 455                 460

Lys Pro Glu Gly Thr Asp Val Gln Ala Ala Tyr Leu Lys Ala Thr Thr
465                 470                 475                 480

Thr Thr Ala Gln Asn Thr Thr Val Thr Thr Asn Pro Thr Ala Gly
                485                 490                 495

Ala Gly Thr Val Ser Ile Ala Asp Val Pro Asn Thr Lys Leu Gly Glu
            500                 505                 510

Leu Pro Ser Thr Gly Gly Met Gly Thr Tyr Leu Phe Thr Phe Ile Gly
        515                 520                 525

Val Leu Val Leu Thr Val Gly Leu Gly Leu Tyr Phe Thr Lys Asn Lys
    530                 535                 540

Lys Ala
545

<210> SEQ ID NO 97
<211> LENGTH: 1364
<212> TYPE: PRT
<213> ORGANISM: S. suis

<400> SEQUENCE: 97

Met Phe Pro Asn Gly Asn Val Ala Asn Ser Ile Pro Gln Ser Ile Glu
1               5                   10                  15

Leu Tyr Val Ala Asp Gly Thr Lys Ala Met Ser Tyr Ser Lys Asp Ser
            20                  25                  30
```

-continued

Leu Glu Lys Leu Thr Tyr Lys Gly Thr Ser Asn Asn Gly Asn Ile His
     35                  40                  45

His Tyr Tyr Leu Pro Gly Thr Asp Ile Gly Ile Ser Val Arg Val Tyr
 50                  55                  60

Ser Glu Arg Asn Ser Tyr Pro Ala Phe Asp Gly Phe Glu Ser Thr His
 65                  70                  75                  80

Thr Ile Glu Phe Tyr Gln Gly Trp Lys Leu Gly Asn Lys Ala Ile
                 85                  90                  95

Val Val Arg Leu Lys Glu Arg Lys Lys Phe Gln Lys Asn Gly Leu Tyr
                100                 105                 110

Tyr Asn Gly Met Ser Val Pro Trp Asn Ser Pro Val Met Gly Gly Gly
            115                 120                 125

Arg Thr Thr Asn Ile Tyr Arg Arg Glu Gly Asp Thr Val Ser Gln Gly
        130                 135                 140

Gly Ala Tyr Pro Val Asp Trp Tyr Gly Phe Lys Leu Lys Lys Val Gly
145                 150                 155                 160

Ile Lys Asn Gly Gln Lys Ile Pro Leu Ser Gly Ala Ile Phe Thr Leu
                165                 170                 175

Tyr Lys Gly Asn Glu Pro Tyr Arg Thr Ala Val Ser Asp Asp Asn Gly
            180                 185                 190

Asp Ile Gln Phe Ser Glu Ile Ile Gly Gly Thr Tyr Thr Phe Lys Glu
        195                 200                 205

Thr Ser Ala Pro Ser Gly Tyr Ile Leu Asp Pro Thr Glu His Thr Ile
210                 215                 220

Val Val Thr Asp Asn Gln Asn Ile Thr Ile Asp Gly Lys Lys Tyr Asp
225                 230                 235                 240

Val Asn Lys Pro Thr Glu Val Val Asn Thr Lys Ser Thr Thr Leu Gln
                245                 250                 255

Ile Asn Lys Phe Glu Phe Gly Glu Ser Lys Pro Leu Lys Gly Ala Val
                260                 265                 270

Phe Arg Leu Gln Ser Lys Asn Gly Gly Asn Tyr Asp Val Thr Ile Gly
            275                 280                 285

Asp Val Leu Pro Ala Ser Gln Phe Ile Phe Ser Asn Leu Ala Lys Gly
        290                 295                 300

Ile Tyr Thr Leu Thr Glu Thr Lys Ala Pro Ala Gly Tyr Lys Thr Ile
305                 310                 315                 320

Pro Pro Leu Asp Ile Glu Val Tyr Glu Glu Asn Gly Glu Leu Lys Val
                325                 330                 335

Arg Lys Leu Thr Asp Thr Ser Asn Thr Gln Thr Gly Ala Val Glu Val
            340                 345                 350

Val Asn Gly Asn Phe Ser Ile Asn Val Val Asp Glu Asp Phe Ser Thr
        355                 360                 365

Glu Phe Thr Lys Val Asn Glu Gln Gly Gln Pro Leu Ala Asp Ala Val
370                 375                 380

Phe Glu Leu Arg Gln Ile Thr Gln Thr Gly Tyr Lys Arg Val Leu Thr
385                 390                 395                 400

Gly Leu Thr Ser Asn Ser Gln Gly Lys Leu Arg Val Asp His Leu Gln
            405                 410                 415

Gly Gly Ile Thr Tyr Glu Leu Trp Glu Thr Ser Ala Pro Ala Gly Tyr
        420                 425                 430

Ser Lys Leu Thr Thr Ala Ala Ala Arg Phe Thr Val Ser Glu Thr Gly
435                 440                 445

Thr Ile Ser Phe Glu Ser Gly Thr Ser Glu Arg Ile Ile Asn Arg Pro

```
                450             455             460
Pro Thr Tyr Lys Val Lys Val Gln Lys Ile Asp Ala Leu Thr Gly Gln
465             470             475             480

Lys Val Thr Val Gln Thr Arg Ile Gly Ile Thr Asp Ser Gln Gly Asn
            485             490             495

Val Ile Asp Gly Gln Ile Ala Asn Phe Asp Asn Gly Glu Phe Ser Phe
            500             505             510

Pro Lys Asn Phe Thr Pro Gly Thr Tyr Tyr Ile Lys Glu Glu Lys Thr
            515             520             525

Pro Ser Gly Tyr Ile Gly Leu Ser Gly Leu Val Pro Phe Thr Ile Arg
            530             535             540

Ala Asp Gly Ile Val Glu Val Asn Ser Asp Tyr Leu Glu Gly Ile Asp
545             550             555             560

Val Thr Thr Ser Ser Pro Asp Thr Ile Thr Ile Lys Val Lys Asn Tyr
            565             570             575

Pro Leu Gly Lys Phe Lys Val Ser Lys Arg Val Lys Gly Ile Ser Asp
            580             585             590

Leu Thr Asn Leu Ile Thr Gly Gln Met Thr Phe Thr Leu Thr Lys Asn
            595             600             605

Asp Asp Val Asn Phe Ala Pro Ile Val Lys Gln Gln Ala Ala Asn Gln
            610             615             620

Asp Phe Val Phe Glu Asn Leu Gln Pro Gly Val Tyr Thr Leu Thr Glu
625             630             635             640

Thr Gln Ala Pro Ser Gly Tyr Val Lys Ser Thr Glu Asn Tyr Thr Ile
            645             650             655

Tyr Val Asn Arg Asp Gly Ser Val Arg Phe Tyr Ser Asp Ser Asp Ile
            660             665             670

Ser Ser His Ile Ala Arg Gly Leu His Val Ile Lys Ser Ala Glu Ile
            675             680             685

Ala Met Ala Ser Thr Tyr Gly Ser Ser Thr Glu Asp Lys Ala Leu Asp
            690             695             700

Gly Asp Leu Thr Thr Gly Ala Leu Tyr Gln Leu Pro Ser Ser Thr Leu
705             710             715             720

Asn Glu Gly Gln Trp Trp Gly Val Asn Leu Gly Ser Pro Gln Arg Val
            725             730             735

Thr Gln Ile Arg Phe Ala Gln Gly Lys Asn Thr Thr Asn Gly Ser Asp
            740             745             750

His Asp Lys Met Asp Ser Tyr Ala Leu Glu Tyr Ser Pro Asp Gly Ile
            755             760             765

Thr Tyr Gln Ser Ile Gly Asn Phe Thr Glu Thr Asp Leu Thr Gln Thr
            770             775             780

Val Asp Ile Tyr Ala Gln Tyr Ile Arg Val Arg Asn Leu Gln Thr Gly
785             790             795             800

Thr Asn Arg Trp Leu Gly Ile Arg Glu Leu Gln Val Ser Val Arg Asp
            805             810             815

Ala Thr Gln Thr Ile Glu Ala Gly Gly Ser Asp Ala Ala Ala Asn Val
            820             825             830

Ile Lys Ile Gly Asn Ile Glu Asn Pro Glu Phe Lys Ile Glu Lys Val
            835             840             845

Asp Ala Asn Asn Lys Gln Ile Ser Lys Pro Val Thr Phe Lys Leu Tyr
            850             855             860

Lys Val Asp Asp Ser Thr Thr Glu Ala Thr Val Ser Ser Thr Ser Leu
865             870             875             880
```

```
Asp Asp Thr Asn Leu Val Gln Thr Leu Thr Phe Thr Gly Gln Ser Ser
                885                 890                 895
Leu Thr Arg Leu Thr Ala Thr Ala Leu Gly Lys Tyr Val Leu Val Glu
            900                 905                 910
Thr Gln Ala Pro Glu Gly Tyr Asp Gly Leu Ser Ala Pro Val Leu Leu
            915                 920                 925
Glu Leu Tyr Glu Thr Thr Gln Ala Tyr Ala Val Thr Gln Gln Lys Ala
        930                 935                 940
Val Thr Arg Phe Arg Val Leu Ser Gln Thr Asn Ser Val Ser Val Thr
945                 950                 955                 960
Asp Leu Pro Gly Val Ser Gly Ala Leu Ala Asn Ala Ile Ser Ile Lys
                965                 970                 975
Val Lys Asn Asn Glu Arg Arg Tyr Asn Leu Lys Ile Lys Lys Arg Asp
            980                 985                 990
Tyr His His Pro Thr Leu Gly Leu Asn Ala Arg Phe Glu Leu Val Thr
        995                 1000                1005
Glu Ala Gly His Pro Val Val Ile Asp Gly Val Asn Met Lys Gly Asp
    1010                1015                1020
Thr Asn Ser Ala Asp Asn Ser Ile Thr Phe Ser Asn Leu Pro Val Gly
1025                1030                1035                1040
Val Tyr Ile Leu Lys Glu Thr Val Val Pro Thr Gly Gly Tyr Arg Pro
                1045                1050                1055
Val Asn Gln Leu Gln Asp Thr Lys Phe Glu Ile Arg Pro Asp Gly Ser
            1060                1065                1070
Leu Gln Ile Leu Glu Ser Asp Ser Asn Met Val Thr Val Asp Thr Ser
        1075                1080                1085
Gln Gly Ala Thr Phe Glu Ile Thr Ile Lys Asn Phe Lys Gln Phe Lys
    1090                1095                1100
Phe Arg Leu Gln Lys Thr Asp Asn Arg Asp Glu Asn His Leu Leu Asn
1105                1110                1115                1120
Gly Ala Thr Phe Lys Ile Tyr Ser Asp Pro Asn Asn Asp Gly Val Glu
                1125                1130                1135
Asp Thr Glu Val Ala Ser Gly Val Thr Thr Asn Gly Leu Phe Glu Thr
            1140                1145                1150
Ser Leu Ser Phe Gly Tyr Tyr Ile Leu Glu Glu Thr Val Ala Pro Thr
        1155                1160                1165
Gly Tyr Gln Leu Asn Pro Lys Lys Tyr Arg Phe Gln Ile Asn His Asp
    1170                1175                1180
Gly Thr Thr Lys Leu His Asn Gly Asp Asn Gln Val Thr Leu Ala Glu
1185                1190                1195                1200
Arg Val Asp Gly Asp Asn Val Ile Leu Phe Asn Met Lys Asn Thr Lys
                1205                1210                1215
Gln Thr Thr His Ile Lys Leu Ala Lys Arg Ser Tyr Ser Asp Pro Thr
            1220                1225                1230
Gln Arg Leu Val Ala Thr Phe Glu Leu Arg Glu Ser Asp Asn Pro Gln
        1235                1240                1245
Ala Thr Ala Val Val Lys Thr Thr Thr Thr Gly Asp Glu Val Leu
    1250                1255                1260
Phe Asp Asn Leu Ala Val Gly Lys Thr Tyr Ile Leu Lys Glu Ile Val
1265                1270                1275                1280
Ala Pro Asp Gly Tyr Gln Lys Ile Glu Lys Glu Phe His Ile Asn Ile
                1285                1290                1295
```

-continued

Gly Ala Asp Gly Ala Ile Ser Ile Gln Asp Gly Glu Asp Leu Val Ser
            1300                1305                1310

Leu Asp Asn Met Asp Asn His Leu Ile Ile Val Lys Asn Leu Arg Lys
        1315                1320                1325

Gly Glu Tyr Pro Lys Thr Gly Gly Met Gly Ile Ile Pro Tyr Ile Ala
        1330                1335                1340

Leu Gly Gly Val Met Met Phe Ile Ala Phe Ala Val Glu Gln Arg Arg
1345                1350                1355                1360

Lys Tyr Thr Arg

<210> SEQ ID NO 98
<211> LENGTH: 304
<212> TYPE: PRT
<213> ORGANISM: S. equi

<400> SEQUENCE: 98

Met Ile Leu Gly Val Val Phe Arg Phe Pro Lys Gln Ile Trp Ala Gln
1               5                   10                  15

Glu Ala Glu His Ser Leu Ile Val Thr His Leu Glu Ala Arg Asp Ile
            20                  25                  30

Asp Arg Pro Asp Pro Lys Leu Asp Val Ala Pro Lys Ser Gly Glu Pro
        35                  40                  45

Ile Glu Gly Ile Arg Tyr Gln Leu Tyr Gln Leu Lys Gln Leu Glu Asp
    50                  55                  60

Val Ala Ile Leu Ser Gln Leu Asp Asn Leu Ser Leu Glu Gly Leu Ala
65                  70                  75                  80

His Gln Ala Gln Arg Val Phe Gln Glu Thr Thr Asp Ser Glu Gly Arg
                85                  90                  95

Ala Arg Phe Thr Gln Leu Pro Ser Gly Ile Tyr Tyr Gly Ile Ala Val
            100                 105                 110

Lys Ala Asn Gln Arg Asp Lys Gln Val Ser Ser Phe Leu Val Asp Met
        115                 120                 125

Ile Gly Asn Gln Lys Glu Pro Leu Leu Val Tyr Pro Lys Ile Ile Trp
    130                 135                 140

Glu Thr Gly Ala Phe Asp Leu Phe Lys Ile Gly Val Asp Gly Lys Glu
145                 150                 155                 160

Ser Leu Pro Leu Ser Gly Val Thr Phe Glu Leu Tyr Glu Arg Asn Gly
                165                 170                 175

Leu Ser Pro Ile Arg Val Lys Lys Gly Ile His Ser Tyr Asp Leu Asp
            180                 185                 190

Ala Pro Thr Thr Leu Thr Thr Asp His Thr Gly His Ile Lys Val Ser
        195                 200                 205

Gly Leu Ile Pro Gly Tyr Tyr Leu Lys Glu Gln Glu Thr Val Lys
    210                 215                 220

Gly Tyr Leu Ile Asp Lys Thr Asp Ile Pro Ile Thr Val Glu Ala His
225                 230                 235                 240

Glu Thr Ser His Ile Thr Ile Lys Asn Ile Lys Glu Asn Thr Pro Pro
                245                 250                 255

Pro Arg Lys Gly Gly Phe Ile Pro Tyr Thr Gly Glu Leu Lys Ala Ile
            260                 265                 270

Leu Phe Leu Met Ile Gly Gly Ser Leu Ile Val Leu Ala Phe Ile Leu
        275                 280                 285

Ile Arg Arg Tyr Arg Lys Asp Glu Ser Ser Asn Asp Lys Lys Lys Ser
    290                 295                 300

```
<210> SEQ ID NO 99
<211> LENGTH: 967
<212> TYPE: PRT
<213> ORGANISM: S. equi

<400> SEQUENCE: 99

Met Ile Lys Lys Arg Lys Leu Leu Ser Leu Val Ala Thr Ala Gly Leu
 1               5                  10                  15

Leu Met Ala Gln Phe Ser Val Pro Leu Gly Gln Ala Gly Val Leu Met
             20                  25                  30

Gly His Ala Glu Ala Lys Asp Pro Thr Ser Glu Val Val Thr Ser Asp
         35                  40                  45

Pro Ser Lys Pro Gln Ala Glu Ala Val Thr Gly Asn Lys Arg Glu Leu
     50                  55                  60

Val Ser Asp Thr Asn Asp Val Thr Val Ser Val Lys Ser Glu Ala Gly
 65                  70                  75                  80

Phe Gly Ser Ala Asp Thr Ile Thr Ala Ser Leu Ala Ala Ala Lys Thr
                 85                  90                  95

Asp Ala Asp Tyr Lys Ser Tyr Ser Gln Asp Ile Ala Lys Val Ser Leu
            100                 105                 110

Ala Leu Ser Lys Gln Gly Leu Ala Ile Val Asp Ala Gln Val Ile Asp
        115                 120                 125

Leu His Tyr Gln Val Asn Gln Ala Ala Ala Val Thr Met Ala Leu His
130                 135                 140

Ile Lys Lys Asp Leu Ser Leu Asn Gly Ile Ser Asp Asp His Lys Asn
145                 150                 155                 160

Ile Lys Val Gly Leu Ile Thr Ser Asp Asp Met Val Gln Ile Val Glu
                165                 170                 175

Ala Thr Ile Gly Leu Ser His Ala Asn Ala Val Asn Ser Ile Gly Cys
            180                 185                 190

Ala Gly Ser Leu Ser Lys Arg Val Val Val Thr Thr Ala Lys Leu
        195                 200                 205

Glu Glu Asp Lys Thr Leu Ala Leu Gly Lys Tyr Gly Lys Leu Val Val
    210                 215                 220

Asp Gly Ala Val Gly Val Ala Gln Gln Lys Val Ser Pro Tyr Ser Lys
225                 230                 235                 240

Pro Ile Thr Val Thr Ile Leu Thr Pro Lys Pro Ser Ala Leu Glu Ser
                245                 250                 255

Ser Leu Asp Ser Lys Asp Phe Glu Val Val Lys Thr Ile Asp Lys Leu
            260                 265                 270

Tyr Thr Trp Asp Glu His Phe Tyr Leu Leu Asp Phe Leu Ser Asp Asp
        275                 280                 285

Tyr Glu Val Leu Lys Thr Glu Tyr Gln Ser Ala Lys Asp Ser Glu Pro
    290                 295                 300

Lys Leu Gln Asp Leu Leu Phe Gly Glu Tyr Glu Pro Asn Pro Leu Ala
305                 310                 315                 320

Thr Asp Lys Gly His Ser Asn Thr Val Asn Ile Tyr Ile Arg Pro Arg
                325                 330                 335

Lys Pro Leu Gly Leu Lys Pro Met Pro Phe Ala Ala Asn Gly Ile Gln
            340                 345                 350

Pro Arg Ala Phe Arg Ser Arg Ser Val Asp Ser Ala Ser Gln Gly Glu
        355                 360                 365

Leu Glu His His Lys Arg Ile Asp Tyr Leu Gly Asp Asn Gln Asn Asn
    370                 375                 380
```

-continued

```
Pro Asp Thr Ser Val Asp Asp Pro Gly Ser Gln His Asp Thr Ser Asp
385                 390                 395                 400

Leu Tyr Arg Leu Tyr Leu Asp Met Thr Gly Lys Lys Gln Pro Leu Asp
            405                 410                 415

Val Leu Val Val Val Asp Arg Ser Ala Ser Met Lys Glu Gly Ile Ser
        420                 425                 430

Gln Asn Asp Ile Pro Arg Asp Gln Ala Val Lys Asn Ala Leu Thr Gly
    435                 440                 445

Ala Gly Gly Leu Leu Gln Lys Phe Ile Asn Ile Asn Ala Glu Asn Lys
450                 455                 460

Leu Ser Val Ile Gly Phe Gln Gly Ser Leu Asn Tyr Asn Ser Arg Glu
465                 470                 475                 480

Gly Lys Pro Glu Arg Ile Ser Trp Arg Ser Ile Tyr Gln Pro Ser
            485                 490                 495

Ile Asn Asn Asn Lys Asp Ala Asp Val Leu Lys Asn Trp Glu Ser Ser
            500                 505                 510

Ser Ala Leu Asn Arg Asp Asp Leu Ser Tyr Lys Asp Lys Asn Gly Thr
        515                 520                 525

Asn Tyr His Ala Ala Leu Val Lys Ala Asp Glu Met Leu Asn Lys Val
    530                 535                 540

Ala Asp Asp Gly His Arg Lys Ile Met Val Phe Val Ser Asp Gly Val
545                 550                 555                 560

Pro Thr Phe Tyr Phe Gly Ser Asp His Tyr Arg Ala Gly Asn Gly Thr
                565                 570                 575

Ser Asp Ala Ser Asn Ile Lys Ser Ser Gln Asp Gly Thr Arg Ala Ala
            580                 585                 590

Ile Asp Asp Phe Lys Lys Lys His Pro Asn Leu Ser Ile Tyr Ser Leu
        595                 600                 605

Gly Val Ser Lys Asp Ile Asn Ser Asp Thr Ala Ser Ser Ser Pro Val
610                 615                 620

Val Leu Lys Tyr Leu Ser Gly Glu Asp His Tyr Tyr Gly Ile Thr Asn
625                 630                 635                 640

Thr Val Glu Leu Glu Lys Ile Ala Asn Lys Ile Val Glu Asp Ser Lys
                645                 650                 655

Val Ser His Leu Glu Ile Ser Asp Thr Leu Ser Gln Tyr Val Asp Tyr
            660                 665                 670

Tyr Glu Lys Gln Pro Asp Val Val Thr Arg Ile Ser Lys Ala Asp
        675                 680                 685

Lys Ser Lys Val Glu Thr Leu Tyr Lys Asp Asn Thr Leu Thr Ser Glu
    690                 695                 700

Gly Gln Lys Ile Ile Lys Ser Val Thr Phe Thr Pro Lys Glu Thr Gln
705                 710                 715                 720

Asn Ser Ser Gly Lys Val Thr Leu Thr Phe Lys Pro Asp Tyr Lys Ile
                725                 730                 735

Asp Asp Glu Tyr Thr Tyr Thr Leu Ser Phe Asn Val Lys Val Ser Asp
            740                 745                 750

Lys Ala Tyr Glu Lys Tyr Lys Asn Gln Gln Gly Lys Tyr Thr Thr Lys
        755                 760                 765

Gly Asp Val Asp Thr Asp Tyr Gly Ser Asn Asn Thr Ser Ser Gly Gln
    770                 775                 780

Asp Gly Phe Tyr Ser Asn Gln Glu Ala Ser Val Asn Tyr Met Ala Asp
785                 790                 795                 800
```

Gly Arg Trp Gln Lys Leu Thr Tyr Lys Arg Pro Val Val Gln Leu Lys
                805                 810                 815

Thr Ile Pro Ala Ala Phe Ser Lys Ile Asp Ala Asn Asp Asp Lys Lys
                820                 825                 830

Thr Leu Asp Gly Val Glu Phe Glu Leu Arg Lys Glu Asn Arg Thr Ala
                835                 840                 845

Val Trp Glu Lys Gly Thr Thr Ala Lys Asn Gly Arg Leu Val Phe Asn
                850                 855                 860

Tyr Leu Gln Lys Gly Lys Thr Tyr Tyr Leu Tyr Glu Thr Lys Ala Arg
865                 870                 875                 880

Ala Gly Tyr Thr Leu Pro Glu Asn Pro Trp Lys Ile Lys Val Asp Asp
                885                 890                 895

Lys Gly Lys Ile Arg Leu Thr His Pro Ile Glu Gly Glu Leu Gln Ser
                900                 905                 910

Asn His Gly Ala Tyr Val Ile Lys Asn His Lys Ile Tyr Gln Leu Pro
                915                 920                 925

Ser Ser Gly Gly Arg Gly Ser Gln Leu Phe Leu Ile Phe Gly Ser Met
                930                 935                 940

Val Ile Thr Thr Thr Ala Leu Leu Tyr Arg Arg Arg Tyr Asn Arg Lys
945                 950                 955                 960

Gln Arg Gln Gln Ser Ile Met
                965

<210> SEQ ID NO 100
<211> LENGTH: 549
<212> TYPE: PRT
<213> ORGANISM: S. equi

<400> SEQUENCE: 100

Met Lys Asp Asn Ile Leu Ile Ile Ile Lys Lys Val Met Ile Ala Phe
1               5                   10                  15

Leu Val Ile Leu Thr Val Ile Gly Phe Ser Val Thr Thr Ile Ser Ala
                20                  25                  30

Leu Ser Lys Asp Asp Lys Ala Glu Leu Thr Ile Thr Asn Ile Lys Gly
                35                  40                  45

Lys Pro Thr Val Thr Leu Tyr Gln Ile Gly Glu Gly Lys Tyr Ser Glu
                50                  55                  60

Arg Gly Asp Ser Phe Ile Arg Phe Glu Leu Lys Glu Gly Val Lys Leu
65                  70                  75                  80

Thr Lys Glu Lys Pro Thr Ser Gln Glu Ile Asn Lys Ile Ala Asn Asp
                85                  90                  95

Val Ile Ser Gly Thr Leu Lys Gly Val His Lys Val Glu Glu Lys Gln
                100                 105                 110

Ser Val Gly Asp Thr Tyr Val Ser Gln Lys Val Ser Ala Gly Ile Tyr
                115                 120                 125

Ile Ala Met Leu Thr Gly Ala Ala Asp Gly Phe Val Tyr Asn Pro Ile
                130                 135                 140

Leu Leu Thr Ala Ser Tyr Ser Gly Glu Gln Pro Leu Lys Gly Gly Lys
145                 150                 155                 160

Ile Asp Val Thr Ser Lys Tyr Leu Tyr Gly Glu Ala Val Ala Lys
                165                 170                 175

Ser Ser Gln Pro Thr Ile His Lys Asp Ile Thr Lys Ser Thr Lys Asp
                180                 185                 190

Gly Asp Lys Ala Thr Ala Ser Val Gly Asp Lys Val Asp Tyr Ser Leu
                195                 200                 205

```
Thr Val Gln Leu Pro Ser Tyr Ser Lys Glu Ala Thr Asn Lys Thr Val
    210                 215                 220

Phe Val Ser Asp Thr Met Ser Glu Gly Leu Thr Phe Leu Ala Gly Ser
225                 230                 235                 240

Leu Arg Val Lys Trp Asn Gly Gln Thr Leu Thr Ala Lys His Asn Val
                245                 250                 255

Phe Glu His Lys Gly Lys Thr Ile Ala Glu Leu Lys Leu Thr Gly Asn
            260                 265                 270

Gly Phe Asn Ile Asn Phe Asn Tyr Asp Asn Leu Glu Ser His Asn Pro
        275                 280                 285

Glu Leu Thr Tyr Ser Ala Val Leu Asn Glu Lys Ala Ala Val Gly Lys
    290                 295                 300

Glu Gly Asn Ala Asn Asn Val Asp Tyr Tyr Ser Asn Asn Pro Asn
305                 310                 315                 320

Lys Gly Glu Thr His Lys Thr Ala Glu Lys Pro Gln Glu Gly Gln Asp
                325                 330                 335

Ile Thr Lys Lys Thr Asn Gln Lys Thr Val Tyr Thr Tyr Arg Val Ala
            340                 345                 350

Phe Lys Lys Thr Asp Lys Asp Asn Lys Pro Leu Ala Asn Ala Val Phe
        355                 360                 365

Gly Ile Tyr Ser Asp Lys Ala Ala Thr Ser Leu Ile Asp Val Val Val
    370                 375                 380

Thr Asn Gln Glu Gly Tyr Ala Thr Ser Ser Gln Val Gly Ala Gly Thr
385                 390                 395                 400

Tyr Tyr Leu Lys Glu Ile Lys Ala Pro Lys Gly Tyr Ser Leu Asn Thr
                405                 410                 415

Lys Ile Tyr Ala Leu Glu Ala Ser Trp Thr Ser Ala Asp Thr Arg Ser
            420                 425                 430

Thr Ser Asn Arg Gln Glu Thr Ile Tyr Thr Ser Asp Asn Asn Gln Lys
        435                 440                 445

Ser Pro Gly Thr Lys Ala Val Gly Trp Leu Val Gly Asp Val Phe Tyr
    450                 455                 460

Lys Glu Lys Pro Glu Ala Lys Asp Ala Lys Pro Ala Tyr Ile Lys Lys
465                 470                 475                 480

Ser Thr Glu Glu Ala Ser Thr Thr Thr Glu Val Lys Asp Asn Gln Gly
                485                 490                 495

Asp Gly Ser Gly Thr Ala Leu Leu Lys Glu Pro Ile Pro Asn Thr Lys
            500                 505                 510

Leu Gly Glu Leu Pro Ser Thr Gly Ser Ile Gly Thr Tyr Ile Phe Thr
        515                 520                 525

Ala Val Gly Ala Ala Ala Met Val Gly Ala Val Gly Ile Tyr Ile Val
    530                 535                 540

Lys Arg Arg Lys Ala
545

<210> SEQ ID NO 101
<211> LENGTH: 830
<212> TYPE: PRT
<213> ORGANISM: S. equi

<400> SEQUENCE: 101

Met Ser Lys Glu Lys Leu Lys Lys Ile Leu Val Lys Leu Ala Ala Leu
1               5                   10                  15

Leu Ala Ile Ile Gln Leu Ile Leu Pro Thr Ser Leu Thr Ala Ala Thr
```

```
                    20                  25                  30
Val Leu Ser Glu Gln Ile Asn Thr Glu Asn Pro Ala Ser Val Ala Thr
                35                  40                  45
Ala Thr Gly Glu Thr Ile Thr Ala Asp Asn Leu Asp Phe Lys Lys Ala
         50                  55                  60
Ala Ser Glu Ser Gly Ala Ala Leu Lys Asn Gly Ser Ile Arg Trp Leu
 65                  70                  75                  80
Gln Ile Thr Tyr Asn Lys Gly Asp Asn Asp Leu Ala Lys Gln Asp Leu
                 85                  90                  95
Phe Leu Thr Val Pro Lys Gly Met Ile Val Glu Gly Ile Gly Gln Asp
            100                 105                 110
Asn Arg Leu Glu Val Gly Gly Ile Thr Val Pro Glu Asp Leu Ala Phe
            115                 120                 125
Ala Lys Asn Asn Thr Thr Ile Asn Asn Ala Lys Leu Val Ser Gly Phe
        130                 135                 140
Glu Lys Ile Ala Asp Gln Val Tyr Lys Ile Ser Phe Glu Pro Thr Thr
145                 150                 155                 160
Glu Met Val Asn Leu Val Phe Lys Val Asn Asp Thr Ile Thr Asp Glu
                165                 170                 175
Pro Arg Glu Leu Leu Arg Asp His Gln Glu Gln Glu Lys Ala Ser
            180                 185                 190
Leu Ile Lys Arg Leu Val Leu Gly Ala Gly Gln Asp Glu Asp Arg Ala
        195                 200                 205
Ser Ile Asp Ser Ser Ser Gln Arg Pro Thr Ile Gln Pro Arg Ala Ala
        210                 215                 220
Arg Ala Thr Glu Arg Val Gly Asn Gln Gly Val Ser Ser Lys Leu Thr
225                 230                 235                 240
Ala Thr Glu Lys Thr Gly Asp Gln Lys Ile Lys Val Val Lys Arg Asp
                245                 250                 255
Glu Leu Thr Gly Gln Pro Leu Ala Asn Ala Lys Phe Gln Leu Lys Ala
            260                 265                 270
Ser Asp Gly Ala Leu Tyr His Gly Thr Thr Asn Glu Lys Gly Glu Leu
        275                 280                 285
Ile Phe Asp Lys Leu Pro Tyr Gly Gln Tyr Val Leu Thr Glu Thr Glu
    290                 295                 300
Ala Pro Pro Gly Tyr Val Leu Asp Pro Ile Pro Arg Asp Ile Asn Ile
305                 310                 315                 320
Thr Glu Val Gly Ile Pro Glu Thr Glu Val Val Ala Ser Gly Asn Ala
                325                 330                 335
Ile Asp Leu Asn Ser Thr Ser Ile Thr Arg Ala Ala Val Ala Asn Ser
            340                 345                 350
Val Pro Glu Ser Met Ile Gly Lys Asn Val Ser Asn Gln Ile Thr Ile
        355                 360                 365
Lys Asn Leu Asp Ile Thr Ser Ser Asn Glu Asp Thr Pro Tyr Asn Val
        370                 375                 380
Arg Pro Asn Asn Gly Glu Asn Ile Leu Ile Arg Ala Asp Phe Thr Ile
385                 390                 395                 400
Glu Ser Gly Ser Asp Ile Lys Glu Gly Asp Phe Phe Thr Leu Thr Leu
                405                 410                 415
Pro Asn Thr Ile Asp Pro Phe Gly Ile Ser Ala Pro Glu Asn Val Asn
            420                 425                 430
Phe Arg Ile Leu Gly Pro Leu Gly Thr Leu Ala Leu Gly Thr Tyr Asp
        435                 440                 445
```

```
Ser Asp Thr Arg Thr Ile Thr Tyr Arg Phe Thr Asn Tyr Ile Thr Arg
450                 455                 460

Tyr Glu Val Ala Asn Phe Ser Ile Ile Ser Pro Phe Phe Val Asp Arg
465                 470                 475                 480

Tyr Thr Val Lys Ser Thr Gln Asn Ile Asp Leu Tyr Leu Lys Ile Gly
                485                 490                 495

Asp Lys Thr Ser Gln Ser Lys Val Phe Phe Ile Asn Tyr Asp Pro Tyr
                500                 505                 510

Tyr Gly Thr Met Asp Thr Asn Asn Pro Val Asn Ile Gly Ser Ser Ile
            515                 520                 525

Thr Arg Leu Asn Gln Asp Thr Gly Glu Phe Val Asn Tyr Ile Tyr Ile
530                 535                 540

Asn Pro Ala Gly Gln Ser Leu Glu Gln Ala Ser Leu Thr Phe Thr Gly
545                 550                 555                 560

Asn Gly Ser Ser Ile Ile Asp Ser Thr Thr Glu Ile Gln Ile Phe Glu
                565                 570                 575

Val Thr Asp Ser His Leu Gln Met Pro Ser Ser Trp Gly Val Asn Glu
                580                 585                 590

Lys Leu Leu Arg Glu Thr Thr Ser Tyr His Ile Asp Lys Gln Val Gly
                595                 600                 605

Arg Ile Asn Ile Asn Phe Tyr Asn Asp Leu Leu Asp Arg Arg Ser Tyr
610                 615                 620

Ile Ile Lys Val Ser Gly Lys Ser Asp Leu Ser Asn Ser Ala Pro Ile
625                 630                 635                 640

Gln Thr Ser Ala Ile Leu Thr Gln Arg Tyr Phe Asn Tyr Phe Pro Tyr
                645                 650                 655

His Thr Pro Ser Gly Arg Tyr Ile Pro Tyr Gly Pro Tyr Thr Glu Thr
                660                 665                 670

Phe Thr Phe Thr Ala Gly Val Leu Lys Lys Ser Gly Glu Ser Asn Ala
                675                 680                 685

Asp Gly Ala Val Val Asn Met Thr Asn Arg Lys Asn Tyr Ile Gly
690                 695                 700

Phe Val Lys Thr Asp Ala Gln Gly Glu Ser Leu Glu Ala Thr Phe Glu
705                 710                 715                 720

Leu Arg Lys Lys Thr Ala Asn Gly Leu Glu Thr Val Gly Asp Ser Val
                725                 730                 735

Thr Ser Asp Lys Thr Gly Lys Phe Tyr Phe Glu Gly Leu Pro Gln
                740                 745                 750

Gly Asp Tyr Glu Leu Trp Glu Ile Lys Ala Pro Asn Gly Tyr Ile Lys
                755                 760                 765

Pro Ile Glu Ala Val Ala Thr Phe Lys Val Thr Ala Ala Gly Glu Ile
770                 775                 780

Val Asp Lys Ser Leu Lys Asp Gly Arg Ile Ile Asn Tyr Lys Arg Thr
785                 790                 795                 800

Glu Leu Pro Ala Thr Gly Gly Pro Ser Ile Leu Pro Tyr Phe Leu Ile
                805                 810                 815

Gly Ser Phe Leu Cys Phe Val Ala Ile Phe Trp Lys Asn Ser
                820                 825                 830

<210> SEQ ID NO 102
<211> LENGTH: 675
<212> TYPE: PRT
<213> ORGANISM: S. agalactiae
```

```
<400> SEQUENCE: 102

Met Lys Lys Ile Asn Lys Tyr Phe Ala Val Phe Ser Ala Leu Leu Leu
 1               5                  10                  15

Thr Val Thr Ser Leu Phe Ser Val Ala Pro Val Phe Ala Glu Glu Ala
             20                  25                  30

Lys Thr Thr Asp Thr Val Thr Leu His Lys Ile Val Met Pro Arg Thr
             35                  40                  45

Ala Phe Asp Gly Phe Thr Ala Gly Thr Lys Gly Lys Asp Asn Thr Asp
         50                  55                  60

Tyr Val Gly Lys Gln Ile Glu Asp Leu Lys Thr Tyr Phe Gly Ser Gly
 65                  70                  75                  80

Glu Ala Lys Glu Ile Ala Gly Ala Tyr Phe Ala Phe Lys Asn Glu Ala
                 85                  90                  95

Gly Thr Lys Tyr Ile Thr Glu Asn Gly Glu Val Asp Thr Leu Asp
            100                 105                 110

Thr Thr Asp Ala Lys Gly Cys Ala Val Leu Lys Gly Leu Thr Thr Asp
            115                 120                 125

Asn Gly Phe Lys Phe Asn Thr Ser Lys Leu Thr Gly Thr Tyr Gln Ile
        130                 135                 140

Val Glu Leu Lys Glu Lys Ser Thr Tyr Asn Asn Asp Gly Ser Ile Leu
145                 150                 155                 160

Ala Asp Ser Lys Ala Val Pro Val Lys Ile Thr Leu Pro Leu Val Asn
                165                 170                 175

Asp Asn Gly Val Val Lys Asp Ala His Val Tyr Pro Lys Asn Thr Glu
            180                 185                 190

Thr Lys Pro Gln Val Asp Lys Asn Phe Ala Asp Lys Glu Leu Asp Tyr
        195                 200                 205

Ala Asn Asn Lys Lys Asp Lys Gly Thr Val Ser Ala Ser Val Gly Asp
    210                 215                 220

Val Lys Lys Tyr His Val Gly Thr Lys Ile Leu Lys Gly Ser Asp Tyr
225                 230                 235                 240

Lys Lys Leu Ile Trp Thr Asp Ser Met Thr Lys Gly Leu Thr Phe Asn
                245                 250                 255

Asn Asp Ile Ala Val Thr Leu Asp Gly Ala Thr Leu Asp Ala Thr Asn
            260                 265                 270

Tyr Lys Leu Val Ala Asp Asp Gln Gly Phe Arg Leu Val Leu Thr Asp
        275                 280                 285

Lys Gly Leu Glu Ala Val Ala Lys Ala Ala Lys Thr Lys Asp Val Glu
    290                 295                 300

Ile Lys Ile Thr Tyr Ser Ala Thr Leu Asn Gly Ser Ala Val Val Glu
305                 310                 315                 320

Val Leu Glu Thr Asn Asp Val Lys Leu Asp Tyr Gly Asn Asn Pro Thr
                325                 330                 335

Ile Glu Asn Glu Pro Lys Glu Gly Ile Pro Val Asp Lys Lys Ile Thr
            340                 345                 350

Val Asn Lys Thr Trp Ala Val Asp Gly Asn Glu Val Asn Lys Ala Asp
        355                 360                 365

Glu Thr Val Asp Ala Val Phe Thr Leu Gln Val Lys Asp Gly Asp Lys
    370                 375                 380

Trp Val Asn Val Asp Ser Ala Lys Ala Thr Ala Thr Ser Phe Lys
385                 390                 395                 400

His Thr Phe Glu Asn Leu Asp Asn Ala Lys Thr Tyr Arg Val Ile Glu
                405                 410                 415
```

```
Arg Val Ser Gly Tyr Ala Pro Glu Tyr Val Ser Phe Val Asn Gly Val
                420                 425                 430

Val Thr Ile Lys Asn Asn Lys Asp Ser Asn Glu Pro Thr Pro Ile Asn
            435                 440                 445

Pro Ser Glu Pro Lys Val Val Thr Tyr Gly Arg Lys Phe Val Lys Thr
        450                 455                 460

Asn Lys Asp Gly Lys Glu Arg Leu Ala Gly Ala Thr Phe Leu Val Lys
465                 470                 475                 480

Lys Asp Gly Lys Tyr Leu Ala Arg Lys Ser Gly Val Ala Thr Asp Ala
                485                 490                 495

Glu Lys Ala Ala Val Asp Ser Thr Lys Ser Ala Leu Asp Ala Ala Val
                500                 505                 510

Lys Ala Tyr Asn Asp Leu Thr Lys Glu Lys Gln Glu Gly Gln Asp Gly
            515                 520                 525

Lys Ser Ala Leu Ala Thr Val Ser Glu Lys Gln Lys Ala Tyr Asn Asp
        530                 535                 540

Ala Phe Val Lys Ala Asn Tyr Ser Tyr Glu Trp Val Glu Asp Lys Asn
545                 550                 555                 560

Ala Lys Asn Val Val Lys Leu Ile Ser Asn Asp Lys Gly Gln Phe Glu
                565                 570                 575

Ile Thr Gly Leu Thr Glu Gly Gln Tyr Ser Leu Glu Glu Thr Gln Ala
            580                 585                 590

Pro Thr Gly Tyr Ala Lys Leu Ser Gly Asp Val Ser Phe Asn Val Asn
        595                 600                 605

Ala Thr Ser Tyr Ser Lys Gly Ser Ala Gln Asp Ile Glu Tyr Thr Gln
610                 615                 620

Gly Ser Lys Thr Lys Asp Ala Gln Gln Val Ile Asn Lys Lys Val Thr
625                 630                 635                 640

Ile Pro Gln Thr Gly Gly Ile Gly Thr Ile Phe Phe Thr Ile Ile Gly
                645                 650                 655

Leu Ser Ile Met Leu Gly Ala Val Val Ile Met Lys Arg Arg Gln Ser
            660                 665                 670

Glu Glu Val
        675

<210> SEQ ID NO 103

<400> SEQUENCE: 103

000

<210> SEQ ID NO 104
<211> LENGTH: 15
<212> TYPE: PRT
<213> ORGANISM: S. agalactiae

<400> SEQUENCE: 104

Gly Lys Asp Tyr Lys Gly Gly Ala Ile Ser Asp Leu Ala Gly Tyr
1               5                   10                  15

<210> SEQ ID NO 105
<211> LENGTH: 200
<212> TYPE: PRT
<213> ORGANISM: S. pyogenes

<400> SEQUENCE: 105

Pro Leu Asp Ile Leu Val Val Val Asp Lys Ser Gly Ser Met Gln Glu
```

```
            1               5                  10                 15
        Gly Ile Gly Ser Val Gln Arg Tyr Arg Tyr Tyr Ala Gln Arg Trp Asp
                        20                 25                 30

Asp Tyr Tyr Ser Gln Trp Val Tyr His Gly Thr Phe Asp Tyr Ser Ser
                        35                 40                 45

Tyr Gln Gly Glu Ser Phe Asn Arg Gly Gln Ile His Tyr Arg Tyr Arg
                        50                 55                 60

Gly Ile Val Ser Val Ser Asp Gly Ile Arg Arg Asp Asp Ala Val Lys
         65                 70                 75                 80

Asn Ser Leu Leu Gly Val Asn Gly Leu Leu Gln Arg Phe Val Asn Ile
                        85                 90                 95

Asn Pro Glu Asn Lys Leu Ser Val Ile Gly Phe Gln Gly Ser Ala Asp
                        100                105                110

Tyr His Ala Gly Lys Trp Tyr Pro Asp Gln Ser Pro Arg Gly Gly Phe
                        115                120                125

Tyr Gln Pro Asn Leu Asn Asn Ser Arg Asp Ala Glu Leu Leu Lys Gly
                        130                135                140

Trp Ser Thr Asn Ser Leu Leu Asp Pro Asn Thr Leu Thr Ala Leu His
        145                150                155                160

Asn Asn Gly Thr Asn Tyr His Ala Ala Leu Leu Lys Ala Lys Glu Ile
                        165                170                175

Leu Asn Glu Val Lys Asp Asp Gly Arg Arg Lys Ile Met Ile Phe Ile
                        180                185                190

Ser Asp Gly Val Pro Thr Phe Tyr
                        195                200

<210> SEQ ID NO 106
<211> LENGTH: 175
<212> TYPE: PRT
<213> ORGANISM: S. agalactiae

<400> SEQUENCE: 106

Pro Leu Asp Val Val Phe Val Leu Asp Asn Ser Asn Ser Met Asn Asn
         1                 5                 10                 15

Asp Gly Pro Asn Phe Gln Arg His Asn Lys Ala Lys Lys Ala Ala Glu
                        20                 25                 30

Ala Leu Gly Thr Ala Val Lys Asp Ile Leu Gly Ala Asn Ser Asp Asn
                        35                 40                 45

Arg Val Ala Leu Val Thr Tyr Gly Ser Asp Ile Phe Asp Gly Arg Ser
                        50                 55                 60

Val Asp Val Val Lys Gly Phe Lys Glu Asp Lys Tyr Tyr Gly Leu
         65                 70                 75                 80

Gln Thr Lys Phe Thr Ile Gln Thr Glu Asn Tyr Ser His Lys Gln Leu
                        85                 90                 95

Thr Asn Asn Ala Glu Glu Ile Ile Lys Arg Ile Pro Thr Glu Ala Pro
                        100                105                110

Lys Ala Lys Trp Gly Ser Thr Thr Asn Gly Leu Thr Pro Glu Gln Gln
                        115                120                125

Lys Glu Tyr Tyr Leu Ser Lys Val Gly Glu Thr Phe Thr Met Lys Ala
                        130                135                140

Phe Met Glu Ala Asp Asp Ile Leu Ser Gln Val Asn Arg Asn Ser Gln
        145                150                155                160

Lys Ile Ile Val His Val Thr Asp Gly Val Pro Thr Arg Ser Tyr
                        165                170                175
```

<210> SEQ ID NO 107
<211> LENGTH: 174
<212> TYPE: PRT
<213> ORGANISM: S. pneumoniae

<400> SEQUENCE: 107

Pro Leu Asp Val Val Ile Leu Leu Asp Asn Ser Asn Ser Met Ser Asn
1               5                   10                  15

Ile Arg Asn Lys Asn Ala Arg Arg Ala Glu Arg Ala Gly Glu Ala Thr
            20                  25                  30

Arg Ser Leu Ile Asp Lys Ile Thr Ser Asp Pro Glu Asn Arg Val Ala
        35                  40                  45

Leu Val Thr Tyr Ala Ser Thr Ile Phe Asp Gly Thr Glu Phe Thr Val
50                  55                  60

Glu Lys Gly Val Ala Asp Lys Asn Gly Lys Arg Leu Asn Asp Ser Leu
65                  70                  75                  80

Phe Trp Asn Tyr Asp Gln Thr Ser Phe Thr Thr Asn Thr Lys Asp Tyr
                85                  90                  95

Ser Tyr Leu Lys Leu Thr Asn Asp Lys Asn Asp Ile Val Glu Leu Lys
            100                 105                 110

Asn Lys Val Leu Thr Glu Ala Glu Asp His Asp Gly Asn Arg Leu Met
        115                 120                 125

Tyr Gln Phe Gly Ala Thr Phe Thr Gln Lys Ala Leu Met Lys Ala Asp
130                 135                 140

Glu Ile Leu Thr Gln Gln Ala Arg Gln Asn Ser Gln Lys Val Ile Phe
145                 150                 155                 160

His Ile Thr Asp Gly Val Pro Thr Met Ser Tyr Pro Ile Asn
                165                 170

<210> SEQ ID NO 108
<211> LENGTH: 366
<212> TYPE: PRT
<213> ORGANISM: Artificial Sequence
<220> FEATURE:
<223> OTHER INFORMATION: fusion protein

<400> SEQUENCE: 108

Leu Gly Gly Ala Glu Phe Asp Leu Leu Ala Ser Asp Gly Thr Ala Val
1               5                   10                  15

Lys Trp Thr Asp Ala Leu Ile Lys Ala Asn Thr Asn Lys Asn Tyr Ile
            20                  25                  30

Ala Gly Glu Ala Val Thr Gly Gln Pro Ile Lys Leu Lys Ser His Thr
        35                  40                  45

Asp Gly Thr Phe Glu Ile Lys Gly Leu Ala Tyr Ala Val Asp Ala Asn
    50                  55                  60

Ala Glu Gly Thr Ala Val Thr Tyr Lys Leu Lys Glu Thr Lys Ala Pro
65                  70                  75                  80

Glu Gly Tyr Val Ile Pro Asp Lys Glu Ile Glu Phe Thr Val Ser Gln
                85                  90                  95

Thr Ser Tyr Asn Thr Lys Pro Thr Asp Ile Thr Val Asp Ser Gly Ser
            100                 105                 110

Gly Gly Gly Gly Leu Gln Gly Ala Ile Phe Val Leu Lys Asn Ala Thr
        115                 120                 125

Gly Gln Phe Leu Asn Phe Asn Asp Thr Asn Asn Val Glu Trp Gly Thr
130                 135                 140

Glu Ala Asn Ala Thr Glu Tyr Thr Thr Gly Ala Asp Gly Ile Ile Thr

```
              145                 150                 155                 160
Ile Thr Gly Leu Lys Glu Gly Thr Tyr Tyr Leu Val Glu Lys Lys Ala
                    165                 170                 175
Pro Leu Gly Tyr Asn Leu Leu Asp Asn Ser Gln Lys Val Ile Leu Gly
                180                 185                 190
Asp Gly Ala Thr Asp Thr Thr Asn Ser Asp Gly Ser Gly Gly Gly
            195                 200                 205
Leu Ser Lys Ala Thr Phe Val Leu Lys Thr Thr Ala His Pro Glu Ser
    210                 215                 220
Lys Ile Glu Lys Val Thr Ala Glu Leu Thr Gly Glu Ala Thr Phe Asp
225                 230                 235                 240
Asn Leu Ile Pro Gly Asp Tyr Thr Leu Ser Glu Glu Thr Ala Pro Glu
                245                 250                 255
Gly Tyr Lys Lys Thr Asn Gln Thr Trp Gln Val Lys Val Glu Ser Asn
                260                 265                 270
Gly Lys Thr Thr Ile Gln Asn Ser Gly Leu Lys Gly Ala Thr Phe Glu
            275                 280                 285
Leu Gln Glu Phe Asn Glu Asp Tyr Lys Leu Tyr Leu Pro Ile Lys Asn
    290                 295                 300
Asn Asn Ser Lys Val Val Thr Gly Glu Asn Gly Lys Ile Ser Tyr Lys
305                 310                 315                 320
Asp Leu Lys Asp Gly Lys Tyr Gln Leu Ile Glu Ala Val Ser Pro Glu
                325                 330                 335
Asp Tyr Gln Lys Ile Thr Asn Lys Pro Ile Leu Thr Phe Glu Val Val
                340                 345                 350
Lys Gly Ser Ile Lys Asn Ile Ile Ala Val Asn Lys Gln Ile
            355                 360                 365

<210> SEQ ID NO 109
<211> LENGTH: 448
<212> TYPE: PRT
<213> ORGANISM: Artificial Sequence
<220> FEATURE:
<223> OTHER INFORMATION: fusion protein

<400> SEQUENCE: 109

Leu Gly Gly Ala Glu Phe Asp Leu Leu Ala Ser Asp Gly Thr Ala Val
1               5                   10                  15
Lys Trp Thr Asp Ala Leu Ile Lys Ala Asn Thr Asn Lys Asn Tyr Ile
                20                  25                  30
Ala Gly Glu Ala Val Thr Gly Gln Pro Ile Lys Leu Lys Ser His Thr
            35                  40                  45
Asp Gly Thr Phe Glu Ile Lys Gly Leu Ala Tyr Ala Val Asp Ala Asn
        50                  55                  60
Ala Glu Gly Thr Ala Val Thr Tyr Lys Leu Lys Glu Thr Lys Ala Pro
65                  70                  75                  80
Glu Gly Tyr Val Ile Pro Asp Lys Glu Ile Glu Phe Thr Val Ser Gln
                85                  90                  95
Thr Ser Tyr Asn Thr Lys Pro Thr Asp Ile Thr Val Asp Ser Gly Ser
                100                 105                 110
Gly Gly Gly Gly Leu Gln Gly Ala Ile Phe Val Leu Lys Asn Ala Thr
            115                 120                 125
Gly Gln Phe Leu Asn Phe Asn Asp Thr Asn Asn Val Glu Trp Gly Thr
        130                 135                 140
Glu Ala Asn Ala Thr Glu Tyr Thr Thr Gly Ala Asp Gly Ile Ile Thr
```

```
                145                 150                 155                 160
        Ile Thr Gly Leu Lys Glu Gly Thr Tyr Tyr Leu Val Glu Lys Lys Ala
                        165                 170                 175

Pro Leu Gly Tyr Asn Leu Leu Asp Asn Ser Gln Lys Val Ile Leu Gly
                        180                 185                 190

Asp Gly Ala Thr Asp Thr Thr Asn Ser Asp Gly Ser Gly Gly Gly Gly
                        195                 200                 205

Ile Ala Gly Ala Tyr Phe Ala Phe Lys Asn Glu Ala Gly Thr Lys Tyr
                        210                 215                 220

Ile Thr Glu Asn Gly Glu Glu Val Asp Thr Leu Asp Thr Thr Asp Ala
        225                 230                 235                 240

Lys Gly Cys Ala Val Leu Lys Gly Leu Thr Thr Asp Asn Gly Phe Lys
                        245                 250                 255

Phe Asn Thr Ser Lys Leu Thr Gly Thr Tyr Gln Ile Val Glu Leu Lys
                        260                 265                 270

Glu Lys Ser Thr Tyr Asn Asn Asp Gly Ser Ile Leu Ala Asp Ser Lys
                        275                 280                 285

Ala Val Pro Val Lys Ile Thr Leu Pro Leu Leu Ala Gly Ala Thr Phe
                        290                 295                 300

Leu Val Lys Lys Asp Gly Lys Tyr Leu Ala Arg Lys Ser Gly Val Ala
        305                 310                 315                 320

Thr Asp Ala Glu Lys Ala Ala Val Asp Ser Thr Lys Ser Ala Leu Asp
                        325                 330                 335

Ala Ala Val Lys Ala Tyr Asn Asp Leu Thr Lys Glu Lys Gln Glu Gly
                        340                 345                 350

Gln Asp Gly Lys Ser Ala Leu Ala Thr Val Ser Glu Lys Gln Lys Ala
                        355                 360                 365

Tyr Asn Asp Ala Phe Val Lys Ala Asn Tyr Ser Tyr Glu Trp Val Glu
                        370                 375                 380

Asp Lys Asn Ala Lys Asn Val Val Lys Leu Ile Ser Asn Asp Lys Gly
        385                 390                 395                 400

Gln Phe Glu Ile Thr Gly Leu Thr Glu Gly Gln Tyr Ser Leu Glu Glu
                        405                 410                 415

Thr Gln Ala Pro Thr Gly Tyr Ala Lys Leu Ser Gly Asp Val Ser Phe
                        420                 425                 430

Asn Val Asn Ala Thr Ser Tyr Ser Lys Gly Ser Ala Gln Asp Ile Glu
                        435                 440                 445

<210> SEQ ID NO 110
<211> LENGTH: 70
<212> TYPE: PRT
<213> ORGANISM: S. agalactiae

<400> SEQUENCE: 110

Leu Ser Lys Ala Thr Phe Val Leu Lys Thr Thr Ala His Pro Glu Ser
        1               5                   10                  15

Lys Ile Glu Lys Val Thr Ala Glu Leu Thr Gly Glu Ala Thr Phe Asp
                        20                  25                  30

Asn Leu Ile Pro Gly Asp Tyr Thr Leu Ser Glu Glu Thr Ala Pro Glu
                        35                  40                  45

Gly Tyr Lys Lys Thr Asn Gln Thr Trp Gln Val Lys Val Glu Ser Asn
                        50                  55                  60

Gly Lys Thr Thr Ile Gln
        65                  70
```

```
<210> SEQ ID NO 111
<211> LENGTH: 82
<212> TYPE: PRT
<213> ORGANISM: S. agalactiae

<400> SEQUENCE: 111

Leu Lys Gly Ala Thr Phe Glu Leu Gln Glu Phe Asn Glu Asp Tyr Lys
 1               5                  10                  15

Leu Tyr Leu Pro Ile Lys Asn Asn Ser Lys Val Val Thr Gly Glu
                20                  25                  30

Asn Gly Lys Ile Ser Tyr Lys Asp Leu Lys Asp Gly Lys Tyr Gln Leu
            35                  40                  45

Ile Glu Ala Val Ser Pro Glu Asp Tyr Gln Lys Ile Thr Asn Lys Pro
50                  55                  60

Ile Leu Thr Phe Glu Val Val Lys Gly Ser Ile Lys Asn Ile Ile Ala
65                  70                  75                  80

Val Asn

<210> SEQ ID NO 112
<211> LENGTH: 107
<212> TYPE: PRT
<213> ORGANISM: S. agalactiae

<400> SEQUENCE: 112

Leu Gly Gly Ala Glu Phe Asp Leu Leu Ala Ser Asp Gly Thr Ala Val
 1               5                  10                  15

Lys Trp Thr Asp Ala Leu Ile Lys Ala Asn Thr Asn Lys Asn Tyr Ile
                20                  25                  30

Ala Gly Glu Ala Val Thr Gly Gln Pro Ile Lys Leu Lys Ser His Thr
            35                  40                  45

Asp Gly Thr Phe Glu Ile Lys Gly Leu Ala Tyr Ala Val Asp Ala Asn
50                  55                  60

Ala Glu Gly Thr Ala Val Thr Tyr Lys Leu Lys Glu Thr Lys Ala Pro
65                  70                  75                  80

Glu Gly Tyr Val Ile Pro Asp Lys Glu Ile Glu Phe Thr Val Ser Gln
                85                  90                  95

Thr Ser Tyr Asn Thr Lys Pro Thr Asp Ile Thr
            100                 105

<210> SEQ ID NO 113
<211> LENGTH: 86
<212> TYPE: PRT
<213> ORGANISM: S. agalactiae

<400> SEQUENCE: 113

Leu Gln Gly Ala Ile Phe Val Leu Lys Asn Ala Thr Gly Gln Phe Leu
 1               5                  10                  15

Asn Phe Asn Asp Thr Asn Asn Val Glu Trp Gly Thr Glu Ala Asn Ala
                20                  25                  30

Thr Glu Tyr Thr Thr Gly Ala Asp Gly Ile Ile Thr Ile Thr Gly Leu
            35                  40                  45

Lys Glu Gly Thr Tyr Tyr Leu Val Glu Lys Lys Ala Pro Leu Gly Tyr
            50                  55                  60

Asn Leu Leu Asp Asn Ser Gln Lys Val Ile Leu Gly Asp Gly Ala Thr
65                  70                  75                  80

Asp Thr Thr Asn Ser Asp
                85
```

```
<210> SEQ ID NO 114
<211> LENGTH: 87
<212> TYPE: PRT
<213> ORGANISM: S. agalactiae

<400> SEQUENCE: 114

Ile Ala Gly Ala Tyr Phe Ala Phe Lys Asn Glu Ala Gly Thr Lys Tyr
 1               5                  10                  15

Ile Thr Glu Asn Gly Glu Val Asp Thr Leu Asp Thr Asp Ala
            20                  25                  30

Lys Gly Cys Ala Val Leu Lys Gly Leu Thr Thr Asp Asn Gly Phe Lys
            35                  40                  45

Phe Asn Thr Ser Lys Leu Thr Gly Thr Tyr Gln Ile Val Glu Leu Lys
50                  55                  60

Glu Lys Ser Thr Tyr Asn Asn Asp Gly Ser Ile Leu Ala Asp Ser Lys
65                  70                  75                  80

Ala Val Pro Val Lys Ile Thr
                85

<210> SEQ ID NO 115
<211> LENGTH: 147
<212> TYPE: PRT
<213> ORGANISM: S. agalactiae

<400> SEQUENCE: 115

Leu Ala Gly Ala Thr Phe Leu Val Lys Lys Asp Gly Lys Tyr Leu Ala
 1               5                  10                  15

Arg Lys Ser Gly Val Ala Thr Asp Ala Glu Lys Ala Ala Val Asp Ser
            20                  25                  30

Thr Lys Ser Ala Leu Asp Ala Ala Val Lys Ala Tyr Asn Asp Leu Thr
            35                  40                  45

Lys Glu Lys Gln Glu Gly Gln Asp Gly Lys Ser Ala Leu Ala Thr Val
        50                  55                  60

Ser Glu Lys Gln Lys Ala Tyr Asn Asp Ala Phe Val Lys Ala Asn Tyr
65                  70                  75                  80

Ser Tyr Glu Trp Val Glu Asp Lys Asn Ala Lys Asn Val Val Lys Leu
                85                  90                  95

Ile Ser Asn Asp Lys Gly Gln Phe Glu Ile Thr Gly Leu Thr Glu Gly
            100                 105                 110

Gln Tyr Ser Leu Glu Glu Thr Gln Ala Pro Thr Gly Tyr Ala Lys Leu
        115                 120                 125

Ser Gly Asp Val Ser Phe Asn Val Asn Ala Thr Ser Tyr Ser Lys Gly
    130                 135                 140

Ser Ala Gln
145

<210> SEQ ID NO 116
<211> LENGTH: 69
<212> TYPE: PRT
<213> ORGANISM: S. agalactiae

<400> SEQUENCE: 116

Leu Ser Val Ala Pro Ala Phe Ala Asp Glu Ala Thr Thr Asn Thr Val
 1               5                  10                  15

Thr Leu His Lys Ile Leu Gln Thr Glu Ser Asn Leu Asn Lys Ser Asn
            20                  25                  30
```

Phe Pro Gly Thr Thr Gly Leu Asn Gly Lys Asp Tyr Lys Gly Gly Ala
                35                  40                  45

Ile Ser Asp Leu Ala Gly Tyr Phe Gly Glu Gly Ser Lys Glu Ile Glu
 50                  55                  60

Gly Ala Phe Phe Ala
 65

<210> SEQ ID NO 117
<211> LENGTH: 161
<212> TYPE: PRT
<213> ORGANISM: S. agalactiae

<400> SEQUENCE: 117

Glu Thr His Gly Lys Lys Phe Val Lys Thr Asn Glu Gln Gly Asp Arg
 1               5                  10                  15

Leu Ala Gly Ala Gln Phe Val Val Lys Asn Ser Ala Gly Lys Tyr Leu
                20                  25                  30

Ala Leu Lys Ala Asp Gln Ser Glu Gly Gln Lys Thr Leu Ala Ala Lys
            35                  40                  45

Lys Ile Ala Leu Asp Glu Ala Ile Ala Tyr Asn Lys Leu Ser Ala
 50                  55                  60

Thr Asp Gln Lys Gly Glu Lys Gly Ile Thr Ala Lys Glu Leu Ile Lys
 65                  70                  75                  80

Thr Lys Gln Ala Asp Tyr Asp Ala Ala Phe Ile Glu Ala Arg Thr Ala
                85                  90                  95

Tyr Glu Trp Ile Thr Asp Lys Ala Arg Ala Ile Thr Tyr Thr Ser Asn
            100                 105                 110

Asp Gln Gly Gln Phe Glu Val Thr Gly Leu Ala Asp Gly Thr Tyr Asn
        115                 120                 125

Leu Glu Glu Thr Leu Ala Pro Ala Gly Phe Ala Lys Leu Ala Gly Asn
    130                 135                 140

Ile Lys Phe Val Val Asn Gln Gly Ser Tyr Ile Thr Gly Gly Asn Ile
145                 150                 155                 160

Asp

<210> SEQ ID NO 118
<211> LENGTH: 705
<212> TYPE: PRT
<213> ORGANISM: S. agalactiae

<400> SEQUENCE: 118

Met Lys Arg Ile Asn Lys Tyr Phe Ala Met Phe Ser Ala Leu Leu Leu
 1               5                  10                  15

Thr Leu Thr Ser Leu Leu Ser Val Ala Pro Ala Phe Ala Asp Glu Ala
                20                  25                  30

Thr Thr Asn Thr Val Thr Leu His Lys Ile Leu Gln Thr Glu Ser Asn
            35                  40                  45

Leu Asn Lys Ser Asn Phe Pro Gly Thr Thr Gly Leu Asn Gly Lys Asp
 50                  55                  60

Tyr Lys Gly Gly Ala Ile Ser Asp Leu Ala Gly Tyr Phe Gly Glu Gly
 65                  70                  75                  80

Ser Lys Glu Ile Glu Gly Ala Phe Phe Ala Leu Ala Leu Lys Glu Asp
                85                  90                  95

Lys Ser Gly Lys Val Gln Tyr Val Lys Ala Lys Glu Gly Asn Lys Leu
            100                 105                 110

Thr Pro Ala Leu Ile Asn Lys Asp Gly Thr Pro Glu Ile Thr Val Asn

```
            115                 120                 125
Ile Asp Glu Ala Val Ser Gly Leu Thr Pro Glu Gly Asp Thr Gly Leu
130                 135                 140

Val Phe Asn Thr Lys Gly Leu Lys Gly Glu Phe Lys Ile Val Glu Val
145                 150                 155                 160

Lys Ser Lys Ser Thr Tyr Asn Asn Asn Gly Ser Leu Leu Ala Ala Ser
                    165                 170                 175

Lys Ala Val Pro Val Asn Ile Thr Leu Pro Leu Val Asn Glu Asp Gly
                180                 185                 190

Val Val Ala Asp Ala His Val Tyr Pro Lys Asn Thr Glu Glu Lys Pro
            195                 200                 205

Glu Ile Asp Lys Asn Phe Ala Lys Thr Asn Asp Leu Thr Ala Leu Thr
210                 215                 220

Asp Val Asn Arg Leu Leu Thr Ala Gly Ala Asn Tyr Gly Asn Tyr Ala
225                 230                 235                 240

Arg Asp Lys Ala Thr Ala Thr Ala Glu Ile Gly Lys Val Val Pro Tyr
                    245                 250                 255

Glu Val Lys Thr Lys Ile His Lys Gly Ser Lys Tyr Glu Asn Leu Val
                260                 265                 270

Trp Thr Asp Ile Met Ser Asn Gly Leu Thr Met Gly Ser Thr Val Ser
            275                 280                 285

Leu Lys Ala Ser Gly Thr Thr Glu Thr Phe Ala Lys Asp Thr Asp Tyr
290                 295                 300

Glu Leu Ser Ile Asp Ala Arg Gly Phe Thr Leu Lys Phe Thr Ala Asp
305                 310                 315                 320

Gly Leu Gly Lys Leu Glu Lys Ala Ala Lys Thr Ala Asp Ile Glu Phe
                    325                 330                 335

Thr Leu Thr Tyr Ser Ala Thr Val Asn Gly Gln Ala Ile Ile Asp Asn
                340                 345                 350

Pro Glu Ser Asn Asp Ile Lys Leu Ser Tyr Gly Asn Lys Pro Gly Lys
            355                 360                 365

Asp Leu Thr Glu Leu Pro Val Thr Pro Ser Lys Gly Glu Val Thr Val
370                 375                 380

Ala Lys Thr Trp Ser Asp Gly Ile Ala Pro Asp Gly Val Asn Val Val
385                 390                 395                 400

Tyr Thr Leu Lys Asp Lys Asp Lys Thr Val Ala Ser Val Ser Leu Thr
                    405                 410                 415

Lys Thr Ser Lys Gly Thr Ile Asp Leu Gly Asn Gly Ile Lys Phe Glu
                420                 425                 430

Val Ser Gly Asn Phe Ser Gly Lys Phe Thr Gly Leu Glu Asn Lys Ser
            435                 440                 445

Tyr Met Ile Ser Glu Arg Val Ser Gly Tyr Gly Ser Ala Ile Asn Leu
450                 455                 460

Glu Asn Gly Lys Val Thr Ile Thr Asn Thr Lys Asp Ser Asp Asn Pro
465                 470                 475                 480

Thr Pro Leu Asn Pro Thr Glu Pro Lys Val Glu Thr His Gly Lys Lys
                    485                 490                 495

Phe Val Lys Thr Asn Glu Gln Gly Asp Arg Leu Ala Gly Ala Gln Phe
                500                 505                 510

Val Val Lys Asn Ser Ala Gly Lys Tyr Leu Ala Leu Lys Ala Asp Gln
            515                 520                 525

Ser Glu Gly Gln Lys Thr Leu Ala Ala Lys Lys Ile Ala Leu Asp Glu
530                 535                 540
```

```
Ala Ile Ala Ala Tyr Asn Lys Leu Ser Ala Thr Asp Gln Lys Gly Glu
545                 550                 555                 560

Lys Gly Ile Thr Ala Lys Glu Leu Ile Lys Thr Lys Gln Ala Asp Tyr
            565                 570                 575

Asp Ala Ala Phe Ile Glu Ala Arg Thr Ala Tyr Glu Trp Ile Thr Asp
                580                 585                 590

Lys Ala Arg Ala Ile Thr Tyr Thr Ser Asn Asp Gln Gly Gln Phe Glu
            595                 600                 605

Val Thr Gly Leu Ala Asp Gly Thr Tyr Asn Leu Glu Glu Thr Leu Ala
610                 615                 620

Pro Ala Gly Phe Ala Lys Leu Ala Gly Asn Ile Lys Phe Val Val Asn
625                 630                 635                 640

Gln Gly Ser Tyr Ile Thr Gly Gly Asn Ile Asp Tyr Val Ala Asn Ser
                645                 650                 655

Asn Gln Lys Asp Ala Thr Arg Val Glu Asn Lys Lys Val Thr Ile Pro
                660                 665                 670

Gln Thr Gly Gly Ile Gly Thr Ile Leu Phe Thr Ile Ile Gly Leu Ser
            675                 680                 685

Ile Met Leu Gly Ala Val Val Ile Met Lys Arg Arg Gln Ser Lys Glu
    690                 695                 700

Ala
705

<210> SEQ ID NO 119
<211> LENGTH: 3486
<212> TYPE: DNA
<213> ORGANISM: S. pyogenes

<400> SEQUENCE: 119
atgacacaaa aaatagcta taagttaagc ttcctgttat ccctaacagg atttatttta      60
ggtttattat tggtttttat aggattgtcc ggagtatcag taggacatgc ggaaacaaga    120
aatggagcaa acaaacaagg atcttttgaa atcaagaaag tcgaccaaaa caataagcct    180
ttaccgggag caactttttc actgacatca aaggatggca aggaacatc tgttcaaacg     240
ttcacttcaa atgataaagg tattgtagat gctcaaaatc tccaaccagg gacttatacc    300
ttaaaagaag aaacagcacc agatggttat gataaaacca gccggacttg acagtgact    360
gtttatgaga acggctatac caagttggtt gaaaatccct ataatgggga atcatcagt    420
aaagcagggt caaagatgt tagtagttct ttacagttgg aaaatcccaa atgtcagtt     480
gtttctaaat atgggaaaac agaggttagt agtggcgcag cggatttcta ccgcaaccat    540
gccgcctatt ttaaaatgtc ttttgagttg aaacaaaagg ataaatctga acaatcaac    600
ccaggtgata ccttgtgtt acagctggat agacgtctca atcctaaagg tatcagtcaa    660
gatatcccta aaatcattta cgacagtgca aatagtccgc ttgcgattgg aaaataccat    720
gctgagaacc atcaacttat ctatactttc acagattata ttgcgggttt agataaagtc    780
cagttgtctg cagaattgag cttattccta gagaataagg aagtgttgga aaatactagt    840
atctcaaatt ttaagagtac cataggtggg caggagatca cctataaagg aacggttaat    900
gttctttatg gaaatgagag cactaaagaa agcaattata ttactaatgg attgagcaat    960
gtgggtggga gtattgaaag ctacaacacc gaaacgggag aatttgtctg gtatgtttat   1020
gtcaatccaa accgtaccaa tattccttat gcgaccatga atttatgggg atttggaagg   1080
gctcgttcaa atacaagcga cttagaaaac gacgctaata caagtagtgc tgagcttgga   1140
```

```
gagattcagg tctatgaagt acctgaagga gaaaaattac catcaagtta tggggttgat   1200
gttacaaaac ttactttaag aacggatatc acagcaggcc taggaaatgg ttttcaaatg   1260
accaaacgtc agcgaattga ctttggaaat aatatccaaa ataaagcatt tatcatcaaa   1320
gtaacaggga aaacagacca atctggtaag ccattggttg ttcaatccaa tttggcaagt   1380
tttcgtggtg cttctgaata tgctgctttt actccagttg gaggaaatgt ctacttccaa   1440
aacgaaattg ccttgtctcc ttctaagggt agtggttctg ggaaaagtga atttactaag   1500
ccctctatta cagtagcaaa tctaaaacga gtggctcagc ttcgctttaa gaaaatgtca   1560
actgacaatg tgccattgcc agaagcggct tttgagctgc gttcatcaaa tggtaatagt   1620
cagaaattag aagccagttc aaacacacaa ggagaggttc actttaagga cctgacctcg   1680
ggcacatatg acctgtatga acaaaaagcg ccaaaaggtt atcagcaggt gacagagaaa   1740
ttggcgaccg ttactgttga tactaccaaa cctgctgagg aaatggtcac ttggggaagc   1800
ccacattcgt ctgtaaaagt agaagctaac aaagaagtca cgattgtcaa ccataaagaa   1860
acccttacgt tttcagggaa gaaaatttgg gagaatgaca gaccagatca acgcccagca   1920
aagattcaag tgcaactgtt gcaaaatggt caaaagatgc ctaaccagat tcaagaagta   1980
acgaaggata acgattggtc ttatcacttc aaagacttgc ctaagtacga tgccaagaat   2040
caggagtata agtactcagt tgaagaagta aatgttccag acggctacaa ggtgtcgtat   2100
ttaggaaatg atatatttaa caccagagaa acagaatttg tgtttgaaca gaataacttt   2160
aaccttgaat ttggaaatgc tgaaataaaa ggtcaatctg ggtcaaaaat cattgatgaa   2220
gacacgctaa cgtctttcaa aggtaagaaa atttggaaaa atgatacggc agaaaatcgt   2280
ccccaagcca ttcaagtgca gctttatgct gatggagtgg ctgtggaagg tcaaaccaaa   2340
tttatttctg gctcaggtaa tgagtggtca tttgagttta aaaacttgaa gaagtataat   2400
ggaacaggta atgacatcat ttactcagtt aaagaagtaa ctgttccaac aggttatgat   2460
gtgacttact cagctaatga tattattaat accaaacgtg aggttattac acaacaagga   2520
ccgaaactag agattgaaga aacgcttccg ctagaatcag gtgcttcagg cggtaccact   2580
actgtcgaag actcacgccc agttgatacc ttatcaggtt tatcaagtga gcaaggtcag   2640
tccggtgata tgacaattga agaagatagt gctacccata ttaaattctc aaaacgtgat   2700
attgacggca aagagttagc tggtgcaact atggagttgc gtgattcatc tggtaaaact   2760
attagtacat ggatttcaga tggacaagtg aaagatttct acctgatgcc aggaaaatat   2820
acatttgtcg aaaccgcagc accagacggt tatgagatag caactgctat tacctttaca   2880
gttaatgagc aaggtcaggt tactgtaaat ggcaaagcaa ctaaaggtga cactcatatt   2940
gtcatggttg atgcttacaa gccaactaag ggttcaggtc aggttattga tattgaagaa   3000
aagcttccag acgagcaagg tcattctggt tcaactactg aaatagaaga cagtaaatct   3060
tcagacctta tcattggcgg tcaaggtgaa gttgttgaca caacagaaga cacacaaagt   3120
ggtatgacgg gccattctgg ctcaactact gaaatagaag atagcaagtc ttcagacgtt   3180
atcattggtg gtcaggggca ggttgtcgag acaacagagg atacccaaac tggcatgtac   3240
ggggattctg gttgtaaaac ggaagtcgaa gatactaaac tagtacaatc cttccacttt   3300
gataacaagg aaccagaaag taactctgag attcctaaaa aagataagcc aaagagtaat   3360
actagtttac cagcaactgg tgagaagcaa cataatatgt tctttggat ggttacttct   3420
tgctcactta ttagtagtgt ttttgtaata tcactaaaat ccaaaaaacg cctatcatca   3480
```

```
tgttaa                                                                  3486
```

<210> SEQ ID NO 120
<211> LENGTH: 216
<212> TYPE: DNA
<213> ORGANISM: S. pyogenes

<400> SEQUENCE: 120

```
cttgcaggtg ttgagtttga actccgtaaa gaggacaaga agatcgtctg ggaaaaggga    60
acaacaggtt caaatggcca actcaacttt aagtaccttc aaaaaggcaa aacctattat   120
ctgtatgaga cgaaggcaaa acttggatac actcttccag aaaatccatg ggaagttgcc   180
gttgctaaca acggtgatat aaaagtaaaa cacccg                             216
```

<210> SEQ ID NO 121
<211> LENGTH: 1161
<212> TYPE: PRT
<213> ORGANISM: S. pyogenes

<400> SEQUENCE: 121

| Met | Thr | Gln | Lys | Asn | Ser | Tyr | Lys | Leu | Ser | Phe | Leu | Leu | Ser | Leu | Thr |
|---|---|---|---|---|---|---|---|---|---|---|---|---|---|---|---|
| 1 | | | | 5 | | | | | 10 | | | | | 15 | |

| Gly | Phe | Ile | Leu | Gly | Leu | Leu | Leu | Val | Phe | Ile | Gly | Leu | Ser | Gly | Val |
| | | | 20 | | | | | 25 | | | | | 30 | | |

| Ser | Val | Gly | His | Ala | Glu | Thr | Arg | Asn | Gly | Ala | Asn | Lys | Gln | Gly | Ser |
| | | 35 | | | | | 40 | | | | | 45 | | | |

| Phe | Glu | Ile | Lys | Lys | Val | Asp | Gln | Asn | Lys | Pro | Leu | Pro | Gly | Ala |
| 50 | | | | | 55 | | | | | 60 | | | | | |

| Thr | Phe | Ser | Leu | Thr | Ser | Lys | Asp | Gly | Lys | Gly | Thr | Ser | Val | Gln | Thr |
| 65 | | | | 70 | | | | | 75 | | | | | 80 | |

| Phe | Thr | Ser | Asn | Asp | Lys | Gly | Ile | Val | Asp | Ala | Gln | Asn | Leu | Gln | Pro |
| | | | | 85 | | | | | 90 | | | | | 95 | |

| Gly | Thr | Tyr | Thr | Leu | Lys | Glu | Glu | Thr | Ala | Pro | Asp | Gly | Tyr | Asp | Lys |
| | | | 100 | | | | | 105 | | | | | 110 | | |

| Thr | Ser | Arg | Thr | Trp | Thr | Val | Thr | Val | Tyr | Glu | Asn | Gly | Tyr | Thr | Lys |
| | | 115 | | | | | 120 | | | | | 125 | | | |

| Leu | Val | Glu | Asn | Pro | Tyr | Asn | Gly | Glu | Ile | Ile | Ser | Lys | Ala | Gly | Ser |
| | 130 | | | | | 135 | | | | | 140 | | | | |

| Lys | Asp | Val | Ser | Ser | Leu | Gln | Leu | Glu | Asn | Pro | Lys | Met | Ser | Val |
| 145 | | | | | 150 | | | | | 155 | | | | | 160 |

| Val | Ser | Lys | Tyr | Gly | Lys | Thr | Glu | Val | Ser | Ser | Gly | Ala | Ala | Asp | Phe |
| | | | 165 | | | | | 170 | | | | | 175 | | |

| Tyr | Arg | Asn | His | Ala | Ala | Tyr | Phe | Lys | Met | Ser | Phe | Glu | Leu | Lys | Gln |
| | | | 180 | | | | | 185 | | | | | 190 | | |

| Lys | Asp | Lys | Ser | Glu | Thr | Ile | Asn | Pro | Gly | Asp | Thr | Phe | Val | Leu | Gln |
| | | 195 | | | | | 200 | | | | | 205 | | | |

| Leu | Asp | Arg | Arg | Leu | Asn | Pro | Lys | Gly | Ile | Ser | Gln | Asp | Ile | Pro | Lys |
| | 210 | | | | | 215 | | | | | 220 | | | | |

| Ile | Ile | Tyr | Asp | Ser | Ala | Asn | Ser | Pro | Leu | Ala | Ile | Gly | Lys | Tyr | His |
| 225 | | | | | 230 | | | | | 235 | | | | | 240 |

| Ala | Glu | Asn | His | Gln | Leu | Ile | Tyr | Thr | Phe | Thr | Asp | Tyr | Ile | Ala | Gly |
| | | | 245 | | | | | 250 | | | | | 255 | | |

| Leu | Asp | Lys | Val | Gln | Leu | Ser | Ala | Glu | Leu | Ser | Leu | Phe | Leu | Glu | Asn |
| | | | 260 | | | | | 265 | | | | | 270 | | |

| Lys | Glu | Val | Leu | Glu | Asn | Thr | Ser | Ile | Ser | Asn | Phe | Lys | Ser | Thr | Ile |
| | | 275 | | | | | 280 | | | | | 285 | | | |

```
Gly Gly Gln Glu Ile Thr Tyr Lys Gly Thr Val Asn Val Leu Tyr Gly
    290                 295                 300

Asn Glu Ser Thr Lys Glu Ser Asn Tyr Ile Thr Asn Gly Leu Ser Asn
305                 310                 315                 320

Val Gly Gly Ser Ile Glu Ser Tyr Asn Thr Glu Thr Gly Glu Phe Val
                325                 330                 335

Trp Tyr Val Tyr Val Asn Pro Asn Arg Thr Asn Ile Pro Tyr Ala Thr
            340                 345                 350

Met Asn Leu Trp Gly Phe Gly Arg Ala Arg Ser Asn Thr Ser Asp Leu
        355                 360                 365

Glu Asn Asp Ala Asn Thr Ser Ser Ala Glu Leu Gly Glu Ile Gln Val
370                 375                 380

Tyr Glu Val Pro Glu Gly Glu Lys Leu Pro Ser Ser Tyr Gly Val Asp
385                 390                 395                 400

Val Thr Lys Leu Thr Leu Arg Thr Asp Ile Thr Ala Gly Leu Gly Asn
                405                 410                 415

Gly Phe Gln Met Thr Lys Arg Gln Arg Ile Asp Phe Gly Asn Asn Ile
            420                 425                 430

Gln Asn Lys Ala Phe Ile Ile Lys Val Thr Gly Lys Thr Asp Gln Ser
        435                 440                 445

Gly Lys Pro Leu Val Val Gln Ser Asn Leu Ala Ser Phe Arg Gly Ala
    450                 455                 460

Ser Glu Tyr Ala Ala Phe Thr Pro Val Gly Gly Asn Val Tyr Phe Gln
465                 470                 475                 480

Asn Glu Ile Ala Leu Ser Pro Ser Lys Gly Ser Gly Ser Gly Lys Ser
                485                 490                 495

Glu Phe Thr Lys Pro Ser Ile Thr Val Ala Asn Leu Lys Arg Val Ala
            500                 505                 510

Gln Leu Arg Phe Lys Lys Met Ser Thr Asp Asn Val Pro Leu Pro Glu
        515                 520                 525

Ala Ala Phe Glu Leu Arg Ser Ser Asn Gly Asn Ser Gln Lys Leu Glu
    530                 535                 540

Ala Ser Ser Asn Thr Gln Gly Glu Val His Phe Lys Asp Leu Thr Ser
545                 550                 555                 560

Gly Thr Tyr Asp Leu Tyr Glu Thr Lys Ala Pro Lys Gly Tyr Gln Gln
                565                 570                 575

Val Thr Glu Lys Leu Ala Thr Val Thr Val Asp Thr Thr Lys Pro Ala
            580                 585                 590

Glu Glu Met Val Thr Trp Gly Ser Pro His Ser Ser Val Lys Val Glu
        595                 600                 605

Ala Asn Lys Glu Val Thr Ile Val Asn His Lys Glu Thr Leu Thr Phe
    610                 615                 620

Ser Gly Lys Lys Ile Trp Glu Asn Asp Arg Pro Asp Gln Arg Pro Ala
625                 630                 635                 640

Lys Ile Gln Val Gln Leu Leu Gln Asn Gly Gln Lys Met Pro Asn Gln
                645                 650                 655

Ile Gln Glu Val Thr Lys Asp Asn Asp Trp Ser Tyr His Phe Lys Asp
            660                 665                 670

Leu Pro Lys Tyr Asp Ala Lys Asn Gln Glu Tyr Lys Tyr Ser Val Glu
        675                 680                 685

Glu Val Asn Val Pro Asp Gly Tyr Lys Val Ser Tyr Leu Gly Asn Asp
    690                 695                 700
```

-continued

Ile Phe Asn Thr Arg Glu Thr Glu Phe Val Phe Glu Gln Asn Asn Phe
705                 710                 715                 720

Asn Leu Glu Phe Gly Asn Ala Glu Ile Lys Gly Gln Ser Gly Ser Lys
            725                 730                 735

Ile Ile Asp Glu Asp Thr Leu Thr Ser Phe Lys Gly Lys Lys Ile Trp
        740                 745                 750

Lys Asn Asp Thr Ala Glu Asn Arg Pro Gln Ala Ile Gln Val Gln Leu
            755                 760                 765

Tyr Ala Asp Gly Val Ala Val Glu Gly Gln Thr Lys Phe Ile Ser Gly
    770                 775                 780

Ser Gly Asn Glu Trp Ser Phe Glu Phe Lys Asn Leu Lys Lys Tyr Asn
785                 790                 795                 800

Gly Thr Gly Asn Asp Ile Ile Tyr Ser Val Lys Glu Val Thr Val Pro
                805                 810                 815

Thr Gly Tyr Asp Val Thr Tyr Ser Ala Asn Asp Ile Ile Asn Thr Lys
            820                 825                 830

Arg Glu Val Ile Thr Gln Gln Gly Pro Lys Leu Glu Ile Glu Glu Thr
        835                 840                 845

Leu Pro Leu Glu Ser Gly Ala Ser Gly Gly Thr Thr Thr Val Glu Asp
    850                 855                 860

Ser Arg Pro Val Asp Thr Leu Ser Gly Leu Ser Ser Glu Gln Gly Gln
865                 870                 875                 880

Ser Gly Asp Met Thr Ile Glu Glu Asp Ser Ala Thr His Ile Lys Phe
                885                 890                 895

Ser Lys Arg Asp Ile Asp Gly Lys Glu Leu Ala Gly Ala Thr Met Glu
            900                 905                 910

Leu Arg Asp Ser Ser Gly Lys Thr Ile Ser Thr Trp Ile Ser Asp Gly
        915                 920                 925

Gln Val Lys Asp Phe Tyr Leu Met Pro Gly Lys Tyr Thr Phe Val Glu
    930                 935                 940

Thr Ala Ala Pro Asp Gly Tyr Glu Ile Ala Thr Ala Ile Thr Phe Thr
945                 950                 955                 960

Val Asn Glu Gln Gly Gln Val Thr Val Asn Gly Lys Ala Thr Lys Gly
                965                 970                 975

Asp Thr His Ile Val Met Val Asp Ala Tyr Lys Pro Thr Lys Gly Ser
            980                 985                 990

Gly Gln Val Ile Asp Ile Glu Glu Lys Leu Pro Asp Glu Gln Gly His
        995                 1000                1005

Ser Gly Ser Thr Thr Glu Ile Glu Asp Ser Lys Ser Ser Asp Leu Ile
    1010                1015                1020

Ile Gly Gly Gln Gly Glu Val Val Asp Thr Thr Glu Asp Thr Gln Ser
1025                1030                1035                1040

Gly Met Thr Gly His Ser Gly Ser Thr Thr Glu Ile Glu Asp Ser Lys
                1045                1050                1055

Ser Ser Asp Val Ile Ile Gly Gly Gln Gly Val Val Glu Thr Thr
            1060                1065                1070

Glu Asp Thr Gln Thr Gly Met Tyr Gly Asp Ser Gly Cys Lys Thr Glu
        1075                1080                1085

Val Glu Asp Thr Lys Leu Val Gln Ser Phe His Phe Asp Asn Lys Glu
    1090                1095                1100

Pro Glu Ser Asn Ser Glu Ile Pro Lys Lys Asp Lys Pro Lys Ser Asn
1105                1110                1115                1120

Thr Ser Leu Pro Ala Thr Gly Glu Lys Gln His Asn Met Phe Phe Trp

-continued

```
                     1125                1130                1135
Met Val Thr Ser Cys Ser Leu Ile Ser Ser Val Phe Val Ile Ser Leu
              1140                1145                1150

Lys Ser Lys Lys Arg Leu Ser Ser Cys
         1155                1160

<210> SEQ ID NO 122
<211> LENGTH: 70
<212> TYPE: PRT
<213> ORGANISM: S. pyogenes

<400> SEQUENCE: 122

Leu Pro Gly Ala Thr Phe Ser Leu Thr Ser Lys Asp Gly Lys Gly Thr
  1               5                  10                  15

Ser Val Gln Thr Phe Thr Ser Asn Asp Lys Gly Ile Val Asp Ala Gln
             20                  25                  30

Asn Leu Gln Pro Gly Thr Tyr Thr Leu Lys Glu Glu Thr Ala Pro Asp
         35                  40                  45

Gly Tyr Asp Lys Thr Ser Arg Thr Trp Thr Val Thr Val Tyr Glu Asn
     50                  55                  60

Gly Tyr Thr Lys Leu Val
 65                  70

<210> SEQ ID NO 123
<211> LENGTH: 74
<212> TYPE: PRT
<213> ORGANISM: S. pyogenes

<400> SEQUENCE: 123

Leu Pro Glu Ala Ala Phe Glu Leu Arg Ser Ser Asn Gly Asn Ser Gln
  1               5                  10                  15

Lys Leu Glu Ala Ser Ser Asn Thr Gln Gly Glu Val His Phe Lys Asp
             20                  25                  30

Leu Thr Ser Gly Thr Tyr Asp Leu Tyr Glu Thr Lys Ala Pro Lys Gly
         35                  40                  45

Tyr Gln Gln Val Thr Glu Lys Leu Ala Thr Val Thr Val Asp Thr Thr
     50                  55                  60

Lys Pro Ala Glu Glu Met Val Thr Trp Gly
 65                  70

<210> SEQ ID NO 124
<211> LENGTH: 71
<212> TYPE: PRT
<213> ORGANISM: S. pyogenes

<400> SEQUENCE: 124

Pro Ala Lys Ile Gln Val Gln Leu Leu Gln Asn Gly Gln Lys Met Pro
  1               5                  10                  15

Asn Gln Ile Gln Glu Val Thr Lys Asp Asn Asp Trp Ser Tyr His Phe
             20                  25                  30

Lys Asp Leu Pro Lys Tyr Asp Ala Lys Asn Gln Glu Tyr Lys Tyr Ser
         35                  40                  45

Val Glu Glu Val Asn Val Pro Asp Gly Tyr Lys Val Ser Tyr Leu Gly
     50                  55                  60

Asn Asp Ile Phe Asn Thr Arg
 65                  70

<210> SEQ ID NO 125
```

```
<211> LENGTH: 62
<212> TYPE: PRT
<213> ORGANISM: S. pyogenes

<400> SEQUENCE: 125

Asp Gly Val Ala Val Glu Gly Gln Thr Lys Phe Ile Ser Gly Ser Gly
 1               5                  10                  15

Asn Glu Trp Ser Phe Glu Phe Lys Asn Leu Lys Lys Tyr Asn Gly Thr
            20                  25                  30

Gly Asn Asp Ile Ile Tyr Ser Val Lys Glu Val Thr Val Pro Thr Gly
        35                  40                  45

Tyr Asp Val Thr Tyr Ser Ala Asn Asp Ile Ile Asn Thr Lys
    50                  55                  60

<210> SEQ ID NO 126
<211> LENGTH: 67
<212> TYPE: PRT
<213> ORGANISM: S. pyogenes

<400> SEQUENCE: 126

Leu Ala Gly Ala Thr Met Glu Leu Arg Asp Ser Ser Gly Lys Thr Ile
 1               5                  10                  15

Ser Thr Trp Ile Ser Asp Gly Gln Val Lys Asp Phe Tyr Leu Met Pro
            20                  25                  30

Gly Lys Tyr Thr Phe Val Glu Thr Ala Ala Pro Asp Gly Tyr Glu Ile
        35                  40                  45

Ala Thr Ala Ile Thr Phe Thr Val Asn Glu Gln Gly Gln Val Thr Val
    50                  55                  60

Asn Gly Lys
65

<210> SEQ ID NO 127
<211> LENGTH: 272
<212> TYPE: PRT
<213> ORGANISM: Artificial Sequence
<220> FEATURE:
<223> OTHER INFORMATION: His-tagged chimeric Cna_B antigen

<400> SEQUENCE: 127

His His His His His His Leu Ala Gly Ala Thr Phe Leu Val Lys Lys
 1               5                  10                  15

Asp Gly Lys Tyr Leu Ala Arg Lys Ser Gly Val Ala Thr Asp Ala Glu
            20                  25                  30

Lys Ala Ala Val Asp Ser Thr Lys Ser Ala Leu Asp Ala Ala Val Lys
        35                  40                  45

Ala Tyr Asn Asp Leu Thr Lys Glu Lys Gln Glu Gly Gln Asp Gly Lys
    50                  55                  60

Ser Ala Leu Ala Thr Val Ser Glu Lys Gln Lys Ala Tyr Asn Asp Ala
65                  70                  75                  80

Phe Val Lys Ala Asn Tyr Ser Tyr Glu Trp Val Glu Asp Lys Asn Ala
                85                  90                  95

Lys Asn Val Val Lys Leu Ile Ser Asn Asp Lys Gly Gln Phe Glu Ile
            100                 105                 110

Thr Gly Leu Thr Glu Gly Gln Tyr Ser Leu Glu Glu Thr Gln Ala Pro
        115                 120                 125

Thr Gly Tyr Ala Lys Leu Ser Gly Asp Val Ser Phe Asn Val Asn Ala
    130                 135                 140

Thr Ser Tyr Ser Lys Gly Ser Ala Gln Asp Ile Glu Gly Ser Gly Gly
```

```
145                 150                 155                 160
Gly Gly Leu Gly Gly Ala Glu Phe Asp Leu Leu Ala Ser Asp Gly Thr
                165                 170                 175

Ala Val Lys Trp Thr Asp Ala Leu Ile Lys Ala Asn Thr Asn Lys Asn
            180                 185                 190

Tyr Ile Ala Gly Glu Ala Val Thr Gly Gln Pro Ile Lys Leu Lys Ser
        195                 200                 205

His Thr Asp Gly Thr Phe Glu Ile Lys Gly Leu Ala Tyr Ala Val Asp
    210                 215                 220

Ala Asn Ala Glu Gly Thr Ala Val Thr Tyr Lys Leu Lys Glu Thr Lys
225                 230                 235                 240

Ala Pro Glu Gly Tyr Val Ile Pro Asp Lys Glu Ile Glu Phe Thr Val
                245                 250                 255

Ser Gln Thr Ser Tyr Asn Thr Lys Pro Thr Asp Ile Thr Val Asp Ser
            260                 265                 270

<210> SEQ ID NO 128
<211> LENGTH: 248
<212> TYPE: PRT
<213> ORGANISM: Artificial Sequence
<220> FEATURE:
<223> OTHER INFORMATION: His-tagged chimeric Cna_B antigen

<400> SEQUENCE: 128

His His His His His Leu Ala Gly Ala Thr Phe Leu Val Lys Lys
  1               5                  10                  15

Asp Gly Lys Tyr Leu Ala Arg Lys Ser Gly Val Ala Thr Asp Ala Glu
            20                  25                  30

Lys Ala Ala Val Asp Ser Thr Lys Ser Ala Leu Asp Ala Ala Val Lys
        35                  40                  45

Ala Tyr Asn Asp Leu Thr Lys Glu Lys Gln Glu Gly Gln Asp Gly Lys
    50                  55                  60

Ser Ala Leu Ala Thr Val Ser Glu Lys Gln Lys Ala Tyr Asn Asp Ala
65                  70                  75                  80

Phe Val Lys Ala Asn Tyr Ser Tyr Glu Trp Val Glu Asp Lys Asn Ala
                85                  90                  95

Lys Asn Val Val Lys Leu Ile Ser Asn Asp Lys Gly Gln Phe Glu Ile
            100                 105                 110

Thr Gly Leu Thr Glu Gly Gln Tyr Ser Leu Glu Glu Thr Gln Ala Pro
        115                 120                 125

Thr Gly Tyr Ala Lys Leu Ser Gly Asp Val Ser Phe Asn Val Asn Ala
    130                 135                 140

Thr Ser Tyr Ser Lys Gly Ser Ala Gln Asp Ile Glu Gly Ser Gly Gly
145                 150                 155                 160

Gly Gly Leu Gln Gly Ala Ile Phe Val Leu Lys Asn Ala Thr Gly Gln
                165                 170                 175

Phe Leu Asn Phe Asn Asp Thr Asn Asn Val Glu Trp Gly Thr Glu Ala
            180                 185                 190

Asn Ala Thr Glu Tyr Thr Thr Gly Ala Asp Gly Ile Ile Thr Ile Thr
        195                 200                 205

Gly Leu Lys Glu Gly Thr Tyr Tyr Leu Val Glu Lys Lys Ala Pro Leu
    210                 215                 220

Gly Tyr Asn Leu Leu Asp Asn Ser Gln Lys Val Ile Leu Gly Asp Gly
225                 230                 235                 240

Ala Thr Asp Thr Thr Asn Ser Asp
```

<210> SEQ ID NO 129
<211> LENGTH: 320
<212> TYPE: PRT
<213> ORGANISM: Artificial Sequence
<220> FEATURE:
<223> OTHER INFORMATION: His-tagged chimeric Cna_B antigen

<400> SEQUENCE: 129

```
His His His His His His Leu Ala Gly Ala Thr Phe Leu Val Lys Lys
  1               5                  10                  15

Asp Gly Lys Tyr Leu Ala Arg Lys Ser Gly Val Ala Thr Asp Ala Glu
             20                  25                  30

Lys Ala Ala Val Asp Ser Thr Lys Ser Ala Leu Asp Ala Ala Val Lys
         35                  40                  45

Ala Tyr Asn Asp Leu Thr Lys Glu Lys Gln Glu Gly Gln Asp Gly Lys
     50                  55                  60

Ser Ala Leu Ala Thr Val Ser Glu Lys Gln Lys Ala Tyr Asn Asp Ala
 65                  70                  75                  80

Phe Val Lys Ala Asn Tyr Ser Tyr Glu Trp Val Glu Asp Lys Asn Ala
                 85                  90                  95

Lys Asn Val Val Lys Leu Ile Ser Asn Asp Lys Gly Gln Phe Glu Ile
            100                 105                 110

Thr Gly Leu Thr Glu Gly Gln Tyr Ser Leu Glu Thr Gln Ala Pro
        115                 120                 125

Thr Gly Tyr Ala Lys Leu Ser Gly Asp Val Ser Phe Asn Val Asn Ala
    130                 135                 140

Thr Ser Tyr Ser Lys Gly Ser Ala Gln Asp Ile Glu Gly Ser Gly Gly
145                 150                 155                 160

Gly Gly Leu Ser Lys Ala Thr Phe Val Leu Lys Thr Thr Ala His Pro
                165                 170                 175

Glu Ser Lys Ile Glu Lys Val Thr Ala Glu Leu Thr Gly Glu Ala Thr
            180                 185                 190

Phe Asp Asn Leu Ile Pro Gly Asp Tyr Thr Leu Ser Glu Glu Thr Ala
        195                 200                 205

Pro Glu Gly Tyr Lys Lys Thr Asn Gln Thr Trp Gln Val Lys Val Glu
    210                 215                 220

Ser Asn Gly Lys Thr Thr Ile Gln Asn Ser Gly Leu Lys Gly Ala Thr
225                 230                 235                 240

Phe Glu Leu Gln Glu Phe Asn Glu Asp Tyr Lys Leu Tyr Leu Pro Ile
                245                 250                 255

Lys Asn Asn Ser Lys Val Val Thr Gly Glu Asn Gly Lys Ile Ser
            260                 265                 270

Tyr Lys Asp Leu Lys Asp Gly Lys Tyr Gln Leu Ile Glu Ala Val Ser
        275                 280                 285

Pro Glu Asp Tyr Gln Lys Ile Thr Asn Lys Pro Ile Leu Thr Phe Glu
    290                 295                 300

Val Val Lys Gly Ser Ile Lys Asn Ile Ile Ala Val Asn Lys Gln Ile
305                 310                 315                 320
```

<210> SEQ ID NO 130
<211> LENGTH: 364
<212> TYPE: PRT
<213> ORGANISM: Artificial Sequence
<220> FEATURE:
<223> OTHER INFORMATION: His-tagged chimeric Cna_B antigen

<400> SEQUENCE: 130

```
His His His His His His Leu Ala Gly Ala Thr Phe Leu Val Lys Lys
  1               5                  10                  15

Asp Gly Lys Tyr Leu Ala Arg Lys Ser Gly Val Ala Thr Asp Ala Glu
             20                  25                  30

Lys Ala Ala Val Asp Ser Thr Lys Ser Ala Leu Asp Ala Ala Val Lys
         35                  40                  45

Ala Tyr Asn Asp Leu Thr Lys Glu Lys Gln Gly Gln Asp Gly Lys
     50                  55                  60

Ser Ala Leu Ala Thr Val Ser Glu Lys Gln Lys Ala Tyr Asn Asp Ala
 65                  70                  75                  80

Phe Val Lys Ala Asn Tyr Ser Tyr Glu Trp Val Glu Asp Lys Asn Ala
                 85                  90                  95

Lys Asn Val Val Lys Leu Ile Ser Asn Asp Lys Gly Gln Phe Glu Ile
            100                 105                 110

Thr Gly Leu Thr Glu Gly Gln Tyr Ser Leu Glu Thr Gln Ala Pro
        115                 120                 125

Thr Gly Tyr Ala Lys Leu Ser Gly Asp Val Ser Phe Asn Val Asn Ala
        130                 135                 140

Thr Ser Tyr Ser Lys Gly Ser Ala Gln Asp Ile Glu Leu Gly Gly Ala
145                 150                 155                 160

Glu Phe Asp Leu Leu Ala Ser Asp Gly Thr Ala Val Lys Trp Thr Asp
                165                 170                 175

Ala Leu Ile Lys Ala Asn Thr Asn Lys Asn Tyr Ile Ala Gly Glu Ala
            180                 185                 190

Val Thr Gly Gln Pro Ile Lys Leu Lys Ser His Thr Asp Gly Thr Phe
        195                 200                 205

Glu Ile Lys Gly Leu Ala Tyr Ala Val Asp Ala Asn Ala Glu Gly Thr
    210                 215                 220

Ala Val Thr Tyr Lys Leu Lys Glu Thr Lys Ala Pro Glu Gly Tyr Val
225                 230                 235                 240

Ile Pro Asp Lys Glu Ile Glu Phe Thr Val Ser Gln Thr Ser Tyr Asn
                245                 250                 255

Thr Lys Pro Thr Asp Ile Thr Val Asp Ser Gly Ser Gly Gly Gly
            260                 265                 270

Leu Gln Gly Ala Ile Phe Val Leu Lys Asn Ala Thr Gly Gln Phe Leu
        275                 280                 285

Asn Phe Asn Asp Thr Asn Asn Val Glu Trp Gly Thr Glu Ala Asn Ala
    290                 295                 300

Thr Glu Tyr Thr Thr Gly Ala Asp Gly Ile Ile Thr Ile Thr Gly Leu
305                 310                 315                 320

Lys Glu Gly Thr Tyr Tyr Leu Val Glu Lys Lys Ala Pro Leu Gly Tyr
                325                 330                 335

Asn Leu Leu Asp Asn Ser Gln Lys Val Ile Leu Gly Asp Gly Ala Thr
            340                 345                 350

Asp Thr Thr Asn Ser Asp Gly Ser Gly Gly Gly
        355                 360
```

<210> SEQ ID NO 131
<211> LENGTH: 521
<212> TYPE: PRT
<213> ORGANISM: Artificial Sequence
<220> FEATURE:
<223> OTHER INFORMATION: His-tagged chimeric Cna_B antigen

<400> SEQUENCE: 131

```
His His His His His Val Gly Asn Val Thr Val Thr Val Phe Asp
  1               5                  10                  15

Asn Asn Thr Asn Thr Lys Val Gly Glu Ala Val Thr Lys Glu Asp Gly
              20                  25                  30

Ser Tyr Leu Ile Pro Asn Leu Pro Asn Gly Asp Tyr Arg Val Glu Phe
          35                  40                  45

Ser Asn Leu Pro Lys Gly Tyr Glu Val Thr Pro Ser Lys Gln Gly Asn
 50                  55                  60

Asn Glu Glu Leu Asp Ser Asn Gly Leu Ser Ser Val Ile Thr Val Asn
 65                  70                  75                  80

Gly Lys Asp Asn Leu Ser Ala Asp Leu Gly Ile Tyr Lys Pro Lys Tyr
              85                  90                  95

Asn Leu Gly Asp Tyr Val Trp Glu Asp Thr Asn Lys Asn Gly Ile Gln
         100                 105                 110

Asp Gln Asp Glu Lys Gly Ile Ser Gly Val Thr Val Thr Leu Lys Asp
         115                 120                 125

Glu Asn Gly Asn Val Leu Lys Thr Val Thr Thr Asp Ala Asp Gly Lys
130                 135                 140

Tyr Lys Phe Thr Asp Leu Asp Asn Gly Asn Tyr Lys Val Glu Phe Thr
145                 150                 155                 160

Thr Pro Glu Gly Tyr Thr Pro Thr Thr Val Thr Ser Gly Ser Asp Ile
             165                 170                 175

Glu Lys Asp Ser Asn Gly Leu Thr Thr Thr Gly Val Ile Asn Gly Ala
         180                 185                 190

Asp Asn Met Thr Leu Asp Ser Gly Phe Tyr Lys Thr Pro Lys Tyr Asn
         195                 200                 205

Leu Gly Asn Tyr Val Trp Glu Asp Thr Asn Lys Asp Gly Lys Gln Asp
210                 215                 220

Ser Thr Glu Lys Gly Ile Ser Gly Val Thr Val Thr Leu Lys Asn Glu
225                 230                 235                 240

Asn Gly Glu Val Leu Gln Thr Thr Lys Thr Asp Lys Asp Gly Lys Tyr
             245                 250                 255

Gln Phe Thr Gly Leu Glu Asn Gly Thr Tyr Lys Val Glu Phe Glu Thr
         260                 265                 270

Pro Ser Gly Tyr Thr Pro Thr Gln Val Gly Ser Gly Thr Asp Glu Gly
         275                 280                 285

Ile Asp Ser Asn Gly Thr Ser Thr Thr Gly Val Ile Lys Asp Lys Asp
290                 295                 300

Asn Asp Thr Ile Asp Ser Gly Phe Tyr Lys Pro Thr Tyr Asn Leu Gly
305                 310                 315                 320

Asp Tyr Val Trp Glu Asp Thr Asn Lys Asn Gly Val Gln Asp Lys Asp
             325                 330                 335

Glu Lys Gly Ile Ser Gly Val Thr Val Thr Leu Lys Asp Glu Asn Asp
         340                 345                 350

Lys Val Leu Lys Thr Val Thr Thr Asp Glu Asn Gly Lys Tyr Gln Phe
         355                 360                 365

Thr Asp Leu Asn Asn Gly Thr Tyr Lys Val Glu Phe Glu Thr Pro Ser
370                 375                 380

Gly Tyr Thr Pro Thr Ser Val Thr Ser Gly Asn Asp Thr Glu Lys Asp
385                 390                 395                 400

Ser Asn Gly Leu Thr Thr Thr Gly Val Ile Lys Asp Ala Asp Asn Met
```

```
                        405                 410                 415
Thr Leu Asp Ser Gly Phe Tyr Lys Thr Pro Lys Tyr Ser Leu Gly Asp
            420                 425                 430

Tyr Val Trp Tyr Asp Ser Asn Lys Asp Gly Lys Gln Asp Ser Thr Glu
            435                 440                 445

Lys Gly Ile Lys Asp Val Lys Val Thr Leu Leu Asn Glu Lys Gly Glu
            450                 455                 460

Val Ile Gly Thr Thr Lys Thr Asp Glu Asn Gly Lys Tyr Cys Phe Asp
465                 470                 475                 480

Asn Leu Asp Ser Gly Lys Tyr Lys Val Ile Phe Glu Lys Pro Ala Gly
            485                 490                 495

Leu Thr Gln Thr Val Thr Asn Thr Thr Glu Asp Asp Lys Asp Ala Asp
            500                 505                 510

Gly Gly Glu Val Asp Val Thr Ile Thr
            515                 520

<210> SEQ ID NO 132
<211> LENGTH: 1349
<212> TYPE: PRT
<213> ORGANISM: S. aureus

<400> SEQUENCE: 132

Met Leu Asn Arg Glu Asn Lys Thr Ala Ile Thr Arg Lys Gly Met Val
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Leu Ile Glu
            100                 105                 110

Lys Glu Ser Val Gln Ser Thr Thr Gly Asn Lys Val Glu Val Ser Thr
        115                 120                 125

Ala Lys Ser Asp Glu Gln Ala Ser Pro Lys Ser Thr Asn Glu Asp Leu
    130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Asp Glu Thr Leu Val Asp Asn Asn Ser Asn
        195                 200                 205

Ser Asn Asn Glu Asn Asn Ala Asp Ile Ile Leu Pro Lys Ser Thr Ala
    210                 215                 220

Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255
```

-continued

```
Leu Thr Val Val Asp Ala Asp Lys Asn Asn Lys Ile Val Pro Ala Gln
            260                 265                 270

Asp Tyr Leu Ser Leu Lys Ser Gln Ile Thr Val Asp Asp Lys Val Lys
        275                 280                 285

Ser Gly Asp Tyr Phe Thr Ile Lys Tyr Ser Asp Thr Val Gln Val Tyr
    290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Gln Met Gly Ile Asn Tyr Ser Ile Tyr Met Asp Ala Asp Thr Ile Pro
        355                 360                 365

Val Ser Lys Asn Asp Val Glu Phe Asn Val Thr Ile Gly Asn Thr Thr
    370                 375                 380

Thr Lys Thr Thr Ala Asn Ile Gln Tyr Pro Asp Tyr Val Val Asn Glu
385                 390                 395                 400

Lys Asn Ser Ile Gly Ser Ala Phe Thr Glu Thr Val Ser His Val Gly
                405                 410                 415

Asn Lys Glu Asn Pro Gly Tyr Tyr Lys Gln Thr Ile Tyr Val Asn Pro
            420                 425                 430

Ser Glu Asn Ser Leu Thr Asn Ala Lys Leu Lys Val Gln Ala Tyr His
        435                 440                 445

Ser Ser Tyr Pro Asn Asn Ile Gly Gln Ile Asn Lys Asp Val Thr Asp
    450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
                485                 490                 495

Lys Ile Thr Tyr Gly Asp Asn Asn Ser Ala Val Ile Asp Phe Gly Asn
            500                 505                 510

Ala Asp Ser Ala Tyr Val Val Met Val Asn Thr Lys Phe Gln Tyr Thr
        515                 520                 525

Asn Ser Glu Ser Pro Thr Leu Val Gln Met Ala Thr Leu Ser Ser Thr
    530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590

Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
    610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
            660                 665                 670

Ala Asp Leu Gly Ile Tyr Lys Pro Lys Tyr Asn Leu Gly Asp Tyr Val
```

-continued

```
            675                 680                 685
Trp Glu Asp Thr Asn Lys Asn Gly Ile Gln Asp Gln Asp Glu Lys Gly
            690                 695                 700
Ile Ser Gly Val Thr Val Thr Leu Lys Asp Glu Asn Gly Asn Val Leu
705                 710                 715                 720
Lys Thr Val Thr Thr Asp Ala Asp Gly Lys Tyr Lys Phe Thr Asp Leu
                    725                 730                 735
Asp Asn Gly Asn Tyr Lys Val Glu Phe Thr Thr Pro Glu Gly Tyr Thr
                740                 745                 750
Pro Thr Thr Val Thr Ser Gly Ser Asp Ile Glu Lys Asp Ser Asn Gly
                755                 760                 765
Leu Thr Thr Gly Val Ile Asn Gly Ala Asp Asn Met Thr Leu Asp
770                 775                 780
Ser Gly Phe Tyr Lys Thr Pro Lys Tyr Asn Leu Gly Asn Tyr Val Trp
785                 790                 795                 800
Glu Asp Thr Asn Lys Asp Gly Lys Gln Asp Ser Thr Glu Lys Gly Ile
                    805                 810                 815
Ser Gly Val Thr Val Thr Leu Lys Asn Glu Asn Gly Glu Val Leu Gln
                820                 825                 830
Thr Thr Lys Thr Asp Lys Asp Gly Lys Tyr Gln Phe Thr Gly Leu Glu
                835                 840                 845
Asn Gly Thr Tyr Lys Val Glu Phe Glu Thr Pro Ser Gly Tyr Thr Pro
850                 855                 860
Thr Gln Val Gly Ser Gly Thr Asp Glu Gly Ile Asp Ser Asn Gly Thr
865                 870                 875                 880
Ser Thr Thr Gly Val Ile Lys Asp Lys Asp Asn Asp Thr Ile Asp Ser
                    885                 890                 895
Gly Phe Tyr Lys Pro Thr Tyr Asn Leu Gly Asp Tyr Val Trp Glu Asp
                900                 905                 910
Thr Asn Lys Asn Gly Val Gln Asp Lys Asp Glu Lys Gly Ile Ser Gly
                915                 920                 925
Val Thr Val Thr Leu Lys Asp Glu Asn Asp Lys Val Leu Lys Thr Val
930                 935                 940
Thr Thr Asp Glu Asn Gly Lys Tyr Gln Phe Thr Asp Leu Asn Asn Gly
945                 950                 955                 960
Thr Tyr Lys Val Glu Phe Glu Thr Pro Ser Gly Tyr Thr Pro Thr Ser
                    965                 970                 975
Val Thr Ser Gly Asn Asp Thr Glu Lys Asp Ser Asn Gly Leu Thr Thr
                980                 985                 990
Thr Gly Val Ile Lys Asp Ala Asp Asn Met Thr Leu Asp Ser Gly Phe
                995                 1000                1005
Tyr Lys Thr Pro Lys Tyr Ser Leu Gly Asp Tyr Val Trp Tyr Asp Ser
            1010                1015                1020
Asn Lys Asp Gly Lys Gln Asp Ser Thr Glu Lys Gly Ile Lys Asp Val
1025                1030                1035                1040
Lys Val Thr Leu Leu Asn Glu Lys Gly Glu Val Ile Gly Thr Thr Lys
                    1045                1050                1055
Thr Asp Glu Asn Gly Lys Tyr Cys Phe Asp Asn Leu Ser Gly Lys
                1060                1065                1070
Tyr Lys Val Ile Phe Glu Lys Pro Ala Gly Leu Thr Gln Thr Val Thr
                1075                1080                1085
Asn Thr Thr Glu Asp Asp Lys Asp Ala Asp Gly Gly Glu Val Asp Val
                1090                1095                1100
```

```
Thr Ile Thr Asp His Asp Asp Phe Thr Leu Asp Asn Gly Tyr Phe Glu
1105                1110                1115                1120

Glu Asp Thr Ser Asp Ser Asp Ser Asp Ser Asp Ser Asp Ser Asp Ser
                1125                1130                1135

Asp Ser Asp Ser Asp Ser Asp Ser Asp Ser Asp Ser Asp Ser Asp Ser
            1140                1145                1150

Asp Ser Asp Ser Asp Ser Asp Ser Asp Ser Asp Ser Asp Ser Asp Ser
            1155                1160                1165

Asp Ser Asp Ser Asp Ser Asp Ser Asp Ser Asp Ser Asp Ser Asp Ser
            1170                1175                1180

Asp Ser Asp Ser Asp Ser Asp Ser Asp Ser Asp Ser Asp Ser Asp Ser
1185                1190                1195                1200

Asp Ser Asp Ser Asp Ser Asp Ser Asp Ser Asp Ser Asp Ser Asp Ser
            1205                1210                1215

Asp Ser Asp Ser Asp Ser Asp Ser Asp Ser Asp Ser Asp Ser Asp Ser
            1220                1225                1230

Asp Ser Asp Ser Asp Ser Asp Ser Asp Ser Asp Ser Asp Ser Asp Ser
            1235                1240                1245

Asp Ser Asp Ser Asp Ser Asp Ser Asp Ser Asp Ser Asp Ser Asp Ser
            1250                1255                1260

Asp Ser Asp Ser Asp Ser Asp Ser Asp Ser Asp Ser Asp Ser Asp Ser
1265                1270                1275                1280

Asp Ser Asp Ser Asp Ser Asp Ser Asp Ala Gly Lys His Thr Pro Val
            1285                1290                1295

Lys Pro Met Ser Thr Thr Lys Asp His His Asn Lys Ala Lys Ala Leu
            1300                1305                1310

Pro Glu Thr Gly Ser Glu Asn Asn Gly Ser Asn Asn Ala Thr Leu Phe
            1315                1320                1325

Gly Gly Leu Phe Ala Ala Leu Gly Ser Leu Leu Leu Phe Gly Arg Arg
            1330                1335                1340

Lys Lys Gln Asn Lys
1345

<210> SEQ ID NO 133
<211> LENGTH: 538
<212> TYPE: PRT
<213> ORGANISM: S. aureus

<400> SEQUENCE: 133

Met His His His His His His Val Gly Asn Val Thr Val Thr Val Phe
  1               5                  10                  15

Asp Asn Asn Thr Asn Thr Lys Val Gly Glu Ala Val Thr Lys Glu Asp
             20                  25                  30

Gly Ser Tyr Leu Ile Pro Asn Leu Pro Asn Gly Asp Tyr Arg Val Glu
         35                  40                  45

Phe Ser Asn Leu Pro Lys Gly Tyr Glu Val Thr Pro Ser Lys Gln Gly
     50                  55                  60

Asn Asn Glu Glu Leu Asp Ser Asn Gly Leu Ser Ser Val Ile Thr Val
65                  70                  75                  80

Asn Gly Lys Asp Asn Leu Ser Ala Asp Leu Gly Ile Tyr Lys Pro Lys
                 85                  90                  95

Tyr Asn Leu Gly Asp Tyr Val Trp Glu Asp Thr Asn Lys Asn Gly Ile
            100                 105                 110

Gln Asp Gln Asp Glu Lys Gly Ile Ser Gly Val Thr Val Thr Leu Lys
```

-continued

```
            115                 120                 125
Asp Glu Asn Gly Asn Val Leu Lys Thr Val Thr Thr Asp Ala Asp Gly
            130                 135                 140
Lys Tyr Lys Phe Thr Asp Leu Asp Asn Gly Asn Tyr Lys Val Glu Phe
145                 150                 155                 160
Thr Thr Pro Glu Gly Tyr Thr Pro Thr Val Thr Ser Gly Ser Asp
                165                 170                 175
Ile Glu Lys Asp Ser Asn Gly Leu Thr Thr Gly Val Ile Asn Gly
                180                 185                 190
Ala Asp Asn Met Thr Leu Asp Ser Gly Phe Tyr Lys Thr Pro Lys Tyr
                195                 200                 205
Asn Leu Gly Asn Tyr Val Trp Glu Asp Thr Asn Lys Asp Gly Lys Gln
            210                 215                 220
Asp Ser Thr Glu Lys Gly Ile Ser Gly Val Thr Val Thr Leu Lys Asn
225                 230                 235                 240
Glu Asn Gly Glu Val Leu Gln Thr Thr Lys Thr Asp Lys Asp Gly Lys
                245                 250                 255
Tyr Gln Phe Thr Gly Leu Glu Asn Gly Thr Tyr Lys Val Glu Phe Glu
                260                 265                 270
Thr Pro Ser Gly Tyr Thr Pro Thr Gln Val Gly Ser Gly Thr Asp Glu
                275                 280                 285
Gly Ile Asp Ser Asn Gly Thr Ser Thr Gly Val Ile Lys Asp Lys
            290                 295                 300
Asp Asn Asp Thr Ile Asp Ser Gly Phe Tyr Lys Pro Thr Tyr Asn Leu
305                 310                 315                 320
Gly Asp Tyr Val Trp Glu Asp Thr Asn Lys Asn Gly Val Gln Asp Lys
                325                 330                 335
Asp Glu Lys Gly Ile Ser Gly Val Thr Val Thr Leu Lys Asp Glu Asn
                340                 345                 350
Asp Lys Val Leu Lys Thr Val Thr Thr Asp Glu Asn Gly Lys Tyr Gln
                355                 360                 365
Phe Thr Asp Leu Asn Asn Gly Thr Tyr Lys Val Glu Phe Glu Thr Pro
            370                 375                 380
Ser Gly Tyr Thr Pro Thr Ser Val Thr Ser Gly Asn Asp Thr Glu Lys
385                 390                 395                 400
Asp Ser Asn Gly Leu Thr Thr Thr Gly Val Ile Lys Asp Ala Asp Asn
                405                 410                 415
Met Thr Leu Asp Ser Gly Phe Tyr Lys Thr Pro Lys Tyr Ser Leu Gly
                420                 425                 430
Asp Tyr Val Trp Tyr Asp Ser Asn Lys Asp Gly Lys Gln Asp Ser Thr
                435                 440                 445
Glu Lys Gly Ile Lys Asp Val Lys Val Thr Leu Leu Asn Glu Lys Gly
            450                 455                 460
Glu Val Ile Gly Thr Thr Lys Thr Asp Glu Asn Gly Lys Tyr Cys Phe
465                 470                 475                 480
Asp Asn Leu Asp Ser Gly Lys Tyr Lys Val Ile Phe Glu Lys Pro Ala
                485                 490                 495
Gly Leu Thr Gln Thr Val Thr Asn Thr Thr Glu Asp Asp Lys Asp Ala
                500                 505                 510
Asp Gly Gly Glu Val Asp Val Thr Ile Thr Asp His Asp Asp Phe Thr
            515                 520                 525
Leu Asp Asn Gly Tyr Phe Glu Glu Asp Thr
            530                 535
```

<210> SEQ ID NO 134
<211> LENGTH: 74
<212> TYPE: PRT
<213> ORGANISM: S. aureus

<400> SEQUENCE: 134

Val Gly Asn Val Thr Val Thr Val Phe Asp Asn Asn Thr Asn Thr Lys
1               5                   10                  15

Val Gly Glu Ala Val Thr Lys Glu Asp Gly Ser Tyr Leu Ile Pro Asn
            20                  25                  30

Leu Pro Asn Gly Asp Tyr Arg Val Glu Phe Ser Asn Leu Pro Lys Gly
        35                  40                  45

Tyr Glu Val Thr Pro Ser Lys Gln Gly Asn Asn Glu Glu Leu Asp Ser
    50                  55                  60

Asn Gly Leu Ser Ser Val Ile Thr Val Asn
65                  70

<210> SEQ ID NO 135
<211> LENGTH: 72
<212> TYPE: PRT
<213> ORGANISM: S. aureus

<400> SEQUENCE: 135

Ile Ser Gly Val Thr Val Thr Leu Lys Asp Glu Asn Gly Asn Val Leu
1               5                   10                  15

Lys Thr Val Thr Thr Asp Ala Asp Gly Lys Tyr Lys Phe Thr Asp Leu
            20                  25                  30

Asp Asn Gly Asn Tyr Lys Val Glu Phe Thr Thr Pro Glu Gly Tyr Thr
        35                  40                  45

Pro Thr Thr Val Thr Ser Gly Ser Asp Ile Glu Lys Asp Ser Asn Gly
    50                  55                  60

Leu Thr Thr Thr Gly Val Ile Asn
65                  70

<210> SEQ ID NO 136
<211> LENGTH: 72
<212> TYPE: PRT
<213> ORGANISM: S. aureus

<400> SEQUENCE: 136

Ile Ser Gly Val Thr Val Thr Leu Lys Asn Glu Asn Gly Glu Val Leu
1               5                   10                  15

Gln Thr Thr Lys Thr Asp Lys Asp Gly Lys Tyr Gln Phe Thr Gly Leu
            20                  25                  30

Glu Asn Gly Thr Tyr Lys Val Glu Phe Glu Thr Pro Ser Gly Tyr Thr
        35                  40                  45

Pro Thr Gln Val Gly Ser Gly Thr Asp Glu Gly Ile Asp Ser Asn Gly
    50                  55                  60

Thr Ser Thr Thr Gly Val Ile Lys
65                  70

<210> SEQ ID NO 137
<211> LENGTH: 72
<212> TYPE: PRT
<213> ORGANISM: S. aureus

<400> SEQUENCE: 137

Ile Ser Gly Val Thr Val Thr Leu Lys Asp Glu Asn Asp Lys Val Leu

```
                1               5                  10                 15
Lys Thr Val Thr Thr Asp Glu Asn Gly Lys Tyr Gln Phe Thr Asp Leu
                    20                  25                 30

Asn Asn Gly Thr Tyr Lys Val Glu Phe Glu Thr Pro Ser Gly Tyr Thr
                    35                  40                 45

Pro Thr Ser Val Thr Ser Gly Asn Asp Thr Glu Lys Asp Ser Asn Gly
 50                      55                     60

Leu Thr Thr Thr Gly Val Ile Lys
 65                  70
```

<210> SEQ ID NO 138
<211> LENGTH: 71
<212> TYPE: PRT
<213> ORGANISM: S. aureus

<400> SEQUENCE: 138

```
Ile Lys Asp Val Lys Val Thr Leu Leu Asn Glu Lys Gly Glu Val Ile
 1               5                  10                 15

Gly Thr Thr Lys Thr Asp Glu Asn Gly Lys Tyr Cys Phe Asp Asn Leu
                    20                  25                 30

Asp Ser Gly Lys Tyr Lys Val Ile Phe Glu Lys Pro Ala Gly Leu Thr
                    35                  40                 45

Gln Thr Val Thr Asn Thr Thr Glu Asp Lys Asp Ala Asp Gly Gly
 50                      55                     60

Glu Val Asp Val Thr Ile Thr
 65                  70
```

<210> SEQ ID NO 139
<211> LENGTH: 531
<212> TYPE: PRT
<213> ORGANISM: S. aureus

<400> SEQUENCE: 139

```
Val Gly Asn Val Thr Val Thr Val Phe Asp Asn Asn Thr Asn Thr Lys
 1               5                  10                 15

Val Gly Glu Ala Val Thr Lys Glu Asp Gly Ser Tyr Leu Ile Pro Asn
                    20                  25                 30

Leu Pro Asn Gly Asp Tyr Arg Val Glu Phe Ser Asn Leu Pro Lys Gly
                    35                  40                 45

Tyr Glu Val Thr Pro Ser Lys Gln Gly Asn Asn Glu Glu Leu Asp Ser
 50                      55                     60

Asn Gly Leu Ser Ser Val Ile Thr Val Asn Gly Lys Asp Asn Leu Ser
 65                  70                     75                 80

Ala Asp Leu Gly Ile Tyr Lys Pro Lys Tyr Asn Leu Gly Asp Tyr Val
                    85                  90                 95

Trp Glu Asp Thr Asn Lys Asn Gly Ile Gln Asp Gln Asp Glu Lys Gly
                   100                 105                110

Ile Ser Gly Val Thr Val Thr Leu Lys Asp Glu Asn Gly Asn Val Leu
                   115                 120                125

Lys Thr Val Thr Thr Asp Ala Asp Gly Lys Tyr Lys Phe Thr Asp Leu
                   130                 135                140

Asp Asn Gly Asn Tyr Lys Val Glu Phe Thr Thr Pro Glu Gly Tyr Thr
145                 150                 155                160

Pro Thr Thr Val Thr Ser Gly Ser Asp Ile Glu Lys Asp Ser Asn Gly
                   165                 170                175

Leu Thr Thr Thr Gly Val Ile Asn Gly Ala Asp Asn Met Thr Leu Asp
```

```
                180                 185                 190
Ser Gly Phe Tyr Lys Thr Pro Lys Tyr Asn Leu Gly Asn Tyr Val Trp
            195                 200                 205

Glu Asp Thr Asn Lys Asp Gly Lys Gln Asp Ser Thr Glu Lys Gly Ile
        210                 215                 220

Ser Gly Val Thr Val Thr Leu Lys Asn Glu Asn Gly Glu Val Leu Gln
225                 230                 235                 240

Thr Thr Lys Thr Asp Lys Asp Gly Lys Tyr Gln Phe Thr Gly Leu Glu
                245                 250                 255

Asn Gly Thr Tyr Lys Val Glu Phe Glu Thr Pro Ser Gly Tyr Thr Pro
            260                 265                 270

Thr Gln Val Gly Ser Gly Thr Asp Glu Gly Ile Asp Ser Asn Gly Thr
        275                 280                 285

Ser Thr Thr Gly Val Ile Lys Asp Lys Asp Asn Asp Thr Ile Asp Ser
        290                 295                 300

Gly Phe Tyr Lys Pro Thr Tyr Asn Leu Gly Asp Tyr Val Trp Glu Asp
305                 310                 315                 320

Thr Asn Lys Asn Gly Val Gln Asp Lys Asp Glu Lys Gly Ile Ser Gly
                325                 330                 335

Val Thr Val Thr Leu Lys Asp Glu Asn Asp Lys Val Leu Lys Thr Val
            340                 345                 350

Thr Thr Asp Glu Asn Gly Lys Tyr Gln Phe Thr Asp Leu Asn Asn Gly
        355                 360                 365

Thr Tyr Lys Val Glu Phe Glu Thr Pro Ser Gly Tyr Thr Pro Thr Ser
        370                 375                 380

Val Thr Ser Gly Asn Asp Thr Glu Lys Asp Ser Asn Gly Leu Thr Thr
385                 390                 395                 400

Thr Gly Val Ile Lys Asp Ala Asp Asn Met Thr Leu Asp Ser Gly Phe
                405                 410                 415

Tyr Lys Thr Pro Lys Tyr Ser Leu Gly Asp Tyr Val Trp Tyr Asp Ser
            420                 425                 430

Asn Lys Asp Gly Lys Gln Asp Ser Thr Glu Lys Gly Ile Lys Asp Val
        435                 440                 445

Lys Val Thr Leu Leu Asn Glu Lys Gly Glu Val Ile Gly Thr Thr Lys
        450                 455                 460

Thr Asp Glu Asn Gly Lys Tyr Cys Phe Asp Asn Leu Asp Ser Gly Lys
465                 470                 475                 480

Tyr Lys Val Ile Phe Glu Lys Pro Ala Gly Leu Thr Gln Thr Val Thr
                485                 490                 495

Asn Thr Thr Glu Asp Asp Lys Asp Ala Asp Gly Gly Glu Val Asp Val
            500                 505                 510

Thr Ile Thr Asp His Asp Asp Phe Thr Leu Asp Asn Gly Tyr Phe Glu
        515                 520                 525

Glu Asp Thr
        530

<210> SEQ ID NO 140
<211> LENGTH: 266
<212> TYPE: PRT
<213> ORGANISM: Artificial Sequence
<220> FEATURE:
<223> OTHER INFORMATION: chimeric Cna_B domain antigen

<400> SEQUENCE: 140

Leu Ala Gly Ala Thr Phe Leu Val Lys Lys Asp Gly Lys Tyr Leu Ala
```

```
                1               5                   10                  15
            Arg Lys Ser Gly Val Ala Thr Asp Ala Glu Lys Ala Ala Val Asp Ser
                            20                  25                  30

Thr Lys Ser Ala Leu Asp Ala Ala Val Lys Ala Tyr Asn Asp Leu Thr
                            35                  40                  45

Lys Glu Lys Gln Glu Gly Gln Asp Gly Lys Ser Ala Leu Ala Thr Val
                            50                  55                  60

Ser Glu Lys Gln Lys Ala Tyr Asn Asp Ala Phe Val Lys Ala Asn Tyr
             65                 70                  75                  80

Ser Tyr Glu Trp Val Glu Asp Lys Asn Ala Lys Asn Val Val Lys Leu
                                85                  90                  95

Ile Ser Asn Asp Lys Gly Gln Phe Glu Ile Thr Gly Leu Thr Glu Gly
                            100                 105                 110

Gln Tyr Ser Leu Glu Glu Thr Gln Ala Pro Thr Gly Tyr Ala Lys Leu
                            115                 120                 125

Ser Gly Asp Val Ser Phe Asn Val Asn Ala Thr Ser Tyr Ser Lys Gly
                            130                 135                 140

Ser Ala Gln Asp Ile Glu Gly Ser Gly Gly Gly Leu Gly Gly Ala
            145                 150                 155                 160

Glu Phe Asp Leu Leu Ala Ser Asp Gly Thr Ala Val Lys Trp Thr Asp
                            165                 170                 175

Ala Leu Ile Lys Ala Asn Thr Asn Lys Asn Tyr Ile Ala Gly Glu Ala
                            180                 185                 190

Val Thr Gly Gln Pro Ile Lys Leu Lys Ser His Thr Asp Gly Thr Phe
                            195                 200                 205

Glu Ile Lys Gly Leu Ala Tyr Ala Val Asp Ala Asn Ala Glu Gly Thr
                            210                 215                 220

Ala Val Thr Tyr Lys Leu Lys Glu Thr Lys Ala Pro Glu Gly Tyr Val
            225                 230                 235                 240

Ile Pro Asp Lys Glu Ile Glu Phe Thr Val Ser Gln Thr Ser Tyr Asn
                            245                 250                 255

Thr Lys Pro Thr Asp Ile Thr Val Asp Ser
                            260                 265

<210> SEQ ID NO 141
<211> LENGTH: 242
<212> TYPE: PRT
<213> ORGANISM: Artificial Sequence
<220> FEATURE:
<223> OTHER INFORMATION: chimeric Cna_B domain antigen

<400> SEQUENCE: 141

Leu Ala Gly Ala Thr Phe Leu Val Lys Lys Asp Gly Lys Tyr Leu Ala
             1                  5                  10                  15

Arg Lys Ser Gly Val Ala Thr Asp Ala Glu Lys Ala Ala Val Asp Ser
                            20                  25                  30

Thr Lys Ser Ala Leu Asp Ala Ala Val Lys Ala Tyr Asn Asp Leu Thr
                            35                  40                  45

Lys Glu Lys Gln Glu Gly Gln Asp Gly Lys Ser Ala Leu Ala Thr Val
                            50                  55                  60

Ser Glu Lys Gln Lys Ala Tyr Asn Asp Ala Phe Val Lys Ala Asn Tyr
             65                 70                  75                  80

Ser Tyr Glu Trp Val Glu Asp Lys Asn Ala Lys Asn Val Val Lys Leu
                                85                  90                  95

Ile Ser Asn Asp Lys Gly Gln Phe Glu Ile Thr Gly Leu Thr Glu Gly
```

```
            100                 105                 110
Gln Tyr Ser Leu Glu Glu Thr Gln Ala Pro Thr Gly Tyr Ala Lys Leu
            115                 120                 125

Ser Gly Asp Val Ser Phe Asn Val Asn Ala Thr Ser Tyr Ser Lys Gly
        130                 135                 140

Ser Ala Gln Asp Ile Glu Gly Ser Gly Gly Gly Leu Gln Gly Ala
145                 150                 155                 160

Ile Phe Val Leu Lys Asn Ala Thr Gly Gln Phe Leu Asn Phe Asn Asp
                165                 170                 175

Thr Asn Asn Val Glu Trp Gly Thr Glu Ala Asn Ala Thr Glu Tyr Thr
            180                 185                 190

Thr Gly Ala Asp Gly Ile Ile Thr Ile Thr Gly Leu Lys Glu Gly Thr
        195                 200                 205

Tyr Tyr Leu Val Glu Lys Lys Ala Pro Leu Gly Tyr Asn Leu Leu Asp
    210                 215                 220

Asn Ser Gln Lys Val Ile Leu Gly Asp Gly Ala Thr Asp Thr Thr Asn
225                 230                 235                 240

Ser Asp

<210> SEQ ID NO 142
<211> LENGTH: 314
<212> TYPE: PRT
<213> ORGANISM: Artificial Sequence
<220> FEATURE:
<223> OTHER INFORMATION: chimeric Cna_B domain antigen

<400> SEQUENCE: 142

Leu Ala Gly Ala Thr Phe Leu Val Lys Lys Asp Gly Lys Tyr Leu Ala
1               5                   10                  15

Arg Lys Ser Gly Val Ala Thr Asp Ala Glu Lys Ala Ala Val Asp Ser
            20                  25                  30

Thr Lys Ser Ala Leu Asp Ala Ala Val Lys Ala Tyr Asn Asp Leu Thr
        35                  40                  45

Lys Glu Lys Gln Glu Gly Gln Asp Gly Lys Ser Ala Leu Ala Thr Val
    50                  55                  60

Ser Glu Lys Gln Lys Ala Tyr Asn Asp Ala Phe Val Lys Ala Asn Tyr
65                  70                  75                  80

Ser Tyr Glu Trp Val Glu Asp Lys Asn Ala Lys Asn Val Val Lys Leu
                85                  90                  95

Ile Ser Asn Asp Lys Gly Gln Phe Glu Ile Thr Gly Leu Thr Glu Gly
            100                 105                 110

Gln Tyr Ser Leu Glu Glu Thr Gln Ala Pro Thr Gly Tyr Ala Lys Leu
        115                 120                 125

Ser Gly Asp Val Ser Phe Asn Val Asn Ala Thr Ser Tyr Ser Lys Gly
    130                 135                 140

Ser Ala Gln Asp Ile Glu Gly Ser Gly Gly Gly Leu Ser Lys Ala
145                 150                 155                 160

Thr Phe Val Leu Lys Thr Thr Ala His Pro Glu Ser Lys Ile Glu Lys
                165                 170                 175

Val Thr Ala Glu Leu Thr Gly Glu Ala Thr Phe Asp Asn Leu Ile Pro
            180                 185                 190

Gly Asp Tyr Thr Leu Ser Glu Glu Thr Ala Pro Glu Gly Tyr Lys Lys
        195                 200                 205

Thr Asn Gln Thr Trp Gln Val Lys Val Glu Ser Asn Gly Lys Thr Thr
    210                 215                 220
```

```
Ile Gln Asn Ser Gly Leu Lys Gly Ala Thr Phe Glu Leu Gln Glu Phe
225                 230                 235                 240

Asn Glu Asp Tyr Lys Leu Tyr Leu Pro Ile Lys Asn Asn Ser Lys
            245                 250                 255

Val Val Thr Gly Glu Asn Gly Lys Ile Ser Tyr Lys Asp Leu Lys Asp
            260                 265                 270

Gly Lys Tyr Gln Leu Ile Glu Ala Val Ser Pro Glu Asp Tyr Gln Lys
            275                 280                 285

Ile Thr Asn Lys Pro Ile Leu Thr Phe Glu Val Val Lys Gly Ser Ile
            290                 295                 300

Lys Asn Ile Ile Ala Val Asn Lys Gln Ile
305                 310

<210> SEQ ID NO 143
<211> LENGTH: 358
<212> TYPE: PRT
<213> ORGANISM: Artificial Sequence
<220> FEATURE:
<223> OTHER INFORMATION: chimeric Cna_B domain antigen

<400> SEQUENCE: 143

Leu Ala Gly Ala Thr Phe Leu Val Lys Lys Asp Gly Lys Tyr Leu Ala
1               5                   10                  15

Arg Lys Ser Gly Val Ala Thr Asp Ala Glu Lys Ala Ala Val Asp Ser
            20                  25                  30

Thr Lys Ser Ala Leu Asp Ala Ala Val Lys Ala Tyr Asn Asp Leu Thr
            35                  40                  45

Lys Glu Lys Gln Glu Gly Gln Asp Gly Lys Ser Ala Leu Ala Thr Val
        50                  55                  60

Ser Glu Lys Gln Lys Ala Tyr Asn Asp Ala Phe Val Lys Ala Asn Tyr
65                  70                  75                  80

Ser Tyr Glu Trp Val Glu Asp Lys Asn Ala Lys Asn Val Val Lys Leu
            85                  90                  95

Ile Ser Asn Asp Lys Gly Gln Phe Glu Ile Thr Gly Leu Thr Glu Gly
            100                 105                 110

Gln Tyr Ser Leu Glu Glu Thr Gln Ala Pro Thr Gly Tyr Ala Lys Leu
        115                 120                 125

Ser Gly Asp Val Ser Phe Asn Val Asn Ala Thr Ser Tyr Ser Lys Gly
    130                 135                 140

Ser Ala Gln Asp Ile Glu Leu Gly Gly Ala Glu Phe Asp Leu Leu Ala
145                 150                 155                 160

Ser Asp Gly Thr Ala Val Lys Trp Thr Asp Ala Leu Ile Lys Ala Asn
            165                 170                 175

Thr Asn Lys Asn Tyr Ile Ala Gly Glu Ala Val Thr Gly Gln Pro Ile
            180                 185                 190

Lys Leu Lys Ser His Thr Asp Gly Thr Phe Glu Ile Lys Gly Leu Ala
        195                 200                 205

Tyr Ala Val Asp Ala Asn Ala Glu Gly Thr Ala Val Thr Tyr Lys Leu
    210                 215                 220

Lys Glu Thr Lys Ala Pro Glu Gly Tyr Val Ile Pro Asp Lys Glu Ile
225                 230                 235                 240

Glu Phe Thr Val Ser Gln Thr Ser Tyr Asn Thr Lys Pro Thr Asp Ile
            245                 250                 255

Thr Val Asp Ser Gly Ser Gly Gly Gly Leu Gln Gly Ala Ile Phe
            260                 265                 270
```

```
Val Leu Lys Asn Ala Thr Gly Gln Phe Leu Asn Phe Asn Asp Thr Asn
            275                 280                 285

Asn Val Glu Trp Gly Thr Glu Ala Asn Ala Thr Glu Tyr Thr Thr Gly
            290                 295                 300

Ala Asp Gly Ile Ile Thr Ile Thr Gly Leu Lys Glu Gly Thr Tyr Tyr
305                 310                 315                 320

Leu Val Glu Lys Lys Ala Pro Leu Gly Tyr Asn Leu Leu Asp Asn Ser
                325                 330                 335

Gln Lys Val Ile Leu Gly Asp Gly Ala Thr Asp Thr Asn Ser Asp
            340                 345                 350

Gly Ser Gly Gly Gly
            355

<210> SEQ ID NO 144
<211> LENGTH: 515
<212> TYPE: PRT
<213> ORGANISM: Artificial Sequence
<220> FEATURE:
<223> OTHER INFORMATION: chimeric Cna_B domain antigen

<400> SEQUENCE: 144

Val Gly Asn Val Thr Val Thr Val Phe Asp Asn Asn Thr Asn Thr Lys
1               5                   10                  15

Val Gly Glu Ala Val Thr Lys Glu Asp Gly Ser Tyr Leu Ile Pro Asn
            20                  25                  30

Leu Pro Asn Gly Asp Tyr Arg Val Glu Phe Ser Asn Leu Pro Lys Gly
            35                  40                  45

Tyr Glu Val Thr Pro Ser Lys Gln Gly Asn Asn Glu Glu Leu Asp Ser
    50                  55                  60

Asn Gly Leu Ser Ser Val Ile Thr Val Asn Gly Lys Asp Asn Leu Ser
65                  70                  75                  80

Ala Asp Leu Gly Ile Tyr Lys Pro Lys Tyr Asn Leu Gly Asp Tyr Val
                85                  90                  95

Trp Glu Asp Thr Asn Lys Asn Gly Ile Gln Asp Gln Asp Glu Lys Gly
            100                 105                 110

Ile Ser Gly Val Thr Val Thr Leu Lys Asp Glu Asn Gly Asn Val Leu
            115                 120                 125

Lys Thr Val Thr Thr Asp Ala Asp Gly Lys Tyr Lys Phe Thr Asp Leu
130                 135                 140

Asp Asn Gly Asn Tyr Lys Val Glu Phe Thr Thr Pro Glu Gly Tyr Thr
145                 150                 155                 160

Pro Thr Thr Val Thr Ser Gly Ser Asp Ile Glu Lys Asp Ser Asn Gly
                165                 170                 175

Leu Thr Thr Thr Gly Val Ile Asn Gly Ala Asp Asn Met Thr Leu Asp
            180                 185                 190

Ser Gly Phe Tyr Lys Thr Pro Lys Tyr Asn Leu Gly Asn Tyr Val Trp
            195                 200                 205

Glu Asp Thr Asn Lys Asp Gly Lys Gln Asp Ser Thr Glu Lys Gly Ile
        210                 215                 220

Ser Gly Val Thr Val Thr Leu Lys Asn Glu Asn Gly Glu Val Leu Gln
225                 230                 235                 240

Thr Thr Lys Thr Asp Lys Asp Gly Lys Tyr Gln Phe Thr Gly Leu Glu
                245                 250                 255

Asn Gly Thr Tyr Lys Val Glu Phe Glu Thr Pro Ser Gly Tyr Thr Pro
            260                 265                 270
```

```
Thr Gln Val Gly Ser Gly Thr Asp Glu Gly Ile Asp Ser Asn Gly Thr
        275                 280                 285

Ser Thr Thr Gly Val Ile Lys Asp Lys Asp Asn Thr Ile Asp Ser
        290                 295                 300

Gly Phe Tyr Lys Pro Thr Tyr Asn Leu Gly Asp Tyr Val Trp Glu Asp
305                 310                 315                 320

Thr Asn Lys Asn Gly Val Gln Asp Lys Asp Glu Lys Gly Ile Ser Gly
                325                 330                 335

Val Thr Val Thr Leu Lys Asp Glu Asn Asp Lys Val Leu Lys Thr Val
                340                 345                 350

Thr Thr Asp Glu Asn Gly Lys Tyr Gln Phe Thr Asp Leu Asn Asn Gly
        355                 360                 365

Thr Tyr Lys Val Glu Phe Glu Thr Pro Ser Gly Tyr Thr Pro Thr Ser
        370                 375                 380

Val Thr Ser Gly Asn Asp Thr Glu Lys Asp Ser Asn Gly Leu Thr Thr
385                 390                 395                 400

Thr Gly Val Ile Lys Asp Ala Asp Asn Met Thr Leu Asp Ser Gly Phe
                405                 410                 415

Tyr Lys Thr Pro Lys Tyr Ser Leu Gly Asp Tyr Val Trp Tyr Asp Ser
                420                 425                 430

Asn Lys Asp Gly Lys Gln Asp Ser Thr Glu Lys Gly Ile Lys Asp Val
                435                 440                 445

Lys Val Thr Leu Leu Asn Glu Lys Gly Glu Val Ile Gly Thr Thr Lys
        450                 455                 460

Thr Asp Glu Asn Gly Lys Tyr Cys Phe Asp Asn Leu Asp Ser Gly Lys
465                 470                 475                 480

Tyr Lys Val Ile Phe Glu Lys Pro Ala Gly Leu Thr Gln Thr Val Thr
                485                 490                 495

Asn Thr Thr Glu Asp Asp Lys Asp Ala Asp Gly Gly Glu Val Asp Val
                500                 505                 510

Thr Ile Thr
        515

<210> SEQ ID NO 145
<211> LENGTH: 210
<212> TYPE: DNA
<213> ORGANISM: Artificial Sequence
<220> FEATURE:
<223> OTHER INFORMATION: CnaB antigen

<400> SEQUENCE: 145
ctggctggtg ttgaattcga actgcgtaaa gaagacaaaa aaatcgtttg ggaaaaaggt    60
accaccggtt ccaacggtca gctgaacttc aaataccctgc agaaaggtaa aacctactac   120
ctgtacgaaa ccaaagctaa actgggttac accctgccgg aaaacccgtg ggaagttgct   180
gttgctaaca acggtgacat caaagttaaa                                    210
```